United States Patent
Kitano et al.

(10) Patent No.: US 8,933,413 B2
(45) Date of Patent: Jan. 13, 2015

(54) RADIOLOGICAL IMAGE-CAPTURING DEVICE, RADIOLOGICAL IMAGE-CAPTURING SYSTEM, RADIOLOGICAL IMAGE-CAPTURING METHOD, AND PROGRAM

(71) Applicant: FUJIFILM Corporation, Tokyo (JP)

(72) Inventors: Kouichi Kitano, Kanagawa (JP); Yasunori Ohta, Kanagawa (JP); Kentaro Noma, Kanagawa (JP); Naoto Iwakiri, Kanagawa (JP); Katsumi Shimada, Kanagawa (JP); Keita Watanabe, Kanagawa (JP); Shou Shimizukawa, Kanagawa (JP); Takahiro Iwamoto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/267,192

(22) Filed: May 1, 2014

(65) Prior Publication Data

US 2014/0241502 A1    Aug. 28, 2014

Related U.S. Application Data

(63) Continuation of application No. 13/742,111, filed on Jan. 15, 2013, now Pat. No. 8,759,786, which is a continuation of application No. PCT/JP2011/062518, filed on May 31, 2011.

(30) Foreign Application Priority Data

| Jul. 16, 2010 | (JP) | 2010-161915 |
| Jul. 16, 2010 | (JP) | 2010-161917 |
| Jul. 16, 2010 | (JP) | 2010-161922 |
| Jul. 16, 2010 | (JP) | 2010-161924 |
| Jul. 16, 2010 | (JP) | 2010-161925 |
| Jul. 16, 2010 | (JP) | 2010-161927 |
| Jul. 22, 2010 | (JP) | 2010-164829 |
| Jul. 23, 2010 | (JP) | 2010-165981 |
| Jul. 29, 2010 | (JP) | 2010-170055 |

(51) Int. Cl.
*G01J 1/42* (2006.01)
*G01T 1/00* (2006.01)
*A61B 6/00* (2006.01)

(52) U.S. Cl.
CPC .................................. *A61B 6/4266* (2013.01)
USPC ........................................................ 250/393

(58) Field of Classification Search
CPC ....................................................... A61B 6/4233
USPC ......................................................... 250/393
See application file for complete search history.

(56) References Cited

U.S. PATENT DOCUMENTS 5,513,252 A * 4/1996 Blaschka et al. ............. 378/98.8
5,539,202 A    7/1996 Geagan et al.

(Continued)

FOREIGN PATENT DOCUMENTS

JP    9-131337 A    5/1997
JP    2000-076431 A    3/2000

(Continued)

OTHER PUBLICATIONS

International Search Report issued in PCT/JP2011/062518 on Jul. 5, 2011.

(Continued)

*Primary Examiner* — David Porta
*Assistant Examiner* — Abra Fein
(74) *Attorney, Agent, or Firm* — Jean C. Edwards, Esq.; Edwards Neils PLLC

(57) ABSTRACT

A radiological image-capturing device includes: a first read control section that executes a first read mode in which electric signals stored in a plurality of pixels are read out simultaneously in units of a plurality of rows; and an emission-start determining section that determines that the emission of radiation from a radiation source onto an image-capturing panel has started when the values of the electric signals read by the first read control section have become greater than an arbitrarily settable threshold. If it is determined by the emission-start determining section that the emission of the radiation has started, the first read control section terminates the reading of the electric signals, and thereby brings the image-capturing panel into an exposure state.

7 Claims, 58 Drawing Sheets

(56) References Cited

U.S. PATENT DOCUMENTS

| 5,818,898 | A | 10/1998 | Tsukamoto et al. |
| 6,671,394 | B1 | 12/2003 | Sako |
| 2003/0030004 | A1 | 2/2003 | Dixon et al. |
| 2004/0256567 | A1 | 12/2004 | Nokita |
| 2008/0029688 | A1 | 2/2008 | Yagi et al. |
| 2010/0078583 | A1 | 4/2010 | Tsubota et al. |

FOREIGN PATENT DOCUMENTS

| JP | 2008-132216 A | 6/2001 |
| JP | 2005-028113 A | 2/2005 |
| JP | 2008-237445 A | 10/2008 |
| JP | 2009-219538 A | 10/2009 |
| JP | 2009-219586 A | 10/2009 |
| JP | 2010-071659 A | 4/2010 |
| JP | 2010-081960 A | 4/2010 |
| WO | 2010-073894 A1 | 7/2010 |

OTHER PUBLICATIONS

Written Opinion issued in PCT/JP2011/062518 on Jul. 5, 2011.
Non-Final Office Action issued by the USPTO on May 10, 2013 in parent U.S. Appl. No. 13/742,111.
Final Office Action issued by the USPTO on Nov. 7, 2013 in parent U.S. Appl. No. 13/742,111.
Notice of Allowance and Fees Due issued by the USPTO on Apr. 2, 2014 in parent U.S. Appl. No. 13/742,111.
Japanese Rejection of the Application issued by JPO on Jul. 15, 2014 in connection with corresponding Japanese Patent Application No. 2012-524487.
Partial translation of WO-2010-073894.

* cited by examiner

| IMAGING AREA | DIAGNOSTIC SITE | IRRADIATION TIME | TUBE VOLTAGE | TUBE CURRENT |
|---|---|---|---|---|
| CHEST | CIRCULATORY ORGAN | 200msec | 100kV | 10mA |
| | RIB BONE | — | — | — |
| | HEART | — | — | — |
| ... | ... | ... | ... | ... |
| LOWER ABDOMEN | LUMBER SPINE | 600msec | 100kV | 5mA |
| | ... | ... | ... | ... |
| ... | ... | ... | ... | ... |

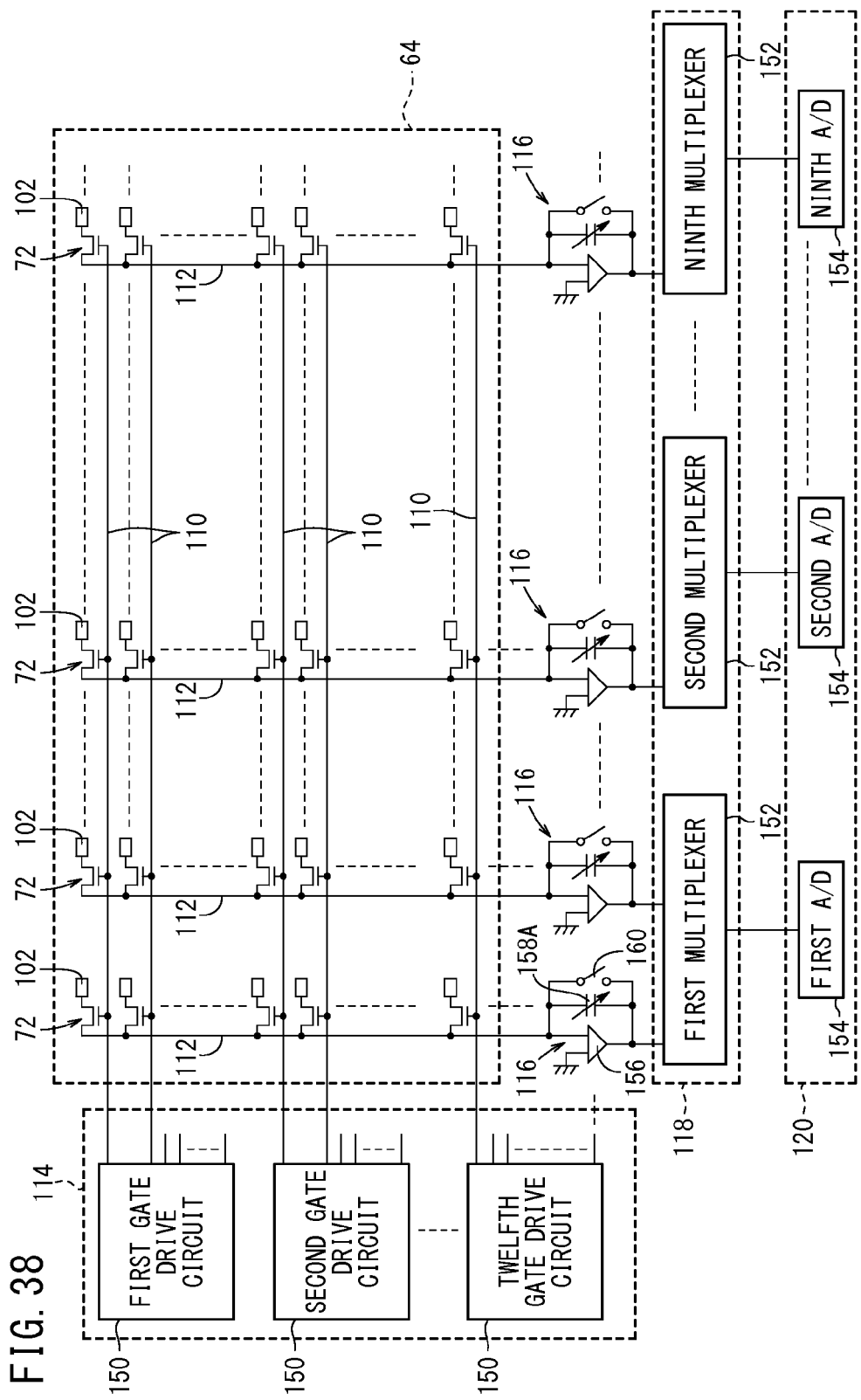

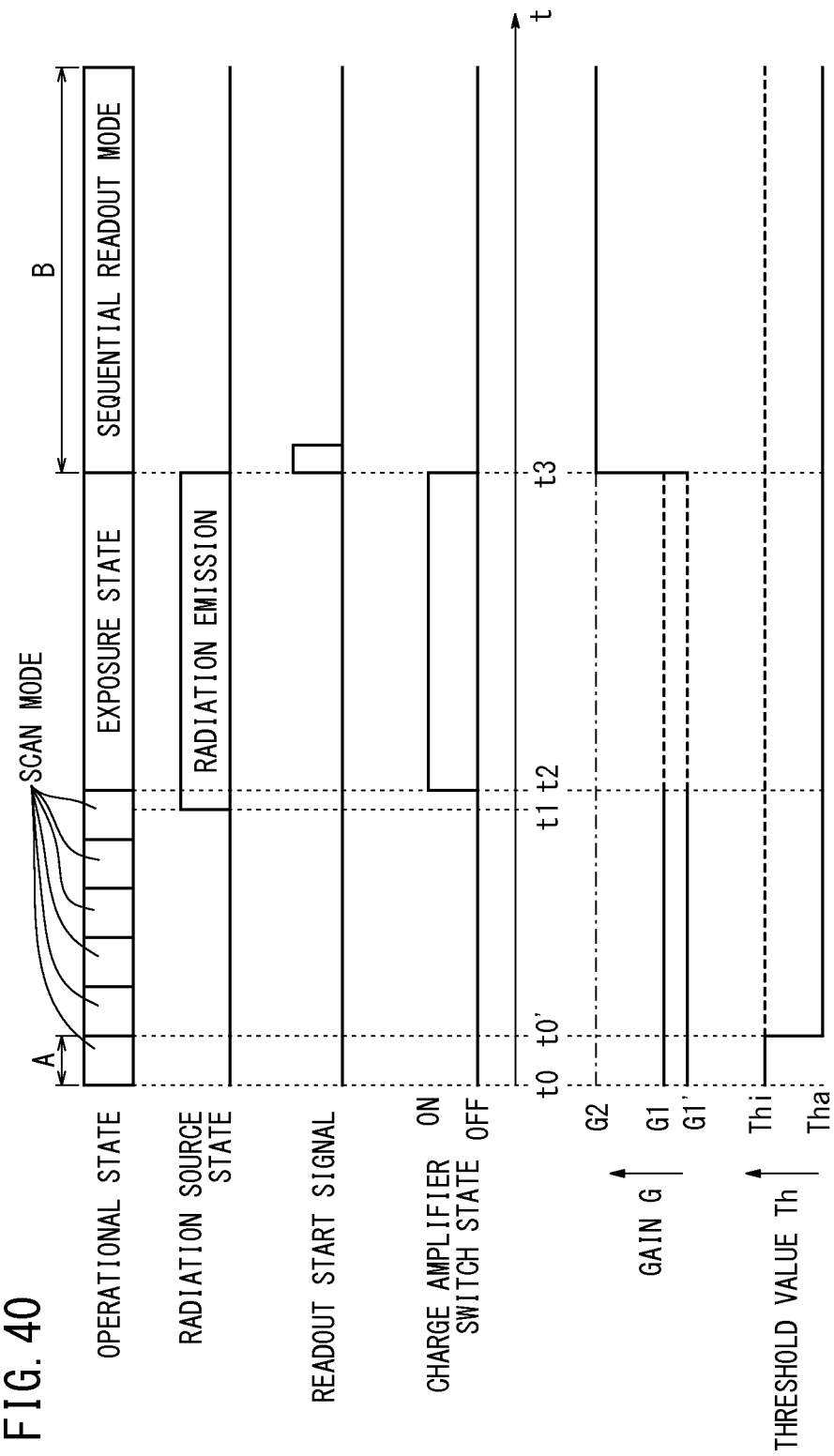

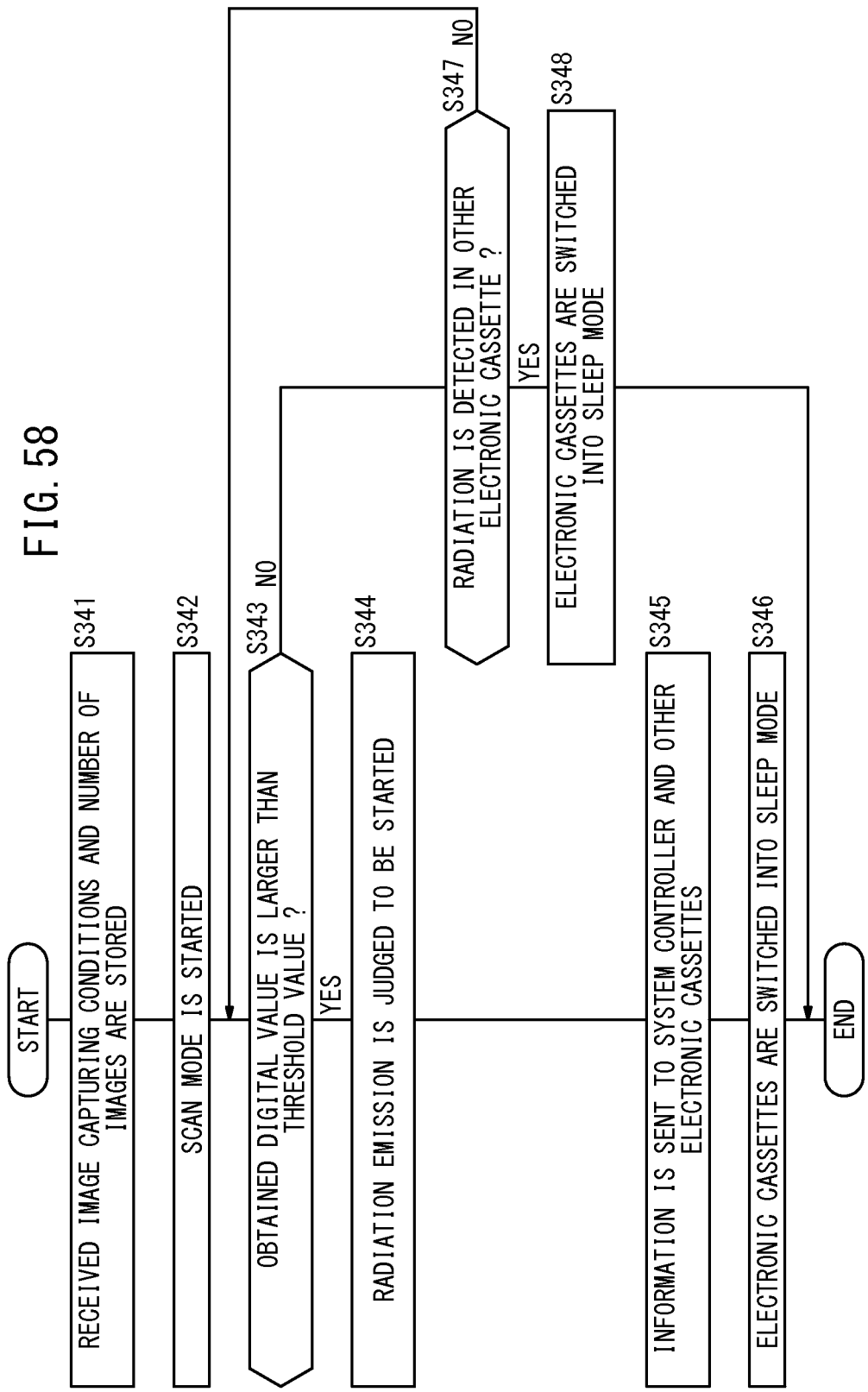

RADIOLOGICAL IMAGE-CAPTURING DEVICE, RADIOLOGICAL IMAGE-CAPTURING SYSTEM, RADIOLOGICAL IMAGE-CAPTURING METHOD, AND PROGRAM

CROSS-REFERENCE TO RELATED APPLICATIONS

This application is a Continuation of U.S. patent application Ser. No. 13/742,111, filed on Jan. 15, 2013, which in turn is a continuation application of International Application No. PCT/JP2011/062518 filed on May 31, 2011, which was published under PCT Article 21(2) in Japanese, which is based upon and claims the benefit of priority from Japanese Patent Applications No. 2010-161927 filed on Jul. 16, 2010, No. 2010-161925 filed on Jul. 16, 2010, No. 2010-161924 filed on Jul. 16, 2010, No. 2010-161922 filed on Jul. 16, 2010, No. 2010-161917 filed on Jul. 16, 2010, No. 2010-161915 filed on Jul. 16, 2010, No. 2010-164829 filed on Jul. 22, 2010, No. 2010-165981 filed on Jul. 23, 2010 and No. 2010-170055 filed on Jul. 29, 2010, the contents all of which are incorporated herein by reference.

TECHNICAL FIELD

The present invention relates to a radiographic (radiological) image capturing apparatus, a radiographic image capturing system, a radiographic image capturing method, and a program for forming an image from a radiation transmitted through a human body.

BACKGROUND ART

In the medical field, there have been used transportable radiographic image capturing apparatuses such as FPDs (Flat Panel Detectors), which detect intensity of a radiation transmitted through a human body to capture an image of an inside portion of the body. The FPD (hereinafter referred to as the electronic cassette) can capture the image while keeping a patient on a bed or the like, can be moved to adjust an area to be captured, and thereby can be flexibly used also for immobile patients.

In the electronic cassette, even if the radiation is not emitted, electric charges are generated by a dark current and stored in each pixel. The dark current appears as noise in the radiographic image. Therefore, in general, in the electronic cassette, a procedure of removing electric charges stored in each pixel is repeatedly carried out before a process of capturing a radiographic image. In a case where the radiographic image capturing process is performed, a control unit sends an image capturing instruction to the electronic cassette and a radiation apparatus for emitting the radiation. In a case where the radiation apparatus receives the image capturing instruction, the radiation apparatus starts to emit the radiation, and the electronic cassette starts to be exposed. When the radiation emission is completed, the electronic cassette reads the electric charges accumulated by the emission. In this process, the radiation emission timing of the radiation apparatus and the exposure timing of the electronic cassette are synchronized. Thus, the image capturing timings are synchronized.

Japanese Laid-Open Patent Publication No. 2010-081960 describes a first time measurement means disposed in a console (the control unit) and a second time measurement means disposed in the electronic cassette. The first and second time measurement means are synchronized with each other. At an exposure start predetermined by the console, the radiation is emitted from the radiation apparatus for a predetermined time. After the predetermined time has elapsed from the exposure start, the electronic cassette reads the electric charges generated in a radiation detector.

Various types and specifications of the electronic cassettes are used depending on the requirements of the image capturing conditions and the like. Also, the electronic cassettes are relatively costly. Therefore, as is often the case, a plurality of the electronic cassettes are not placed in each image capturing room, but are shared by a plurality of the image capturing rooms. In a case where a plurality of the electronic cassettes are shared by a plurality of the image capturing rooms, a user (such as a radiation technician) may make a mistake in selecting the electronic cassette. In the image capturing process, the electronic cassette has to be switched from a sleep mode to an image capturing mode in response to the instruction sent from the control unit (such as a console or a system controller). Therefore, in a case where the user makes the selection mistake, the image capturing process is performed while the electronic cassette remains in the sleep mode, thereby failing to obtain the radiographic image. Thus, Japanese Laid-Open Patent Publication No. 2009-219586 describes a technique, in which the image capturing process can be performed even if the user makes the selection mistake.

In Japanese Laid-Open Patent Publication No. 2009-219586, considering the possibility of the selection mistake, all the electronic cassettes (1) are switched from a standby mode to a capturing mode in the radiographic image capturing process. Thus, all the cassettes and their radiation detection means (22), located outside the subject area, are made ready for the radiation detection. Then, when the radiation detection means of one electronic cassette detects the radiation, the other electronic cassettes are returned to the standby mode (see, abstract, FIG. 8, and paragraphs 0054 to 0065 of the document).

SUMMARY OF INVENTION

To synchronize the image capturing timings, the control unit and the radiation apparatus have to be electrically connected. In this case, a manufacturer serviceman has to make the electrical connection between the control unit and the radiation apparatus at the system installation, resulting in high installation and maintenance costs. In addition, in a case where the control unit and the radiation apparatus are obtained from different manufacturers, they often cannot be electrically connected in view of safety. On the contrary, in a case where the control unit and the radiation apparatus are not electrically connected, the image capturing timings cannot be synchronized. In this case, the electronic cassette is exposed for a time longer than the irradiation time of the radiation, and the radiation is emitted while the electronic cassette is exposed, whereby the electronic cassette can be exposed to all the emitted radiation to capture the radiographic image.

In the case where the control unit and the radiation apparatus are not electrically connected, the image capturing timings cannot be synchronized as described above. Therefore, in this case, the electronic cassette is excessively exposed even in a period in which the radiation is not emitted, whereby the resultant radiographic image has a high noise content. Furthermore, the procedure of removing the unnecessary electric charges stored in the pixels cannot be carried out before the radiation emission, whereby the noise content of the resultant radiographic image is further increased. In addition, because the image capturing timings cannot be synchronized, the radiation cannot be emitted to the patient at a suitable timing. In a case where the radiation is emitted at an inaccurate timing, the resultant radiographic image often has a high noise content as described above, requiring the retaking of the radiographic image.

Assuming that the procedure of removing the unnecessary electric charges stored in the pixels can be carried out before the radiation emission, in a case where the radiation emission is not started even after a long time has elapsed from the start of the removal procedure, electric power used in the procedure is wasted. The unnecessary electric charges stored in the pixels before the radiation emission may contain electric charges corresponding to a residual image formed in a previous image capturing process (residual electric charges). When the residual electric charges cannot be reliably removed, the resultant radiographic image overlaps with the residual image.

In Japanese Laid-Open Patent Publication No. 2009-219586, the radiation detection means is located outside the subject area (paragraph 0038). Therefore, the electronic cassette is likely to have a large size.

Furthermore, Japanese Laid-Open Patent Publication No. 2009-219586 does not describes the structure of the radiation detection means. Thus, preferred structures and methods for detecting the radiation emission are not studied in this document.

Accordingly, in view of the above conventional problems, an object of the present invention is to provide a radiographic image capturing apparatus, a radiographic image capturing system, a radiographic image capturing method, and a program, capable of forming the radiographic image with a lowered noise content at low cost without synchronizing the image capturing timings. Another object of the present invention is to emit the radiation to the subject at the suitable timing without synchronizing the image capturing timings. A further object of the invention is to prevent the excessive electric power waste in the procedure of removing the unnecessary electric charges from the pixels before the radiation emission. A still further object of the invention is to reduce the overlap of the residual image with the radiographic image. A still further object of the invention is to form the radiographic image more appropriately even if the mistake is made in the selection of the radiographic image capturing apparatus such as the electronic cassette. A still further object of the invention is to improve the quality and S/N ratio of the radiographic image.

A radiographic image capturing apparatus according to a first aspect of the present invention has an image capturing panel containing a plurality of pixels arranged in a matrix for converting a radiation (which is emitted from a radiation source and transmitted through a subject) into electric signals and storing the electric signals, a first readout control part for executing a first readout mode for reading the electric signals stored in the pixels in a plurality of rows simultaneously, and an irradiation start judgment part for judging start of the radiation emission from the radiation source to the image capturing panel in a case where a value of the electric signals read by the first readout control part becomes larger than an arbitrarily settable threshold value. In a case where the radiation emission is judged to be started by the irradiation start judgment part, the first readout control part acts to stop the reading of the electric signals and to switch the image capturing panel to an exposure state.

The first readout control part may read the electric signals stored in the pixels in the rows arranged at a predetermined row interval simultaneously.

In a case where the radiation emission is judged to be started by the irradiation start judgment part, the first readout control part may stop the reading of the electric signals stored in the pixels at a timing of completion of the reading.

In a case where the radiation emission is judged to be started by the irradiation start judgment part, the first readout control part may stop the reading of the electric signals at a timing of the judgment.

The radiographic image capturing apparatus may further have an elapsed time judgment part for judging whether a predetermined time has elapsed or not after the start of the radiation emission, and a second readout control part for executing a second readout mode for reading the electric signals stored in the pixels sequentially row by row. The second readout mode is executed if elapse of the predetermined time is judged by the elapsed time judgment part.

A number of images to be captured may be set beforehand, and the first and second readout control parts may execute the first readout mode, the exposure state, and the second readout mode repeatedly based on the setup number.

A radiographic image capturing system according to the first aspect has the above radiographic image capturing apparatus, a table storing irradiation times of the radiation corresponding to at least imaging areas, and an irradiation time setting part for setting an irradiation time corresponding to an imaging area selected by a user. The elapsed time judgment part judges whether the irradiation time set by the irradiation time setting part has elapsed or not after the radiation emission is judged to be started.

The table may store the irradiation times of the radiation corresponding to at least the imaging areas and diagnostic sites, and the irradiation time setting part may set an irradiation time corresponding to an imaging area and a diagnostic site selected by the user.

The radiographic image capturing system may further have an image number setting part for setting a number of images to be captured selected by the user. The first and second readout control parts may execute the first readout mode, the exposure state, and the second readout mode repeatedly based on the number set by the image number setting part.

The table may store the irradiation times of the radiation and numbers of images to be captured corresponding to at least the imaging areas, and the first and second readout control parts may execute the first readout mode, the exposure state, and the second readout mode repeatedly based on the number of images corresponding to an imaging area selected by the user.

A method for capturing a radiographic image according to the first aspect is performed using a computer equipped with an image capturing panel. The image capturing panel contains a plurality of pixels arranged in a matrix for converting a radiation (which is emitted from a radiation source and transmitted through a subject) into electric signals and storing the electric signals. The method contains the steps of executing a first readout mode for reading the electric signals stored in the pixels in a plurality of rows simultaneously, judging start of the radiation emission from the radiation source to the image capturing panel in a case where a value of the electric signals read in the first readout mode becomes larger than a threshold value, and stopping the reading of the electric signals to switch the image capturing panel to an exposure state in a case where the radiation emission is judged to be started.

A program according to the first aspect is for using a computer equipped with an image capturing panel. The image capturing panel contains a plurality of pixels arranged in a matrix for converting a radiation (which is emitted from a radiation source and transmitted through a subject) into electric signals and storing the electric signals. The computer is used as a first readout control part for executing a first readout mode for reading the electric signals stored in the pixels in a plurality of rows simultaneously and as an irradiation start judgment part for judging start of the radiation emission from the radiation source to the image capturing panel. In a case where a value of the electric signals read by the first readout control part becomes larger than a threshold value, the radiation emission is judged to be started. In a case where the radiation emission is judged to be started by the irradiation start judgment part, the first readout control part acts to stop the reading of the electric signals and to switch the image capturing panel to an exposure state.

In the first aspect, in the first readout mode, the electric charges stored in the pixels in a plurality of rows are read out as electric signals simultaneously, and the start of the radiation emission is detected based on the read electric signals. In a case where the radiation emission is judged to be started, the reading of the electric charges is stopped, and the image capturing panel is switched to an accumulation state. Therefore, in the first aspect, it is not necessary to synchronize the image capturing timings, resulting in low cost. Since the first readout mode is performed until the radiation emission is judged to be started, the unnecessary electric charges stored in the pixels can be removed to lower the noise content of the resultant radiographic image.

A radiographic image capturing apparatus according to a second aspect of the present invention has an image capturing panel containing a plurality of pixels arranged in a matrix for converting a radiation (which is emitted from a radiation source and transmitted through a subject) into electric charges and storing the electric charges, a first readout control part for executing a first readout mode for reading the electric signals stored in the pixels in a predetermined row, an irradiation start judgment part for judging start of the radiation emission from the radiation source to the image capturing panel, the radiation emission being judged to be started in a case where a value of the electric signals read by the first readout control part becomes larger than a threshold value, an elapsed time judgment part for judging whether a predetermined time has elapsed or not after the start of the radiation emission, and a second readout control part for executing a second readout mode for reading the electric signals stored in the pixels sequentially row by row, the second readout mode being executed in a case where elapse of the predetermined time is judged by the elapsed time judgment part. In a case where the radiation emission is judged to be started by the irradiation start judgment part, the first readout control part acts to stop the reading of the electric signals and to switch the image capturing panel to an exposure state.

The first readout control part may read the electric signals stored in the pixels in the predetermined row sequentially row by row in the first readout mode.

The pixels in the image capturing panel may include pixels for storing electric signals to be read in the first readout mode and pixels for storing electric signals to be read in the second readout mode. The pixels in the predetermined row may be the pixels for storing electric signals to be read in the first readout mode executed by the first readout control part.

The pixels in the predetermined row may be pixels in a row arbitrarily selected by a user.

A number of images to be captured may be set beforehand, and the first and second readout control parts may execute the first readout mode, the exposure state, and the second readout mode repeatedly based on the setup number.

A radiographic image capturing system according to the second aspect has the above radiographic image capturing apparatus, a table storing irradiation times of the radiation corresponding to at least imaging areas, and an irradiation time setting part for setting an irradiation time corresponding to an imaging area selected by a user. The elapsed time judgment part judges whether the irradiation time set by the irradiation time setting part has elapsed or not after the radiation emission is judged to be started.

The table may store the irradiation times of the radiation corresponding to at least the imaging areas and diagnostic sites, and the irradiation time setting part may set an irradiation time corresponding to an imaging area and a diagnostic site selected by the user.

The radiographic image capturing system may further have an image number setting part for setting a number of images to be captured selected by the user. The first and second readout control parts may execute the first readout mode, the exposure state, and the second readout mode repeatedly based on the number set by the image number setting part.

The table may store the irradiation times of the radiation and numbers of images to be captured corresponding to at least the imaging areas, and the first and second readout control parts may execute the first readout mode, the exposure state, and the second readout mode repeatedly based on the number corresponding to an imaging area selected by the user.

A method for capturing a radiographic image according to the second aspect is performed using a computer equipped with an image capturing panel. The image capturing panel contains a plurality of pixels arranged in a matrix for converting a radiation (which is emitted from a radiation source and transmitted through a subject) into electric signals and storing the electric signals. The method contains the steps of executing a first readout mode for reading the electric signals stored in the pixels in a predetermined row, judging start of the radiation emission from the radiation source to the image capturing panel in a case where a value of the electric signals read in the first readout mode becomes larger than a threshold value, stopping the reading of the electric signals to switch the image capturing panel to an exposure state in a case where the radiation emission is judged to be started, judging whether a predetermined time has elapsed or not after the start of the radiation emission, and executing a second readout mode for reading the electric signals stored in the pixels sequentially row by row, the second readout mode being executed in a case where elapse of the predetermined time after the start of the radiation emission is judged.

A program according to the second aspect is for using a computer equipped with an image capturing panel. The image capturing panel contains a plurality of pixels arranged in a matrix for converting a radiation (which is emitted from a radiation source and transmitted through a subject) into electric signals and storing the electric signals. The computer is used as a first readout control part for executing a first readout mode for reading the electric signals stored in the pixels in a predetermined row, an irradiation start judgment part for judging start of the radiation emission from the radiation source to the image capturing panel in a case where a value of the electric signals read by first readout control part becomes larger than a threshold value, an elapsed time judgment part for judging whether a predetermined time has elapsed or not after the start of the radiation emission, and a second readout control part for executing a second readout mode for reading the electric signals stored in the pixels sequentially row by row. The second readout mode is executed in a case where elapse of the predetermined time is judged by the elapsed time judgment part. In a case where the radiation emission is judged to be started by the irradiation start judgment part, the first readout control part acts to stop the reading of the electric signals and to switch the image capturing panel to an exposure state.

In the second aspect, the first readout mode for reading the electric signals stored in the predetermined pixels is performed until the radiation emission is judged to be started, and the start of the radiation emission is detected based on the read electric signals. In a case where the radiation emission is judged to be started, the image capturing panel is switched to the exposure state. After the predetermined time has elapsed, the second readout mode for reading the electric signals stored in the pixels sequentially row by row is performed. Therefore, in the second aspect, it is not necessary to synchronize the image capturing timings, resulting in low cost. Since the second readout mode is performed after the predetermined time has elapsed, considering the predetermined time as the irradiation time of the radiation, the image capturing panel can be prevented from being excessively exposed after the completion of the radiation emission, lowering the noise content of the resultant radiographic image. Furthermore, since the electric signals stored in the predetermined pixels are read out, the power consumption in the first readout mode can be reduced. In addition, the pixels other than the predetermined pixels are in the exposure state even during the first readout mode, so that the radiographic image can be captured without wasting the radiation.

A radiographic image capturing apparatus according to a third aspect of the present invention has an image capturing panel containing a plurality of pixels arranged in a matrix for converting a radiation (which is emitted from a radiation source and transmitted through a subject) into electric signals and storing the electric signals, a first readout control part for executing a first readout mode for reading the electric signals stored in the pixels, an irradiation start judgment part for judging start of the radiation emission from the radiation source to the image capturing panel, the radiation emission being judged to be started in a case where a value of the electric signals read by the first readout control part becomes larger than an arbitrarily settable threshold value, and a first readout mode stop judgment part for stopping the first readout mode in a case where the values of the electric signals do not reach the threshold value even after a predetermined time has elapsed from the start of the first readout mode.

In the third aspect, the first readout control part preferably acts to switch the image capturing panel into the exposure state after the stop of the first readout mode.

In this case, it is preferred that the radiographic image capturing apparatus further has a transfer detection device for detecting the transfer of the radiographic image capturing apparatus, a light detection device for detecting a visible light for indicating an irradiation field of the radiation (which is emitted from an irradiation field lamp before the radiation emission from the radiation source), a second readout control part for executing a second readout mode for reading the electric signals stored in the pixels sequentially row by row, and an image acquirement judgment part for judging whether the second readout mode should be executed or not based on a detection result from the transfer detection device or the light detection device. In a case where the image acquirement judgment part judges that the second readout mode should be executed, the second readout control part preferably acts to read the electric signals in the pixels in the exposure state sequentially row by row.

In this case, in a case where a value of the electric signals read by the second readout control part reaches a predetermined value, the image acquirement judgment part may acquire the electric signals as a radiographic image of the subject. On the other hand, in a case where a value of the electric signals does not reach the predetermined value, the image acquirement judgment part may act to discharge the electric signals to the ground and to stop the second readout mode.

Alternatively, the radiographic image capturing apparatus may further have a second readout control part for executing a second readout mode for reading the electric signals stored in the pixels sequentially row by row, and the second readout control part may act to perform a reset operation for discharging the electric signals stored in the pixels to the ground after the stop of the first readout mode.

In this case, it is preferred that the radiographic image capturing apparatus further has a sleep state switch judgment part, which judges at least the operation stop of the image capturing panel and switches the radiographic image capturing apparatus to a sleep state in a case where the first readout mode is stopped or the reset operation is completed.

In this case, the radiographic image capturing apparatus may further have a transfer detection device for detecting the transfer of the apparatus, a light detection device for detecting a visible light for indicating an irradiation field of the radiation (which is emitted from an irradiation field lamp before the radiation emission from the radiation source), and a first readout mode restart judgment part for judging whether the first readout mode should be restarted or not based on a detection result from the transfer detection device or the light detection device. In a case where the first readout mode restart judgment part judges that the first readout mode should be restarted, the first readout control part may act to restart the first readout mode.

In the above described structures, the first readout control part may read the electric signals stored in the pixels in a plurality of rows simultaneously, or alternatively may read the electric signals stored in the pixels in a predetermined row.

In this case, the radiographic image capturing apparatus may further have a first announcement device for announcing the stop of the first readout mode to the outside. The first announcement device preferably includes at least one of a sound output device for outputting a sound indicating the stop of the first readout mode, a light output device for outputting a light indicating the stop of the first readout mode, and a first communication device for sending a communication signal indicating the stop of the first readout mode to the outside.

A radiographic image capturing system according to the third aspect has the above radiographic image capturing apparatus, a table storing image capturing conditions including at least irradiation times of the radiation, an image capturing menu setting unit for setting an image capturing menu associated with the radiation emission based on the image capturing conditions, a second communication device for sending at least the image capturing menu to the first communication device and receiving the communication signal from the first communication device, and a second announcement device for announcing the stop of the first readout mode based on the communication signal.

In this case, the radiographic image capturing system may further have an input device for receiving an input operation by a user to select image capturing conditions corresponding to an imaging area of the subject from the conditions stored in the table. The image capturing menu setting unit may set an image capturing menu including the image capturing conditions selected based on the input operation by the user. The second communication device may send the setup image capturing menu to the first communication device.

The radiographic image capturing system may further have an instruction signal generation unit, which generates an instruction signal for restarting the first readout mode in a case where the image capturing menu setting unit resets the image capturing menu or in a case where the user operates the input device, after the second communication device receives the communication signal. The second communication device sends the reset image capturing menu and the instruction signal or only the instruction signal to the first communication device. The radiographic image capturing apparatus may further have a first readout mode restart judgment part for judging whether the first readout mode should be restarted or not based on the instruction signal entered into the first communication device. The first readout control part may restart the first readout mode based on the reset image capturing menu entered into the first communication device and the judgment result from the first readout mode restart judgment part or only the judgment result.

In this case, the second announcement device preferably includes at least one of a display device for displaying a screen indicating the stop of the first readout mode, a sound output device for outputting a sound indicating the stop, and a light output device for outputting a light indicating the stop of the first readout mode.

A method for capturing a radiographic image according to the third aspect is performed using a computer equipped with an image capturing panel. The image capturing panel contains a plurality of pixels arranged in a matrix for converting a radiation (which is emitted from a radiation source and transmitted through a subject) into electric signals and storing the electric signals. The method contains the steps of executing a first readout mode for reading the electric signals stored in the pixels, judging whether or not a value of the electric signals read in the first readout mode becomes larger than an arbitrarily settable threshold value, and stopping the first readout mode in a case where the value of the electric signals does not reach the threshold value even after a predetermined time has elapsed from the start of the first readout mode, based on a judgment that the radiation emission from the radiation source to the image capturing panel is not started.

A program according to the third aspect is for using a computer equipped with an image capturing panel. The image capturing panel contains a plurality of pixels arranged in a matrix for converting a radiation (which is emitted from a radiation source and transmitted through a subject) into electric signals and storing the electric signals. The computer is used as a first readout control part for executing a first readout mode for reading the electric signals stored in the pixels, an irradiation start judgment part for judging the start of the radiation emission from the radiation source to the image capturing panel in a case where a value of the electric signals read by first readout control part becomes larger than an arbitrarily settable threshold value, and a first readout mode stop judgment part for stopping the first readout mode in a case where the values of the electric signals do not reach the threshold value even after a predetermined time has elapsed from the start of the first readout mode.

In the third aspect, the start of the radiation emission is detected based on the read electric signals stored in the pixels in the first readout mode. Therefore, it is not necessary to synchronize the image capturing timings, resulting in low cost. Since the first readout mode is performed before the start of the radiation emission, the unnecessary electric charges stored in the pixels can be removed to lower the noise content of the resultant radiographic image.

Furthermore, in the third aspect, the first readout mode is stopped in a case where the values of the electric signals do not reach the threshold value even after the predetermined time has elapsed from the start of the first readout mode.

Therefore, wasteful power consumption can be prevented in the first readout mode executed before the radiation emission.

A radiographic image capturing apparatus according to a fourth aspect of the present invention has an image capturing panel containing a plurality of pixels arranged in a matrix for converting a radiation (which is emitted from a radiation source and transmitted through a subject) into electric signals and storing the electric signals, a first readout control part for executing a first readout mode for reading the electric signals stored in the pixels based on an image capturing menu associated with the emission of the radiation, a mode switch judgment part for judging whether the first readout mode is started or not, and a first announcement device for announcing a judgment result from the mode switch judgment part to the outside in a case where the first readout mode is judged to be started by the mode switch judgment part.

In the fourth aspect, the first readout control part may read the electric signals stored in the pixels in a plurality of rows simultaneously, or alternatively may read the electric signals stored in the pixels in a predetermined row.

The radiographic image capturing apparatus may further have an irradiation start judgment part. In a case where a value of the electric signals read by first readout control part becomes larger than an arbitrarily settable threshold value, the irradiation start judgment part judges that the radiation emission from the radiation source to the image capturing panel is started, and sends an instruction to the first readout control part to stop the reading of the electric signals and switch the image capturing panel into the exposure state.

The first announcement device preferably includes at least one of a sound output device for outputting a sound indicating the judgment result, a light output device for outputting a light indicating the judgment result, and a first communication device for sending a communication signal indicating the judgment result to the outside.

A radiographic image capturing system according to the fourth aspect has the above radiographic image capturing apparatus, a table storing image capturing conditions including at least irradiation times of the radiation, an image capturing menu setting unit for setting an image capturing menu based on the image capturing conditions, a second communication device for sending the image capturing menu to the first communication device and receiving the communication signal from the first communication device, and a second announcement device for announcing start of the first readout mode based on the communication signal.

In this case, the radiographic image capturing system may further have an input device for receiving an input operation by a user to select image capturing conditions corresponding to an imaging area of the subject from the conditions stored in the table. The image capturing menu setting unit may set an image capturing menu including the image capturing conditions selected based on the input operation by the user. The second communication device may send the setup image capturing menu to the first communication device. In a case where the first communication device receives the image capturing menu, the first readout control part may execute the first readout mode based on the image capturing menu.

The radiographic image capturing apparatus may further have a second readout control part for executing a second readout mode for reading the electric signals stored in the pixels sequentially row by row, and an imaging control device for controlling the first readout control part to start the first readout mode or controlling the first and second readout control parts to switch from the second readout mode to the first readout mode in a case where the first communication device receives the image capturing menu.

In this case, the second readout control part preferably acts to execute the second readout mode for reading the electric signals stored in the pixels as offset signals sequentially row by row or to perform a reset operation for discharging the electric signals stored in the pixels to the ground, before the execution of the first readout mode by the first readout control part.

The second announcement device may include at least one of a display device for displaying a screen indicating the start of the first readout mode, a sound output device for outputting a sound indicating the start of the first readout mode, and a light output device for outputting a light indicating the start of the first readout mode.

The radiographic image capturing system preferably has the radiation source and a radiation switch, which is operated by a user to emit the radiation from the radiation source. The first announcement device and/or the second announcement device preferably announces that the user can operate the radiation switch.

A method for capturing a radiographic image according to the fourth aspect is performed using a computer equipped with an image capturing panel. The image capturing panel contains a plurality of pixels arranged in a matrix for converting a radiation (which is emitted from a radiation source and transmitted through a subject) into electric signals and storing the electric signals. The method contains the steps of executing a first readout mode for reading the electric signals stored in the pixels based on an image capturing menu associated with the radiation emission, judging the start of the start of the first readout mode, and announcing the judgment result from the first readout mode start to the outside.

A program according to the fourth aspect is for using a computer equipped with an image capturing panel. The image capturing panel contains a plurality of pixels arranged in a matrix for converting a radiation (which is emitted from a radiation source and transmitted through a subject) into electric signals and storing the electric signals. The computer is used as a first readout control part for executing a first readout mode for reading the electric signals stored in the pixels based on an image capturing menu associated with the emission of the radiation, a mode switch judgment part for judging whether the first readout mode is started or not, and a first announcement device for announcing a judgment result from the mode switch judgment part to the outside in a case where the first readout mode is judged to be started by the mode switch judgment part.

In the fourth aspect, in a case where the first readout mode is started, the reading of the electric signals stored in the pixels are started, thus the procedure of removing the electric charges is started, and the radiographic image capturing apparatus is switched to a state in which the radiation can be emitted. Then, in the fourth aspect, the start of the first readout mode is judged, and the judgment result is announced to the outside, so that suitable radiation emission timing can be announced to the outside. Thus, the radiation is emitted to the subject after the announcement of the judgment result, whereby the radiographic image can be formed with high quality. The radiation can be emitted at a suitable timing to avoid retaking.

Consequently, in the fourth aspect, the radiation can be emitted to the subject at the suitable timing without synchronizing the image capturing timings, so that the radiographic image can be formed with a lowered noise content at low cost.

A radiographic image capturing apparatus according to a fifth aspect of the present invention has an image capturing panel containing a plurality of pixels arranged in a matrix for converting a radiation (which is emitted from a radiation source and transmitted through a subject) into electric signals and storing the electric signals, a first readout control part for executing a first readout mode for reading the electric signals stored in the pixels corresponding to an imaging region of the subject set in an image capturing menu associated with the emission of the radiation, an irradiation start judgment part for judging the start of the radiation emission from the radiation source to the image capturing panel and for sending an instruction to stop the reading of the electric signals and switch the image capturing panel to an exposure state to the first readout control part, the radiation emission being judged to be started in a case where a value of the electric signals read by the first readout control part becomes larger than an arbitrarily settable threshold value, and a second readout control part for executing a second readout mode for reading the electric signals stored in the pixels corresponding to the imaging region sequentially row by row, the second readout mode being executed after a predetermined time has elapsed from the start of the radiation emission.

In this case, the first readout control part may read the electric signals stored in the pixels corresponding to the imaging region at a predetermined row interval simultaneously, or alternatively may read the electric signals stored in the pixels corresponding to the imaging region in a predetermined row sequentially row by row.

In a case where the radiation emission is judged to be started by the irradiation start judgment part, the first readout control part may stop the reading of the electric signals stored in the pixels at a timing of completion of the reading or a timing of the judgment of the radiation emission as being started.

The first readout control part may read the electric signals stored in the pixels in rows and columns corresponding to the imaging region at a predetermined row interval simultaneously. Alternatively, the first readout control part may read the electric signals stored in the pixels in a predetermined row, among the rows and columns corresponding to the imaging region, sequentially row by row. The second readout control part may read the electric signals stored in the pixels in the rows and columns corresponding to the imaging region sequentially row by row.

In this case, before the first readout mode performed by the first readout control part, the second readout control part may act to execute an offset signal readout mode for reading the electric signals stored in the pixels in the rows and columns corresponding to the imaging region as offset signals sequentially row by row or a reset operation for discharging the electric signals stored in the pixels to the ground.

The radiographic image capturing apparatus may further have a communication device for sending signals to and receiving signals from the outside and an imaging control device for controlling the image capturing panel, the first readout control part, the irradiation start judgment part, the second readout control part, and the communication device. In a case where the communication device receives the image capturing menu from the outside, the imaging control device may, based on the imaging region set in the image capturing menu, detect the pixels in the rows and columns corresponding to the imaging region and send an instruction to the first and second readout control parts to read the electric signals stored in the pixels in the detected rows and columns.

In this case, the communication device may send signals to and receive signals from the outside via wireless communication. The radiographic image capturing apparatus may further have an electric power supply for supplying electric power to each component, and the electric power supply may be a battery. In addition, the radiographic image capturing apparatus is preferably a transportable image capturing apparatus.

A radiographic image capturing system according to the fifth aspect has the above radiographic image capturing apparatus, a table storing image capturing conditions including at least irradiation times of the radiation associated with imaging areas of the subject, an image capturing menu setting unit for setting an image capturing menu including the imaging region based on the image capturing conditions, and a transmission unit for sending the image capturing menu to the communication device.

A method for capturing a radiographic image according to the fifth aspect is performed using a computer equipped with an image capturing panel. The image capturing panel contains a plurality of pixels arranged in a matrix for converting a radiation (which is emitted from a radiation source and transmitted through a subject) into electric signals and storing the electric signals. The method contains the steps of executing a first readout mode for reading the electric signals stored in the pixels corresponding to an imaging region of the subject set in an image capturing menu associated with the radiation emission, judging the start of the radiation emission from the radiation source to the image capturing panel in a case where a value of the electric signals read in the first readout mode becomes larger than an arbitrarily settable threshold value, stopping the reading of the electric signals to switch the image capturing panel to an exposure state in a case where the radiation emission is judged to be started, and executing a second readout mode for reading the electric signals stored in the pixels corresponding to the imaging region sequentially row by row in a case where a predetermined time has elapsed from the start of the radiation emission.

A program according to the fifth aspect is for using a computer equipped with an image capturing panel. The image capturing panel contains a plurality of pixels arranged in a matrix for converting a radiation (which is emitted from a radiation source and transmitted through a subject) into electric signals and storing the electric signals. The computer is used as a first readout control part for executing a first readout mode for reading the electric signals stored in the pixels corresponding to an imaging region of the subject set in an image capturing menu associated with the emission of the radiation, an irradiation start judgment part for judging start of the radiation emission from the radiation source to the image capturing panel and for sending an instruction to stop the reading of the electric signals and switch the image capturing panel to an exposure state to the first readout control part, the radiation emission being judged to be started when a value of the electric signals read by the first readout control part becomes larger than an arbitrarily settable threshold value, and a second readout control part for executing a second readout mode for reading the electric signals stored in the pixels corresponding to the imaging region sequentially row by row, the second readout mode being executed after a predetermined time has elapsed from the start of the radiation emission.

In the fifth aspect, the start of the radiation emission is judged based on the electric signals read from the pixels in the first readout mode. In a case where the radiation emission is judged to be started, the reading of the electric signals is stopped, and the image capturing panel is switched to an accumulation state. Therefore, it is not necessary to synchronize the image capturing timings, resulting in low cost. Since the first readout mode is performed until the radiation emission is judged to be started, the unnecessary electric charges stored in the pixels can be removed to lower the noise content of the resultant radiographic image.

Furthermore, in the fifth aspect, the electric signals stored in all the pixels in the image capturing panel are not read out, and only the electric signals stored in the pixels corresponding to the imaging region of the subject set in the image capturing menu are read out by the first or second readout control part. Therefore, the power consumption required for reading the electric signals can be lowered, and the radiographic image of the imaging region can be reliably acquired.

A radiographic image capturing apparatus according to a sixth aspect of the present invention has an image capturing panel containing a plurality of pixels arranged in a matrix for converting a radiation (which is emitted from a radiation source and transmitted through a subject) into electric signals and storing the electric signals, a first readout control part for executing a first readout mode for reading the electric signals stored in the pixels in a plurality of rows simultaneously or reading the electric signals stored in the pixels in a predetermined row, a second readout control part for executing a second readout mode for reading the electric signals stored in the pixels sequentially row by row, and an imaging control device for deciding to execute the first or second readout mode with reference to an image capturing history contained in an image capturing menu associated with the emission of the radiation and making the first or second readout control part to read the electric signals in the decided mode.

With reference to the image capturing history, in a case where the last image capturing process is carried out using a relatively high radiation dose, the imaging control device may make the first and second readout control parts to read the electric signals in the pixels in the second readout mode, the first readout mode, and the second readout mode in this order.

Alternatively, with reference to the image capturing history, in a case where a predetermined time has elapsed from the last image capturing process, this image capturing process is carried out using a relatively low radiation dose, or this image capturing process is carried out using a relatively short irradiation time, the imaging control device may make the first and second readout control parts to read the electric signals in the pixels in the first readout mode and the second readout mode in this order.

In this case, with reference to the irradiation time and the image capturing history contained in the image capturing menu, the imaging control device may control the first readout control part to change a row interval at which the electric signals are read out simultaneously and use the changed row interval in the first readout mode. Alternatively, the imaging control device may control the first readout control part to change the predetermined row and read the electric signals in the pixels in the changed row in the first readout mode.

The first readout control part may read the electric signals stored in the pixels in rows arranged at a predetermined row interval simultaneously, or read the electric signals stored in the pixels in the predetermined row sequentially row by row. The radiographic image capturing apparatus may further have an irradiation start judgment part. In a case where a value of the electric signals read by first readout control part becomes larger than an arbitrarily settable threshold value, the irradiation start judgment part judges that the radiation emission from the radiation source to the image capturing panel is started, and sends an instruction to the first readout control part to stop the reading of the electric signals and switch the image capturing panel into an exposure state. The second readout control part may act to execute the second readout mode for reading the electric signals stored in the pixels in a case where a predetermined time has elapsed from the start of the radiation emission.

In this case, in a case where the radiation emission is judged to be started by the irradiation start judgment part, the first readout control part may stop the reading of the electric signals stored in the pixels at a timing of completion of the reading or a timing of the judgment of the radiation emission as being started.

A radiographic image capturing system according to the sixth aspect has the above radiographic image capturing apparatus, a table storing image capturing conditions including at least irradiation times of the radiation associated with imaging areas of the subject, an image capturing history recording unit for recording the image capturing history, and an image capturing menu setting unit for setting the image capturing menu based on the image capturing conditions and the image capturing history.

A method for capturing a radiographic image according to the sixth aspect is performed using a computer equipped with an image capturing panel. The image capturing panel contains a plurality of pixels arranged in a matrix for converting a radiation (which is emitted from a radiation source and transmitted through a subject) into electric signals and storing the electric signals. The method contains the steps of deciding to execute one of first and second readout modes, and reading the electric signals stored in the pixels in the decided mode. In the first readout mode, the electric signals stored in the pixels in a plurality of rows are read out simultaneously, or alternatively the electric signals stored in the pixels in a predetermined row are read out. In the second readout mode, the electric signals stored in the pixels are read sequentially row by row.

A program according to the sixth aspect is for using a computer equipped with an image capturing panel. The image capturing panel contains a plurality of pixels arranged in a matrix for converting a radiation (which is emitted from a radiation source and transmitted through a subject) into electric signals and storing the electric signals. The computer is used as a first readout control part for executing a first readout mode for reading the electric signals stored in the pixels in a plurality of rows simultaneously or reading the electric signals stored in the pixels in a predetermined row, a second readout control part for executing a second readout mode for reading the electric signals stored in the pixels sequentially row by row, and an imaging control device for deciding to execute the first or second readout mode with reference to an image capturing history contained in an image capturing menu associated with the emission of the radiation and making the first or second readout control part to read the electric signals in the decided mode.

In the sixth aspect, the radiation emission is judged to be started based on the electric signals read from the pixels in the first readout mode. In a case where the radiation emission is judged to be started, the reading of the electric charges is stopped, and the image capturing panel is switched to an accumulation state. Therefore, in the sixth aspect, it is not necessary to synchronize the image capturing timings, resulting in low cost. Since the first readout mode is performed until the radiation emission is judged to be started, the unnecessary electric charges stored in the pixels can be removed to lower the noise content of the resultant radiographic image.

Furthermore, in the sixth aspect, the execution of the first or second readout mode is decided with reference to the image capturing history contained in the image capturing menu, and the first or second readout control means reads the electric charges (electric signals) in the decided mode. Therefore, residual electric charges stored in a previous image capturing process can be reliably removed before the radiation emission, and the radiographic image can be formed with a high quality without overlap of a residual image.

A radiographic image capturing apparatus according to a seventh aspect of the present invention has an image capturing panel containing a plurality of pixels arranged in a matrix for converting a radiation (which is emitted from a radiation source and transmitted through a subject) into electric signals and storing the electric signals, a first readout control part for executing a first readout mode for reading the electric signals stored in the pixels in a plurality of rows simultaneously through an electric signal amplifier set at a first readout gain, an irradiation start judgment part for judging the start of the emission of the radiation from the radiation source to the image capturing panel, the radiation emission being judged to be started in a case where a value of the electric signals read by the first readout control part becomes larger than an arbitrarily settable threshold value, and the first readout control part acting to stop the reading of the electric signals and to switch the image capturing panel to an exposure state in a case where the radiation emission is judged to be started by the irradiation start judgment part, an emission completion judgment part for judging the completion of the radiation emission, and a second readout control part for executing a second readout mode for reading the electric signals stored in the pixels sequentially row by row through the electric signal amplifier set at a second readout gain, the second readout mode being executed in a case where the radiation emission is judged to be completed by the emission completion judgment part. The first readout gain is set to be lower than the second readout gain.

The emission completion judgment part may be an elapsed time judgment part for judging whether a predetermined time has elapsed or not from the start of the radiation emission. In a case where the predetermined time is judged to have elapsed by the elapsed time judgment part, the second readout control part may act to execute the second readout mode for reading the electric signals stored in the pixels sequentially row by row through the electric signal amplifier at the second readout gain.

The emission completion judgment part may be a radiation detection sensor. In a case where the radiation emission is judged to be completed by the output of the radiation detection sensor, the second readout control part may act to execute the second readout mode for reading the electric signals stored in the pixels sequentially row by row through the electric signal amplifier at the second readout gain.

The first readout control part may simultaneously read the electric signals stored in the pixels in rows arranged at a predetermined row interval.

A radiation dose setting part may be used for setting a low or high radiation dose of the radiation to be emitted to the subject. The first readout control part may control the first readout gain based on information from the radiation dose setting part such that the gain for the high radiation dose is lower than that for the low radiation dose.

The first and second readout control parts may control the first and second readout gains depending on image capturing conditions.

With respect to the setup of the threshold value in the first readout mode executed by the first readout control part, the irradiation start judgment part may set a start threshold value at the start of the first readout mode, and may further set a normal threshold value smaller than the start threshold value. The normal threshold value is a sum of a predetermined value and a value of the electric signals in a plurality of the rows read at the start of the first readout mode. The setup normal threshold value may be used as the above threshold value in the following reading operation in the first readout mode.

The radiographic image capturing apparatus may further have a normal threshold value monitoring part for monitoring the normal threshold value. Then the monitored normal threshold value becomes larger than a predetermined value, the normal threshold value monitoring part may send a notice to the outside.

The first and second readout control parts may execute the first readout mode, the exposure state, and the second readout mode repeatedly based on a number of images to be captured determined beforehand.

In a process of capturing the first image, the irradiation start judgment part may set the start threshold value and the normal threshold value in this order in the first readout mode. In processes of capturing the second and following images, the irradiation start judgment part may set the normal threshold value in first readout mode.

The electric signal amplifier may be a charge amplifier containing a capacitor and an operating amplifier.

A radiographic image capturing system according to the seventh aspect has at least the above radiographic image capturing apparatus and a radiation source.

A method for capturing a radiographic image according to the seventh aspect is performed using a computer equipped with an image capturing panel. The image capturing panel contains a plurality of pixels arranged in a matrix for converting a radiation (which is emitted from a radiation source and transmitted through a subject) into electric signals and storing the electric signals. The method contains a first readout control step of executing a first readout mode for reading the electric signals stored in the pixels in a plurality of rows simultaneously through an electric signal amplifier set at a first readout gain, an irradiation start judgment step of judging the start of the emission of the radiation from the radiation source to the image capturing panel, the radiation emission being judged to be started in a case where a value of the electric signals read by a first readout control part becomes larger than an arbitrarily settable threshold value, and the first readout control part acting to stop the reading of the electric signals and to switch the image capturing panel to an exposure state in a case where the radiation emission is judged to be started in the irradiation start judgment step, an emission completion judgment step of judging the completion of the radiation emission, and a second readout control step of executing a second readout mode for reading the electric signals stored in the pixels sequentially row by row through the electric signal amplifier set at a second readout gain, the second readout mode being executed in a case where the radiation emission is judged to be completed by the emission completion judgment step. The first readout gain is set to be lower than the second readout gain.

A program according to the seventh aspect is for using a computer for controlling an image capturing panel. The image capturing panel contains a plurality of pixels arranged in a matrix for converting a radiation (which is emitted from a radiation source and transmitted through a subject) into electric signals and storing the electric signals. The computer is used as a first readout control part for executing a first readout mode for reading the electric signals stored in the pixels in a plurality of rows simultaneously through an electric signal amplifier set at a first readout gain, an irradiation start judgment part for judging the start of the emission of the radiation from the radiation source to the image capturing panel, the radiation emission being judged to be started in a case where a value of the electric signals read by the first readout control part becomes larger than an arbitrarily settable threshold value, and the first readout control part acting to stop the reading of the electric signals and to switch the image capturing panel to an exposure state in a case where the radiation emission is judged to be started by the irradiation start judgment part, an emission completion judgment part for judging the completion of the radiation emission, and a second readout control part for executing a second readout mode for reading the electric signals stored in the pixels sequentially row by row through the electric signal amplifier set at a second readout gain, the second readout mode being executed in a case where the radiation emission is judged to be completed by the emission completion judgment part. The first readout gain is set to be lower than the second readout gain.

In the seventh aspect, the electric signals stored in the pixels in a plurality of the rows are simultaneously read out through the electric signal amplifier at the first readout gain in the first readout mode, and the start of the radiation emission is judged based on the read electric signals. In a case where the radiation emission is judged to be started, the reading of the electric signals is stopped, and the image capturing panel is switched to an accumulation state. Therefore, in the seventh aspect, it is not necessary to synchronize the image capturing timings, resulting in low cost. Since the first readout mode is performed until the radiation emission is judged to be started, unnecessary electric signals stored in the pixels can be removed, so that the noise content of the resultant radiographic image is lowered. Furthermore, in a case where the radiation emission is completed, the electric signals stored in the pixels are read sequentially row by row through the electric signal amplifier at the second readout gain higher than the first readout gain in the second readout mode. Therefore, even if a value of the electric signals read by the first readout control part becomes larger than the arbitrarily settable threshold value in the first readout mode, the output of the electric signal amplifier can be prevented from being excessively increased or saturated. In addition, the output value of the electric signal amplifier can be made within a suitable range in the second readout mode.

A radiographic image capturing apparatus according to an eighth aspect of the present invention has an image capturing panel containing a plurality of pixels arranged in a matrix for converting a radiation (which is emitted from a radiation source and transmitted through a subject at least in an exposure period) into electric signals and storing the electric signals, a first readout control part for executing a first readout mode for reading the electric signals stored in the pixels in a plurality of rows simultaneously, an irradiation start judgment part for judging the start of the emission of the radiation from the radiation source to the image capturing panel, the radiation emission being judged to be started in a case where a value of the electric signals read by the first readout control part becomes larger than an arbitrarily settable threshold value, and an all-pixel reset control part for performing an all-pixel reset process of discarding the electric signals stored in all the pixels in a case where the radiation emission is judged to be started by the irradiation start judgment part. The image capturing panel is switched to an exposure state in a case where the all-pixel reset process is completed.

After the radiation emission is judged to be started by the irradiation start judgment part, in a case where the first readout mode by the first readout control part is completed, the all-pixel reset control part may perform the all-pixel reset process.

The all-pixel reset control part may have an activation portion for activating all the rows of all the pixels simultaneously after the first readout mode by the first readout control is completed, and a switch control portion for connecting all the columns and drains over the activation period.

The all-pixel reset control part may perform the all-pixel reset process in a case where the radiation emission is judged to be started by the irradiation start judgment part.

The radiographic image capturing apparatus may further have a mask processing portion for disabling the first readout mode by the first readout control part in a case where the radiation emission is judged to be started. The all-pixel reset control part may have an activation portion for activating all the rows of all the pixels simultaneously in a case where the radiation emission is judged to be started by the irradiation start judgment part, and may further have a switch control portion for connecting all the columns and drains over the activation period.

In a case where the all-pixel reset process is completed, the image capturing panel may be switched to the exposure state to start the exposure period.

The radiographic image capturing apparatus may further have an elapsed time judgment part for judging whether a predetermined time has elapsed or not from the start of the exposure period, and a second readout control part for executing a second readout mode for reading the electric signals stored in the pixels sequentially row by row. The second readout mode is executed in a case where the elapsed time judgment part judges that the predetermined time has elapsed.

A number of images to be captured may be set beforehand, and the first and second readout control parts may execute the first readout mode, the exposure state, and the second readout mode repeatedly based on the setup number.

A radiographic image capturing system according to the eighth aspect has the above radiographic image capturing apparatus, a table storing irradiation times of the radiation associated with at least imaging areas, and an irradiation time setting part for setting an irradiation time corresponding to an imaging area selected by a user. The elapsed time judgment part judges whether or not the irradiation time set by the irradiation time setting part has elapsed after the radiation emission is judged to be started.

The table may store the irradiation times of the radiation corresponding to at least the imaging areas and diagnostic sites, and the irradiation time setting part may set an irradiation time corresponding to an imaging area and a diagnostic site selected by the user.

The radiographic image capturing system may further have an image number setting part for setting a number of images to be captured selected by the user. The first and second readout control parts may execute the first readout mode, the exposure state, and the second readout mode repeatedly based on the number set by the image number setting part.

The table may store the irradiation times of the radiation and numbers of images to be captured corresponding to at least the imaging areas, and the first and second readout control parts may execute the first readout mode, the exposure state, and the second readout mode repeatedly based on the number corresponding to an imaging area selected by the user.

A method for capturing a radiographic image according to the eighth aspect is performed using a computer equipped with an image capturing panel. The image capturing panel contains a plurality of pixels arranged in a matrix for converting a radiation (which is emitted from a radiation source and transmitted through a subject in at least an exposure period) into electric signals and storing the electric signals. The method contains the steps of executing a first readout mode for reading the electric signals stored in the pixels in a plurality of rows simultaneously, judging start of the emission of the radiation from the radiation source to the image capturing panel, the radiation emission being judged to be started in a case where a value of the electric signals read in the first readout mode becomes larger than an arbitrarily settable threshold value, and discarding the electric signals stored in all the pixels to switch the image capturing panel to an exposure state in a case where the radiation emission is judged to be started.

A program according to the eighth aspect is for using a computer equipped with an image capturing panel. The image capturing panel contains a plurality of pixels arranged in a matrix for converting a radiation (which is emitted from a radiation source and transmitted through a subject in at least an exposure period) into electric signals and storing the electric signals. The computer is used as a first readout control part for executing a first readout mode for reading the electric signals stored in the pixels in a plurality of rows simultaneously, an irradiation start judgment part for judging start of the emission of the radiation from the radiation source to the image capturing panel, the radiation emission being judged to be started in a case where a value of the electric signals read by the first readout control part becomes larger than an arbitrarily settable threshold value, and an all-pixel reset control part for discarding the electric signals stored in all the pixels to switch the image capturing panel into an exposure state in a case where the radiation emission is judged to be started by the irradiation start judgment part.

In the eighth aspect, the radiation emission is judged to be started based on the electric signals read from the pixels in the first readout mode. In a case where the radiation emission is judged to be started, the reading of the electric charges is stopped, and the image capturing panel is switched to an accumulation state. Therefore, in the eighth aspect, it is not necessary to synchronize the image capturing timings, resulting in low cost. Since the first readout mode is performed until the radiation emission is judged to be started, the unnecessary electric charges stored in the pixels can be removed, lowering the noise content of the resultant radiographic image.

Furthermore, in the eighth aspect, the electric signals stored in all the pixels are discarded in a case where the radiation emission is judged to be started. Therefore, all the pixels can have approximately the same electric signals at the start of the exposure period, and the electric signal difference between the pixels can be mostly removed, to improve the quality and S/N ratio of the radiographic image.

A radiographic image capturing system according to a ninth aspect of the present invention has a radiation source for outputting a radiation, a plurality of radiographic image capturing apparatuses for acquiring a radiographic image, and a control unit for controlling the radiation source and the radiographic image capturing apparatuses. The radiographic image capturing apparatuses have an radiation conversion panel containing a plurality of pixels arranged in a matrix for converting the radiation, transmitted through a subject, into electric charges and storing the electric charges, and a readout control part for controlling the reading of the electric charges stored in the pixels and outputting radiographic image information based on the electric charges. The readout control part is capable of executing a first readout mode and a second readout mode. In the first readout mode, the electric charges stored in the pixels in a plurality of rows are simultaneously read out, and thus the electric charges stored in the pixels are read as first electric signals that are not used for forming the radiographic image. In the second readout mode, the electric charges stored in the pixels are read out row by row, and thus the electric charges stored in the pixels are read as second electric signals that are used for forming the radiographic image. In a process of capturing the radiographic image, the control unit sends an instruction to execute the first readout mode to the readout control part in the radiographic image capturing apparatuses. The readout control part which receives the instruction to execute the first readout mode acts to execute the first readout mode. After that, in a case where the radiation conversion panel detects the radiation, the second readout mode is performed to output the radiographic image information. In this aspect, in the image capturing process, a plurality of the radiographic image capturing apparatuses can be used for forming the radiographic image. Therefore, the image capturing process can be performed even if a user (such as a radiation technician) makes a mistake in selecting the radiographic image capturing apparatus. In addition, the radiation is detected by using the radiation conversion panel for acquiring the radiographic image information. Therefore, a radiation detection means other than the radiation conversion panel is not required, and the radiographic image capturing apparatus can be reduced in size.

Furthermore, the electric charges stored in the pixels in a plurality of the rows are simultaneously read out in the first readout mode, whereby the start of the radiation emission can be judged rapidly and accurately. Thus, since the electric charges stored in the pixels are summed up and read out, a significantly larger value is obtained under the radiation emission than without the radiation emission, whereby the start of the radiation emission can be rapidly judged. Therefore, the radiation conversion panel can be readily switched from the first readout mode for reading the electric charges in a plurality of the rows to the second readout mode for reading the electric charges row by row. Consequently, the start of the radiation emission can be judged in a shorter irradiation time (using a smaller amount of the radiation), so that the energy of the radiation can be efficiently utilized.

Since a plurality of the rows are simultaneously read out in the first readout mode, each row can be controlled in a shorter cycle in the first readout mode than in a row-by-row reading mode. Therefore, at the start of acquiring the radiographic image information (which is practically used as the radiographic image), the electric charge difference between the pixels is smaller in a case where the radiation conversion panel is switched from the first readout mode to the second readout mode than in a case where the start of the radiation emission is detected in the second readout mode. Thus, in the ninth aspect, generation of artifacts can be reduced.

Consequently, in the ninth aspect, the radiographic image can be more appropriately captured even if the user makes a mistake in selecting the radiographic image capturing apparatus such as an electronic cassette.

After the readout control part receives the instruction to execute the first readout mode, in a case where the quantity of the electric charges stored in the pixels in the first readout mode exceeds a threshold value, the readout control part may judge that the radiation is emitted.

In a case where a plurality of the radiographic image capturing apparatuses execute the first readout mode and one of the apparatuses detects the radiation, the one apparatus may send the detection information to the other apparatuses directly or through the control unit. The other apparatuses may stop the first readout mode in a case where they receive the detection information. In this case, the radiographic image capturing apparatuses other than the one apparatus (which has detected the radiation) can stop the first readout mode, making it possible to reduce the subsequent power consumption.

The readout control part may read the electric charges only in a part of the pixels in the first readout mode. In this case, the power consumption or the calculation amount can be reduced in the first readout mode.

The control unit may receive radiographic image capturing conditions entered from the outside, and may select the radiographic image capturing apparatus suitable for the image capturing conditions from a plurality of the apparatuses. The control unit may send, to the radiographic image capturing apparatus suitable for the image capturing conditions, an instruction to execute the second readout mode in a case where the apparatus detects the radiation in the first readout mode. The control unit may send, to the radiographic image capturing apparatus unsuitable for the image capturing conditions, an instruction to send radiation detection information to the control unit without executing the second readout mode in a case where the apparatus detects the radiation in the first readout mode. In a case where the radiation detection information is sent from the apparatus unsuitable for the image capturing conditions to the control unit, the control unit may provide a warning to the user. In a case where the apparatus unsuitable for the image capturing conditions is selected by mistake, the control unit can encourage the user to restart the image capturing.

A radiographic image capturing apparatus according to the ninth aspect has an radiation conversion panel containing a plurality of pixels arranged in a matrix for converting a radiation, transmitted through a subject, into electric charges and storing the electric charges, and a readout control part for controlling the reading of the electric charges stored in the pixels and outputting radiographic image information based on the electric charges. The readout control part is capable of executing a first readout mode and a second readout mode. In the first readout mode, the electric charges stored in the pixels in a plurality of rows are simultaneously read out, and thus the electric charges stored in the pixels are read as first electric signals that are not used for forming the radiographic image. In the second readout mode, the electric charges stored in the pixels are read out row by row, and thus the electric charges stored in the pixels are read as second electric signals that are used for forming the radiographic image. In a case where the readout control part receives an instruction to perform a radiographic image capturing process from the outside, the readout control part acts to execute the first readout mode. Then, in a case where the radiation is detected, the readout control part acts to execute the second readout mode to output the radiographic image information.

A method for capturing a radiographic image according to the ninth aspect is performed using a radiographic image capturing system, which has a radiation source for outputting a radiation, a plurality of radiographic image capturing apparatuses for acquiring a radiographic image, and a control unit for controlling the radiation source and the radiographic image capturing apparatuses. The radiographic image capturing apparatuses have an radiation conversion panel containing a plurality of pixels arranged in a matrix for converting the radiation, transmitted through a subject, into electric charges and storing the electric charges, and a readout control part for controlling the reading of the electric charges stored in the pixels and outputting radiographic image information based on the electric charges. The readout control part is capable of executing a first readout mode and a second readout mode. In the first readout mode, the electric charges stored in the pixels in a plurality of rows are simultaneously read out, and thus the electric charges stored in the pixels are read as first electric signals that are not used for forming the radiographic image. In the second readout mode, the electric charges stored in the pixels are read out row by row, and thus the electric charges stored in the pixels are read as second electric signals that are used for forming the radiographic image. In a process of capturing the radiographic image, the control unit sends an instruction to execute the first readout mode to the radiographic image capturing apparatuses. The radiographic image capturing apparatuses receive the instruction to execute the first readout mode, and then act to execute the first readout mode. In a case where one of the radiographic image capturing apparatuses detects the radiation, the second readout mode is performed to output the radiographic image information.

A program according to the ninth aspect is used for a radiographic image capturing apparatus, which has an radiation conversion panel containing a plurality of pixels arranged in a matrix for converting the radiation, transmitted through a subject, into electric charges and storing the electric charges, and a readout control part for controlling the reading of the electric charges stored in the pixels and outputting radiographic image information based on the electric charges. The readout control part acts to execute a first readout mode and a second readout mode. In the first readout mode, the electric charges stored in the pixels in a plurality of rows are simultaneously read out, and thus the electric charges stored in the pixels are read as first electric signals that are not used for forming the radiographic image. In the second readout mode, the electric charges stored in the pixels are read out row by row, and thus the electric charges stored in the pixels are read as second electric signals that are used for forming the radiographic image. In a case where the radiographic image capturing apparatus receives an instruction to perform a radiographic image capturing process from the outside, the readout control part acts to execute the first readout mode. Then, in a case where the radiation is detected, the readout control part acts to execute the second readout mode to output the radiographic image information.

In the ninth aspect, the radiographic image can be more appropriately captured even if the user makes a mistake in selecting the radiographic image capturing apparatus such as an electronic cassette.

BRIEF DESCRIPTION OF DRAWINGS

FIG. 11 is an example of a table shown in FIG. 10;

FIG. 38 is a detail view of a radiation conversion panel, a gate drive part, charge amplifiers, and a multiplexer part according to Modified Example 11, wherein the gain of the charge amplifier can be modified;

FIG. 40 is a time chart for illustrating charge amplifier gain switching and threshold value setting in a process of capturing one image;

FIG. 58 is a flowchart of the operation of a cassette control device, which does not satisfy image capturing conditions, in an electronic cassette according to Modified Example 17.

DESCRIPTION OF EMBODIMENTS

Radiographic image capturing apparatuses and radiographic image capturing systems containing the apparatus according to preferred embodiments of the present invention will be described in detail below with reference to the accompanying drawings.

Figure 1:
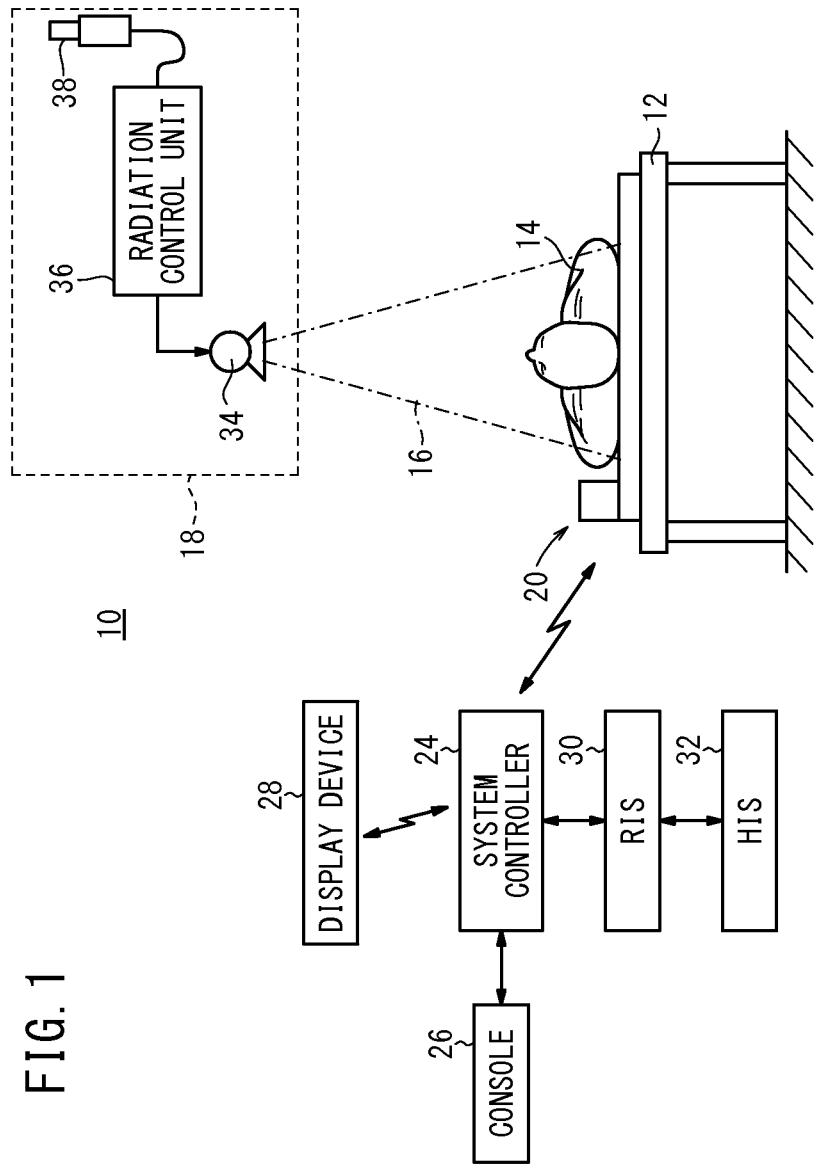
FIG. 1 is a schematic view of a radiographic image capturing system according to an embodiment of the present invention.

FIG. 1 is a schematic view of a radiographic image capturing system 10 according to an embodiment of the present invention. The radiographic image capturing system 10 has a radiation apparatus 18 for applying radiation 16 to a subject 14 of a patient lying on an image capturing base 12 such as a bed, an electronic cassette (radiographic image capturing apparatus) 20 for detecting the radiation 16 that has passed through the subject 14 and converting the detected radiation 16 into a radiographic image, a system controller 24 for controlling the entire radiographic image capturing system 10, a console 26 for receiving operation input by a doctor, a technician, or the like (hereinafter referred to as the user), and a display device 28 for displaying the captured radiographic image and the like.

The system controller 24, the electronic cassette 20, and the display device 28 may send signals to and receive signals from each other via wireless communication using UWB (Ultra Wide Band), wireless LAN according to IEEE 802.11.a/b/g/n standard or the like, millimeter waves, etc. Alternatively, the components may send and receive signals via wired communication using cables.

The system controller 24 is connected to an RIS (radiology information system) 30, which generally manages radiographic images and other information handled in the radiological department of a hospital. The RIS 30 is connected to an HIS (hospital information system) 32, which generally manages medical information in the hospital.

The radiation apparatus 18 has a radiation source 34 for emitting the radiation 16, a radiation control unit 36 for controlling the radiation source 34, and a radiation switch 38. The radiation source 34 applies the radiation 16 to the electronic cassette 20. The radiation 16 emitted from the radiation source 34 may be X-ray, α-ray, β-ray, γ-ray, electron beam, or the like. The radiation switch 38 is of a two stage stroke type. When the radiation switch 38 is pressed halfway by the user, the radiation control unit 36 makes a preparation to emit the radiation 16. When the radiation switch 38 is pressed completely, the radiation 16 is emitted from the radiation source 34. The radiation control unit 36 has an input device (not shown), and the user can operate the input device to set an irradiation time for the radiation 16, a tube voltage, a tube current, and the like. The radiation control unit 36 acts to emit the radiation 16 from the radiation source 34 based on the setup irradiation time and the like.

Figure 2:
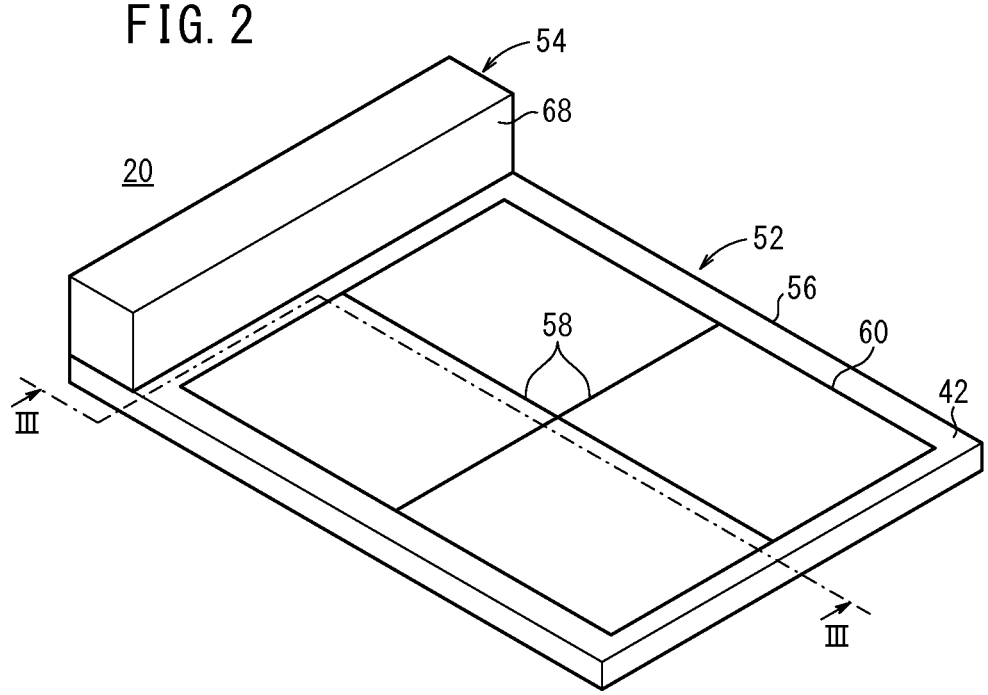
FIG. 2 is a perspective view of an electronic cassette shown in FIG. 1.
Figure 3:
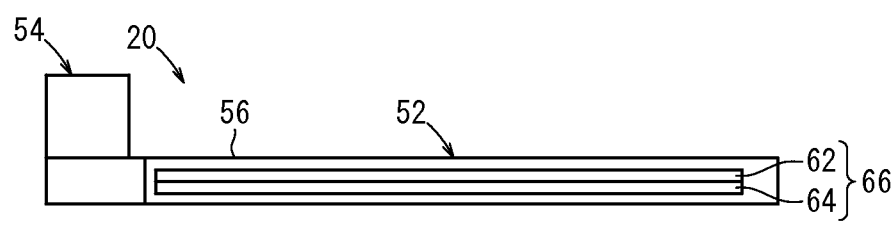
FIG. 3 is a cross-sectional view of the electronic cassette taken along the line III-III of FIG. 2.

FIG. 2 is a perspective view of the electronic cassette 20 shown in FIG. 1, and FIG. 3 is a cross-sectional view of the electronic cassette 20 taken along the line III-III of FIG. 2. The electronic cassette 20 has a panel unit 52 and a control unit 54 disposed thereon. The panel unit 52 is thinner than the control unit 54.

The panel unit 52 has a substantially rectangular casing 56 composed of a material permeable to the radiation 16. The panel unit 52 has an image capturing surface 42, which is irradiated with the radiation 16. The image capturing surface 42 has guide lines 58 substantially at the center as a reference for the image capturing range and position of the subject 14.

The outer frame of the guide lines 58 corresponds to an image capturable area 60 indicative of an irradiation field of the radiation 16. The central position of the guide lines 58 (the crisscross intersection between the guide lines 58) corresponds to the center of the image capturable area 60.

The panel unit 52 has a radiation detector (image capturing panel) 66 containing a scintillator 62 and a radiation conversion panel 64, and further has a drive circuit device 106 for driving the radiation conversion panel 64 to be hereinafter described (see FIG. 6). The scintillator 62 is for converting the radiation 16 transmitted through the subject 14 into a visible fluorescent light. The radiation conversion panel 64 is an indirect conversion panel for converting the fluorescence from the scintillator 62 into electric signals. The scintillator 62 and the radiation conversion panel 64 are arranged in the casing 56 in this order from the image capturing surface 42, which is irradiated with the radiation 16. The radiation conversion panel 64 may be a direct conversion panel for converting the radiation 16 directly into electric signals. In this case, the scintillator 62 is not required, so that the radiation conversion panel 64 corresponds to the radiation detector 66.

The control unit 54 has a substantially rectangular casing 68 composed of a material impermeable to the radiation 16. The casing 68 extends along one side of the image capturing surface 42, and the control unit 54 is located outside of the image capturable area 60 on the image capturing surface 42. In this case, the casing 68 contains a cassette control device (imaging control device) 122 for controlling the panel unit 52, a buffer memory 124 for storing captured radiographic image data, a communication device (first announcement device or first communication device) 126 for sending signals to and receiving signals from the system controller 24 through a wireless communication link, and a power supply device (electric power supply) 128 such as a battery (see FIG. 6). The power supply device 128 supplies electric power to the cassette control device 122 and the communication device 126.

Figure 4:
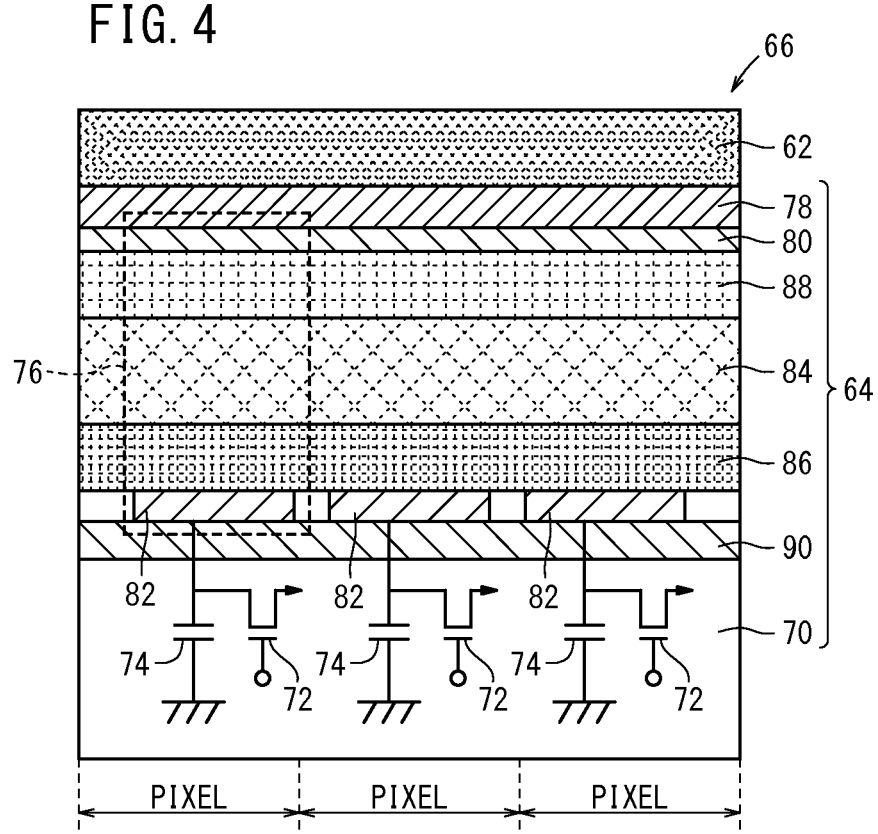
FIG. 4 is a schematic view of a structure of three pixels in a radiation detector shown in FIG. 3.

FIG. 4 is a schematic view of a structure of three pixels in the radiation detector 66. In the radiation detector 66, TFTs (field-effect-type thin film transistors) 72 and charge storage parts 74, sensor parts 76, and the scintillator 62 are stacked in this order on a board 70. The pixels each contain the charge storage part 74 and the sensor part 76, and are arranged in a matrix on the board 70. Each TFT (switching element) 72 outputs electric charges in the charge storage part 74 of the pixel connected therewith. The scintillator 62 is disposed on the sensor parts 76 with a transparent insulating film 78 interposed therebetween. The scintillator 62 is formed as a film from a fluorescent material, which converts the radiation 16 injected from above (to the surface remote from the board 70) into a light.

The light emitted from the scintillator 62 preferably has a wavelength within the visible range (360 to 830 nm), and more preferably has a wavelength within the green range to form a monochrome image using the radiation detector 66. In the case of using an X-ray as the radiation 16 for image capturing, the fluorescent material for the scintillator 62 preferably contains gadolinium oxide sulfur (GOS) or cesium iodide (CsI). The fluorescent material particularly preferably contains CsI(Tl) having an emission spectrum within a range of 420 to 700 nm under X-ray irradiation. The CsI(Tl) exhibits an emission peak wavelength of 565 nm in the visible range.

The sensor part 76 has an upper electrode 80, a lower electrode 82, and a photoelectric conversion film 84 disposed between the upper and lower electrodes 80 and 82. The upper electrode 80 is preferably composed of an electrically conductive material transparent at least to the emission wavelength of the scintillator 62 to inject the light from the scintillator 62 into the photoelectric conversion film 84.

The photoelectric conversion film 84 contains an organic photoconductor (OPC). The photoelectric conversion film 84 absorbs the light from the scintillator 62 to generate an electric charge corresponding to the absorbed light. The photoelectric conversion film 84 containing the organic photoconductor exhibits an absorption spectrum having a sharp peak in the visible range, and thereby hardly absorbs electromagnetic waves other than the light from the scintillator 62. Thus, the photoelectric conversion film 84 can be effectively prevented from absorbing the radiation 16, which otherwise generates noise.

The organic photoconductor in the photoelectric conversion film 84 preferably has an absorption peak wavelength closer to the emission peak wavelength of the scintillator 62 to absorb the light from the scintillator 62 more efficiently. It is ideal that the absorption peak wavelength of the organic photoconductor is equal to the emission peak wavelength of the scintillator 62. When the difference between the peak wavelengths is small enough, the organic photoconductor can satisfactorily absorb the light from the scintillator 62. Specifically, the difference between the absorption peak wavelength of the organic photoconductor and the emission peak wavelength of the scintillator 62 under the radiation 16 is preferably 10 nm or less, more preferably 5 nm or less.

Such organic photoconductors satisfying the above requirement include quinacridone-based organic compounds and phthalocyanine-based organic compounds. For example, quinacridone has an absorption peak wavelength of 560 nm in the visible range. Therefore, when the quinacridone is used as the organic photoconductor and CsI(Ti) is used as the material of the scintillator 62, the difference between the above peak wavelengths can be 5 nm or less, whereby the amount of electric charges generated in the photoelectric conversion film 84 can be substantially maximized.

An electromagnetic wave absorption/photoelectric conversion region may be formed by a pair of the electrodes 80 and 82 and an organic layer containing the photoelectric conversion film 84 sandwiched therebetween. The organic layer may be formed by stacking or combining an electromagnetic wave absorption component, a photoelectric conversion component, an electron transport component, a hole transport component, an electron blocking component, a hole blocking component, a crystallization preventing component, an electrode, an interlayer contact improving component, etc. The organic layer preferably contains an organic p-type or n-type compound.

The organic p-type compound (semiconductor) is an organic donor compound (semiconductor) typified by an organic hole transport compound, which has an electron donating property. More specifically, in a case where two organic compounds are used in contact with each other, the organic donor compound is one compound having a lower ionization potential. Thus, any organic compounds having the electron donating property can be used as the organic donor compound.

The organic n-type compound (semiconductor) is an organic acceptor compound (semiconductor) typified by an organic electron transport compound, which has an electron accepting property. More specifically, in a case where two organic compounds are used in contact with each other, the organic acceptor compound is one compound having a higher electron affinity. Thus, any organic compounds having the electron accepting property can be used as the organic acceptor compound. Compounds usable as the organic p-type and n-type compounds and the structure of the photoelectric conversion film 84 are described in detail in Japanese Laid-Open Patent Publication No. 2009-032854, and therefore explanations thereof are omitted.

The lower electrode 82 contains a thin film divided for each pixel. The lower electrode 82 may be composed of a transparent or opaque conductive material, and preferred examples thereof include aluminum and silver. In the sensor part 76, when a predetermined bias voltage is applied between the upper electrode 80 and the lower electrode 82, one of the electric charges (holes and electrons) generated in the photoelectric conversion film 84 can be transferred to the upper electrode 80, while the other can be transferred to the lower electrode 82. In this embodiment, in the radiation detector 66, a wire is connected to the upper electrode 80, and the bias voltage is applied from the wire to the upper electrode 80. The bias voltage has such a polarity that the electrons are transferred to the upper electrode 80 and the holes are transferred to the lower electrode 82 from the photoelectric conversion film 84. The bias voltage may have a polarity opposite thereto.

The sensor part 76 in each pixel contains at least the lower electrode 82, the photoelectric conversion film 84, and the upper electrode 80. Further, the sensor part 76 preferably contains at least one of an electron blocking film 86 and a hole blocking film 88, and more preferably contains the both, to prevent dark current increase.

The electron blocking film 86 may be disposed between the lower electrode 82 and the photoelectric conversion film 84. When the bias voltage is applied between the lower electrode 82 and the upper electrode 80, the electron blocking film 86 can prevent electron injection from the lower electrode 82 into the photoelectric conversion film 84, and thus can prevent the dark current increase. The electron blocking film 86 may be composed of an organic electron donating material. The material of the electron blocking film 86 may be practically selected depending on the materials of the adjacent lower electrode 82 and photoelectric conversion film 84, etc. It is preferred that the material of the electron blocking film 86 has an electron affinity (Ea) larger by 1.3 eV or more than the work function (Wf) of the material of the adjacent lower electrode 82 and has an ionization potential (Ip) equal to or smaller than that of the material of the adjacent photoelectric conversion film 84. Materials usable as the organic electron donating material are described in detail in Japanese Laid-Open Patent Publication No. 2009-032854, and therefore such materials will not be described in detail below.

The thickness of the electron blocking film 86 is preferably 10 to 200 nm, more preferably 30 to 150 nm, particularly preferably 50 to 100 nm, from the viewpoints of reliably achieving the dark current reducing effect and preventing reduction in the photoelectric conversion efficiency of the sensor part 76.

The hole blocking film 88 may be disposed between the photoelectric conversion film 84 and the upper electrode 80. When the bias voltage is applied between the lower electrode 82 and the upper electrode 80, the hole blocking film 88 can prevent hole injection from the upper electrode 80 into the photoelectric conversion film 84, and thus can prevent the dark current increase.

The hole blocking film 88 may be composed of an organic electron accepting material. The thickness of the hole blocking film 88 is preferably 10 to 200 nm, more preferably 30 to 150 nm, particularly preferably 50 to 100 nm, from the viewpoints of reliably achieving the dark current reducing effect and preventing reduction in the photoelectric conversion efficiency of the sensor part 76.

The material of the hole blocking film 88 may be practically selected depending on the materials of the adjacent upper electrode 80 and photoelectric conversion film 84, etc. It is preferred that the material of the hole blocking film 88 has an ionization potential (Ip) larger by 1.3 eV or more than the work function (Wf) of the material of the adjacent upper electrode 80 and has an electron affinity (Ea) equal to or larger than that of the material of the adjacent photoelectric conversion film 84. Materials usable as the organic electron accepting material are described in detail in Japanese Laid-Open Patent Publication No. 2009-032854, and therefore such materials will not be described in detail below.

Figure 5:
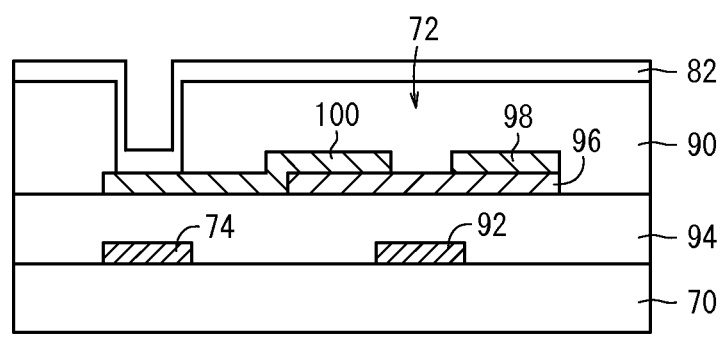
FIG. 5 is a schematic structural view of a TFT and a charge storage part shown in FIG. 4.

FIG. 5 is a schematic structural view of the TFT 72 and the charge storage part 74. The electric charge transferred to the lower electrode 82 is stored in the charge storage part 74, and the electric charge stored in the charge storage part 74 is converted to an electric signal and output by the TFT 72. The region including the charge storage part 74 and the TFT 72 is partially overlapped with the lower electrode 82 as viewed in plan, so that the TFT 72 overlaps with the sensor part 76 in the thicknesswise direction in each pixel. It is preferred that the region including the charge storage part 74 and the TFT 72 is entirely covered with the lower electrode 82 to minimize the plane area of the radiation detector 66.

The charge storage part 74 is electrically connected to the correspondent lower electrode 82 by a conductive material wire, which extends through an insulating film 90 formed between the board 70 and the lower electrode 82. Thus, the electric charges collected in the lower electrode 82 can be transferred to the charge storage part 74.

The TFT 72 contains a stack of a gate electrode 92, a gate insulating film 94, and an active layer (channel layer) 96. A source electrode 98 and a drain electrode 100 are disposed on the active layer 96 at a predetermined distance. The active layer 96 contains an amorphous oxide. The amorphous oxide for the active layer 96 is preferably an oxide containing at least one of In, Ga, and Zn (such as In—O oxide), more preferably an oxide containing at least two of In, Ga, and Zn (such as In—Zn—O, In—Ga, or Ga—Zn—O oxide), particularly preferably an oxide containing all of In, Ga, and Zn. The amorphous In—Ga—Zn—O oxide is preferably an amorphous oxide having a composition of $InGaO_3 (ZnO)_m$ (wherein m is a natural number of less than 6) in a crystalline state, particularly preferably $InGaZnO_4$.

When the active layer 96 of the TFT 72 contains the amorphous oxide, the active layer 96 does not absorb the radiation 16 such as X-ray or absorbs only an extremely small amount of the radiation 16, whereby noise generation can be effectively reduced in the TFT 72. Both of the amorphous oxide for the active layer 96 of the TFT 72 and the organic photoconductor for the photoelectric conversion film 84 can be formed into a film at low temperature. Therefore, the board 70 is not limited to a highly heat-resistant substrate such as a semiconductor substrate, a quartz substrate, or a glass substrate, and may contain a flexible material (such as a plastic), an aramid, or a bionanofiber. Specifically, the board 70 may be a flexible substrate of a polyester (such as a polyethylene terephthalate, a polyethylene phthalate, or a polyethylene naphthalate), a polystyrene, a polycarbonate, a polyethersulfone, a polyarylate, a polyimide, a polycycloolefin, a norbornene resin, a poly(chlorotrifluoroethylene), or the like. In the case of using the flexible plastic substrate, the radiation detector 66 can be made lighter and easier to carry around.

The aramid can undergo a process at a high temperature of 200 degrees or higher. Therefore, in the case of using the aramid, a transparent electrode material can be hardened at a high temperature to lower the resistance, and a driver IC can be automatically mounted using a solder reflow process. Furthermore, the aramid has a thermal expansion coefficient close to those of ITO (Indium Tin Oxide) and glass, whereby the board 70 containing the aramid is less liable to warp and crack after fabrication thereof. In addition, the board 70 of the aramid can be made thinner as compared with glass substrates and the like. The board 70 may be formed by stacking the aramid on an ultrathin glass substrate.

The bionanofiber is prepared by combining a transparent resin with a cellulose microfibril bundle (bacteria cellulose) produced by bacteria (acetic acid bacteria, Acetobacter Xylinum). The cellulose microfibril bundle has a width of 50 nm, which is 1/10 of the visible light wavelength, and exhibits a high strength, a high elasticity, and a low thermal expansion. The bionanofiber can be produced with a light transmittance of about 90% at a wavelength of 500 nm even at a fibril content of 60% to 70% by impregnating the bacteria cellulose with the transparent resin such as an acrylic resin or an epoxy resin and then hardening the resin. The bionanofiber has a low thermal expansion coefficient (3 to 7 ppm) comparable to a silicon crystal, a high strength (460 MPa) comparable to a steel, a high elasticity (30 GPa), and a high flexibility, whereby the board 70 of the bionanofiber can be made thinner as compared with glass substrates and the like.

In this embodiment, the radiation detector 66 is formed by stacking the TFTs 72 and the charge storage parts 74, the sensor parts 76, and the transparent insulating film 78 in this order on the board 70 and by bonding the scintillator 62 to the stack with an adhesive resin having a low light absorbance or the like. The stack containing the board 70 to the transparent insulating film 78 is referred to as the radiation conversion panel 64.

In the radiation detector 66, the photoelectric conversion film 84 composed of the organic photoconductor hardly absorbs the radiation 16. Therefore, in the radiation detector 66 of this embodiment, even in a case where the radiation 16 is transmitted through the radiation conversion panel 64 in a back side irradiation process, the amount of the radiation 16 absorbed by the photoelectric conversion film 84 can be reduced to prevent the deterioration of the sensitivity to the radiation 16. In the back side irradiation process, the radiation 16 passes through the radiation conversion panel 64 and reaches the scintillator 62. When the photoelectric conversion film 84 is composed of the organic photoconductor in the radiation conversion panel 64, the photoelectric conversion film 84 hardly absorbs the radiation 16, so that attenuation of the radiation 16 can be prevented. Therefore, the photoelectric conversion film 84 can be suitably used also in the back side irradiation process.

Figure 6:
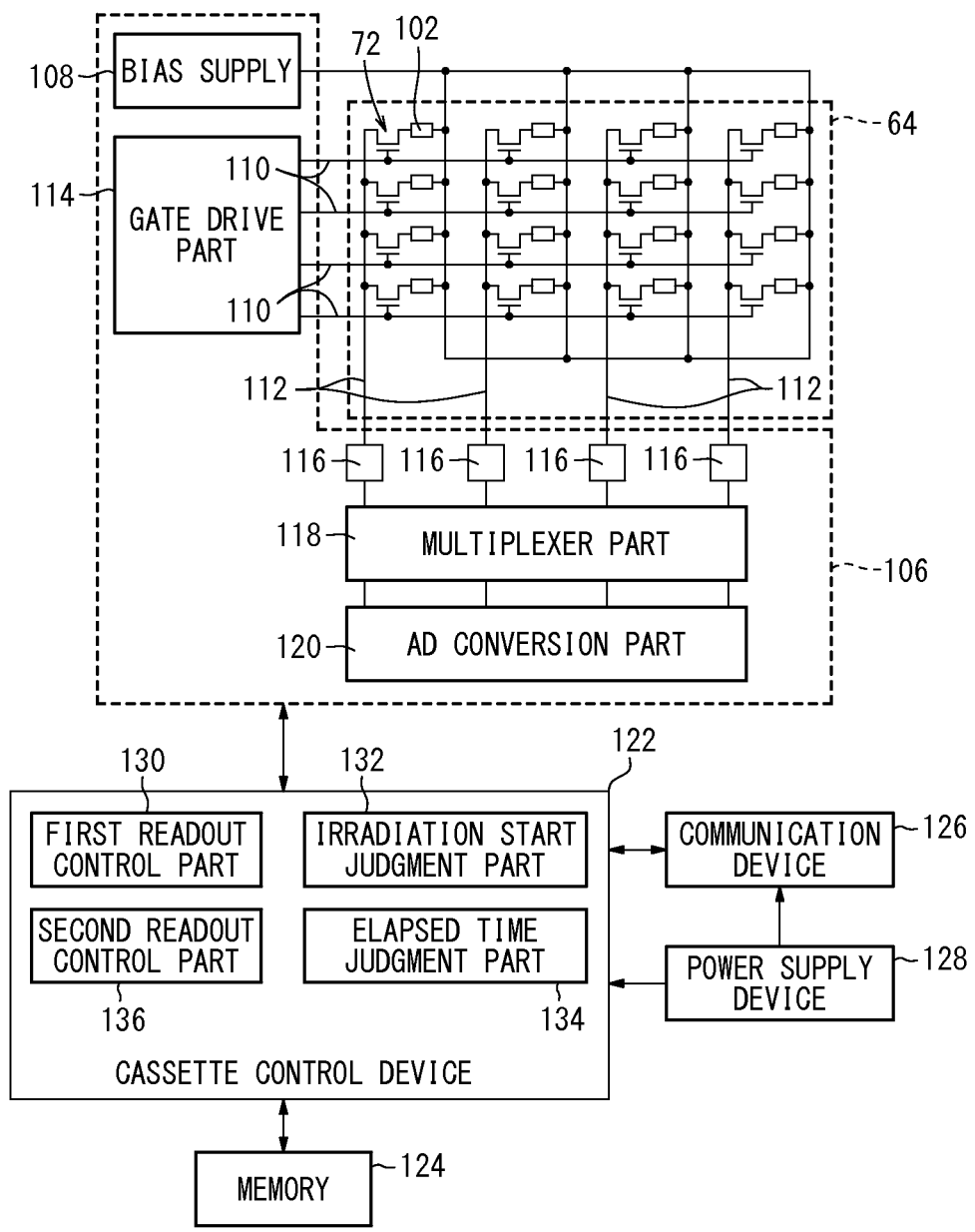
FIG. 6 is a schematic structural view of the electric structure of the electronic cassette shown in FIG. 1.

FIG. 6 is a schematic structural view of the electric structure of the electronic cassette 20 shown in FIG. 1. The electronic cassette 20 has the structure containing pixels 102 disposed on the TFTs 72 arranged in a matrix. The pixels 102 are arranged in a matrix and each have a photoelectric conversion element (not shown). The pixels 102, which are supplied with a bias voltage from a bias supply 108 in the drive circuit device 106, store electric charges generated by photoelectric conversion of a visible light. The TFTs 72 are turned on sequentially column by column, whereby the electric charge signals (electric signals) can be read from signal lines 112 as analog pixel signal values. Though the pixels 102 and the TFTs 72 are arranged vertically and horizontally in a 4×4 matrix in FIG. 6 for the sake of convenience, they are practically arranged vertically and horizontally in a 2880×2304 matrix.

The TFTs 72, connected to the pixels 102, are connected with gate lines 110 extending in the row direction and the signal lines 112 extending in the column direction. The gate lines 110 are connected to a gate drive part 114 in the drive circuit device 106, and the signal lines 112 are connected to a multiplexer part 118 in the drive circuit device 106 through a charge amplifier (electric signal amplifier) 116. The multiplexer part 118 is connected to an AD conversion part 120 for converting the analog electric signals into digital electric signals. The AD conversion part 120 outputs the converted digital electric signals (digital pixel signal values, hereinafter referred to also as digital values) to the cassette control device 122.

The cassette control device 122 is provided for controlling the entire electronic cassette 20. The cassette control device 122 has a clock circuit (not shown) and acts also as a timer. An information processor such as a computer can be used as the cassette control device 122 of this embodiment by installing a predetermined program thereinto.

The cassette control device 122 is connected with the memory 124 and the communication device 126. The memory 124 stores the digital pixel signal values, and the communication device 126 sends signals to and receives signals from the system controller 24. The communication device 126 sends the pixel values sequentially row by row to the system controller 24, and thus sends a packet of one image (one-frame image) containing the pixel values arranged in a matrix. The power supply device 128 supplies electric power to the cassette control device 122, the memory 124, and the communication device 126. The electric power is transferred from the cassette control device 122 to the bias supply 108, and is supplied to the pixels 102 by the bias supply 108.

The cassette control device 122 has a first readout control part 130, an irradiation start judgment part 132, an elapsed time judgment part (emission completion judgment part or exposure completion judgment part) 134, and a second readout control part 136. The first readout control part 130 acts to read the electric charges stored in the pixels 102 in a plurality of the rows (lines) simultaneously in a scan mode (first readout mode). The first readout control part 130 controls the gate drive part 114, the charge amplifiers 116, the multiplexer part 118, and the AD conversion part 120 to execute the scan mode.

The scan mode (first readout mode) is a fast readout mode capable of reading the one-frame image data in a shorter time as compared with a sequential readout mode (second readout mode) to be hereinafter described.

The outline of the scan mode will be described below. In the scan mode, for example, the gate drive part 114 outputs gate signals to the gate lines 110 in 0th and second rows, whereby the TFTs 72 in the 0th and second rows are turned on (the 0th and second rows are activated) to simultaneously read electric charges stored in the pixels 102 in the 0th and second rows through the signal lines 112. The read electric charges in each column are output as electric charge signals (pixel values) to the charge amplifier 116 in each column. Since the electric charges stored in the pixels 102 in the 0th and second rows are simultaneously read out, the electric signals sent to the charge amplifier 116 are the sum of the electric signals stored in the pixels 102 in the 0th and second rows. Thus, the electric signals stored in the pixels 102 in the 0th and second rows are summed up in each column, and the sum of the electric signals is output to the charge amplifier 116 in each column. The electric charges in the pixels 102 in the 0th and second rows can be summed and read out in this manner.

The charge amplifiers 116 convert the entered electric charge signals into voltage signals, and output the voltage signals to the multiplexer part 118. The multiplexer part 118 sequentially selects the entered voltage signals, and outputs the voltage signals to the AD conversion part 120. The AD conversion part 120 converts the entered voltage signals into digital signals, and outputs the digital signals. Consequently, the electric signals (pixel values) stored in the pixels 102 in the 0th and second rows are summed up in each column, and are output from the AD conversion part 120 as the digital electric signals (pixel values). The digital electric signals (pixel values) are transferred from the AD conversion part 120 to the cassette control device 122. In the cassette control device 122, the transferred digital values are stored in the memory 124. Thus, the memory 124 stores image data including the signals of the 0th and second rows summed up in each column.

After the electric charges stored in the pixels 102 in the 0th and second rows are read out as described above, the gate drive part 114 sends gate signals to the gate lines 110 in first and 3rd rows, whereby the TFTs 72 in the first and 3rd rows are turned on (the first and 3rd rows are activated) to simultaneously read electric charges (electric signals) stored in the pixels 102 in the first and 3rd rows through the signal lines 112. The read electric signals are transferred to the cassette control device 122 and stored as digital signals in the memory 124 in the above manner.

When the emission of the radiation 16 is judged to be started by the irradiation start judgment part 132 to be hereinafter described, the first readout control part 130 stops the scan mode. In a case where the reading of the one-frame image data is not completed at this time, the scan mode is stopped after the completion of the reading of the one-frame image data.

Since the electric charges stored in the pixels 102 are read out in the scan mode in this manner, the one-frame image data can be read out in a short time, and noise electric charges in the pixels 102 can be removed in a short time. Since the electric charges stored in the pixels 102 are read out in the scan mode in this manner, the electronic cassette 20 can be readily switched into an exposure state when the emission of the radiation 16 is judged to be started. Furthermore, the loss of the radiation 16 with image information can be reduced. On the contrary, in a case where the noise electric charges in the pixels 102 are removed in the sequential readout mode to be hereinafter described, it takes a long time to read the one-frame image data. In this case, the electronic cassette 20 cannot be readily switched into the exposure state when the emission of the radiation 16 is judged to be started during the process of reading the one-frame image data. Furthermore, the loss of the radiation 16 with image information is increased.

The irradiation start judgment part 132 judges whether or not the digital values, which are read by the first readout control part 130 and stored in the memory 124, are larger than a threshold value. When the digital value becomes larger than the threshold value, the emission of the radiation 16 is judged to be started. Thus, the irradiation start judgment part 132 detects the radiation 16 based on the judgment on whether or not the obtained digital values are larger than the threshold value. In a case where the radiation 16 is not emitted, only a minute amount of the noise electric charges are stored in the pixels 102. In a case where the radiation 16 is emitted and injected into the electronic cassette 20, a larger amount of the electric charges are stored in the pixels 102 compared to the case where the radiation 16 is not emitted. Therefore, in a case where the digital signal converted from the electric signal read in the scan mode becomes larger than the threshold value, the emission of the radiation 16 can be judged to be started.

Since the electric charges stored in the pixels 102 in a plurality of the rows are simultaneously read out in the scan mode, the start of the emission of the radiation 16 can be judged rapidly and accurately. If the radiation 16 is emitted, the obtained digital electric signal has a significantly high intensity because the electric charges in the pixels 102 are summed up. Therefore, the start of the emission of the radiation 16 can be rapidly judged. Even in a case where the electric charges stored in the pixels 102 are not summed up, the start of the emission of the radiation 16 can be rapidly detected by using a smaller threshold value. However, in this case, the ratio of the noise electric signals to the threshold value is increased, whereby the start of the emission of the radiation 16 cannot be accurately detected. The threshold value may be arbitrarily set by the user.

The elapsed time judgment part 134 judges whether a predetermined time has elapsed or not after the start of the emission of the radiation 16. The predetermined time may be a time for which the radiation 16 is emitted from the radiation source 34, and may be a time for which the electronic cassette 20 is exposed to the radiation 16 to form the radiographic image. The predetermined time is stored in the memory 124.

The second readout control part 136 acts to read the electric charges stored in the pixels 102 sequentially row by row in the sequential readout mode (second readout mode). The second readout control part 136 controls the gate drive part 114, the charge amplifiers 116, the multiplexer part 118, and the AD conversion part 120 to perform the sequential readout mode.

The outline of the sequential readout mode will be described below. In the sequential readout mode, the gate drive part 114 outputs a gate signal to the gate line 110 in the 0th row, whereby the TFTs 72 in the 0th row are turned on (the 0th row is activated) to read the electric charges stored in the pixels 102 in the 0th row through the signal lines 112. The read electric charges in each column are output as electric charge signals (pixel values) to the charge amplifier 116 in each column. The charge amplifier 116 converts the entered electric charge signals into voltage signals, and outputs the voltage signals to the multiplexer part 118. The AD conversion part 120 converts the electric signals (pixel values) in the pixels 102 in the 0th row into digital signals, and sends the digital signals to the cassette control device 122. The sent digital signals are stored in the memory 124. Thus, the memory 124 stores image data of the 0th row.

After the electric charges stored in the pixels 102 in the 0th row are read out as described above, the gate drive part 114 sends a gate signal to the gate line 110 in the first row, whereby the TFTs 72 in the first row are turned on (the first row is activated) to read electric charges (electric signals) stored in the pixels 102 in the first row through the signal lines 112. The read electric signals are transferred to the cassette control device 122 and stored as digital signals in the memory 124.

After the electric charges stored in the pixels 102 in the first row are read out, the gate drive part 114 acts to read electric charges stored in the pixels 102 in the second row and then read electric charges stored in the pixels 102 in the 3rd row.

The cassette control device 122 sends image data of each row stored in the memory 124 sequentially to the system controller 24 through the communication device 126. Thus, the one-row image data of the rows are sequentially sent row by row. Alternatively, the one-row image data of the rows may be collectively sent as a one-frame image data.

Figure 7:
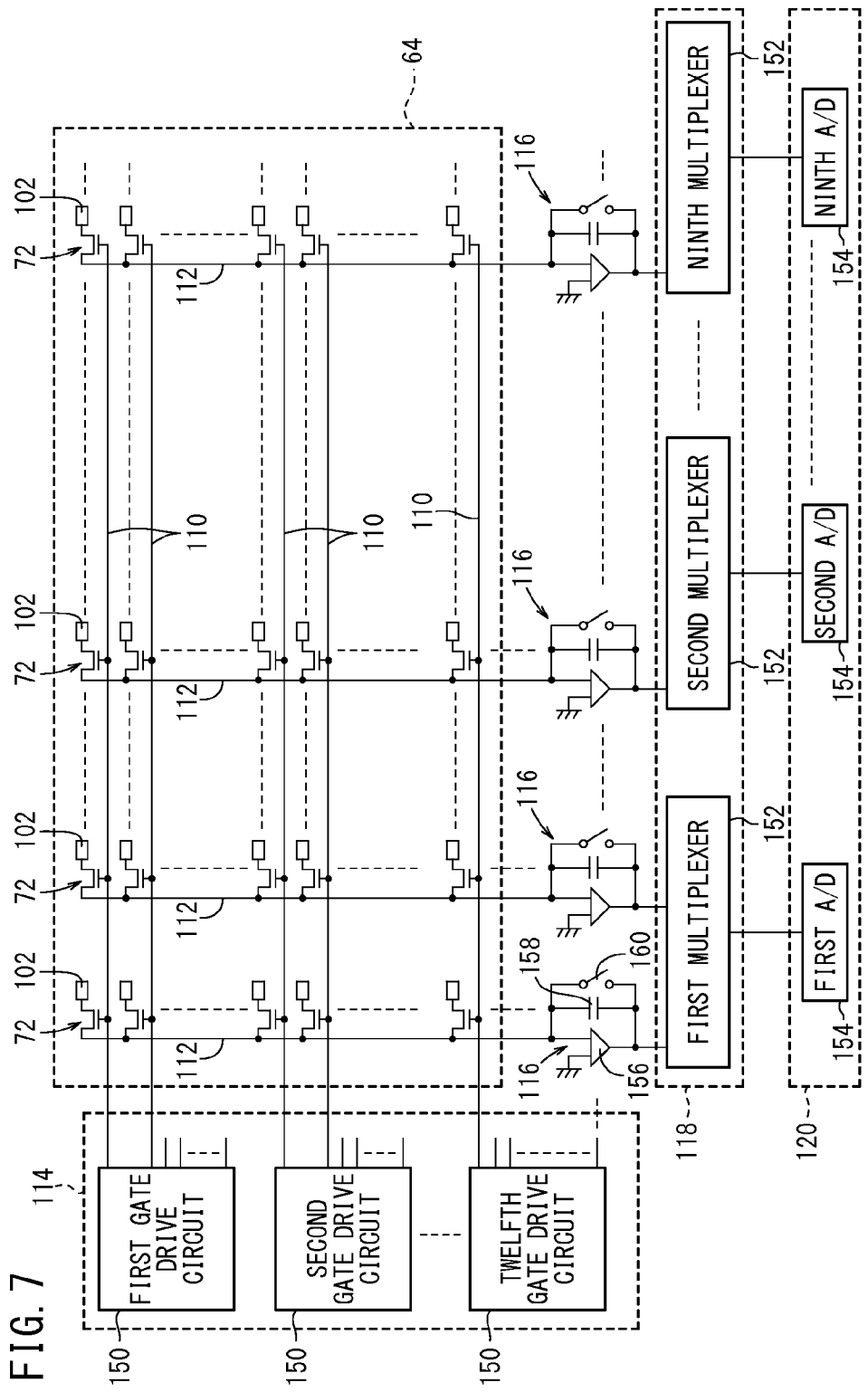
FIG. 7 is a detail view of a radiation conversion panel, a gate drive part, charge amplifiers, and a multiplexer part shown in FIG. 6.

FIG. 7 is a detail view of the radiation conversion panel 64, the gate drive part 114, the charge amplifiers 116, and the multiplexer part 118 shown in FIG. 6. The gate drive part 114 has 12 gate drive circuits 150 (first to twelfth gate drive circuits 150), which are each connected with 240 gate lines 110. The 240 gate lines 110 are connected to the pixels 102 through the TFTs 72, and each gate drive circuit 150 reads electric charges stored in the pixels 102 connected therewith. Thus, each gate drive circuit 150 has an associated readout region (0th to 239th rows), and reads the electric charges stored in the pixels 102 in the region. The first to twelfth gate drive circuits 150 are generally referred to as the gate drive circuits 150.

The multiplexer part 118 contains 9 multiplexers 152 (first to ninth multiplexers 152), which are each connected with 256 signal lines 112. Each multiplexer 152 has an associated readout region (0th to 255th columns), and the electric charge signals in the pixels 102 in the region are input through the charge amplifiers 116 into the multiplexer 152. The first to ninth multiplexers 152 are generally referred to as the multiplexers 152. Consequently, the radiation conversion panel 64 has 2880 (240×12)×2304 (256×9) pixels 102 and TFTs 72 arranged vertically and horizontally.

The AD conversion part 120 contains 9 A/D converters 154 (first to ninth A/D converters 154). The voltage signals are output from the multiplexers 152 to the A/D converters 154. Specifically, the voltage signals output from the first multiplexer 152 are sent to the first A/D converter 154, and the voltage signals output from the second multiplexer 152 are sent to the second A/D converter 154. Thus, the voltage signals output from each multiplexer 152 are sent to the correspondent A/D converter 154 in this manner. The A/D converters 154 convert the entered voltage signals to digital voltage signals. The first to ninth A/D converters 154 are generally referred to as the A/D converters 154.

The TFTs 72 are sequentially turned on row by row by the gate drive circuits 150. Thus, the electric charges stored in the pixels 102 are read sequentially row by row, and are output as charge signals to the charge amplifiers 116 through the signal lines 112. Specifically, each gate drive circuit 150 selects the gate line 110 in the 0th row (to be read in the first procedure) from a plurality of the gate lines 110 connected therewith, and outputs a gate signal to the selected gate line 110, whereby the TFTs 72 in the 0th row are turned on to read the electric charges stored in the pixels 102 in the 0th row. After the electric charges stored in the pixels 102 in the 0th row are read out, the gate drive circuit 150 selects the gate line 110 in the first row (to be read in the second procedure) and outputs a gate signal to the selected gate line 110, whereby the TFTs 72 in the first row are turned on to read the electric charges stored in the pixels 102 in the first row. Then, the gate drive circuit 150 selects the gate lines 110 in the second row, the 3rd row, . . . , and the 239th row (to be read in the final procedure) sequentially, and outputs gate signals to the selected gate lines 110 sequentially, whereby the TFTs 72 in the rows are turned on sequentially row by row to read the electric charges stored in the pixels 102 in the rows.

The read electric charges in each column are input through the signal line 112 into the charge amplifier 116 in the column. The charge amplifier 116 has an operational amplifier (OA) 156, a capacitor 158, and a switch 160. In a case where the switch 160 is in the off state, the charge amplifier 116 converts the electric charge signals entered to the operational amplifier 156 into voltage signals, and outputs the voltage signals. The charge amplifier 116 amplifies the electric signals with a gain set by the cassette control device 122 and outputs the amplified signals. In a case where the switch 160 is in the on state, the electric charges stored in the capacitor 158 are emitted by a closed circuit of the capacitor 158 and the switch 160, and the electric charges stored in the pixels 102 are emitted through the closed switch 160 and the operational amplifier 156 to GND (ground potential). This operation, which contains turning on the switch 160 to emit the electric charges stored in the pixels 102 to the GND (ground potential), is referred to as a reset operation (empty reading operation). Thus, in the reset operation, the voltage signals corresponding to the electric charge signals stored in the pixels 102 are not output to the multiplexer part 118 and the AD conversion part 120, but are discarded. In this embodiment, "the electric charges stored in the pixels 102 are read" means that the voltage signals corresponding to the electric charges stored in the pixels 102 are output to the multiplexer part 118 and the AD conversion part 120.

The voltage signals converted by the charge amplifier 116 are output to the multiplexer 152. The multiplexer 152 selects and outputs the entered voltage signals sequentially based on control signals from the cassette control device 122. The A/D converter 154 converts the voltage signals transferred from the multiplexer 152 into digital signals, and outputs the converted digital signals to the cassette control device 122.

Figure 8:
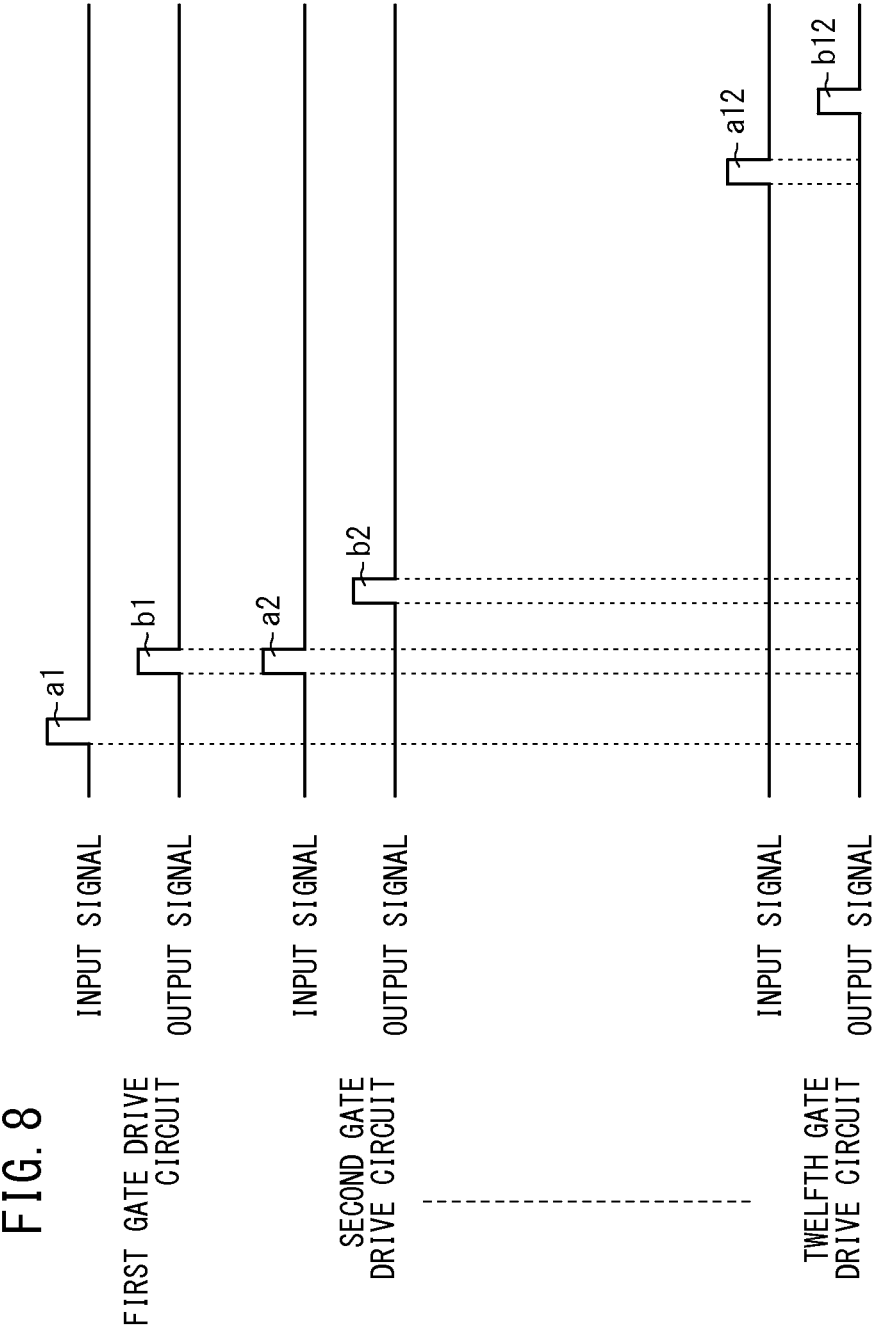
FIG. 8 is a time chart of input signals transferred from a cassette control device to the gate drive part and output signals transferred from the gate drive part to the cassette control device in a sequential readout mode.

FIG. 8 is a time chart of input signals transferred from the cassette control device 122 to the gate drive part 114 and output signals transferred from the gate drive part 114 to the cassette control device 122 in the sequential readout mode. In the normal readout mode, the cassette control device 122 sends an input signal (drive signal) a1 to the first gate drive circuit 150. When the drive signal a1 is entered, the first gate drive circuit 150 selects the associated gate line 110 in the 0th row and then selects those in the other rows sequentially, and outputs the gate signals to the selected gate lines 110 sequentially row by row. Then, the TFTs 72 are turned on sequentially, and the electric charges stored in the pixels 102 are read out row by row. In a case where the final row (the 239th row) is selected, the first gate drive circuit 150 sends an output signal (end signal) b1 to the cassette control device 122. When the cassette control device 122 receives the end signal b1, the cassette control device 122 sends an input signal (drive signal) a2 to the second gate drive circuit 150.

In a case where the input signal a2 is entered, the second gate drive circuit 150 selects the associated gate line 110 in the 0th row and then selects those in the other rows sequentially, and outputs the gate signals to the selected gate lines 110 sequentially row by row. Then, the TFTs 72 are turned on sequentially, and the electric charges stored in the pixels 102 are read out row by row. When the final row (the 239th row) is selected, the second gate drive circuit 150 sends an output signal (end signal) b2 to the cassette control device 122. When the cassette control device 122 receives the end signal b2, the cassette control device 122 sends an input signal (drive signal) a3 to the third gate drive circuit 150. Such a procedure is repeated in the first to twelfth gate drive circuits 150.

Thus, the drive signals a1 to a12 are entered into the first to twelfth gate drive circuits 150 to drive the circuits 150 sequentially, and the electric charges stored in the pixels 102 are read out sequentially row by row. Consequently, the electric charges stored in the pixels 102 in the 0th to 2879th rows on the radiation conversion panel 64 are read out sequentially row by row. In this sequential readout mode, considering the quality of the captured radiographic image, it takes a time of about 173 µsec to read the electric charges stored in the pixels 102 in one row. Therefore, in the sequential readout mode, it takes a time of about 500 msec (173 µsec/1×2880 lines) to read the electric charges in all rows (2880 rows).

Figure 9:
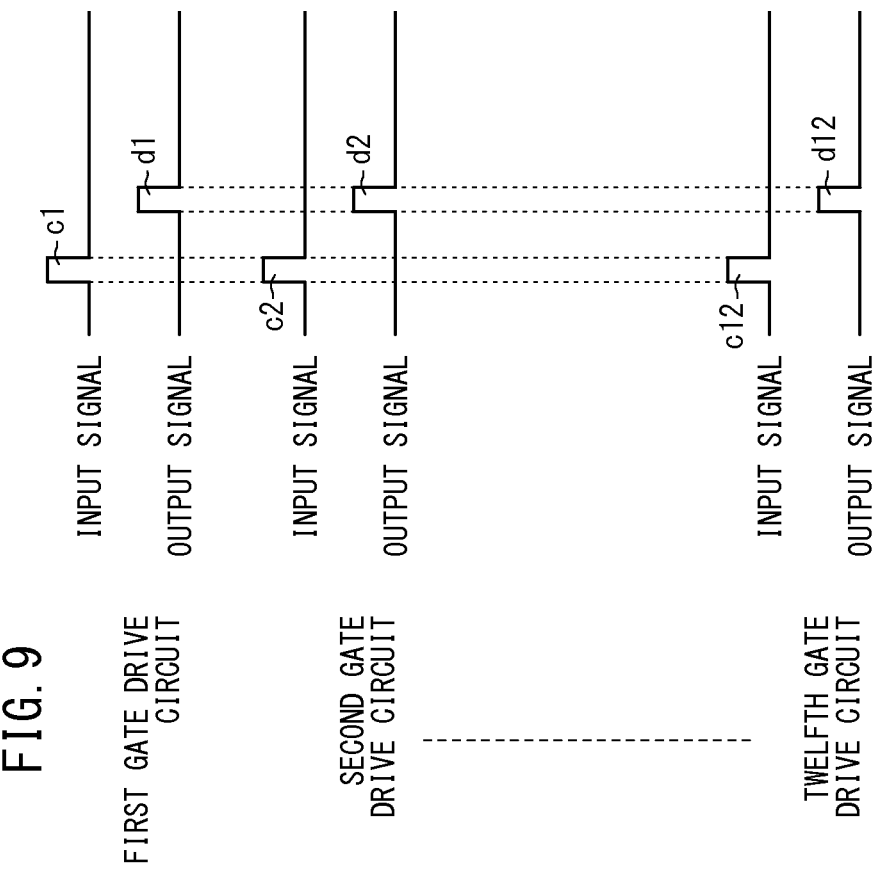
FIG. 9 is a time chart of input signals transferred from the cassette control device to the gate drive part and output signals transferred from the gate drive part to the cassette control device in a scan mode.

FIG. 9 is a time chart of input signals transferred from the cassette control device 122 to the gate drive part 114 and output signals transferred from the gate drive part 114 to the cassette control device 122 in the scan mode. In the scan mode, the cassette control device 122 sends input signals c1 to c12 to the first to twelfth gate drive circuits 150 simultaneously. When the drive signals c1 to c12 are entered, the first to twelfth gate drive circuits 150 each select the associated gate line 110 in the 0th row and then select those in the other rows sequentially, and outputs the gate signals to the selected gate lines 110. Then, in the associated readout region of each gate drive circuit 150, the TFTs 72 are turned on sequentially row by row, and the electric charges stored in the pixels 102 are read out sequentially row by row.

Specifically, in the associated readout regions of the gate drive circuits 150, the electric charges stored in the pixels 102 in the 0th rows are simultaneously read out, and then the electric charges stored in the pixels 102 in the first rows are simultaneously read out. Thus, the procedure of reading the electric charges stored in the pixels 102 sequentially row by row in the associated readout region is performed in the gate drive circuits 150 simultaneously. Consequently, the electric charges in the pixels 102 read by the gate drive circuits 150 are summed up in each column. For example, in a case where the gate drive circuits 150 read the electric charges stored in the pixels 102 in the 0th rows simultaneously, the read electric charges of the 0th rows are summed up in each column. The sum of the electric charges in each column is input to the charge amplifier 116 in each column. When the final row (the 239th row) is selected, the gate drive circuits 150 send output signals (end signals) d1 to d12 to the cassette control device 122.

In the scan mode, it is necessary to shorten the time required to read the electric charges stored in the pixels 102. However, when the time for reading the electric charges is excessively shortened, excess electric charges stored in the pixels 102 cannot be removed, and the radiographic image cannot be captured with excellent quality. To satisfy both the requirements, the electric charges stored in the pixels 102 in one row are read out in a time of 21 μsec. Therefore, in the scan mode, it takes a time of about 5 msec (21 μsec×2880 lines×(1/12)) to read the electric charges in all rows (2880 rows). Thus, the time required to read the electric charges stored in the pixels 102 in all rows in the scan mode is approximately 1/100 of that in the sequential readout mode. It should be noted that (21 μsec×2880 lines) is multiplied by (1/12) because the electric charges stored in the pixels 102 in 12 rows are simultaneously read out in the scan mode.

The electronic cassette 20 has at least a plurality of the pixels 102, which are arranged in matrix, a plurality of the TFTs 72, which are arranged in matrix to read the electric signals stored in the pixels 102, a plurality of the gate lines 110, which extend parallel to the row direction and are each connected to the TFTs 72 in one row, a plurality of the gate drive circuits 150, which are arranged in parallel in the column direction and are each connected with a plurality of the gate lines 110 to send the gate signals to the TFTs 72 row by row, and a plurality of the signal lines 112, which extend parallel to the column direction to read the electric signals stored in the pixels 102.

The TFT 72 has a gate connected to the gate line 110, a source connected to the pixel 102, and a drain connected to the signal line 112. When the drive signal a or c is entered, the gate drive circuit 150 selects the gate lines 110 connected therewith sequentially, sends the gate signals to the selected gate lines 110 to turn on the TFTs 72 sequentially, and reads the electric signals stored in the pixels 102 connected therewith sequentially row by row through the signal lines 112.

In the scan mode, the first readout control part 130 sends the drive signals c to the gate drive circuits 150 simultaneously, and reads the electric signals stored in the pixels 102 in a plurality of the rows simultaneously.

In the sequential readout mode, the second readout control part 136 in the cassette control device 122 sequentially sends the drive signals a to the gate drive circuits 150 to sequentially drive the gate drive circuits 150, and reads the electric signals stored in the pixels 102 sequentially row by row.

Figure 10:
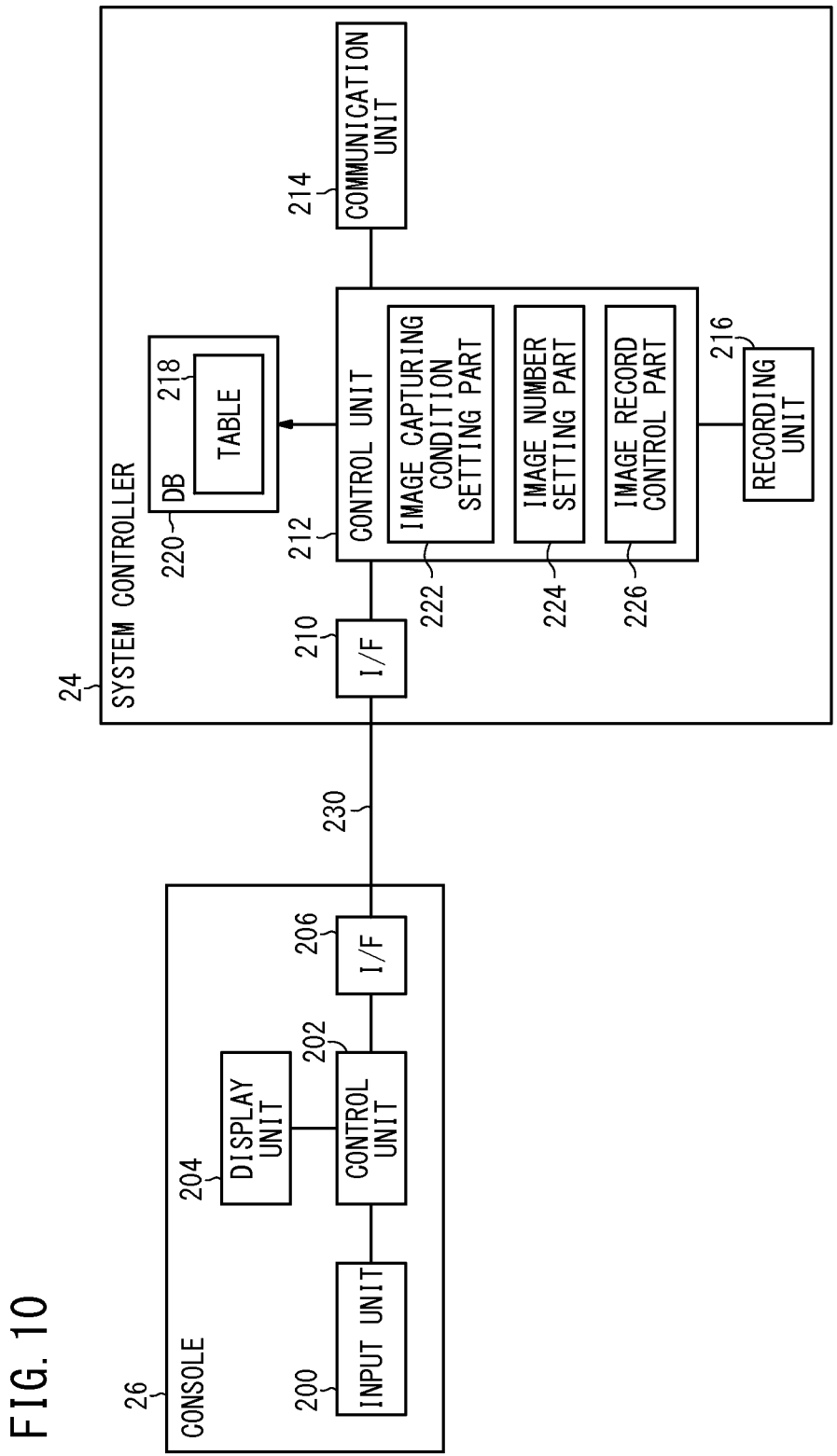
FIG. 10 is a schematic structural view of the electric structures of a system controller and a console.

FIG. 10 is a schematic structural view of the electric structures of the system controller 24 and the console 26. The console 26 has an input unit 200 for receiving an input operation by the user, a control unit 202 for controlling the entire console 26, a display unit (second announcement device) 204 for displaying an image to help the input operation by the user, and an interface I/F 206 for sending signals to and receiving signals from the system controller 24.

The system controller 24 has an interface I/F 210 for sending signals to and receiving signals from the console 26, a control unit (image capturing menu setting unit, instruction signal generation unit, control unit) 212 for controlling the entire radiographic image capturing system 10, a communication unit (second communication device, transmission unit) 214 for sending signals to and receiving signals from the electronic cassette 20 and the display device 28 through a wireless communication link, a recording unit (image capturing history recording unit) 216 for recording the image data transferred from the electronic cassette 20 through the communication unit 214, a program, and the like, and a database 220 having a table 218, which stores image capturing conditions including irradiation times of the radiation 16 associated with imaging areas and diagnostic sites. The interface I/F 206 and the interface I/F 210 are connected by a cable 230. The input unit 200 has a mouse, a keyboard, or the like (not shown), and sends operation signals entered by the user to the control unit 202.

The control unit 202 acts to display a screen (containing an image capturing menu), to which the user inputs the imaging area (imaging region) and the diagnostic site (region of interest) and the number of images to be captured, on the display unit 204, so that the display unit 204 is utilized as a GUI (Graphical User Interface). A doctor operates the input unit 200 while watching the screen (containing the image capturing menu) on the display unit 204, to select the imaging area, the diagnostic site, and the number of images to be captured. The imaging area (imaging region) is a body area of a patient that undergoes the radiographic image capturing process, such as a chest, lower abdomen, or leg. The diagnostic site (the region of interest) is a body site to be examined using an image obtained by the radiographic image capturing process. Even if the imaging area is a chest, the diagnostic site may be different, e.g., circulatory organs, rib bones, the heart, etc.

The control unit 202 sends (the image capturing menu containing) the imaging area, the diagnostic site, and the number of images to be captured, selected by the user, through the interfaces I/F 206 and 210 to the control unit 212 in the system controller 24. In the control unit 212, an image capturing condition setting part (irradiation time setting part) 222 acts to set image capturing conditions corresponding to the imaging area and the diagnostic site sent from the console 26 (selected by the user). Specifically, the image capturing condition setting part 222 reads the image capturing conditions corresponding to the imaging area and the diagnostic site (selected by the user) from the table 218, and sets the read image capturing conditions as conditions for the following radiographic image capturing process. The image capturing condition setting part 222 sends at least the irradiation time condition included in the setup image capturing conditions through the communication unit 214 to the electronic cassette 20. In the electronic cassette 20, the sent irradiation time is stored in the memory 124. The stored irradiation time is used as the above-described predetermined time.

In the control unit 212, an image number setting part 224 acts to set the number of images to be captured, sent from the console 26 (selected by the user). The image number setting part 224 sends the setup number of images through the communication unit 214 to the electronic cassette 20. In the electronic cassette 20, the sent number of images is stored in the memory 124. In the control unit 212, an image record control part 226 acts to record the one-frame image data (sent from the electronic cassette 20 through the communication unit 214) in the recording unit 216.

FIG. 11 is an example of the table 218. In the table 218, the image capturing conditions including the irradiation times, tube voltages, and tube currents are recorded in association with the imaging areas and the diagnostic sites. The imaging areas include a plurality of the diagnostic sites, and the image capturing conditions are recorded in association with the sites. For example, in a case where the imaging area is a chest, it includes a plurality of diagnostic sites such as circulatory organs, rib bones, and the heart, and the image capturing conditions are recorded in association with the sites. If the imaging area is a chest and the diagnostic site is circulatory organs, the irradiation time is 200 msec, the tube voltage is 100 kV, and the tube current is 10 mA. The user may operate the input unit 200 in the console 26 to modify the information recorded on the table 218.

Figure 12:
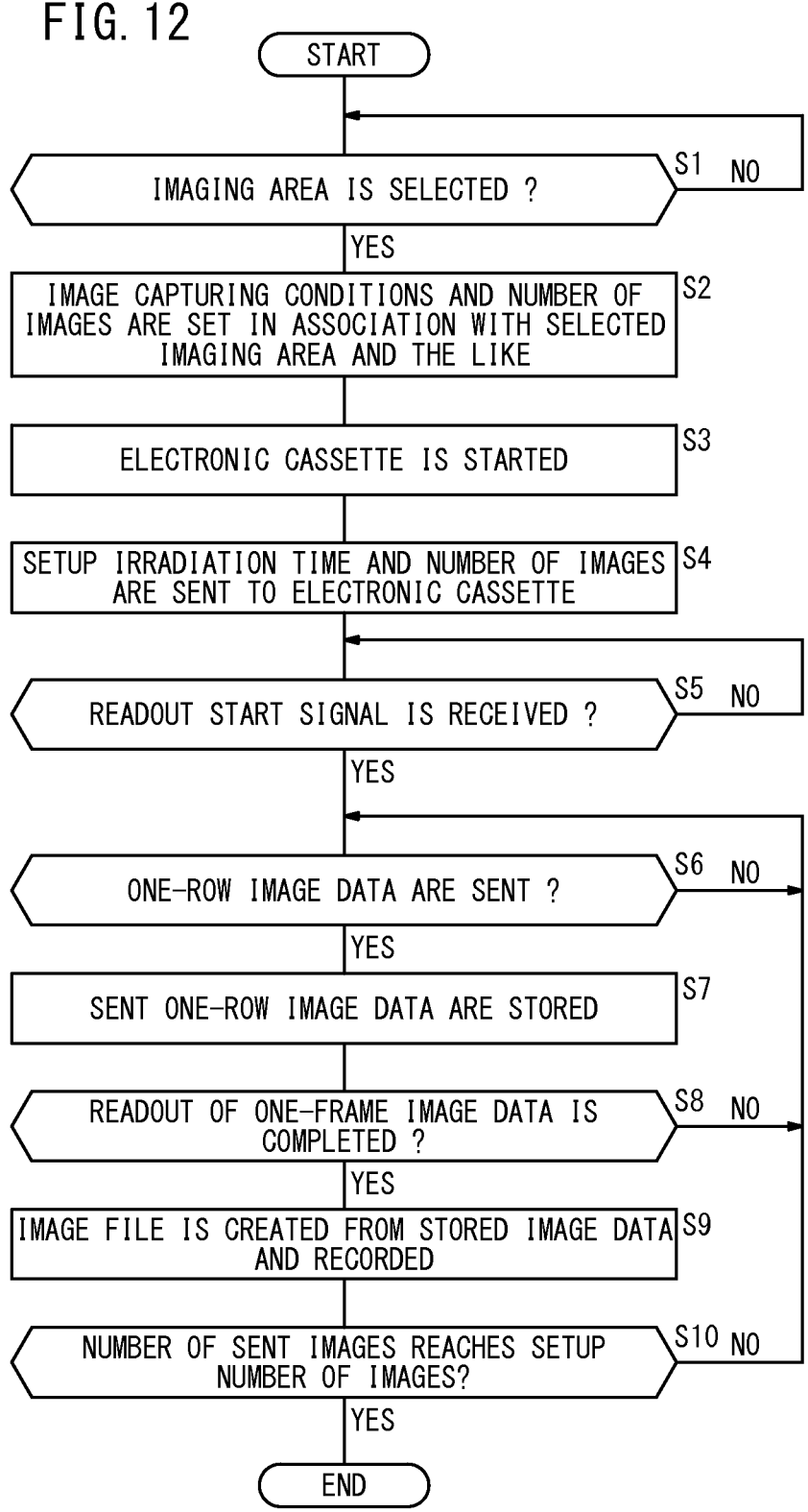
FIG. 12 is a flowchart of the operation of the system controller and the console in the radiographic image capturing system.
Figure 13:
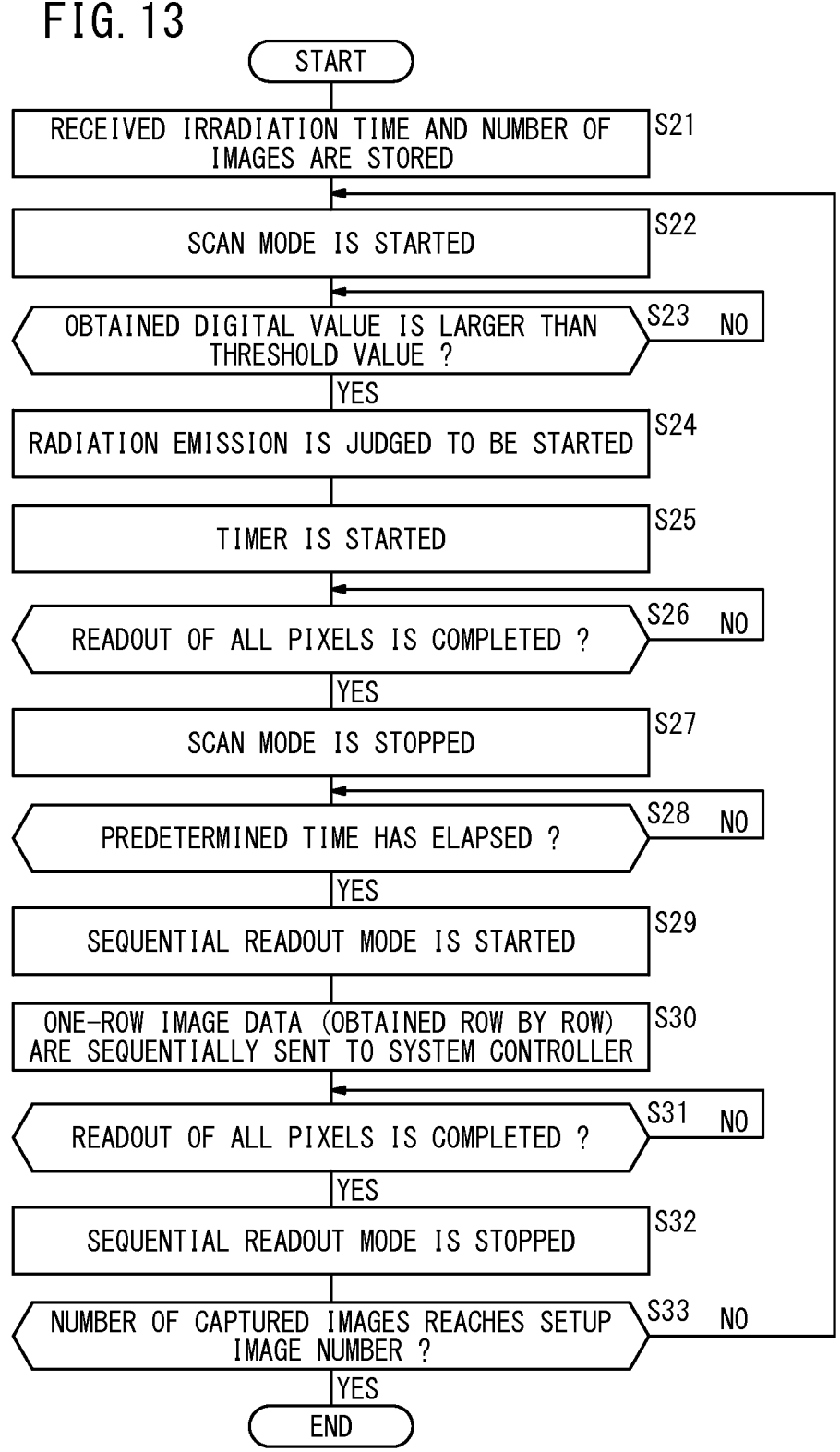
FIG. 13 is a flowchart of the operation of the cassette control device.

Operations of the radiographic image capturing system 10 will be described below with reference to the flowcharts of FIGS. 12 and 13. FIG. 12 is a flowchart of the operation of the system controller 24 and the console 26 in the radiographic image capturing system 10, and FIG. 13 is a flowchart of the operation of the cassette control device 122. The operation of the system controller 24 and the console 26 will be described first, and then the operation of the cassette control device 122 will be described below.

In the console 26, the control unit 202 judges whether or not the user operates the input unit 200 to select the imaging area, the diagnostic site, and the number of images to be captured (step S1). In this step, the control unit 202 acts to display an image on the display unit 204, which is used by the user for selecting the imaging area, the diagnostic site, and the number of images. The user can select, while watching the displayed image, the imaging area and the diagnostic site of a patient that undergoes the radiographic image capturing process.

In a case where the imaging area, the diagnostic site, and the number of images are judged to be not selected in step S1, the radiographic image capturing system 10 remains in step S1 until they are selected.

When the imaging area, the diagnostic site, and the number of images are judged to be selected by the user in step S1, the image capturing condition setting part 222 reads the image capturing conditions corresponding to the imaging area and the diagnostic site selected by the user from the table 218, and sets the read image capturing conditions as conditions for the following radiographic image capturing process, and the image number setting part 224 sets the number of images selected by the user (step S2). Specifically, when the user operates the input unit 200 to select the imaging area and the like, the control unit 202 outputs the selected imaging area and the like to the control unit 212 in the system controller 24 through the interfaces I/F 206 and 210. Then, in the control unit 212, the image capturing condition setting part 222 sets the image capturing conditions corresponding to the imaging area and the diagnostic site sent from the console 26 and sets the number of images sent from the console 26. The system controller 24 may output the setup image capturing conditions to the control unit 202 through the interfaces I/F 210 and 206, and the control unit 202 may act to display the setup image capturing conditions and the setup number of images on the display unit 204. In this case, the user can visually recognize the contents of the setup image capturing conditions.

To emit the radiation 16 from the radiation source 34 under the setup image capturing conditions, the user operates the input device in the radiation control unit 36, so that the radiation control unit 36 sets image capturing conditions equal to the conditions set in the system controller 24. For example, the radiation apparatus 18 may have a table equal to the table 218, and the user may select the imaging area and the diagnostic site from the table to set the equal image capturing conditions. Alternatively, the user may enter the irradiation time, the tube voltage, the tube current, and the like directly.

After the image capturing conditions are set, the control unit 212 sends a startup signal to the electronic cassette 20 through the communication unit 214, whereby the electronic cassette 20 is started up (step S3). The electronic cassette 20 is in the sleep state until the startup signal is sent. The sleep state is such a state that electric power is not supplied to at least the radiation conversion panel 64 and the drive circuit device 106. When the electronic cassette 20 is started up, the electronic cassette 20 acts to execute the scan mode. After the start up, the electronic cassette 20 may act to perform the reset operation before the scan mode.

The image capturing condition setting part 222 and the image number setting part 224 send the setup irradiation time and the setup number of images to the electronic cassette 20 through the communication unit 214 (step S4).

The control unit 212 judges whether a readout start signal from the electronic cassette 20 is received or not (step S5). The readout start signal includes an instruction to start the reading of the electric charges stored in the pixels 102 in the sequential readout mode.

If the readout start signal is judged to be not received in step S5, the radiographic image capturing system 10 remains in step S5 until it is received. When the readout start signal is judged to be received, the image record control part 226 judges whether the one-row image data are sent or not (step S6). The one-row image data are sequentially read out row by row, and the electronic cassette 20 sequentially outputs the one-row image data to the system controller 24. Thus, the one-row image data are sequentially sent to the system controller 24.

If the one-row image data are judged to be sent in step S6, the image record control part 226 acts to store the sent one-row image data in a buffer memory (not shown) in the control unit 212 (step S7).

The image record control part 226 judges whether the readout of the one-frame image data is completed or not (step S8). If the readout of the one-frame image data is completed, the electronic cassette 20 outputs a readout end signal to the system controller 24. In a case where the image record control part 226 receives the readout end signal, the readout of the one-frame image data is judged to be completed.

If the reading of the one-frame image data is judged to be not completed in step S8, the radiographic image capturing system 10 is returned to step S6, and the above steps are repeated.

If the readout of the one-frame image data is judged to be completed in step S8, an image file is created from the one-frame image data stored in the buffer memory, and is recorded in the recording unit 216 (step S9).

The image record control part 226 judges whether or not the sent image data satisfy the required number of images set in step S2 (step S10). If the sent image data are judged to be in short of the set number of images in step S10, the radiographic image capturing system 10 is returned to step S6. When the sent image data are judged to satisfy the set number of images, the process is completed.

The operation of the electronic cassette 20 will be described below with reference to the flowchart of FIG. 13 and the time chart of FIG. 14. When the startup signal is sent from the system controller 24, the electronic cassette 20 is started up, and the cassette control device 122 acts to store the irradiation time and the number of images sent from the system controller 24 in the memory 124 (step S21).

Then, the first readout control part 130 in the cassette control device 122 acts to start the execution of the scan mode (step S22). When the scan mode is started, the first readout control part 130 outputs the drive signals c to the gate drive circuits 150. When the drive signal c is received, each gate drive circuit 150 selects the gate lines 110 connected therewith in the 0th to final rows sequentially, and outputs the gate signals to the selected gate lines 110. Thus, each gate drive circuit 150 reads the electric charges stored in the pixels 102 in the 0th to final rows in the associated readout region sequentially row by row. Consequently, the procedure of reading the electric charges stored in the pixels 102 sequentially row by row in the associated readout region is performed in a plurality of the gate drive circuits 150 simultaneously. The read electric charges are summed up in each column.

Specifically, the electric charges stored in the pixels 102 in the 0th rows in the associated readout regions of the gate drive circuits 150 are simultaneously read out, summed up in each column, and output to the charge amplifier 116 in each column. Then, the electric charges stored in the pixels 102 in the first rows in the associated readout regions of the gate drive circuits 150 are simultaneously read out, summed up in each column, and output to the charge amplifier 116 in each column. The steps are repeated also in the second to 239th rows.

The one-row electric charges, which are read out sequentially row by row and summed up in each column, are send to the charge amplifiers 116, transferred through the multiplexer part 118 and the AD conversion part 120, and stored as the digital electric signals in the memory 124. Thus, the summed one-row image data are sequentially stored in the memory 124. When the electric charges stored in the pixels 102 in the 239th rows are read out, the gate drive circuits 150 sends the end signals d to the cassette control device 122.

The first readout control part 130 controls the switches 160 of the charge amplifiers 116 in the off states while implementing the scan mode. Thus, the charge amplifiers 116 can output the sent electric charge signals as the voltage signals. After the start up, the cassette control device 122 may act to perform the reset operation before the start of the scan mode. The first readout control part 130 may start the scan mode when a predetermined time (e.g. 10 seconds) has elapsed after the start up.

The irradiation start judgment part 132 judges whether or not the digital electric signals stored in the memory 124 are larger than the threshold value (step S23). When the radiation 16 is emitted from the radiation source 34 to the electronic cassette 20, the digital electric signals stored in the memory 124 become larger than the threshold value. Thus, whether the radiation 16 is emitted or not is detected based on whether or not the digital electric signals are larger than the threshold value. When the electric signals are judged to be not larger than the threshold value in step S23, the electronic cassette 20 remains in step S23 until the signal is judged to be larger than the threshold value. When the end signals d1 to d12 are sent from the gate drive circuits 150 to the cassette control device 122 (the one-frame electric charges are read out), the first readout control part 130 outputs the drive signals c1 to c12 to the gate drive circuits 150 again. One cycle of the scan mode include the steps from the input of the drive signals c1 to c12 into the gate drive circuits 150 to the output of the end signals d1 to d12. The end signals d1 to d12 are sent from the gate drive circuits 150 at the same timing.

When the digital electric signal stored in the memory 124 is judged to be larger than the threshold value in step S23, the emission of the radiation 16 from the radiation source 34 is judged to be started by the irradiation start judgment part 132 (step S24).

When the radiation switch 38 is pressed halfway by the user in the scan mode, the radiation control unit 36 makes a preparation to apply the radiation 16. Then, when the radiation switch 38 is pressed completely by the user, the radiation control unit 36 acts to emit the radiation 16 from the radiation source 34 for the predetermined time. Since the radiation control unit 36 acts to emit the radiation 16 under the image capturing conditions corresponding to the imaging area and the diagnostic site selected by the user as described above, the predetermined time is the irradiation time corresponding to the imaging area and the diagnostic site selected by the user. In the case of capturing a plurality of images, the user operates the radiation switch 38 at a certain time interval to apply the radiation 16 from the radiation source 34.

When the emission of the radiation 16 is judged to be started in step S24, the cassette control device 122 acts to start a timer (step S25), and the first readout control part 130 judges whether the electric charges stored in all the pixels 102 are read out completely or not (whether the reading of the one-frame electric charges is completely or not) in the scan mode (step S26). Thus, after the emission of the radiation 16 is judged to be started, the first readout control part 130 judges whether one cycle of the scan mode is completed or not. Specifically, after the emission of the radiation 16 is judged to be started, the first readout control part 130 judges whether or not the end signals d1 to d12 are sent from the gate drive circuits 150.

If the electric charges stored in all the pixels 102 are judged to be not completely read out in step S26, the electronic cassette 20 remains in step S26 until the electric charges are completely read out. In a case where the electric charges stored in all the pixels 102 are judged to be completely read out, the radiographic image capturing process is carried out, and thus the radiation 16 is applied, and the electric charges stored in the pixels 102 by the radiation 16 exposure are read out. Specifically, the first readout control part 130 stops the scan mode to start the exposure, and the electronic cassette 20 is switched to the exposure state (step S27). After this step, the first readout control part 130 does not output the drive signals c1 to c12 to the gate drive circuits 150 even if the end signals d1 to d12 are sent to the cassette control device 122. At the same time as the stop of the scan mode, the first readout control part 130 acts to turn on the switches 160 of the charge amplifiers 116. Consequently, unnecessary electric charges stored in the capacitors 158 can be discarded to improve the radiographic image quality.

Figure 14:
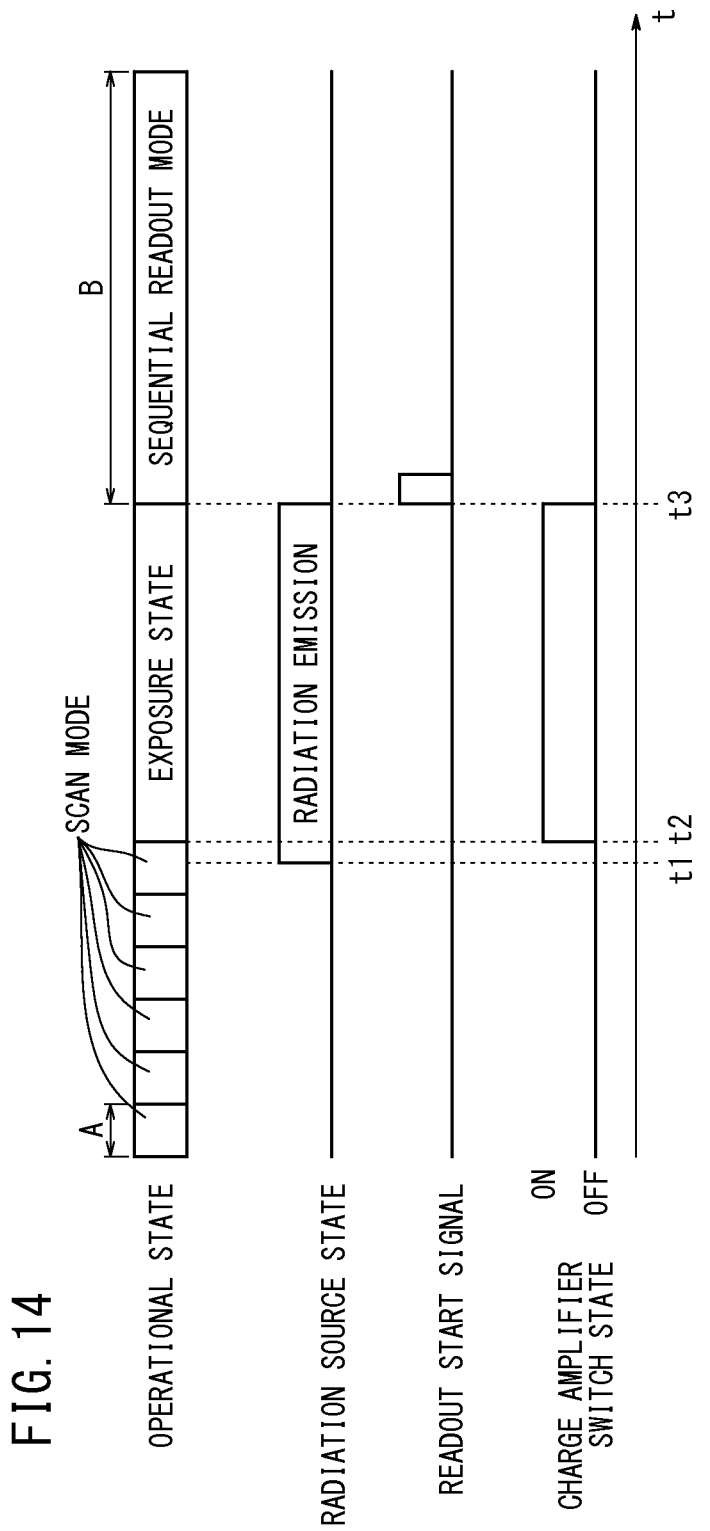
FIG. 14 is a time chart of the operation of the electronic cassette.

As shown in FIG. 14, until the emission of the radiation 16 from the radiation source 34 is judged to be started, the scan mode is repeated. A timing t1 represents a point at which the emission of the radiation 16 is judged to be started, and an arrow A represents one cycle of the scan mode, which is carried out in about 5 msec. After the emission of the radiation 16 is judged to be started, when the ongoing cycle of the scan mode is completed, the scan mode is stopped, so that the electronic cassette 20 is switched to the exposure state.

After the scan mode is stopped in step S27, the elapsed time judgment part 134 judges whether the predetermined time has elapsed or not from the judgment of the emission start of the radiation 16 (step S28). When the elapsed time judgment part 134 judges that the predetermined time has not elapsed from the start of the emission of the radiation 16 in step S28, the electronic cassette 20 remains in step S28 until the predetermined time elapses. The predetermined time is the irradiation time corresponding to the imaging area and diagnosis purpose selected by the user, and therefore the elapsed time judgment part 134 judges whether the emission of the radiation 16 is completed or not in step S28. Thus, after the scan mode is stopped, the exposure for the radiographic image capturing process is continued until the predetermined time elapses.

In a case where elapse of the predetermined time from the start of the emission of the radiation 16 is judged in step S28, the exposure is stopped, and the second readout control part 136 acts to start the sequential readout mode for reading the electric charges generated by the exposure with the radiation 16 (step S29). In this step, the second readout control part 136 outputs the readout start signal to the system controller 24 through the communication device 126 before, at, or after the start of the sequential readout mode. Consequently, the system controller 24 detects that the radiographic image data will be sent from the electronic cassette 20, and makes a preparation to receive the image data.

In the sequential readout mode, the second readout control part 136 outputs the drive signal a1 to the first gate drive circuit 150. When the drive signal a1 is entered, the first gate drive circuit 150 selects the associated gate lines 110 in the 0th to final rows sequentially, outputs the gate signals to the selected gate lines 110, and reads the electric charges stored in the pixels 102 in the 0th to final rows in the associated region sequentially row by row. Thus, the first gate drive circuit 150 reads the electric charges stored in the pixels 102 in the 0th to 239th rows in the associated region sequentially row by row. When the 239th row is selected, the first gate drive circuit 150 sends the end signal b1 to the cassette control device 122.

When the end signal b1 is entered, the second readout control part 136 sends the drive signal a2 to the second gate drive circuit 150. Such a procedure is repeated in the first to twelfth gate drive circuits 150. Consequently, the electric charges stored in the pixels 102 in the 0th to 2879th rows on the radiation conversion panel 64 are read out sequentially row by row. The electric charges, read out sequentially row by row, are input into the charge amplifier 116 in each column, transferred through the multiplexer part 118 and the AD conversion part 120, and stored as the digital electric signals in the memory 124. Thus, the one-row image data, obtained row by row, are sequentially stored in the memory 124.

In FIG. 14, a timing t3 represents a point at which the predetermined time is judged to have elapsed in step S28, and the sequential readout mode is started at approximately the same time as the timing t3 or immediately after the timing t3. The second readout control part 136 outputs the readout start signal to the system controller 24 at the same time as the start of the sequential readout mode. An arrow B represents one cycle of the sequential readout mode, which is carried out in about 500 msec. After the drive signal a1 is entered into the first gate drive circuit 150, one cycle of the sequential readout mode is carried out until the twelfth gate drive circuit 150 outputs the end signal b12.

The cassette control device 122 controls the switches 160 of the charge amplifiers 116 in the off states during implementing the sequential readout mode. Thus, the charge amplifiers 116 can output the sent electric charge signals as voltage signals.

After the start of the sequential readout mode, the cassette control device 122 starts to sequentially send the one-row image data (obtained row by row) to the system controller 24 (step S30). Thus, the one-row image data are stored in the memory 124, and sent to the system controller 24 through the communication device 126.

The second readout control part 136 judges whether the electric charges stored in all the pixels 102 are read out completely or not (whether the one-frame of electric charges are read out completely or not) in the sequential readout mode (step S31). Thus, the second readout control part 136 judges whether one cycle of the sequential readout mode is completed or not. Specifically, the second readout control part 136 judges whether or not the end signal b12 is sent from the twelfth gate drive circuit 150.

In a case where the electric charges stored in all the pixels 102 are judged to be not completely read out in step S31, the electronic cassette 20 remains in step S31 until the electric charges are completely read out. In a case where the electric charges stored in all the pixels 102 are judged to be completely read out, the second readout control part 136 stops the sequential readout mode (step S32). In this step, the second readout control part 136 outputs the readout end signal to the system controller 24 through the communication device 126.

The cassette control device 122 judges whether or not the number of the captured images reaches the setup number of images stored (set by the user) in step S21, thus whether or not the performed exposure and sequential readout procedures satisfy the condition of the setup number of images stored in step S21 (step S33). When the number of the captured images is judged to be in short of the setup number of images in step S33, the electronic cassette 20 is returned to step S22, and the above steps are repeated. When the number of the captured images is judged to reach the setup number of images, the process is completed and stopped.

Figure 15:
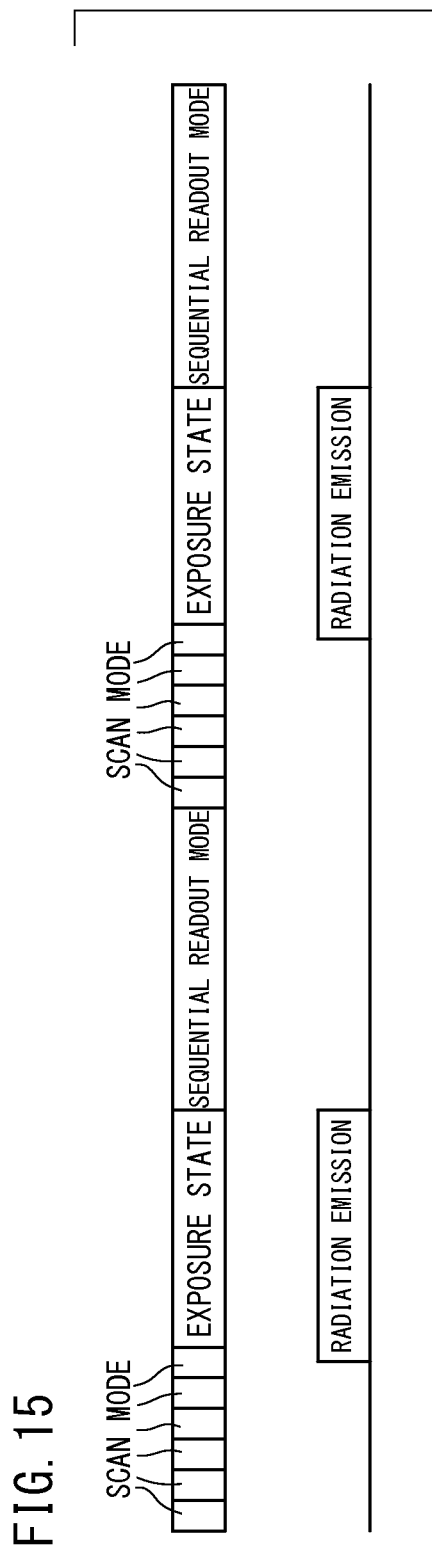
FIG. 15 is a time chart of the operation of the electronic cassette in the case of setting the number of images to be captured to two.

FIG. 15 is a time chart of the operation of the electronic cassette 20 in a case where the setup number of images is 2. In the electronic cassette 20, the first readout control part 130 acts to repeatedly execute the scan mode until the first emission of the radiation 16 is carried out. When the emission of the radiation 16 from the radiation source 34 is started, the emission of the radiation 16 is judged to be started by the irradiation start judgment part 132, and the ongoing cycle of the scan mode is completed, the electronic cassette 20 is switched to the exposure state. When the predetermined time has elapsed (the emission of the radiation 16 is completed), the second readout control part 136 acts to execute the sequential readout mode, and the electric charges stored by the emission of the radiation 16 in the pixels 102 are read out. Then, the first readout control part 130 acts to repeatedly execute the scan mode again. When the emission of the radiation 16 is judged to be started by the irradiation start judgment part 132, and the ongoing cycle of the scan mode is completed, the electronic cassette 20 is switched to the exposure state. When the predetermined time has elapsed (the emission of the radiation 16 is completed), the electric charges stored in the pixels 102 are read out, and thus the process is completed. In this case, the user may operate the radiation switch 38 twice at a certain time interval to apply the radiation 16 twice to the subject 14.

In this manner, before the emission of the radiation 16, the electric charges stored in the pixels 102 are read out in the scan mode, which is capable of more rapid reading than the sequential readout mode. When the digital value obtained by reading the electric charge becomes larger than the threshold value, the emission of the radiation 16 is judged to be started, and the exposure is started. Therefore, it is not necessary to synchronize the image capturing timings (an emission timing of the radiation 16 and an exposure timing of the electronic cassette 20), and the radiographic image can be readily captured.

Since the electric charges stored in the pixels 102 in a plurality of the rows are simultaneously read out in the scan mode, the start of the emission of the radiation 16 can be judged rapidly and accurately. Thus, since the electric charges in the pixels 102 are summed up, the obtained digital electric signal has a significantly higher intensity under the emission of the radiation 16 than without the emission, so that the start of the emission of the radiation 16 can be rapidly judged. Even in a case where the electric charges stored in the pixels 102 are not summed up, the start of the emission of the radiation 16 can be rapidly detected by using a smaller threshold value. However, in this case, the ratio of the noise electric signals to the threshold value is increased, whereby the start of the emission of the radiation 16 cannot be accurately detected.

Since the electric charges in a plurality of the rows are read simultaneously in the scan mode, the one-frame image can be read out at high speed (the one cycle of the scan mode can be shortened). Therefore, when the emission of the radiation 16 is judged to be started, the electronic cassette 20 can be switched to the exposure state in a shorter time.

In the scan mode, the procedure of reading the electric charges stored in the pixels 102 in the 0th to final rows sequentially row by row in the associated readout region is performed in a plurality of the gate drive circuits 150 simultaneously. Therefore, the start of the emission of the radiation 16 can be rapidly detected regardless of area in the radiation conversion panel 64 to which the radiation 16 is emitted. In a case where the electric charges stored in the pixels 102 are read to detect the start of the emission of the radiation 16 in the sequential readout mode, if the radiation 16 is emitted to an area of the 2000th to 2879th rows, the emission of the radiation 16 cannot be detected while the electric charges stored in the pixels 102 in the 0th to 1999th rows are read out. In contrast, since each gate drive circuits 150 read the electric charges stored in the pixels 102 in the 0th to 239th rows row by row in the scan mode, and thus the electric charges stored in the pixels 102 in the rows located at an interval of 240 rows are simultaneously read out in the scan mode, the start of the emission of the radiation 16 can be rapidly detected regardless of the area to which the radiation 16 is emitted.

The electronic cassette 20 perform the scan mode until the emission of the radiation 16 is judged to be started, and is switched to the exposure state when the start of the emission of the radiation 16 is detected. Therefore, it is not necessary to synchronize the image capturing timings, and thus it is not necessary to electrically connect the radiation apparatus 18 and the system controller 24, resulting in lowered cost. Since the scan mode is executed until the emission of the radiation 16 is judged to be started, the unnecessary electric charges stored in the pixels 102 can be removed to reduce the noise content of the radiographic image.

When the emission of the radiation 16 is judged to be started, the scan mode is stopped and switched by the exposure state. Therefore, the loss of the radiation 16 with the image information can be reduced. When the irradiation time (the predetermined time) has elapsed from the start of the emission of the radiation 16, the sequential readout mode is executed. Therefore, the exposure period of the pixels can be shortened to the minimum to further reduce the noise content of the radiographic image. Furthermore, it is not necessary to add another radiation detection sensor, thereby resulting in low cost.

The above embodiment can be modified as follows. Components of the following modified examples, which are identical to those of the above embodiment, are denoted by identical reference characters, and explanations thereof are omitted.

Modified Example 1

In the above embodiment, even when the emission of the radiation 16 is judged to be started in the scan mode, the electronic cassette 20 is not switched into the exposure state until the one cycle is completed. The electronic cassette 20 may be switched into the exposure state immediately after the judgment of the emission of the radiation 16.

Figure 16:
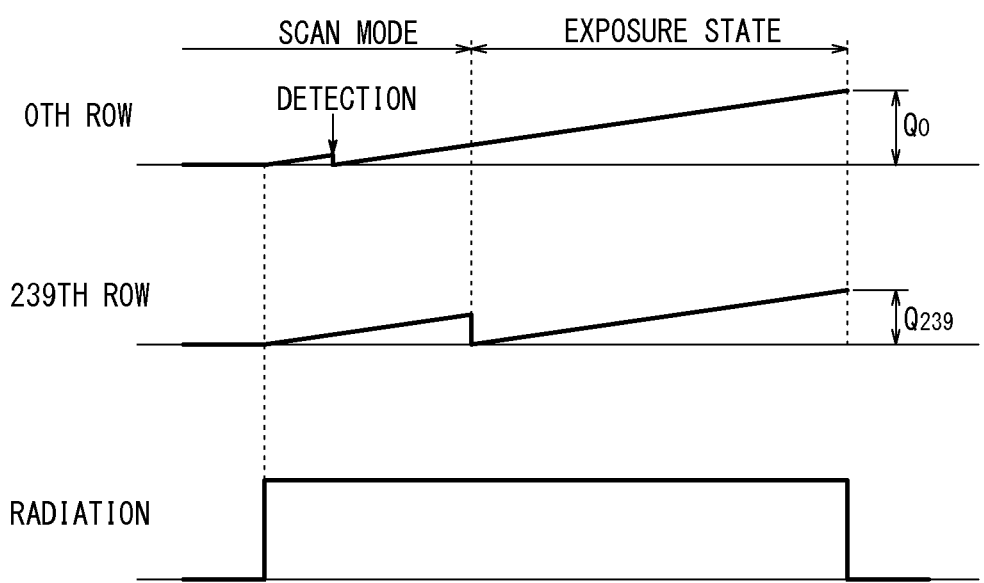
FIG. 16 is a diagram for illustrating electric charges stored in the pixels in some rows in a case where the electronic cassette is switched into an accumulation state after a radiation is detected in a process of reading the electric charges in the 0th row and then one cycle of the scan mode is completed.
Figure 17:
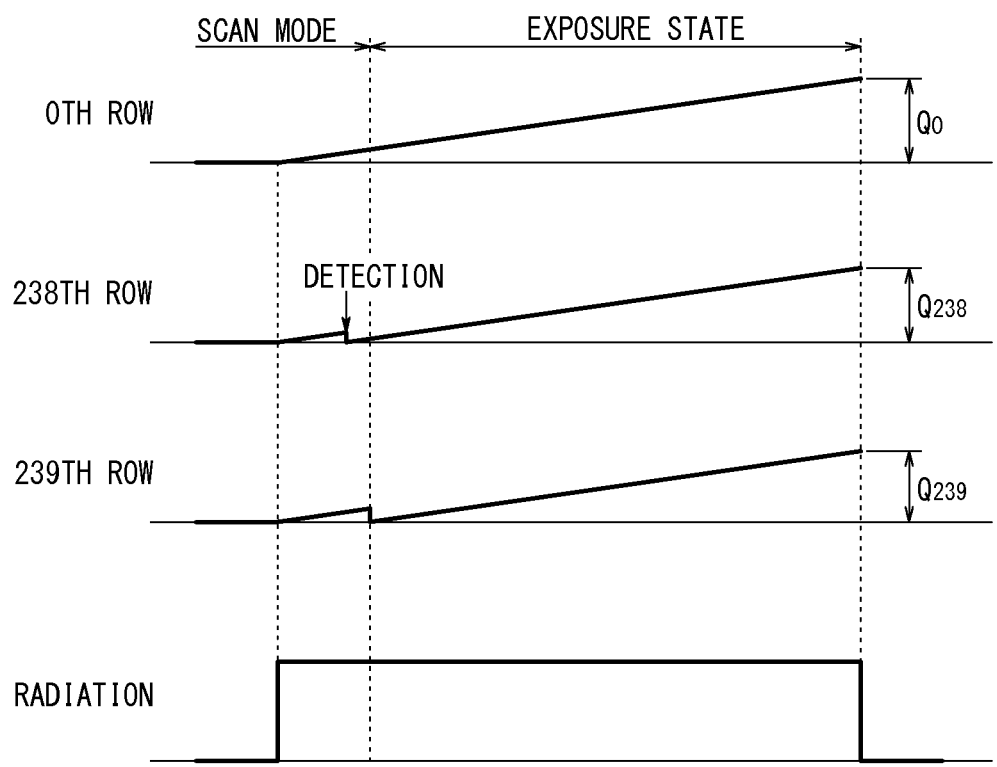
FIG. 17 is a diagram for illustrating electric charges stored in the pixels in some rows in a case where the electronic cassette is switched into the accumulation state after the radiation is detected in a process of reading the electric charges in the 238th row and then one cycle of the scan mode is completed.

FIGS. 16 and 17 are diagrams for illustrating the electric charges in the pixels 102 in some rows in a case where the electronic cassette 20 is switched into the accumulation state after the radiation 16 is detected and then the one cycle of the scan mode is completed. In the scan mode, each of the gate drive circuits 150 reads the electric charges stored in the pixels 102 in the 0th to final rows sequentially row by row. In this case, for example, even if a digital value obtained by reading the electric charges stored in the pixels 102 in the 0th row is judged to be larger than the threshold value and thus the radiation 16 is detected, the scan mode is not switched into the exposure state until the reading of the electric charges stored in the pixels 102 in the 239th row is completed.

Therefore, even after the detection of the radiation 16 in the scan mode, the electric charges stored in the pixels 102 under the radiation 16 are read out (discarded), whereby the loss of the radiation 16 with the image information is increased. The loss is increased significantly when the radiation 16 is detected at an early stage of the one cycle of the scan mode. Thus, as the timing of the detection of the emission of the radiation 16 is closer to the timing of reading the electric charges stored in the pixels 102 in the 239th row, the loss of the radiation 16 is reduced.

Specifically, even when the radiation 16 is detected in the step of reading the electric charges in the pixels 102 in the 0th row as shown in FIG. 16, the electric charges stored in the pixels 102 in the following first to 239th rows are read out sequentially row by row in the scan mode. The electric charges stored in the pixels 102 in the first to 239th rows under the radiation 16 are discarded. Therefore, the electric charges accumulated by the emission of the radiation 16 are wasted. The amount Q0 of the electric charges stored in the pixels 102 in the 0th row by the exposure for capturing the radiographic image and the amount Q239 of the electric charges stored in the pixels 102 in the 239th row satisfy the relation of Q0>Q239, and the difference between the amounts is large. The rows exhibit large variations in the amounts of the electric charges stored in the pixels 102. An amount Qn represents an amount of the electric charges stored in the pixels 102 in the n-th row. For example, the amount of the electric charges stored in the pixels 102 in the 3rd row is represented by Q3, and the amount of the electric charges stored in the pixels 102 in the 200th row is represented by Q200.

When the radiation 16 is detected in the step of reading the electric charges in the 238th row as shown in FIG. 17, the electric charges stored in the pixels 102 only in the following 239th row are read out in the scan mode. Therefore, only the electric charges stored in the pixels 102 in the 239th row under the radiation 16 are discarded. In this case, the amount Q0 of the electric charges stored in the pixels 102 in the 0th row by the exposure for capturing the radiographic image, the amount Q238 of the electric charges stored in the pixels 102 in the 238th row, and the amount Q239 of the electric charges stored in the pixels 102 in the 239th row satisfy the relation of Q0>Q238>Q239, but the difference between the amounts is not large. The rows exhibit small variations in the amounts of the electric charges stored in the pixels 102.

Consequently, the amounts of the electric charges, which are stored in the pixels 102 in the rows by the exposure for capturing the radiographic image, are varied depending on the timing of the emission of the radiation 16.

Accordingly, in Modified Example 1, the electric charges stored in the pixels 102 are not read out after the emission of the radiation 16 is detected, and the electronic cassette 20 is switched into the accumulation state. Specifically, when the start of the emission of the radiation 16 is detected, the cassette control device 122 sends readout stop signals to the gate drive circuits 150. When the drive signals c1 to c12 are sent, each of the gate drive circuits 150 selects the gate lines 110, outputs the gate signals to the selected gate lines 110, and reads the electric charges stored in the pixels 102 sequentially row by row. When the stop signals are sent, a mask processing is carried out, and the gate drive circuits 150 do not output the gate signals. Thus, the first readout control part 130 stops the reading of the electric charges stored in the pixels 102 in the scan mode. In this case, even when the stop signals are sent, each of the gate drive circuits 150 continues to sequentially select the gate lines 110 (the scan mode is continued). However, since the mask processing is carried out, the gate signals are not sent to the selected gate lines 110. Therefore, the electronic cassette 20 can be switched into the exposure state after the detection of the radiation 16.

For example, even in a case where the stop signals are sent after the gate signal is sent to the gate line 110 of the 0th row, each of the gate drive circuits 150 continues to sequentially select the gate lines 110 of the first, second, . . . , and final rows, but does not output the gate signals to the selected gate lines 110. In this case, even if the stop signals are sent, the gate drive circuits 150 sequentially select the gate lines 110, and thereby output the end signals d1 to d12 after the gate lines 110 of the 239th rows are selected. When the end signals d1 to d12 are sent from the gate drive circuits 150, the first readout control part 130 acts to stop the scan mode.

Figure 18:
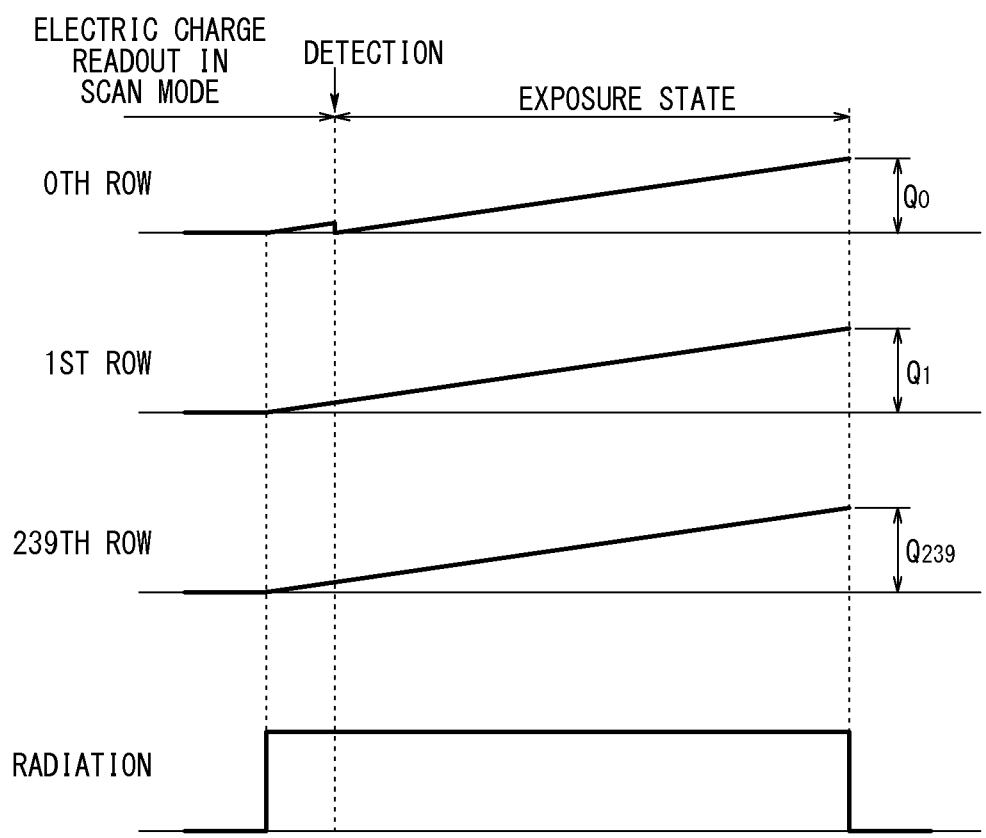
FIG. 18 is a diagram for illustrating electric charges in the pixels in the rows in a case where the electronic cassette is switched into the accumulation state after the radiation is detected and then immediately the reading of the electric charges in the pixels in the scan mode is stopped.

FIG. 18 is a diagram for illustrating the electric charges in the pixels 102 in some rows in a case where the electronic cassette 20 is switched into the accumulation state after the radiation 16 is detected and then immediately the reading of the electric charges in the pixels 102 in the scan mode is stopped.

The electric charges in the pixels 102 in the some rows, stored in a case where the radiation 16 is detected in a process of reading the electric charges stored in the 0th row, are shown in FIG. 18. When the radiation 16 is detected, the cassette control device 122 sends the stop signals to the gate drive circuits 150. Therefore, the electric charges stored in the pixels 102 in the second to final rows under the emission of the radiation 16 are not read out and remain in the rows. In this case, the amount Q0 of the electric charges stored in the pixels 102 in the 0th row by the exposure for capturing the radiographic image, the amount Q1 of the electric charges stored in the pixels 102 in the first row, and the amount Q239 of the electric charges stored in the pixels 102 in the 239th row satisfy the relation of Q0<Q1=Q239, and the difference between the amounts is not large. Thus, the exposure can be performed without wasting the radiation 16 with the image information, and the rows exhibit only small variations in the amounts of the electric charges.

The operation of the cassette control device 122 in Modified Example 1 is approximately equal to that shown in the flowchart of FIG. 13. However, in Modified Example 1, in a case where the emission of the radiation 16 is judged to be started by the irradiation start judgment part 132 in step S24 of FIG. 13, the first readout control part 130 sends the stop signals to the gate drive circuits 150 to perform step S25, so that the electronic cassette 20 can be switched into the exposure state. Then, the first readout control part 130 judges whether or not the end signals d1 to d12 are sent from the gate drive circuits 150 in step S26. When the end signals d1 to d12 are judged to be sent, the scan mode is stopped in step S27.

In this manner, when the emission of the radiation 16 is judged to be started, the electronic cassette 20 outputs the stop signals to the gate drive circuits 150. Though the scan mode is continued until the one cycle is completed, the electric charges stored in the pixels 102 are not read out, whereby the radiation 16 with the image information are not wasted and are utilized for capturing the radiographic image.

Modified Example 2

In the above embodiment and Modified Example 1, the user operates the input unit 200 to input the number of images to be captured, and the image number setting part 224 in the system controller 24 sets the number of images to be captured and sends the number of images to the electronic cassette 20. The numbers of images may be recorded on the table 218 in association with the imaging areas and the diagnosis purposes. In this case, the image capturing condition setting part 222 reads from the table 218 the number of images corresponding to the imaging area and the diagnosis purpose selected by the user, sets the number of images, and sends the setup number of images to the electronic cassette 20.

Modified Example 3

In the above embodiment and Modified Examples 1 and 2, in a case where the radiographic image capturing process is performed multiple times, the user operates the radiation switch 38 to emit the radiation 16 from the radiation source 34 multiple times. In this case, the radiation 16 may be continuously emitted from the radiation source 34 over a predetermined time, and the electronic cassette 20 may act to perform the radiographic image capturing process multiple times in the predetermined time. The user can operate the input device of the radiation control unit 36 to set the predetermined time. The radiation control unit 36 controls the radiation source 34 to emit the radiation 16 for the setup predetermined time.

Figure 19:
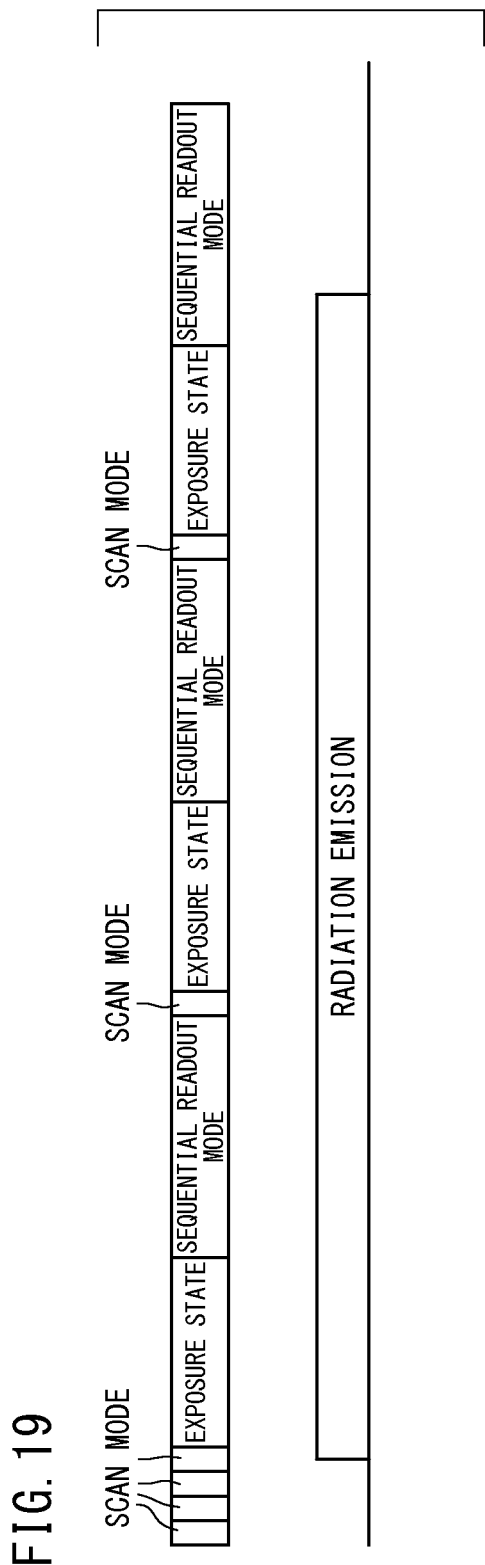
FIG. 19 is a time chart of the operation of the electronic cassette of Modified Example 3.

FIG. 19 is a time chart of the operation of the electronic cassette 20 in Modified Example 3. In the electronic cassette 20, the first readout control part 130 repeatedly executes the scan mode until the emission of the radiation 16. When the emission of the radiation 16 from the radiation source 34 is started, the emission of the radiation 16 is judged to be started by the irradiation start judgment part 132, and the electronic cassette 20 is switched into the exposure state. When the predetermined time has elapsed, the second readout control part 136 acts to execute the sequential readout mode to read the electric charges stored in the pixels 102 under the emission of the radiation 16. Then, the first readout control part 130 acts to execute the scan mode again. However, since the radiation 16 is continuously emitted, the emission of the radiation 16 is immediately detected by the irradiation start judgment part 132, and the electronic cassette 20 is rapidly switched into the exposure state. When the predetermined time has elapsed, the second readout control part 136 acts to execute the sequential readout mode to read the electric charges stored in the pixels 102 under the emission of the radiation 16. The radiographic image capturing process can be performed multiple times while emitting the radiation 16 in this manner. The predetermined time may be an irradiation time corresponding to the imaging area and the diagnosis purpose selected by the user, a default value, or an irradiation time set independently by the user.

Modified Example 4

In the above embodiment and Modified Examples 1 to 3, in the scan mode, the procedures of simultaneously reading a plurality of the rows are sequentially performed to read the electric charges stored in all pixels 102. However, only the pixels in a predetermined row may be read out. Modified Example 4 will be described in detail below.

Figure 20:
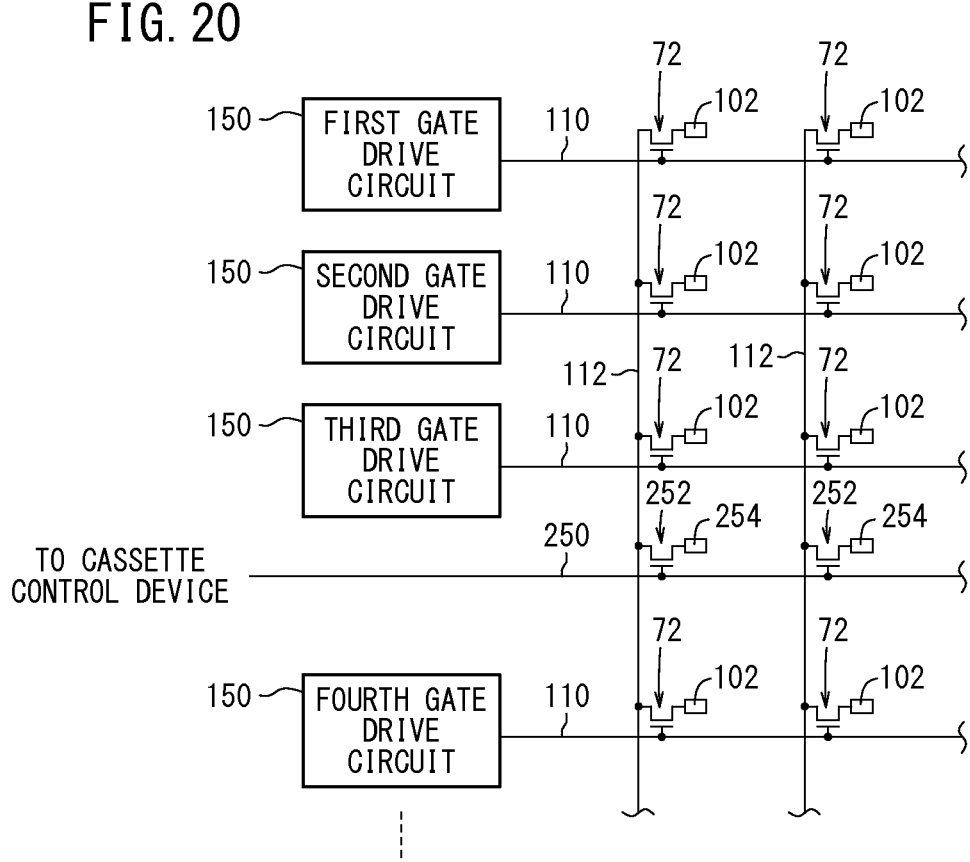
FIG. 20 is a partial detail view of a radiation conversion panel according to Modified Example 4.

FIG. 20 is a partial detail view of a radiation conversion panel 64 according to Modified Example 4. The radiation conversion panel 64 has a gate line 250, which is directly connected to the cassette control device 122. The gate line 250 is connected to pixels 254 through the TFTs 252. When the TFTs 252 are turned on, electric charges stored in the pixels 254 are read out through the signal lines 112. A gate signal for reading the electric charges stored in the pixels 254 in the scan mode is supplied to the TFTs 252 through the gate line 250. Thus, the gate line 250, the TFTs 252, and the pixels 254 are formed to execute the scan mode in addition to the gate lines 110, the TFTs 72, and the pixels 102. The radiation conversion panel 64 may have one gate line 250 or a plurality of the gate lines 250, which are each located between the gate drive circuits 150 or arranged at regular intervals over the entire radiation conversion panel 64. For example, the gate lines 250 may be formed between the first and second gate drive circuits 150, between the sixth and seventh gate drive circuits 150, and between the eleventh and twelfth gate drive circuits 150. In this case, at least one of the pixels 254 can receive the radiation 16 regardless of area in the radiation conversion panel 64 to which the radiation 16 is emitted. The pixels 254 connected to the gate line 250 correspond to the pixels in the predetermined row.

Though not shown in the drawing, each of the gate drive circuits 150 is connected with 240 gate lines 110, and each of the gate lines 110 is connected with the pixels 102 through the TFTs 72.

In Modified Example 4, in the scan mode, the first readout control part 130 outputs the gate signal directly to the gate line 250 to repeatedly read the electric charges stored in the pixels 254 row by row. For example, in the case of forming only one gate line 250, the gate signal is sent to the gate line 250 in the one cycle of the scan mode, and the gate signal is sent again to the gate line 250 in the next cycle of the scan mode after the completion of the one cycle, so that the electric charges stored in the pixels 254 are repeatedly read out.

In the case of forming a plurality of the gate lines 250, the first readout control part 130 sequentially outputs the gate signals directly to the gate lines 250, so that the procedure of sequentially reading the electric charges stored in the pixels 254 row by row is repeatedly performed. For example, in the case of forming three gate lines 250, the gate signal is sent to the gate line 250 of the 0th row, and the electric charges stored in the pixels 254 connected to the gate line 250 of the 0th row are read out. Then, the gate signal is sent to the gate line 250 of the first row, and the electric charges stored in the pixels 254 connected to the gate line 250 of the first row are read out. Finally, the gate signal is sent to the gate line 250 of the second row, and the electric charges stored in the pixels 254 connected to the gate line 250 of the second row are read out. After the gate signal is sent to the gate line 250 of the second row, the one cycle of the scan mode is completed. Then, in the next cycle, the gate signal is sent again to the gate line 250 of the 0th row.

In a case where the emission of the radiation 16 is judged to be started by the irradiation start judgment part 132, the scan mode is immediately stopped, and the electronic cassette 20 is switched into the exposure state. After the emission of the radiation 16 is judged to be started by the irradiation start judgment part 132, the gate drive circuits 150 do not send the gate signal to the gate line 250. For example, in the case of forming three gate lines 250, when the digital value obtained by outputting the gate signal to the gate line 250 of the 0th row is judged to be larger than the threshold value, the scan mode is immediately stopped without sending the gate signals to the gate lines 250 of the first and second rows. Thus, the electric power consumption in the scan mode can be reduced.

In a case where the predetermined time has elapsed from the detection of the radiation 16 (the judgment of the emission start of the radiation 16), i.e. when the emission of the radiation 16 is completed, the second readout control part 136 acts to execute the sequential readout mode.

The electronic cassette 20 has at least a plurality of the pixels (first pixels) 102, which are arranged in the matrix, a plurality of the TFTs (first switching elements) 72, which are arranged in the matrix to read the electric signals stored in the pixels 102, a plurality of the gate lines (first gate lines) 110, which extend parallel to the row direction and are each connected to the TFTs 72 in one row, a plurality of the gate drive circuits 150, which are arranged in parallel in the column direction and are each connected with a plurality of the gate lines 110 to send the gate signals to the TFTs 72 row by row, and a plurality of the signal lines 112, which extend parallel to the column direction to read the electric signals stored in the pixels 102.

The electronic cassette 20 further has a plurality of the pixels (second pixels) 254, which are arranged in the row direction on the surface having the pixels 102, a plurality of the TFTs (second switching elements) 252, which are arranged in the row direction to read the electric signals stored in the pixels 254, and at least one gate line 250, which extends parallel to the row direction and is connected to the TFTs 252.

The TFTs 72 and 252 each have a gate connected to the gate line 110 or 250, a source connected to the pixel 102 or 254, and a drain connected to the signal line 112. When the drive signal a is entered, each gate drive circuit 150 selects the gate lines 110 connected therewith sequentially, sends the gate signals to the selected gate lines 110 to turn on the TFTs 72 sequentially, and reads the electric signals stored in the pixels 102 connected therewith sequentially row by row through the signal lines 112.

The first readout control part 130 sends the gate signal to the gate line 250 sequentially, and thereby acts to execute the scan mode for reading the electric signals stored in the pixels 254 sequentially row by row. The second readout control part 136 sends the drive signals a to the gate drive circuits 150 sequentially to operate the gate drive circuits 150 sequentially, and thereby acts to execute the sequential readout mode for reading the electric signals in the pixels 102 sequentially row by row.

The operation of the cassette control device 122 in Modified Example 4 is approximately equal to that shown in the flowchart of FIG. 13. However, in Modified Example 4, when the emission of the radiation 16 is judged to be started by the irradiation start judgment part 132 in step S24 of FIG. 13, the first readout control part 130 immediately acts to stop the output of the gate signal to the gate line 250 (to stop the scan mode), and step S25 is carried out. The timer is started in step S25, and then step S28 is carried out without performing steps S26 and S27.

In Modified Example 4, the electric charges in the pixels 102 are not read out in the scan mode, whereby the pixels 102 are in the exposure state in the scan mode. Therefore, the radiation 16 with the image information is not wasted, and the electric charges corresponding to the emitted radiation 16 can be stored. Since the start of the emission of the radiation 16 is judged by reading the electric charges stored in the pixels 254, the timing of the emission start of the radiation 16 can be detected. Furthermore, the electronic cassette 20 is switched into the sequential readout mode when the irradiation time has elapsed from the emission start of the radiation 16. Therefore, the electronic cassette 20 is not exposed excessively after the completion of the emission of the radiation 16, whereby the noise content of the radiographic image can be lowered. In addition, since the start of the emission of the radiation 16 is judged by reading the electric charges stored in the pixels 254, the electric power consumption in the scan mode can be reduced.

In Modified Example 4, in the scan mode, the electric charges stored in the pixels 254 in one row may be read out in a time of 173 μsec in the same manner as the sequential mode. Because the electric charges stored in the pixels 254 are read out within 173 μsec in this manner, the emission start of the radiation 16 can be judged with high accuracy without summing the electric charges stored in the pixels 254. The number of the gate lines 250 for the scan mode is smaller than that of the gate lines 110 for the radiographic image capturing process. Therefore, even when the electric charges stored in the pixels 102 in one row are read in the time in the same manner as the sequential readout mode, the one cycle of the scan mode can be performed in a short time. For example, when the number of the gate lines 250 is 29, the one cycle of the scan mode can be performed in a time of about 5 msec in the same manner as the above embodiment.

In the case of forming a plurality of the gate lines 250, the user may operates the input unit 200 of the console 26 to select one, two, or more gate lines 250 for use in the scan mode. The user can expect an area in the electronic cassette 20, which is irradiated with the radiation 16 from the radiation source 34. Therefore, the user may select the gate line 250 corresponding to the area to be irradiated with the radiation 16. The information of the selected gate line 250 is transferred from the console 26 through the system controller 24 to the electronic cassette 20. The first readout control part 130 sends the gate signal only to the selected gate line 250 in the scan mode.

Consequently, the start of the emission of the radiation 16 can be judged rapidly and reliably by the irradiation start judgment part 132. The gate signal is not sent to the gate line 250 in an area, which is not irradiated with the radiation 16. Therefore, the electric power consumption in the scan mode can be further reduced.

Furthermore, in the case of forming a plurality of the gate lines 250, a larger number of the gate lines 250 may be selected in an area, which is likely to be irradiated or is irradiated with the radiation 16. Meanwhile, a smaller number of the gate lines 250 may be selected in an area, which is unlikely to be irradiated or is not irradiated with the radiation 16. In the scan mode, the gate signal is sent only to the selected gate line 250. The user can operate the input unit 200 of the console 26 to specify the area, which is likely to be irradiated or is irradiated with the radiation 16. In this case, the area, which is likely to be irradiated or is irradiated with the radiation 16, may be directly specified by the user. Alternatively, the control unit 212 of the system controller 24 may read from the table 218 and specify the area corresponding to the imaging area and the diagnosis purpose selected by the user. The control unit 212 of the system controller 24 selects the gate line 250 to be used in the scan mode based on the specified area, and sends the information of the selected gate line 250 to the electronic cassette 20.

Modified Example 5

In Modified Example 4, the gate line 250, the TFTs 252, and the pixels 254 for the scan mode are formed independently from the gate lines 110, the TFTs 72, and the pixels 102. However, some of the gate lines 110, the TFTs 72, and the pixels 102 may be predetermined as components to be used also in the scan mode.

Figure 21:
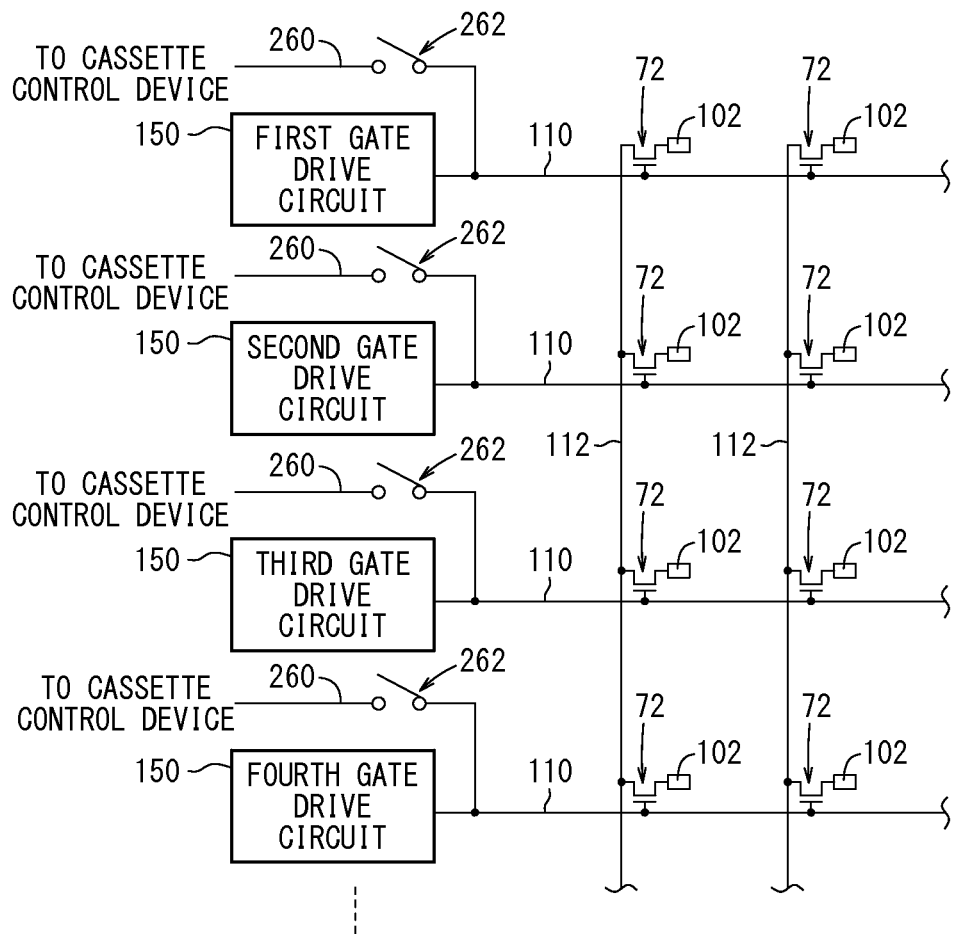
FIG. 21 is a partial detail view of a radiation conversion panel according to Modified Example 5.

FIG. 21 is a partial detail view of a radiation conversion panel 64 according to Modified Example 5. Though not shown in the drawing, each of the gate drive circuits 150 is connected with 240 gate lines 110, and each of the gate lines 110 is connected with the pixels 102 through the TFTs 72. One of the 240 gate lines 110 extending from each gate drive circuit 150 is connected to the cassette control device 122 through a bypass line 260. The bypass line 260 has a switching element 262.

The bypass line 260 connected to the gate line 110 of the first gate drive circuit 150 is referred to as the first bypass line 260, and the bypass line 260 connected to the gate line 110 of the second gate drive circuit 150 is referred to as the second bypass line 260. Similarly, the bypass lines 260 connected to the gate lines 110 of the third to twelfth gate drive circuits 150 are referred to as the third to twelfth bypass lines 260. Furthermore, for the sake of convenience, the gate line 110 connected with the first bypass line 260 is referred to as the first scanning gate line 110, and the gate line 110 connected with the second bypass line 260 is referred to as the second scanning gate line 110. Similarly, the gate lines 110 connected with the third to twelfth bypass lines 260 are referred to as the third to twelfth scanning gate lines 110. Though one of the 240 gate lines 110 connected to each of the gate drive circuits 150 is used as the scanning gate lines 110 for the sake of convenience in Modified Example 5, some of the gate drive circuits 150 may have no scanning gate lines 110 and may have a plurality of the scanning gate lines 110.

In Modified Example 5, in the scan mode, all or part of the switching elements 262 are turned on, and the first readout control part 130 sequentially sends gate signals to the bypass lines 260 with the switching elements 262 turned on, to read the electric charges stored in the pixels 102 sequentially row by row. When the gate signals are sent to all the bypass lines 260 with the switching elements 262 turned on, the one cycle of the scan mode is completed, and the next cycle is performed.

For example, in a case where the switching elements 262 of all the bypass lines 260 are turned on, the first readout control part 130 sends the gate signal to the first bypass line 260 to read the electric charges stored in the pixels 102 connected with the first scanning gate line 110 row by row. Then, the first readout control part 130 sends the gate signal to the second bypass line 260 to read the electric charges stored in the pixels 102 connected with the second scanning gate line 110 row by row. In this manner, the first readout control part 130 sequentially sends the gate signals to the first to twelfth bypass lines 260 to sequentially read the electric charges stored in the pixels 102 connected with the first to twelfth scanning gate lines 110 row by row. When the gate signal is sent to the twelfth bypass line 260, the one cycle of the scan mode is completed, and the gate signal is sent to the first bypass line 260 in the next cycle.

Thus, the electronic cassette 20 has at least a plurality of the pixels 102, which are arranged in the matrix, a plurality of the TFTs 72, which are arranged in the matrix to read the electric signals stored in the pixels 102, a plurality of the gate lines 110, which extend parallel to the row direction and are each connected to the TFTs 72 in one row, a plurality of the gate drive circuits 150, which are arranged in parallel in the column direction and are each connected with a plurality of the gate lines 110 to send the gate signals to the TFTs 72 row by row, and a plurality of the signal lines 112, which extend parallel to the column direction to read the electric signals stored in the pixels 102.

At least one of the gate lines 110 is connected with the bypass line 260 having the switching element 262. Thus, the electronic cassette 20 further has at least one bypass line 260 having the switching element 262 connected to the at least one gate line 110.

The TFTs 72 each have a gate connected to the gate line 110, a source connected to the pixel 102, and a drain connected to the signal line 112. When the drive signal a is entered, each gate drive circuit 150 selects the gate lines 110 connected therewith sequentially, sends the gate signals to the selected gate lines 110 to turn on the TFTs 72 sequentially, and reads the electric signals stored in the pixels 102 connected therewith sequentially row by row through the signal lines 112.

The first readout control part 130 turns on the switching element 262 of the bypass line 260 connected to the predetermined gate line (scanning gate line) 110 and sends the gate signal, and thereby acts to execute the scan mode for reading the electric signals stored in the pixels 102 connected with the predetermined gate line 110 sequentially row by row. The second readout control part 136 sends the drive signals a to the gate drive circuits 150 sequentially to operate the gate drive circuits 150 sequentially, and thereby acts to execute the sequential readout mode for reading the electric signals in the pixels 102 sequentially row by row.

The user operates the input unit 200 of the console 26 to select the scanning gate line 110 to be used in the scan mode. The selected scanning gate line 110 is used as the predetermined gate line 110, and the pixels 102 connected with the selected scanning gate line 110 are used as the pixels 102 in the predetermined row. The user can expect an area in the electronic cassette 20, which is irradiated with the radiation 16 from the radiation source 34. Therefore, the user can select the scanning gate line 110 corresponding to the area to be irradiated with the radiation 16. The information of the selected scanning gate line 110 is transferred from the console 26 through the system controller 24 to the electronic cassette 20. The first readout control part 130 turns on the switching element 262 of the bypass line 260 connected to the scanning gate line 110 selected by the user, while the scan mode is executed. The first readout control part 130 turns off all the switching elements 262 to stop the execution of the scan mode.

In Modified Example 5, the gate signal is sent only to the selected scanning gate line 110 in the scan mode, whereby the pixels 102, other than the predetermined pixels 102 connected with the selected scanning gate line 110, are in the exposure state even in the scan mode. Therefore, the radiation 16 with the image information is not wasted, and the electric charges corresponding to the emitted radiation 16 can be stored. Furthermore, the electronic cassette 20 is switched into the sequential readout mode when the irradiation time has elapsed from the emission start of the radiation 16. Therefore, the electronic cassette 20 is not exposed excessively after the completion of the emission of the radiation 16, whereby the noise content of the radiographic image can be lowered.

The user selects the scanning gate line 110 in the area to be irradiated with the radiation 16. Therefore, the start of the emission of the radiation 16 can be judged rapidly and reliably by the irradiation start judgment part 132. In addition, since the gate signal is sent only to the selected scanning gate line 110, the electric power consumption in the scan mode can be reduced.

In Modified Example 5, in the scan mode, the electric charges stored in the pixels 102 in one row may be read out in a time of 173 μsec in the same manner as the sequential mode. When the electric charges stored in the pixels 102 are read out in 173 μsec in this manner, the emission start of the radiation 16 can be judged with high accuracy without summing the electric charges stored in the pixels 102. Only a small number of the scanning gate lines 110 are used in the scan mode. Therefore, even when the electric charges stored in the pixels 102 in one row are read in the time in the same manner as the sequential readout mode, the one cycle of the scan mode can be performed in a short time.

A larger number of the scanning gate lines 110 may be selected in an area, which is likely to be irradiated or is irradiated with the radiation 16. Meanwhile, a smaller number of the scanning gate lines 110 may be selected in an area, which is unlikely to be irradiated or is not irradiated with the radiation 16. In the scan mode, the gate signal is sent only to the selected scanning gate line 110. The user can operate the input unit 200 of the console 26 to specify the area, which is likely to be irradiated or is irradiated with the radiation 16. In this case, the area, which is likely to be irradiated or is irradiated with the radiation 16, may be directly specified by the user. Alternatively, the control unit 212 of the system controller 24 may read from the table 218 and specify the area corresponding to the imaging area and the diagnosis purpose selected by the user. The control unit 212 of system controller 24 selects the scanning gate line 110 to be used in the scan mode based on the specified area, and sends the information of the selected scanning gate line 110 to the electronic cassette 20.

Modified Example 6

In Modified Example 4, the gate line 250, the TFTs 252, and the pixels 254 for the scan mode are formed independently from the gate lines 110, the TFTs 72, and the pixels 102. However, a predetermined gate drive circuit 150 may be used in the scan mode, so that the gate line 110, the TFTs 72, and the pixels 102 in the associated readout region of the gate drive circuit 150 may be used in the scan mode.

In the scan mode, the first readout control part 130 sends the drive signal c to one predetermined gate drive circuit 150. When the drive signal c is entered, the gate drive circuit 150 reads the electric charges stored in the pixels 102 in the 0th to 239th rows of the associated readout region sequentially row by row. Consequently, the digital electric signals are obtained sequentially row by row. When the digital electric signal is judged to be larger than the threshold value by the irradiation start judgment part 132, the first readout control part 130 stops the scan mode. The first readout control part 130 repeatedly executes the scan mode until the emission is judged to be started. Thus, when the end signal d is sent from the gate drive circuit 150, the drive signal c is sent again to the predetermined gate drive circuit 150. In this case, the electric charges stored in the pixels 102 in one row may be read out in a time of 173 μsec in the same manner as the sequential readout mode or in a time of 21 μsec in the same manner as the scan mode in the above embodiment.

The user can operate the input unit 200 of the console 26 to select the gate drive circuit 150 to be used in the scan mode. The user can expect an area in the electronic cassette 20, which is irradiated with the radiation 16 from the radiation source 34. Therefore, the user can select the gate drive circuit 150 for reading the pixels 102 corresponding to the area to be irradiated with the radiation 16. The information of the gate drive circuit 150 selected by the user is transferred from the console 26 through the system controller 24 to the electronic cassette 20. The first readout control part 130 sends the drive signal c in the scan mode to the gate drive circuit 150 selected by the user, which is used as the predetermined gate drive circuit 150.

The user may select a plurality of the gate drive circuits 150 to be used in the scan mode. In this case, the first readout control part 130 may simultaneously send the drive signals c to the selected gate drive circuits 150. Thus, the gate drive circuits 150 may be simultaneously operated. Furthermore, the first readout control part 130 may sequentially actuate the predetermined gate drive circuits 150. For example, the end signal d is sent from one of the gate drive circuits 150, and then the drive signal c is sent to the next gate drive circuit 150.

In Modified Example 6, the gate drive circuits 150 other than the selected gate drive circuit 150 do not send the gate signals during the execution of the scan mode, whereby the pixels 102, other than the pixels 102 in the associated readout region of the selected gate drive circuit 150, are in the exposure state even in the scan mode. Therefore, the radiation 16 with the image information is not wasted, and the electric charges corresponding to the emitted radiation 16 can be stored. Furthermore, the electronic cassette 20 is switched into the sequential readout mode when the irradiation time has elapsed from the emission start of the radiation 16. Therefore, the electronic cassette 20 is not exposed excessively after the completion of the emission of the radiation 16, whereby the noise content of the radiographic image can be lowered.

The user selects the gate drive circuit 150 for reading the electric charges stored in the pixels 102 in the area to be irradiated with the radiation 16. Therefore, the start of the emission of the radiation 16 can be judged rapidly and reliably by the irradiation start judgment part 132. In addition, since only the selected gate drive circuit 150 acts to read the electric charges stored in the pixels 102, the electric power consumption in the scan mode can be reduced.

Modified Example 7

In Modified Example 7, as described below with reference to FIGS. 22 to 27, when the emission of the radiation 16 cannot be detected even after the predetermined time has elapsed from the start of the scan mode (step S22 of FIG. 13), the scan mode is stopped to avoid wasteful electric power consumption. The scan mode in Modified Example 7 includes those in the above embodiment and Modified Examples 1 to 6.

Figure 22:
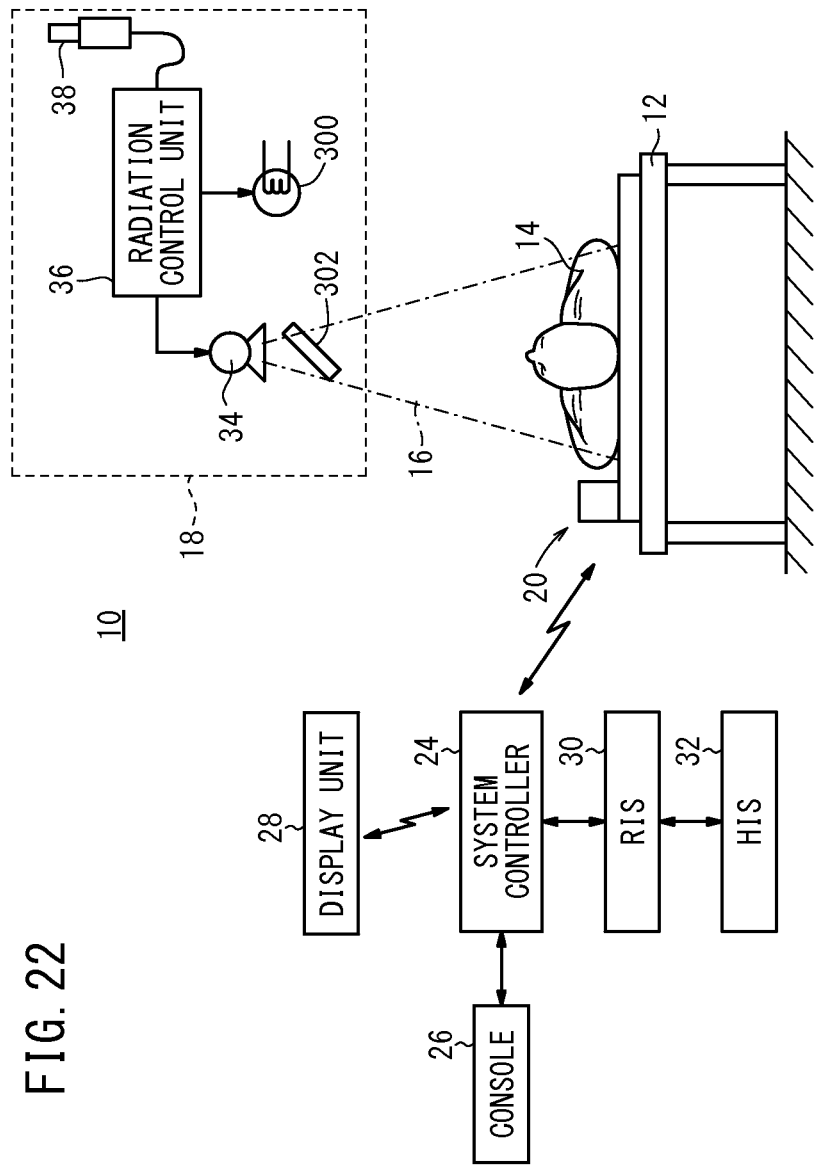
FIG. 22 is a schematic view of a radiographic image capturing system according to Modified Example 7.
Figure 23:
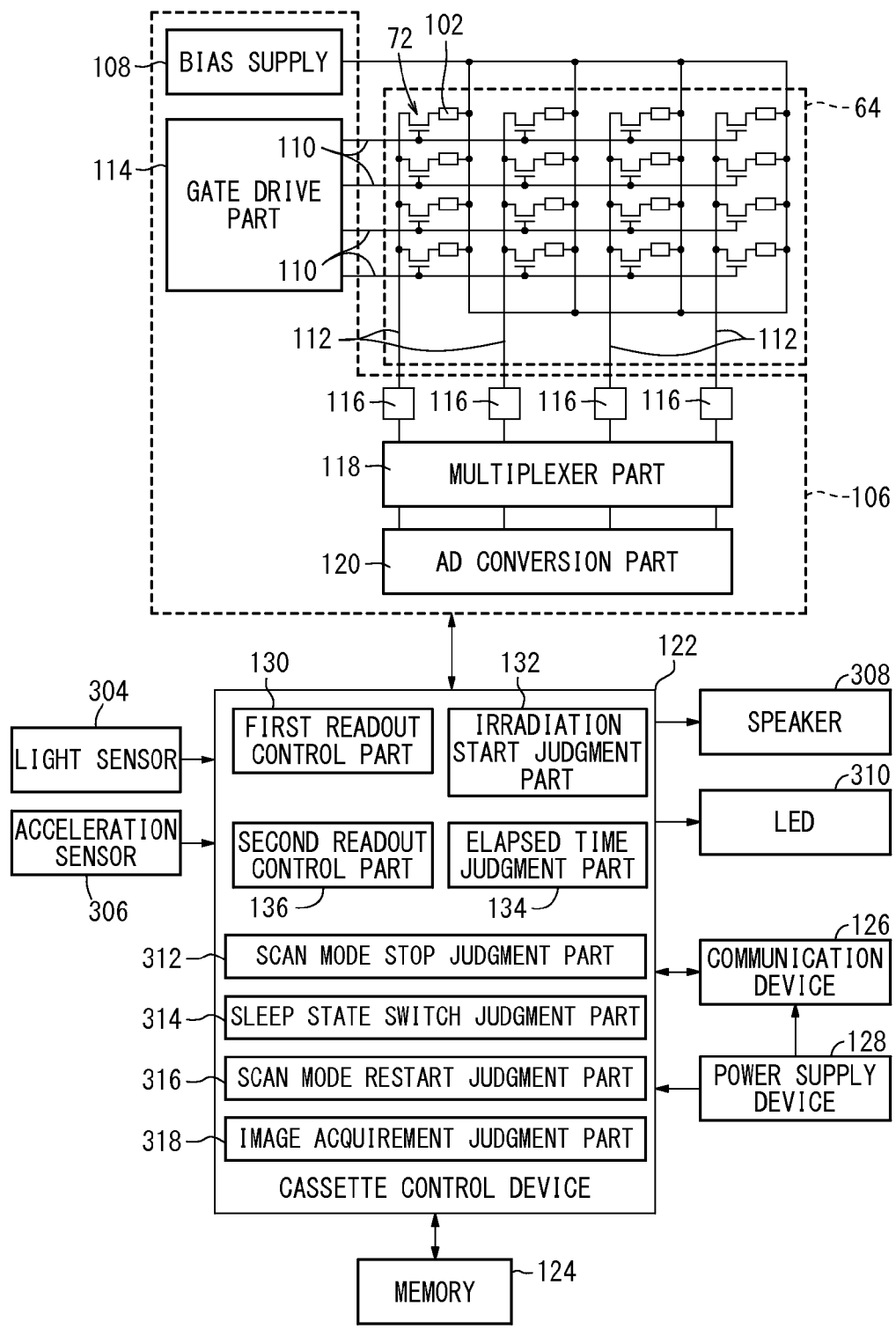
FIG. 23 is a schematic structural view of the electric structure of an electronic cassette shown in FIG. 22.

The components of Modified Example 7 will be described below with reference to FIGS. 22 to 24.

In Modified Example 7, the radiation apparatus 18 further has an irradiation field lamp 300 and a mirror 302. The irradiation field lamp 300 emits an illuminating light before the emission of the radiation 16 according to an instruction from the radiation control unit 36. The illuminating light from the irradiation field lamp 300 is reflected toward the electronic cassette 20 by the mirror 302 composed of a material transmissive to the radiation 16, and is directed onto the image capturing surface 42 of the panel unit 52 (see FIGS. 2 and 22). In this case, when the distance between the radiation source 34 and the radiation conversion panel 64 is controlled at a source to image receptor distance (SID), the emission area of the illuminating light is approximately equal to the image capturable area 60 on the image capturing surface 42. Thus, the illuminating light incident onto the image capturing surface 42 indicates the irradiation field of the radiation 16. When the radiation switch 38 is pressed halfway by the user, the radiation control unit 36 makes a preparation to emit the radiation 16 while the output of the illuminating light from the irradiation field lamp 300 is stopped.

The electronic cassette 20 further has a light sensor (light detection device) 304 for detecting the illuminating light incident onto the image capturing surface 42, an acceleration sensor (transfer detection device) 306 for detecting an acceleration in the transfer of the electronic cassette 20, a speaker (first announcement device, sound output device) 308 for outputting sound corresponding to signals from the cassette control device 122 to the outside, and an LED (first announcement device, light output device) 310 for emitting a light depending on signals from the cassette control device 122. In this case, for example, the light sensor 304 may be disposed in an arbitrary position on the image capturing surface 42 to detect the illuminating light. The acceleration sensor 306 may be disposed in an arbitrary position in the casing 56. The speaker 308 and the LED 310 may be disposed in, for example, the control unit 54 such that the user can recognize the sound and the light.

The cassette control device 122 further has a scan mode stop judgment part (first readout mode stop judgment part) 312, a sleep state switch judgment part 314, a scan mode restart judgment part (first readout mode restart judgment part) 316, and an image acquirement judgment part 318. The scan mode stop judgment part 312 judges whether the scan mode should be halted or not. The sleep state switch judgment part 314 judges after the stop of the scan mode whether or not the electric power supplied from the power supply device 128 to the components in the electronic cassette 20 should be stopped to switch the electronic cassette 20 into the sleep state. The scan mode restart judgment part 316 judges whether or not the halted scan mode should be restarted. The image acquirement judgment part 318 judges, after the scan mode is halted and the pixels 102 are switched into the exposure states, whether or not the second readout control part 136 should act to read the electric signals in the pixels 102 in the sequential readout mode.

Figure 24:
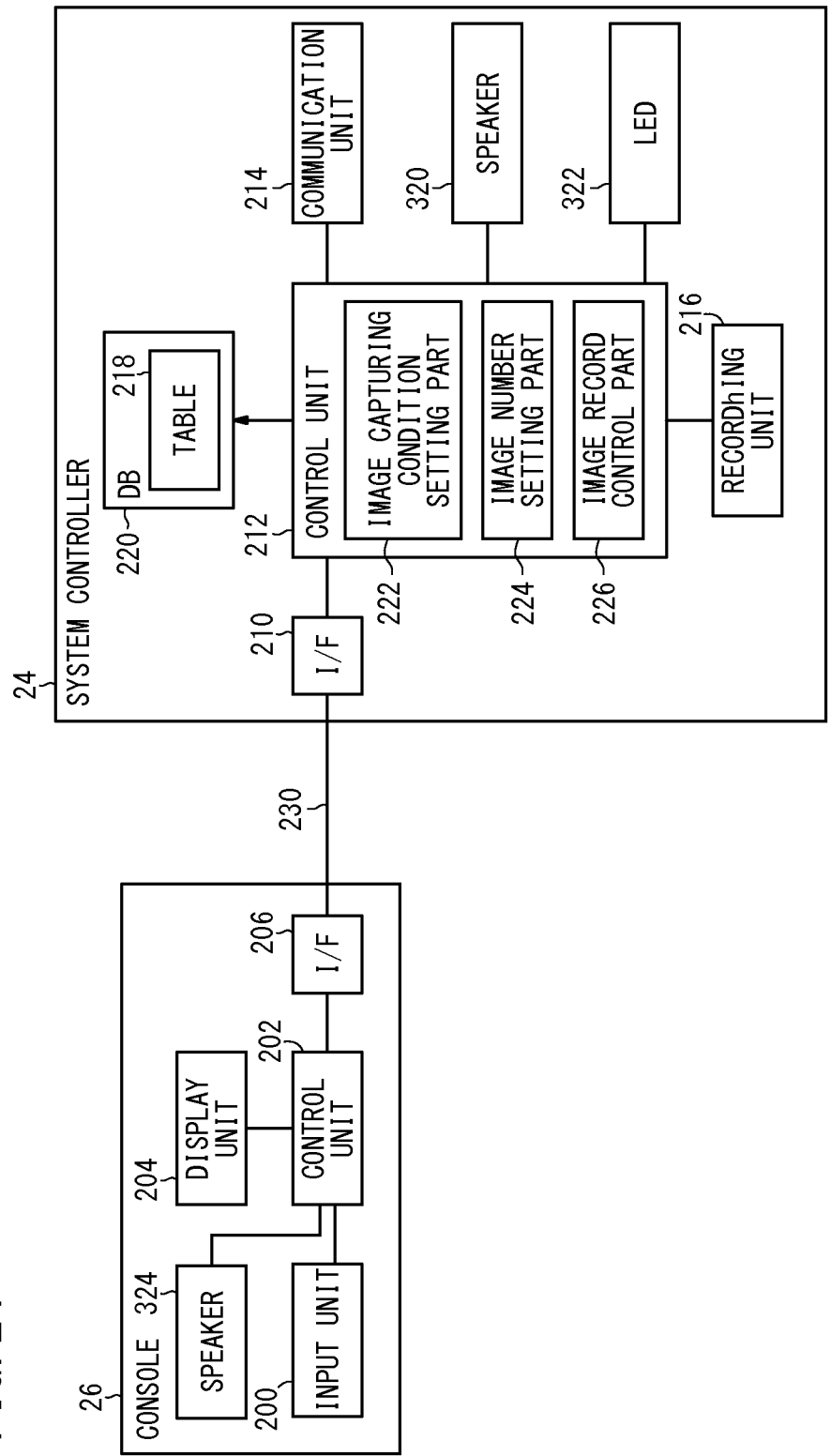
FIG. 24 is a schematic structural view of the electric structures of a system controller and a console shown in FIG. 22.

The system controller 24 further has an LED (second announcement device, light output device) 322 for emitting a light depending on signals from the control unit 212, and a speaker (second announcement device, sound output device) 320 for outputting sound corresponding to signals from the control unit 212 to the outside (see FIG. 24). Also the console 26 further has a speaker (second announcement device, sound output device) 324 for outputting sound corresponding to signals from the control unit 202 to the outside (see FIG. 24).

Operations of the radiographic image capturing system 10 of Modified Example 7 having the above structure will be described below with reference to the flowcharts of FIGS. 25 to 27. The operations are described using the flowcharts of FIGS. 12 and 13 and FIGS. 22 to 24 if necessary.

The scan mode is started in step S22 of FIG. 13, and the irradiation start judgment part 132 judges whether or not the digital electric signals stored in the memory 124 are larger than the threshold value in next step S23. When the electric signals do not reach the threshold value (step S23: NO), step S41 of FIG. 25 is carried out.

In step S41, the scan mode stop judgment part 312 judges whether the predetermined time has elapsed or not from the start of the execution of the scan mode. When the predetermined time is judged to have elapsed (step S41: YES), then the scan mode stop judgment part 312 judges whether or not the cassette control device 122 receives a signal from the system controller 24 or the console 26 (step S42). The signal from the system controller 24 or the console 26 is an instruction signal including an image capturing menu reset (re-entered) by the control unit 212 of the system controller 24, an operation of the input unit 200 by the user, or the like as hereinafter described.

When the cassette control device 122 does not receive the signal from the system controller 24 or the console 26 (step S42: NO), the scan mode stop judgment part 312 judges that the emission of the radiation 16 is not started even after the predetermined time has elapsed from the start of the scan mode, and the electric power will be wasted if the scan mode is further continued. Thus, the scan mode stop judgment part 312 decides to stop the scan mode, and controls the first readout control part 130 to stop the scan mode based on the judgment result (step S43).

After the scan mode is stopped, the scan mode stop judgment part 312 controls the first readout control part 130 to turn off all the TFTs 252, so that all the pixels 102 are switched into the exposure states (step S44). A communication signal, which indicates that the scan mode is stopped and all the pixels 102 are switched into the exposure states, is sent from the communication device 126 to the system controller 24 via wireless communication (step S45), and then step S61 of FIG. 27 is carried out. The scan mode stop judgment part 312 further acts to output a sound (such as a beep sound) corresponding to the communication signal from the speaker 308 to the outside and to emit the light from the LED 310. The user can hear the sound from the speaker 308 or visually recognize the light from the LED 310 to understand that the scan mode is stopped and the pixels 102 are put into the exposure states.

Figure 25:
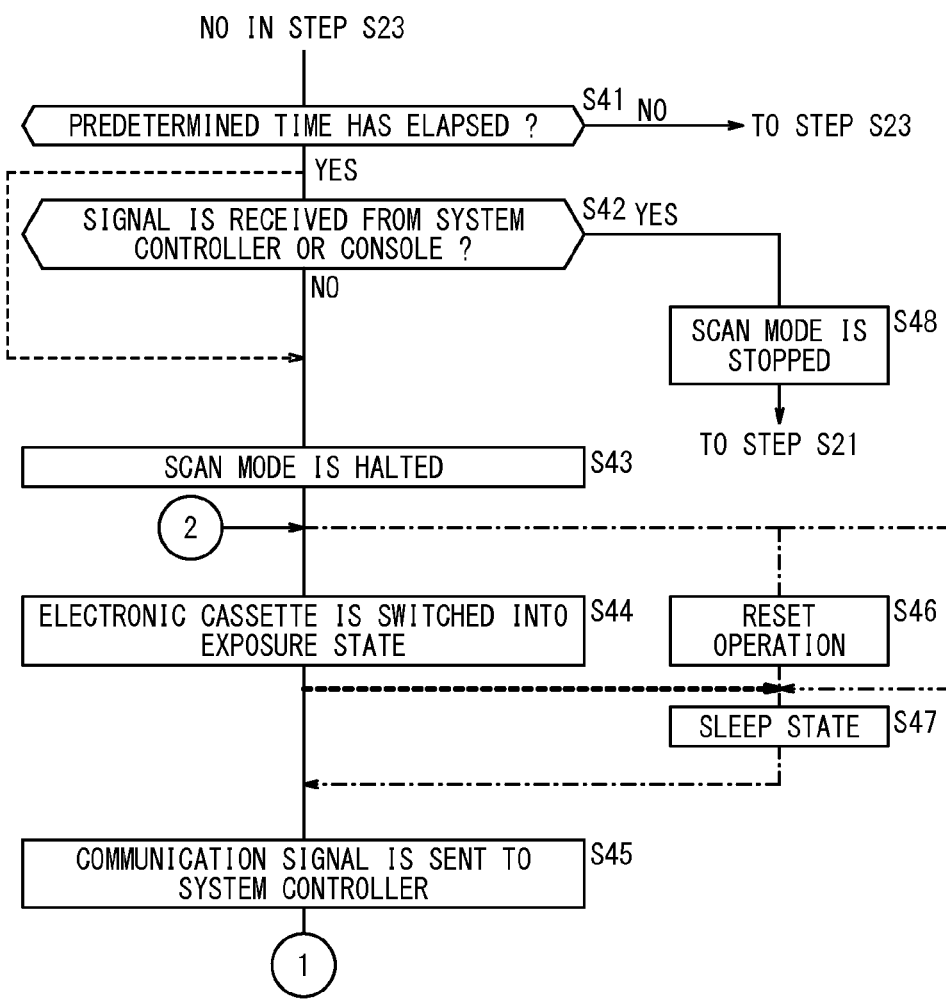
FIG. 25 is a flowchart for illustrating a part of the operation of Modified Example 7.

In a case where the predetermined time has not elapsed in step S41 of FIG. 25 (step S41: NO), the irradiation start judgment part 132 continues to perform the judgment of step S23.

In the above description, steps S41 to S43 are performed by the scan mode stop judgment part 312. Modified Example 7 is not limited to the description, the judgment of step S41 may be performed by the elapsed time judgment part 134. The elapsed time judgment part 134 judges whether the predetermined time has elapsed or not from the start of the emission of the radiation 16 in step S28. Therefore, the elapsed time judgment part 134 may perform this judgment in step S41, and may send the judgment result to the irradiation start judgment part 132 and the scan mode stop judgment part 312.

When the cassette control device 122 receives the signal from the system controller 24 or the console 26 in step S42, the scan mode stop judgment part 312 recognizes that another instruction (re-entered image capturing menu or instruction signal) is sent, and controls the first readout control part 130 to stop the scan mode (step S48). Then, step S21 of FIG. 13 is performed in the cassette control device 122.

Furthermore, after the judgment of step S41, the scan mode stop judgment part 312 may perform step S43 without step S42 as shown by a dashed line in FIG. 25.

In addition, after step S43, steps S46 and S47 to be hereinafter described may be performed instead of the switching to the exposure state (the accumulation state) of step S44 as shown by a dashed-dotted line in FIG. 25.

Thus, after step S43, the scan mode stop judgment part 312 may control the second readout control part 136 to carry out a reset operation (step S46). In this case, the reset operation is performed in the sequential readout mode. It is to be understood that the scan mode stop judgment part 312 may control the first readout control part 130 to carry out a reset operation in the scan mode.

When the sleep state switch judgment part 314 detects the completion of the reset operation, the sleep state switch judgment part 314 acts to stop the electric power supply from the power supply device 128 to the components in the electronic cassette 20, so that the electronic cassette 20 is switched into the sleep state (step S47). Alternatively, after step S43, step S47 may be carried out without the reset operation of step S46 as shown by a dashed-two dotted line in FIG. 25.

Consequently, in step S45 after the operation of step S47, the scan mode stop judgment part 312 acts to send a communication signal, which indicates that the scan mode is stopped and the electronic cassette 20 is switched into the sleep state, from the communication device 126 to the communication unit 214 via wireless communication. Also in this case, the sound is output from the speaker 308 to the outside and the light is emitted from the LED 310. Therefore, the user can hear the sound from the speaker 308 or visually recognize the light from the LED 310 to understand that the scan mode is stopped and the electronic cassette 20 is put into the sleep state.

The switching of the electronic cassette 20 into the sleep state is carried out in order to avoid wasteful electric power consumption before the emission of the radiation 16. Therefore, in the sleep state, power supply to at least the radiation conversion panel 64 and the drive circuit device 106 is stopped, while power supply to the cassette control device 122 and the communication device 126 may be continued. In this case, the electronic cassette 20 and the system controller 24 can send signals to and receive signals from each other also in the sleep state. Furthermore, the electronic cassette 20 can be rapidly switched from the sleep state into the active state based on a signal from the system controller 24.

Figure 26:
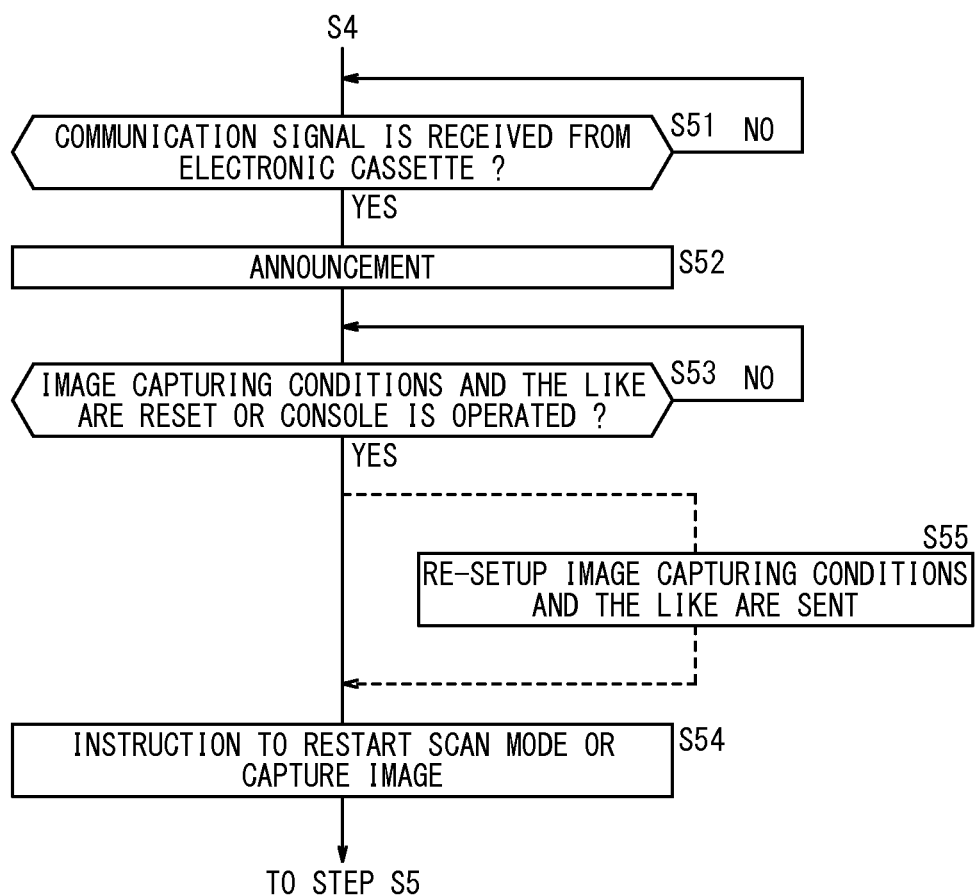
FIG. 26 is a flowchart for illustrating a part of the operation of Modified Example 7.

After step S4 of FIG. 12, step S51 of FIG. 26 is carried out. The control unit 212 of the system controller 24 judges whether or not the communication signal can be received from the electronic cassette 20 through the communication unit 214. When the communication signal can be received (step S51: YES), in step S52, the control unit 212 acts to emit a light from the LED 322 and to output a sound (such as a beep sound) from the speaker 320 to the outside. Furthermore, the control unit 212 sends the communication signal to the console 26. Then, the control unit 202 of the console 26 acts to display the contents of the communication signal as an image (such as a screen-saver display) on the display unit 204, and to output a sound (such as a beep sound) from the speaker 324 to the outside.

Consequently, the user can visually recognize the light emission of the LED 322 and the image on the display unit 204 and can hear the sounds from the speakers 320 and 324 to understand that the scan mode is stopped and that all the pixels 102 are switched into the exposure states or the electronic cassette 20 is switched into the sleep state.

Next, when the user operates the input unit 200 (step S53: YES), the control unit 202 acts to switch the display unit 204 from the screen-saver display to the normal screen, and to send information of the operation to the control unit 212 of the system controller 24.

When the communication signal from the electronic cassette 20 indicates that the scan mode is stopped and all the pixels 102 are switched into the exposure states, the control unit 212 generates, based on the information sent from the control unit 202, an instruction signal for instructing to restart the scan mode or read the electric signals in all the pixels 102 in the sequential scan mode. The control unit 212 sends the generated instruction signal to the electronic cassette 20 through the communication unit 214 via wireless communication (step S54), and then step S5 of FIG. 12 is carried out.

Alternatively, when the communication signal from the electronic cassette 20 indicates that the scan mode is stopped and the electronic cassette 20 is switched into the sleep state, the control unit 212 generates, based on the information sent from the control unit 202, an instruction signal for instructing transition from the sleep state into the active state (startup state) and restart of the scan mode. The control unit 212 sends the generated instruction signal to the electronic cassette 20 through the communication unit 214 via wireless communication (step S54).

When the user operates the input unit 200 to reset the image capturing menu (step S53: YES), as shown by a dashed line in FIG. 26, the control unit 202 sends the image capturing menu reset by the user to the control unit 212. The control unit 212 acts to re-enter the image capturing menu sent from the control unit 202 as a renewed image capturing menu instead of the ongoing image capturing menu that has been sent to the electronic cassette 20. The re-entered image capturing menu is sent to the electronic cassette 20 through the communication unit 214 via wireless communication (step S55). In this case, in addition to image capturing menu, the control unit 212 sends also the instruction signal to the electronic cassette 20 through the communication unit 214 (step S54), and then step S5 of FIG. 12 is carried out.

Figure 27:
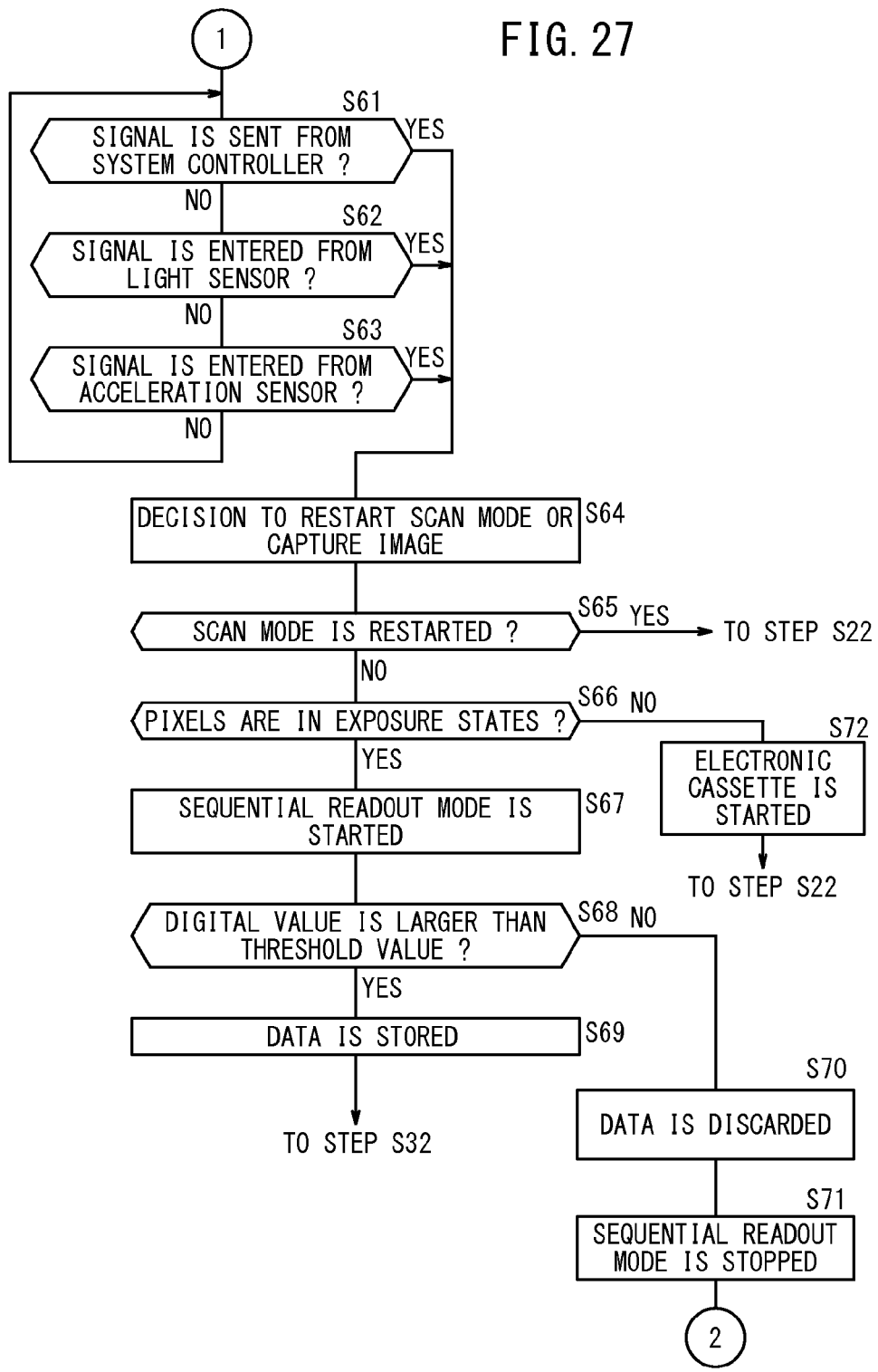
FIG. 27 is a flowchart for illustrating a part of the operation of Modified Example 7.

In step S61 of FIG. 27, the scan mode restart judgment part 316 and/or the image acquirement judgment part 318 sequentially judge whether or not the instruction signal and/or the image capturing menu are sent from the system controller 24 to the communication device 126 (step S61), whether the detection signal corresponding to the illuminating light is entered or not from the light sensor 304 (step S62), and whether the detection signal corresponding to the transfer of the electronic cassette 20 is entered or not from the acceleration sensor 306 (step S63).

In the judgments of steps S61 to S63, when a signal (the image capturing menu, the instruction signal) can be received from the system controller 24 (step S61: YES), when the detection signal is entered from the light sensor 304 (step S62: YES), or when the detection signal is entered from the acceleration sensor 306 (step S63: YES), the scan mode restart judgment part 316 decides to restart the scan mode, and the image acquirement judgment part 318 decides to read the electric signals from all the pixels 102 in the exposure states in the sequential readout mode (step S64).

Then, when the instruction signal includes the instruction to restart the scan mode or the scan mode has to be executed under the new image capturing menu (step S65: YES), the scan mode restart judgment part 316 acts to perform step S22 of FIG. 13, so that the first readout control part 130 acts to restart the scan mode.

In a case where the instruction signal does not include the instruction to restart the scan mode and the new image capturing menu is not received (step S65: NO), and the instruction signal includes the instruction to read the electric signals from all the pixels 102 in the exposure states in the sequential readout mode (step S66: YES), the image acquirement judgment part 318 controls the second readout control part 136 to execute the sequential readout mode in the same manner as steps S29 and S30 of FIG. 13 (step S67).

In a case where the value of the obtained electric signals (digital signal pixel value) becomes larger than the predetermined value (the predetermined threshold value) (step S68: YES), the image acquirement judgment part 318 judges that the radiation 16 is injected from the radiation source 34 through the subject 14 into the electronic cassette 20 in the exposure state and that the electric signals correspond to the radiographic image of the subject 14, and thereby stores the pixel values in the memory 124 (step S69). Thus, the radiographic image of the subject 14 can be reliably acquired without retaking. Thereafter, the cassette control device 122 acts to perform step S32 of FIG. 13.

If the obtained pixel values do not reach the predetermined value (step S68: NO), the radiation 16 is judged to be not emitted during the exposure state. The pixel values are discarded (the electric signals with the pixel values are discharged to the ground) (step S70) to stop the sequential readout mode (step S71). Then, the cassette control device 122 acts to perform step S44, S46, or S47 of FIG. 25.

When the instruction signal includes not the instruction to read the electric signal from all the pixels 102 in the exposure states in the sequential readout mode but the instruction to startup the electronic cassette 20 (step S66: NO), the scan mode restart judgment part 316 acts to restart the electric power supply from the power supply device 128 to each component in the electronic cassette 20, so that the electronic cassette 20 is switched from the sleep state into the active state (step S72). Then, the cassette control device 122 acts to perform step S22 of FIG. 13, whereby the scan mode is restarted.

In Modified Example 7, as described above, the scan mode is stopped when the electric signal values do not reach the threshold value even after the predetermined time has elapsed from the start of the scan mode. Therefore, the wasteful electric power consumption in the scan mode before the emission of the radiation 16 can be reduced. The scan mode is stopped even when the instruction signal or the image capturing menu is not received from the system controller 24. Therefore, the electric power consumption before the emission of the radiation 16 can be efficiently reduced. Thus, the above steps of Modified Example 7 can be performed to reduce the electric power consumption before the emission of the radiation 16 also in the above embodiment and Modified Examples 1 to 6.

After the stop of the scan mode, all the pixels 102 may be switched into the exposure states (the accumulation states). When the radiation 16 is emitted to the subject 14 and the electronic cassette 20 in the exposure state, the electric charges (electric signals) corresponding to the radiographic image of the subject 14 can be reliably stored in the pixels 102.

After the stop of the scan mode, the electronic cassette 20 may be switched into the sleep state after the reset operation or immediately. In this case, the electric power consumption before the emission of the radiation 16 can be further reduced.

In Modified Example 7, the speaker 308 outputs a sound and the LED 310 emits a light depending on the communication signal indicating the stop of the scan mode or the switch into the exposure state or the sleep state. The communication signal is sent from the electronic cassette 20 to the system controller 24. Then, in the system controller 24, the speaker 320 outputs a sound and the LED 322 emits a light depending on the received communication signal. Furthermore, in the console 26, the display unit 204 displays an image and the speaker 324 outputs a sound depending on the communication signal from the system controller 24. Thus, the user can hear the sounds from the speakers 308, 320, 324 and can visually recognize the image on the display unit 204 and the lights from the LEDs 310, 322 to easily understand the stop of the scan mode and the like.

In a case where the image capturing menu is re-entered by the control unit 212 of the system controller 24 or in a case where the user operates the input unit 200 to generate the instruction signal in the control unit 212, the system controller 24 sends the image capturing menu or the instruction signal to the electronic cassette 20. In a case where the illuminating light is emitted from the irradiation field lamp 300 onto the image capturing surface 42 in the preparation for the image capturing process, the light sensor 304 detects the illuminating light and outputs the detection signal to the cassette control device 122. Furthermore, in a case where the user transfers the electronic cassette 20 in the preparation for the image capturing process, the acceleration sensor 306 detects the acceleration in the movement of the electronic cassette 20 and outputs the detection signal to the cassette control device 122.

Thus, based on the entered image capturing menu, instruction signal, and detection signals, the scan mode restart judgment part 316 and the image acquirement judgment part 318 can efficiently and reliably perform the restart of the scan mode, the reading of the electric signals from the pixels 102 in the exposure states in the sequential readout mode, the switch of the electronic cassette 20 from the sleep state into the active state, and the judgment associated with the restart of the scan mode.

The electric signals in all the pixels 102 in the exposure states are read out in the sequential readout mode before the restart of the scan mode. Therefore, in a case where the radiation 16 is emitted to the subject 14 and the electronic cassette 20 during the period of the exposure state, the electric signals corresponding to the radiographic image of the subject 14 can be reliably read out. Since the electric signals corresponding to the radiographic image are read out in this manner, the user can avoid retaking the subject 14.

In this case, the image acquirement judgment part 318 judges whether or not the read electric signals reach the predetermined value. Therefore, the radiographic image can be efficiently acquired. In a case where the electric signals do not reach the predetermined value, the electric signals may be discarded to the ground. Therefore, the memory 124 can be prevented from storing unnecessary data by mistake.

In Modified Example 7, when the radiation 16 cannot be detected even after the predetermined time has elapsed from the switch into the exposure state in step S44, as shown by a thick dashed line in FIG. 25, step S47 may be carried out to switch the electronic cassette 20 into the sleep state. Also in this case, the electric power consumption can be reduced before the emission of the radiation 16.

In Modified Example 7, before the scan mode performed by the first readout control part 130, the second readout control part 136 may act to execute the reset operation or an offset signal readout mode for reading the electric signals stored in the pixels 102 as image correction offset signals (non-exposure signals) sequentially row by row. Also in this case, the electric charges can be reliably removed from the pixels 102 before the emission of the radiation 16, whereby the radiographic image can be obtained with high quality. In addition, the quality of the radiographic image can be further improved by performing an image correction processing using the offset signals.

Modified Example 8

Figure 28:
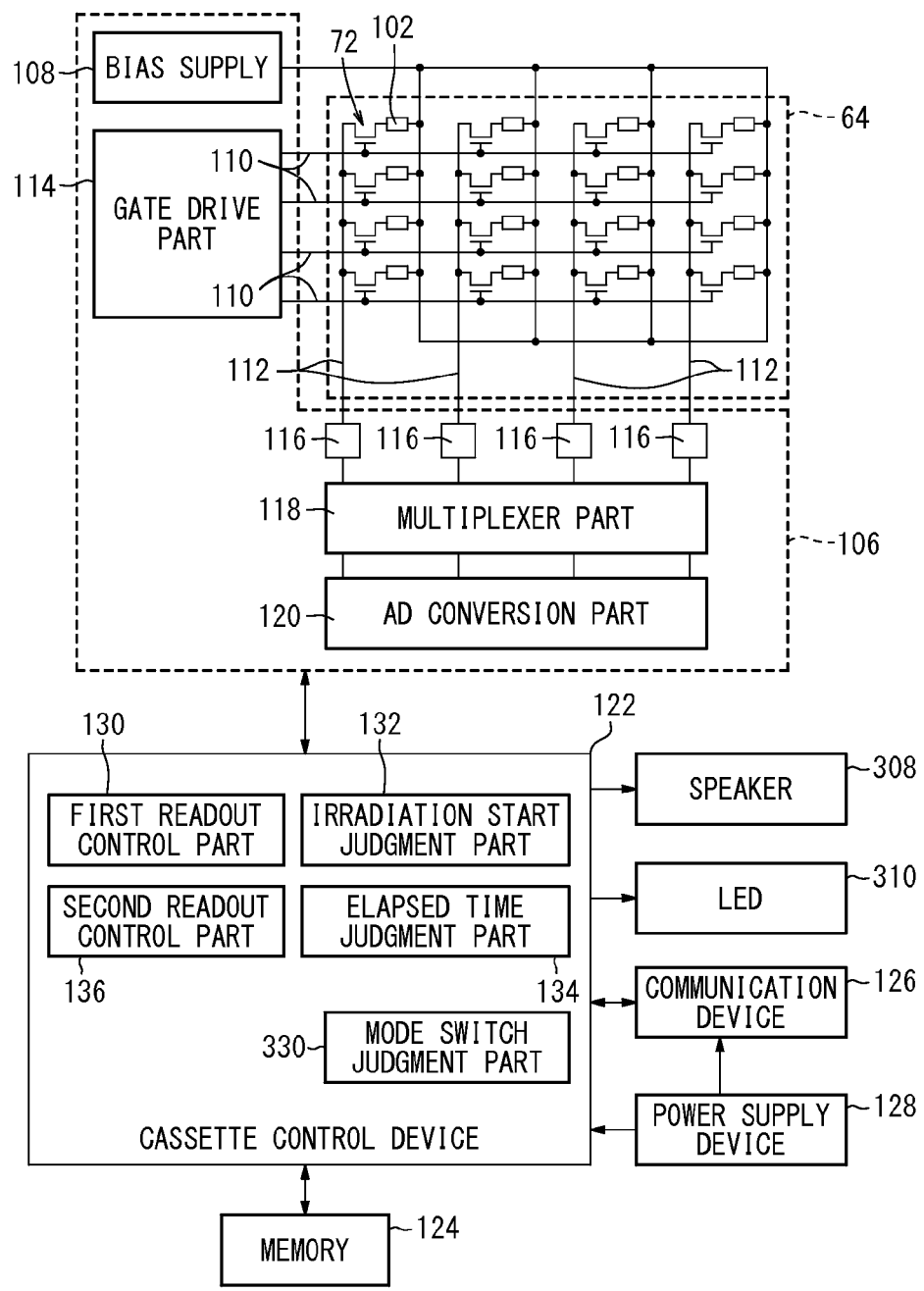
FIG. 28 is a schematic structural view of the electric structure of an electronic cassette according to Modified Example 8.

FIG. 28 is a schematic structural view of the electric structure of an electronic cassette 20 according to Modified Example 8. The control unit 54 has the cassette control device 122, the memory 124, the communication device 126, and the power supply device 128, and further has the speaker (the first announcement device, the sound output device) 308 for outputting sound corresponding to signals from the cassette control device 122 to the outside, and the LED (the first announcement device, the light output device) 310 for emitting a light depending on signals from the cassette control device 122. The speaker 308 and the LED 310 are disposed in the casing 68 of the control unit 54.

The cassette control device 122 has the first readout control part 130, the irradiation start judgment part 132, the elapsed time judgment part 134, and the second readout control part 136, and further has a mode switch judgment part 330. The mode switch judgment part 330 judges whether the readout mode for reading the electric charges stored in the pixels 102 is switched into the scan mode or not. Specifically, in a case where the first readout control part 130 acts to start the scan mode, the mode switch judgment part 330 judges that the electronic cassette 20 is switched into the first readout mode, and sends a scan mode switch signal (communication signal) including the judgment result to the speaker 308, the LED 310, and the communication device 126. The speaker 308 outputs a sound (such as a beep sound) corresponding to the scan mode switch signal to the outside, the LED 310 emits a light corresponding to the scan mode switch signal, and the communication device 126 sends the scan mode switch signal to the system controller 24 via wireless communication.

As described above, the readout mode may be the scan mode or the sequential readout mode. Before the emission of the radiation 16, not only the scan mode but also the sequential readout mode may be performed in some cases.

In the electronic cassette 20, for example, the scan mode may be started when the image capturing menu is received from the system controller 24. Alternatively, the sequential readout mode is executed before the image capturing menu is received, and then the sequential readout mode may be switched into the scan mode when the image capturing menu is received. The sequential readout mode executed before the scan mode may be the reset operation or the offset signal readout mode for reading the electric signals stored in the pixels 102 as image correction offset signals (non-exposure signals) sequentially row by row.

Thus, to handle these cases, the mode switch judgment part 330 detects the start of the scan mode executed by the first readout control part 130 for judging that the electronic cassette 20 is switched into the scan mode (from the sequential readout mode).

Figure 29:
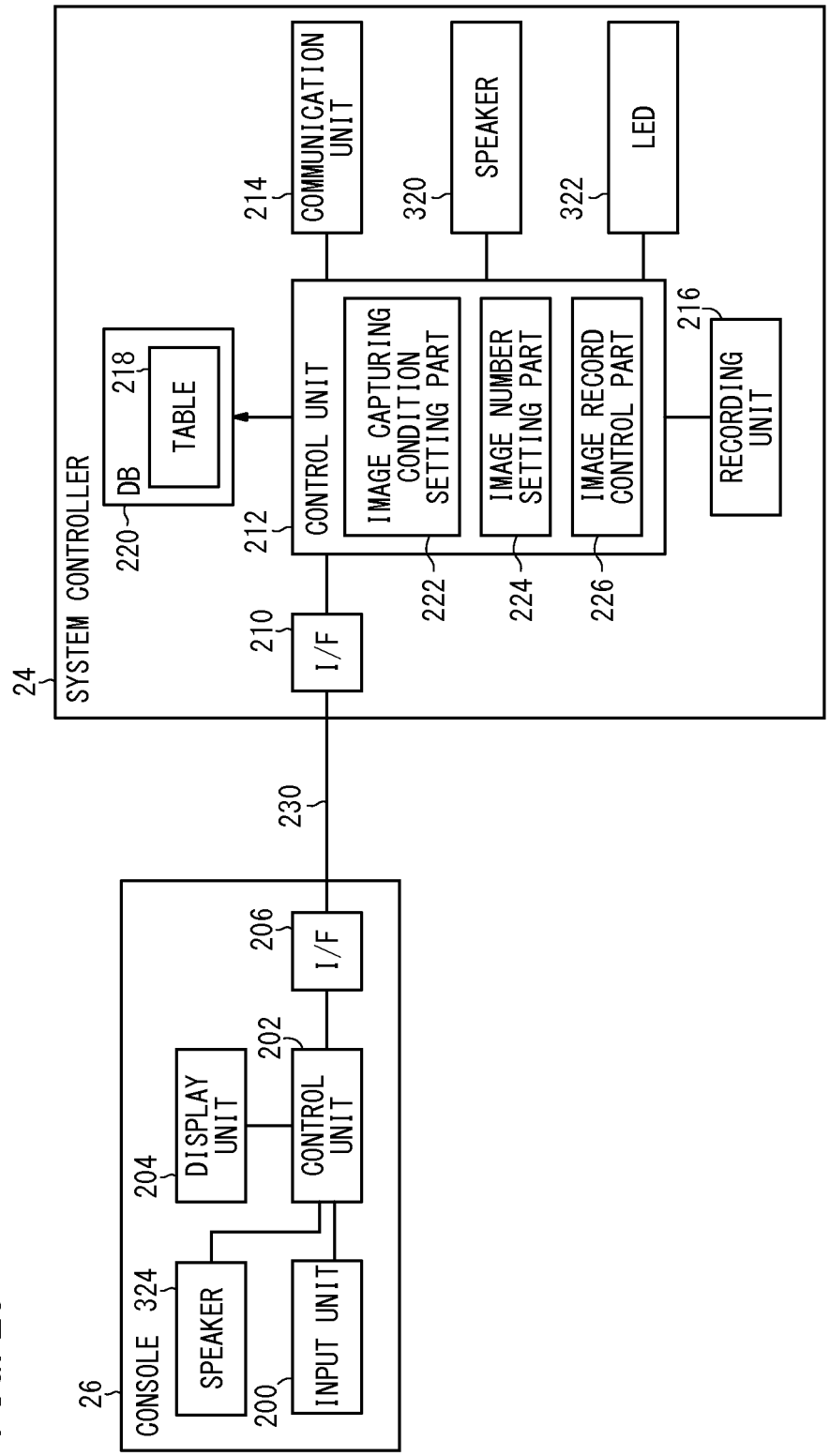
FIG. 29 is a schematic structural view of the electric structures of a system controller and a console according to Modified Example 8.

FIG. 29 is a schematic structural view of the electric structures of the system controller 24 and the console 26 of Modified Example 8.

The console 26 has the input unit 200, the control unit 202, the display unit 204, and the interface I/F 206, and further has the speaker (the second announcement device, the sound output device) 324 for outputting sound corresponding to signals from the control unit 202.

The system controller 24 has the interface I/F 210, the control unit 212, the communication unit 214, the recording unit 216, and the database 220 containing the table 218, and further has the speaker (the second announcement device, the sound output device) 320 for outputting sound corresponding to signals from the control unit 212 to the outside and the LED (the second announcement device, the light output device) 322 for emitting a light depending on signals from the control unit 212.

When the communication unit 214 receives the scan mode switch signal from the electronic cassette 20, the control unit 212 sends the scan mode switch signal to the control unit 202 of the console 26, the speaker 320, and the LED 322. The speaker 320 outputs a sound (such as a beep sound) corresponding to the scan mode switch signal to the outside, and the LED 322 emits a light corresponding to the scan mode switch signal. The control unit 202 acts to display an image corresponding to the scan mode switch signal from the control unit 212 on the display unit 204, and to output a sound (such as a beep sound) corresponding to the scan mode switch signal from the speaker 324 to the outside.

Figure 30:
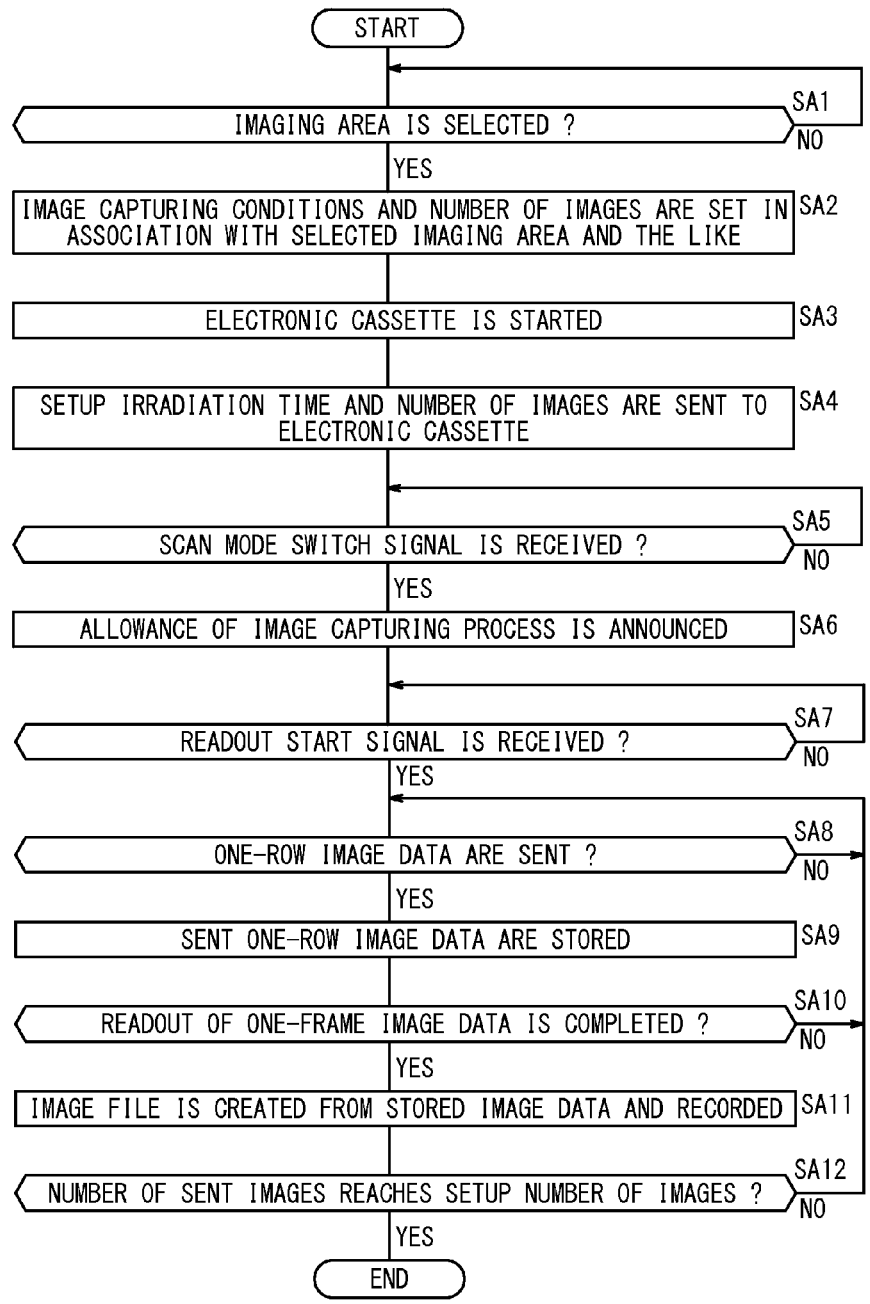
FIG. 30 is a flowchart of the operation of the system controller and the console in a radiographic image capturing system according to Modified Example 8.
Figure 31:
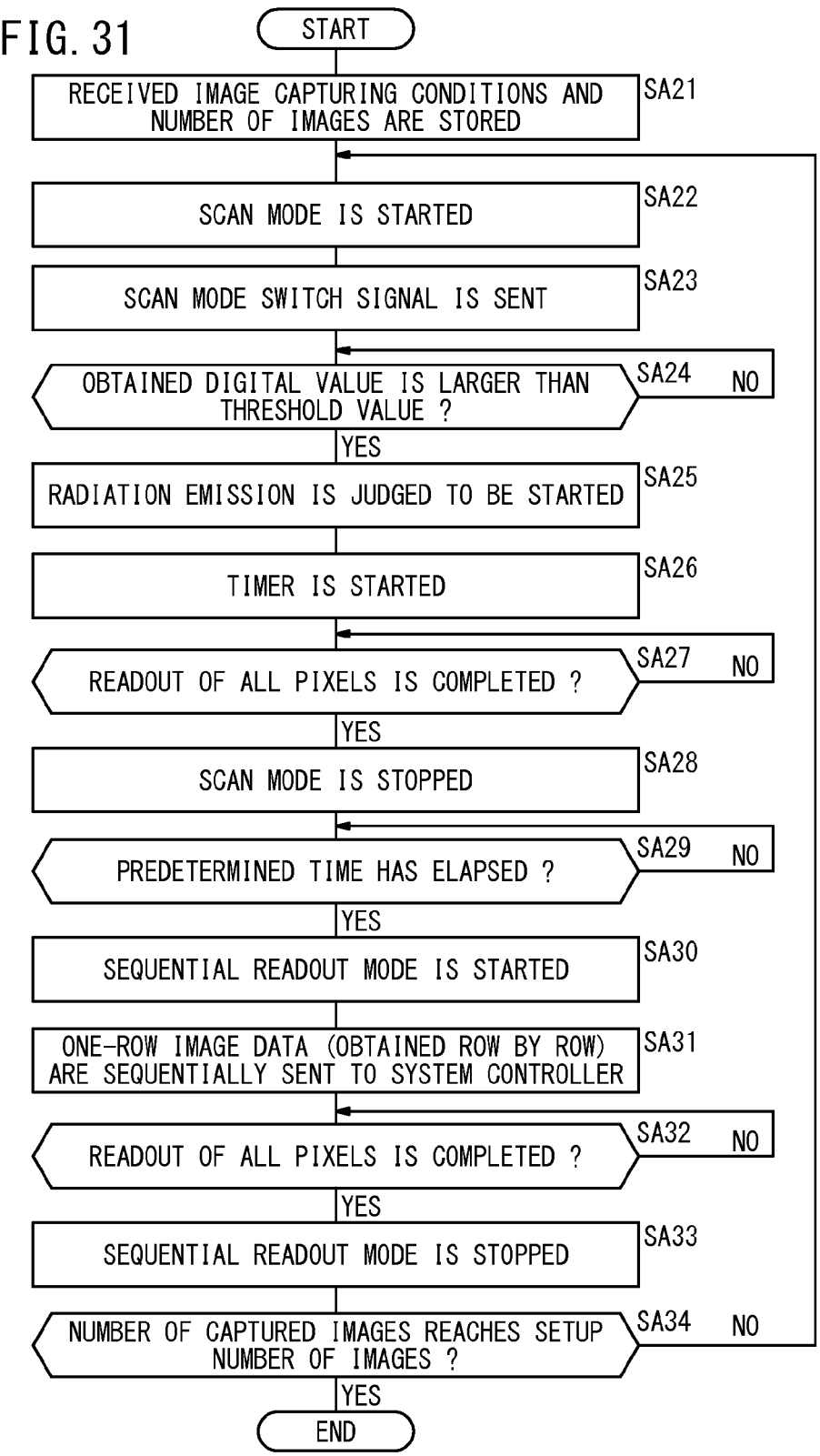
FIG. 31 is a flowchart of the operation of a cassette control device according to Modified Example 8.

Operations of the radiographic image capturing system 10 of Modified Example 8 will be described below with reference to the flowcharts of FIGS. 30 and 31. FIG. 30 is a flowchart of the operation of the system controller 24 and the console 26, and FIG. 31 is a flowchart of the operation of the cassette control device 122 in the radiographic image capturing system 10. The operation of the system controller 24 and the console 26 will be described first, and then the operation of the cassette control device 122 will be described below.

In the console 26, the control unit 202 judges whether or not the user operates the input unit 200 to select the imaging area, the diagnostic site, and the number of images to be captured (step SA1). In this step, the control unit 202 acts to display, on the display unit 204, an image (image capturing menu), which is used by the user for selecting the imaging area, the diagnostic site, and the number of images. The user can select, while watching the displayed image, the imaging area and the diagnostic site of a patient that undergoes the radiographic image capturing process.

In a case where the imaging area, the diagnostic site, and the number of images are judged to be not selected in step SA1, the radiographic image capturing system 10 remains in step SA1 until they are selected.

In a case where the imaging area, the diagnostic site, and the number of images are judged to be selected by the user in step SA1, the image capturing condition setting part 222 reads the image capturing conditions corresponding to the imaging area and the diagnostic site selected by the user from the table 218, and sets the read image capturing conditions as conditions for the following radiographic image capturing process, and the image number setting part 224 sets the number of images selected by the user (step SA2). Specifically, when the user operates the input unit 200 to select the imaging area and the like, the control unit 202 outputs (the image capturing menu containing) the selected imaging area and the like to the control unit 212 in the system controller 24 through the interfaces I/F 206, 210. Then, in the control unit 212, the image capturing condition setting part 222 sets the image capturing conditions corresponding to the imaging area and the diagnostic site sent from the console 26, and sets the number of images sent from the console 26. The system controller 24 may output the setup image capturing conditions to the control unit 202 through the interfaces I/F 210, 206, and the control unit 202 may act to display the setup image capturing conditions and the setup number of images on the display unit 204. In this case, the user can visually recognize the contents of the setup image capturing conditions.

To emit the radiation 16 from the radiation source 34 under the setup image capturing conditions, the user operates the input device in the radiation control unit 36, so that the radiation control unit 36 sets image capturing conditions equal to the conditions set in the system controller 24. For example, the radiation apparatus 18 may have a table equal to the table 218, and the user may select the imaging area and the diagnostic site from the table to set the equal image capturing conditions. Alternatively, the user may enter the irradiation time, the tube voltage, the tube current, and the like directly.

After the image capturing conditions are set, the control unit 212 sends a startup signal to the electronic cassette 20 through the communication unit 214, whereby the electronic cassette 20 is started up (step SA3). The electronic cassette 20 is in the sleep state until the startup signal is sent. The sleep state is such a state that electric power is not supplied to at least the radiation conversion panel 64 and the drive circuit device 106. In a case where the electronic cassette 20 is started up, the electronic cassette 20 acts to execute the scan mode, and the mode switch judgment part 330 judges the execution of the scan mode and generates a scan mode switch signal including the judgment result. After the start up, the electronic cassette 20 may act to perform the reset operation before the scan mode.

The image capturing condition setting part 222 and the image number setting part 224 send the setup irradiation time and the setup number of images to the electronic cassette 20 through the communication unit 214 (step SA4).

The control unit 212 judges whether or not the communication unit 214 receives the scan mode switch signal from the electronic cassette 20 (step SA5).

If the scan mode switch signal is received in step SA5, the control unit 212 acts to output the sound (the beep sound) for indicating the scan mode switch signal from the speaker 320 to the outside and to emit the light from the LED 322. Furthermore, the control unit 212 sends the scan mode switch signal to the control unit 202 of the console 26. The control unit 202 acts to display an image corresponding to the received scan mode switch signal on the display unit 204 and to output the sound (the beep sound) for indicating the scan mode switch signal from the speaker 324 to the outside (step SA6). The user can understand that the scan mode is started and the electronic cassette 20 is switched into a state, in which the radiation 16 can be emitted (the image capturing process is allowed) by at least one of hearing the sound from the speaker 320 or 324 and visually recognizing the light from the LED 322 or the image on the display unit 204. If the control unit 212 judges that the scan mode switch signal is not received in step SA5, the radiographic image capturing system 10 remains in step SA5 until it is received.

The control unit 212 judges whether a readout start signal from the electronic cassette 20 is received or not (step SA7). The readout start signal includes an instruction to start the reading of the electric charges stored in the pixels 102 in the sequential readout mode.

IF the readout start signal is judged to be not received in step SA7, the radiographic image capturing system 10 remains in step SA7 until it is received. If the readout start signal is judged to be received, the image record control part 226 judges whether the one-row image data are sent or not (step SA8). The one-row image data are sequentially read out row by row, and the electronic cassette 20 sequentially outputs the one-row image data to the system controller 24. Thus, the one-row image data are sequentially sent to the system controller 24.

When the one-row image data are judged to be sent in step SA8, the image record control part 226 acts to store the sent one-row image data in a buffer memory (not shown) in the control unit 212 (step SA9).

The image record control part 226 judges whether the readout of the one-frame image data is completed or not (step SA10). If the readout of the one-frame image data is completed, the electronic cassette 20 outputs a readout end signal to the system controller 24. When the image record control part 226 receives the readout end signal, the readout of the one-frame image data is judged to be completed.

If the reading of the one-frame image data is judged to be not completed in step SA10, the radiographic image capturing system 10 is returned to step SA8, and the above steps are repeated.

If the readout of the one-frame image data is judged to be completed in step SA10, an image file is created from the one-frame image data stored in the buffer memory, and is recorded in the recording unit 216 (step SA11).

The image record control part 226 judges whether or not the sent image data satisfy the condition of the number of images set in step SA2 (step SA12). In a case where it is judged that the sent image data are not sufficient to meet the condition of the setup number of images in step SA12, the radiographic image capturing system 10 is returned to step SA8. If the sent image data are judged to be sufficient to meet the condition of the setup number of images, the process is completed.

The operation of the electronic cassette 20 will be described below with reference to the flowchart of FIG. 31. When the startup signal is sent from the system controller 24, the electronic cassette 20 is started up, and the cassette control device 122 acts to store the irradiation time and the number of images sent from the system controller 24 in the memory 124 (step SA21).

Then, the first readout control part 130 in the cassette control device 122 acts to start the execution of the scan mode (step SA22). Consequently, the mode switch judgment part 330 judges that the scan mode is started, and sends the scan mode switch signal including the judgment result to the communication device 126, the speaker 308, and the LED 310. The communication device 126 sends the scan mode switch signal to the system controller 24 via wireless communication. The speaker 308 outputs the sound (the beep sound) corresponding to the scan mode switch signal to the outside, and the LED 310 emits the light corresponding to the scan mode switch signal (step SA23). In the same manner as step SA6 described above, the user can understand that the scan mode is started and the electronic cassette 20 is switched into a state, in which the radiation 16 can be emitted (the image capturing process is allowed) by at least one of hearing the sound from the speaker 308 and visually recognizing the light from the LED 310.

When the scan mode is started, the first readout control part 130 outputs the drive signals c to the gate drive circuits 150. When the drive signal c is received, each gate drive circuit 150 selects the gate lines 110 connected therewith in the 0th to final rows sequentially, and outputs the gate signals to the selected gate lines 110. Thus, each gate drive circuit 150 reads the electric charges stored in the pixels 102 in the 0th to final rows in the associated readout region sequentially row by row. Consequently, the procedure of reading the electric charges stored in the pixels 102 sequentially row by row in the associated readout region is performed in a plurality of the gate drive circuits 150 simultaneously. The read electric charges are summed up in each column.

Specifically, the electric charges stored in the pixels 102 in the 0th rows in the associated readout regions of the gate drive circuits 150 are simultaneously read out, summed up in each column, and output to the charge amplifier 116 in each column. Then, the electric charges stored in the pixels 102 in the first rows in the associated readout regions of the gate drive circuits 150 are simultaneously read out, summed up in each column, and output to the charge amplifier 116 in each column. The steps are repeated also in the second to 239th rows.

The one-row electric charges, which are read out sequentially row by row and summed up in each column, are send to the charge amplifiers 116, transferred through the multiplexer part 118 and the AD conversion part 120, and stored as the digital electric signals in the memory 124. Thus, the summed one-row image data are sequentially stored in the memory 124. When the electric charges stored in the pixels 102 in the 239th rows are read out, the gate drive circuits 150 send the end signals d to the cassette control device 122.

The first readout control part 130 controls the switches 160 of the charge amplifiers 116 in the off states in the scan mode. Thus, the charge amplifiers 116 can output the sent electric charge signals as the voltage signals. After the start up, the cassette control device 122 may act to perform the reset operation before the start of the scan mode. The first readout control part 130 may start the scan mode when a predetermined time (e.g. 10 seconds) has elapsed after the start up.

The irradiation start judgment part 132 judges whether or not the digital electric signals stored in the memory 124 are larger than the threshold value (step SA24). If the radiation 16 is emitted from the radiation source 34 to the electronic cassette 20, the digital electric signals stored in the memory 124 become larger than the threshold value. Thus, whether the radiation 16 is emitted or not is detected based on whether the digital electric signals are larger or not than the threshold value. In a case where the electric signals are judged to be not larger than the threshold value in step SA24, the electronic cassette 20 remains in step SA24 until the signal is judged to be larger than the threshold value. When the end signals d1 to d12 are sent from the gate drive circuits 150 to the cassette control device 122 (the one-frame electric charges are read out), the first readout control part 130 outputs the drive signals c1 to c12 to the gate drive circuits 150 again. One cycle of the scan mode include the steps from the input of the drive signals c1 to c12 into the gate drive circuits 150 to the output of the end signals d1 to d12. The end signals d1 to d12 are sent from the gate drive circuits 150 at the same timing.

If the digital electric signal stored in the memory 124 is judged to be larger than the threshold value in step SA24, the emission of the radiation 16 from the radiation source 34 is judged to be started by the irradiation start judgment part 132 (step SA25).

Thus, the user confirms at least one of the beep sound from one of the speakers 308, 320, 324, the light from one of the LEDs 310, 322, and the image on the display unit 204, and thereby understands that the scan mode is started (the image capturing process is allowed). When the radiation switch 38 is pressed halfway by the user in the scan mode, the radiation control unit 36 makes preparations to emit the radiation 16. Then, when the radiation switch 38 is pressed completely by the user, the radiation control unit 36 acts to emit the radiation 16 from the radiation source 34 for the predetermined time. Since the radiation control unit 36 acts to emit the radiation 16 under the image capturing conditions corresponding to the imaging area and the diagnostic site selected by the user as described above, the predetermined time is the irradiation time corresponding to the imaging area and the diagnostic site selected by the user. In the case of capturing a plurality of images, the user operates the radiation switch 38 at a certain time interval to apply the radiation 16 from the radiation source 34.

If the emission of the radiation 16 is judged to be started in step SA25, the cassette control device 122 acts to start a timer (step SA26), and the first readout control part 130 judges whether the electric charges stored in all the pixels 102 are read out completely or not (whether the one-frame electric charges are read out completely or not) in the scan mode (step SA27). Thus, after the emission of the radiation 16 is judged to be started, the first readout control part 130 judges whether the one cycle of the scan mode is completed or not. Specifically, after the emission of the radiation 16 is judged to be started, the first readout control part 130 judges whether or not the end signals d1 to d12 are sent from the gate drive circuits 150.

If the electric charges stored in all the pixels 102 are judged to be not completely read out in step SA27, the electronic cassette 20 remains in step SA27 until the electric charges are judged to be completely read out. If the electric charges stored in all the pixels 102 are judged to be completely read out, the radiographic image capturing process is carried out, and thus the radiation 16 is applied, and the electric charges stored in the pixels 102 by the radiation 16 exposure are read out. Specifically, the first readout control part 130 stops the scan mode to start the exposure, and the electronic cassette 20 is switched to the exposure state (step SA28). After this step, the first readout control part 130 does not output the drive signals c1 to c12 to the gate drive circuits 150 when the end signals d1 to d12 are sent to the cassette control device 122. At the same time as the stop of the scan mode, the first readout control part 130 acts to turn on the switches 160 of the charge amplifiers 116. Consequently, unnecessary electric charges stored in the capacitors 158 can be discarded to improve the radiographic image quality.

After the scan mode is stopped in step SA28, the elapsed time judgment part 134 judges whether the predetermined time has elapsed or not from the judgment of the emission start of the radiation 16 (step SA29). If the elapsed time judgment part 134 judges that the predetermined time has not elapsed from the start of the emission of the radiation 16 in step SA29, the electronic cassette 20 remains in step SA29 until the predetermined time elapses. The predetermined time is the irradiation time corresponding to the imaging area and diagnosis purpose selected by the user, and therefore the elapsed time judgment part 134 judges whether the emission of the radiation 16 is completed or not in step SA29. Thus, after the scan mode is stopped, the exposure for the radiographic image capturing process is continued until the predetermined time elapses.

In a case where the predetermined time is judged to have elapsed from the start of the emission of the radiation 16 in step SA29, the exposure is stopped, and the second readout control part 136 acts to start the sequential readout mode for reading the electric charges generated by the exposure with the radiation 16 (step SA30). In this step, the second readout control part 136 outputs the readout start signal to the system controller 24 through the communication device 126 before, at, or after the start of the sequential readout mode. Consequently, the system controller 24 detects that the radiographic image data will be sent from the electronic cassette 20, and makes preparations to receive the image data.

In the sequential readout mode, the second readout control part 136 outputs the drive signal a1 to the first gate drive circuit 150. When the drive signal a1 is entered, the first gate drive circuit 150 selects the associated gate lines 110 in the 0th to final rows sequentially, outputs the gate signals to the selected gate lines 110, and reads the electric charges stored in the pixels 102 in the 0th to final rows in the associated region sequentially row by row. Thus, the first gate drive circuit 150 reads the electric charges stored in the pixels 102 in the 0th to 239th rows in the associated region sequentially row by row. When the 239th row is selected, the first gate drive circuit 150 sends the end signal b1 to the cassette control device 122.

When the end signal b1 is entered, the second readout control part 136 sends the drive signal a2 to the second gate drive circuit 150. Such a procedure is repeated in the first to twelfth gate drive circuits 150. Consequently, the electric charges stored in the pixels 102 in the 0th to 2879th rows on the radiation conversion panel 64 are read out sequentially row by row. The electric charges, read out sequentially row by row, are input into the charge amplifier 116 in each column, transferred through the multiplexer part 118 and the AD conversion part 120, and stored as the digital electric signals in the memory 124. Thus, the one-row image data, obtained row by row, are sequentially stored in the memory 124.

The cassette control device 122 controls the switches 160 of the charge amplifiers 116 in the off states during the sequential readout mode. Thus, the charge amplifiers 116 can output the sent electric charge signals as voltage signals.

After the start of the sequential readout mode, the cassette control device 122 starts to sequentially send the one-row image data (obtained row by row) to the system controller 24 (step SA31). Thus, the one-row image data are stored in the memory 124, and sent to the system controller 24 through the communication device 126.

The second readout control part 136 judges whether the electric charges stored in all the pixels 102 are read out completely or not (whether the one-frame electric charges are read out completely or not) in the sequential readout mode (step SA32). Thus, the second readout control part 136 judges whether the one cycle of the sequential readout mode is completed or not. Specifically, the second readout control part 136 judges whether or not the end signal b12 is sent from the twelfth gate drive circuit 150.

If the electric charges stored in all the pixels 102 are judged to be not completely read out in step SA32, the electronic cassette 20 remains in step SA32 until the electric charges are judged to be completely read out. If the electric charges stored in all the pixels 102 are judged to be completely read out, the second readout control part 136 stops the sequential readout mode (step SA33). In this step, the second readout control part 136 outputs the readout end signal to the system controller 24 through the communication device 126.

The cassette control device 122 judges whether or not the number of the captured images reaches the setup number of images stored (set by the user) in step SA21, thus whether or not the performed exposure and sequential readout procedures satisfy the condition of the setup number of images stored in step SA34 (step SA34). In a case where it is judged that the number of the captured images does not reach the setup number of images in step SA34, the electronic cassette 20 is returned to step SA22, and the above steps are repeated. In a case where it is judged that the number of the captured images reaches the setup number of images, the process is completed and stopped.

In Modified Example 8, the mode switch judgment part 330 acts to judge the start of the scan mode and to announce the judgment result to the outside from the speakers 308, 320, 324, the LEDs 310, 322, and the display unit 204. Therefore, the user can receive the information of the start of the scan mode (the information of the image capturing allowance including the suitable timing of the emission of the radiation 16). Thus, after the announcement, the user can operate the radiation switch 38 to start the emission of the radiation 16 to the subject 14, whereby the radiographic image can be obtained with high quality. Since the radiation 16 can be emitted at the suitable timing, the user can avoid retaking of the image. Consequently, in Modified Example 8, the radiation 16 can be emitted at the suitable timing without synchronizing the image capturing timings, so that the radiographic image can be formed with a lowered noise content at low cost.

In Modified Example 8, before the scan mode performed by the first readout control part 130, the second readout control part 136 may act to execute the reset operation or the offset signal readout mode for reading the electric signals stored in the pixels 102 as image correction offset signals (non-exposure signals) sequentially row by row. Also in this case, the electric charges can be reliably removed from the pixels 102 before the emission of the radiation 16, whereby the radiographic image can be obtained with high quality. In addition, the quality of the radiographic image can be further improved by performing the image correction processing using the offset signals.

In Modified Example 8, the sound, light, image, and the like are used as described above, whereby the user can receive, through the eye or ear, the information of the scan mode start (the image capturing allowance). Therefore, for example, a speaker or a display device may be connected to a wireless access point, which can be connected to the electronic cassette 20 via wireless communication. In this case, when the wireless access point receives the scan mode switch signal, the speaker or the display device performs a predetermined announcement processing (e.g. of outputting a beep sound or an image capturing allowance screen). It is to be understood that Modified Examples 1 to 7 can be modified as Modified Example 8.

Modified Example 9

In Modified Example 9, as shown in FIGS. 32 to 35, in a case where an imaging area (imaging region) 352, 356 of the subject 14, included in the image capturing menu, is smaller than the plane area of the radiation conversion panel 64, the reading of the electric signals and the judgment of the emission start of the radiation 16 are performed only in the pixels 102 corresponding to the imaging area 352, 356, to reduce the electric power consumption in the reading and the judgment.

First, an example of FIG. 32 will be described below. As described above, the gate drive circuits 150 and the multiplexers 152 (see FIG. 7) each have predetermined readout subject pixels 102 (a predetermined associated readout region). Thus, with respect to all the pixels 102 on the radiation conversion panel 64, one gate drive circuit 150 and one multiplexer 152 have an associated pixel region 350 containing a plurality of the pixels 102 (in 240 rows×256 columns) and read the electric signals from the pixels 102 in the associated pixel region 350. Thus, the radiation conversion panel 64 is divided into the pixel regions 350 each containing a plurality of the pixels 102, and each combination of the gate drive circuit 150 and the multiplexer 152 is responsible for one pixel region 350.

Figure 32:
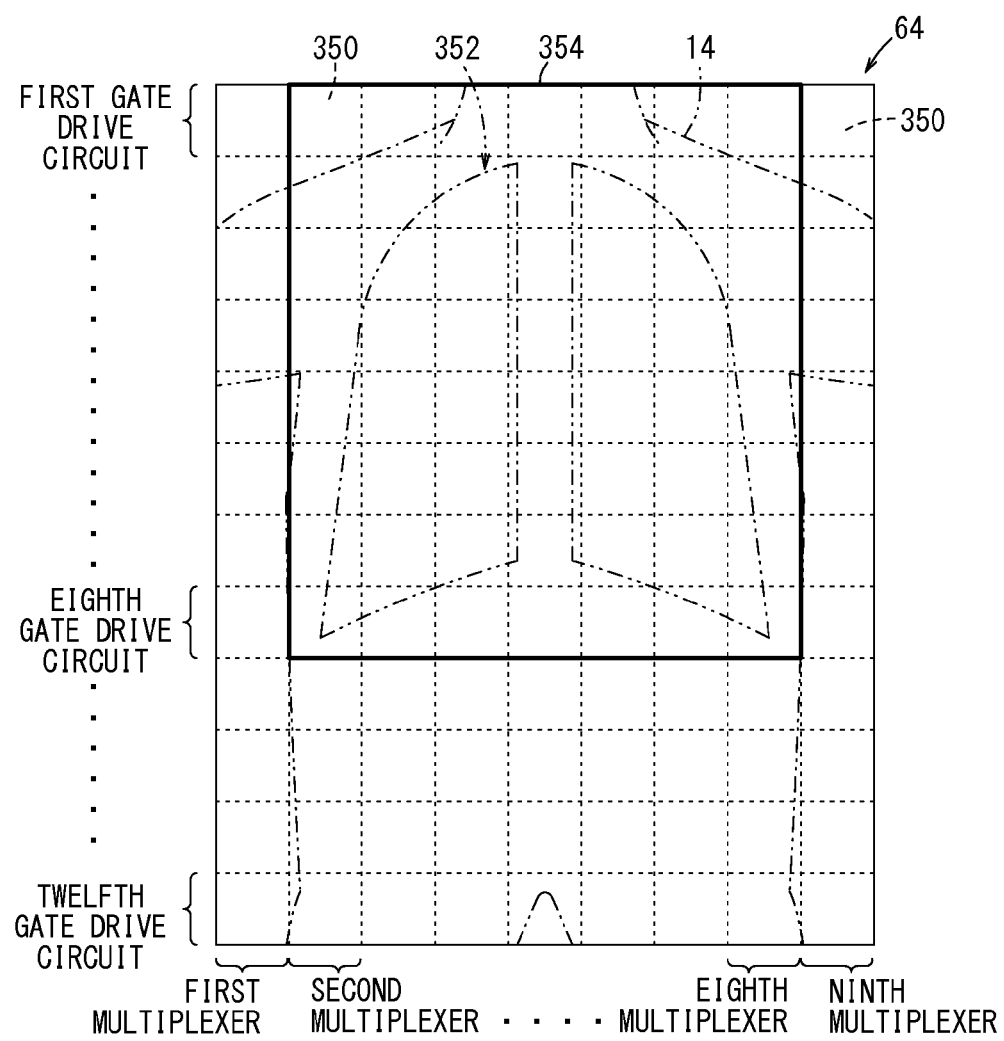
FIG. 32 is a schematic explanatory view of a radiation conversion panel according to Modified Example 9.

In the case of FIG. 32, the user operates the input unit 200 to select the chest of the subject 14 as the imaging area 352, and the control unit 212 of the system controller 24 (see FIG. 10) registers (sets) the image capturing menu corresponding to the imaging area 352 and sends the setup image capturing menu to the electronic cassette 20 (see FIG. 6). The cassette control device 122 of the electronic cassette 20 detects the imaging area 352 in the received image capturing menu and sets a thick frame 354 corresponding to a matrix of the pixels 102 containing the imaging area 352 as viewed in plan. Thus, the cassette control device 122 sets the associated pixel regions 350 in the thick frame 354.

The cassette control device 122 acts to actuate the first to eighth gate drive circuits 150 and the second to eighth multiplexers 152 corresponding to the associated pixel regions 350 in the thick frame 354. Thus, the cassette control device 122 controls the first readout control part 130 and the second readout control part 136 to read the electric charges from the pixels 102 in the associated pixel regions 350 in the thick frame 354, and controls the irradiation start judgment part 132 to judge the start of the emission of the radiation 16 only in the pixels 102 in the associated pixel regions 350 in the thick frame 354.

Consequently, on the radiation conversion panel 64, the reading of the electric signals and the judgment of the emission start of the radiation 16 are not performed in the pixels 102 in the pixel regions 350 located outside the thick frame 354. Therefore, the electric power consumption can be lowered in this case as compared with a case where the reading of the electric signals and the judgment of the emission start of the radiation 16 are performed in all the pixels 102. The electronic cassette 20 is a transportable apparatus, which is driven by the electric power supply from the battery of the power supply device 128. The communication device 126 sends signals to and receives signals from the outside (the system controller 24) via wireless communication. Therefore, it is desirable to reduce wasteful electric power consumption. Thus, the reading of the electric signals and the judgment of the emission start of the radiation 16 are performed only in the pixels 102 in the thick frame 354, which are necessary for acquiring the radiographic image of the imaging area 352. The electric power is not supplied to the ninth to twelfth gate drive circuits 150 and the first and ninth multiplexers 152, other than the first to eighth gate drive circuits 150 and the second to eighth multiplexers 152, so that electric power saving can be achieved in the entire electronic cassette 20.

Furthermore, since the reading of the electric signals and the judgment of the emission start of the radiation 16 are performed only in the pixels 102 in the associated pixel regions 350 in the thick frame 354 corresponding to the imaging area 352, the radiographic image of the imaging area 352 can be reliably formed, and the time required to read the electric charges (electric signals) can be shortened.

Modified Example 9 is similar to the above embodiment and Modified Examples 1 to 8 except that the reading of the electric signals and the judgment of the emission start of the radiation 16 are performed only in the pixels 102 in the associated pixel regions 350 in the thick frame 354. Therefore, the reading and the judgment in each pixel 102 may be carried out in the same manner as the above embodiment and Modified Examples 1 to 8.

Figure 33:
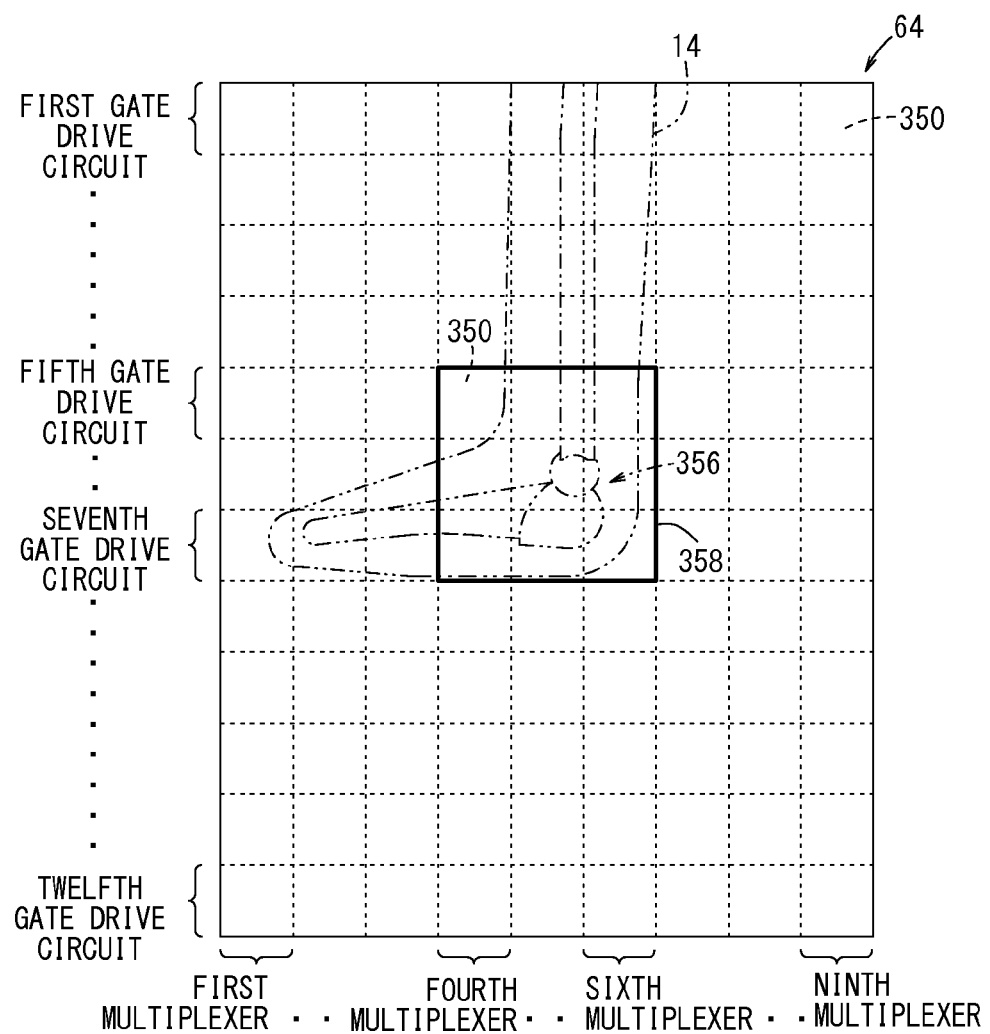
FIG. 33 is a schematic explanatory view of the radiation conversion panel of Modified Example 9.

In the case of FIG. 33, the ankle of the subject 14 is selected as the imaging area 356. The imaging area 356 is smaller than the imaging area 352 of the chest shown in FIG. 32. In this case, the reading of the electric signals and the judgment of the emission start of the radiation 16 are performed in the pixels 102 in the associated pixel regions 350 in a thick frame 358 surrounding the imaging area 356 as viewed in plan, so that the radiographic image of the imaging area 356 can be reliably formed, and the above effects can be achieved in the same manner as FIG. 32.

Figure 34:
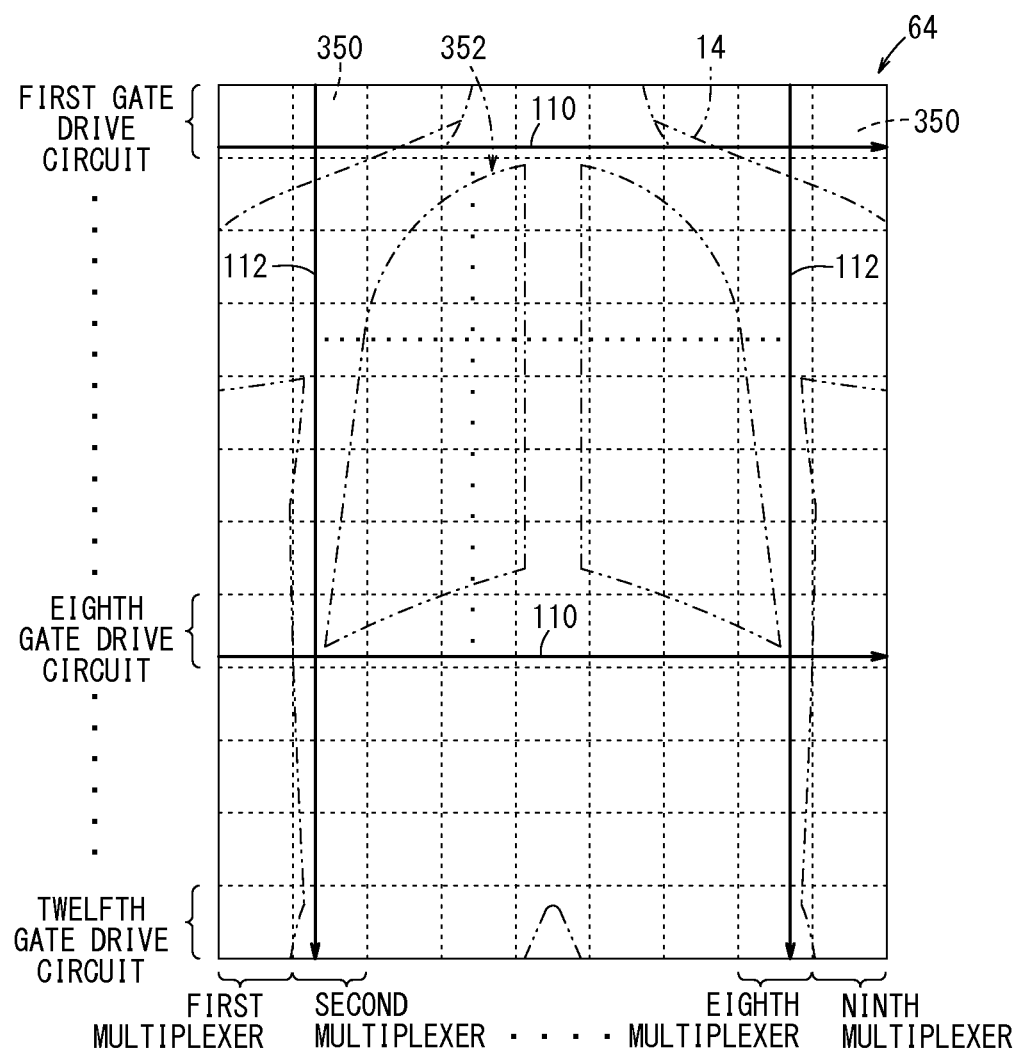
FIG. 34 is a schematic explanatory view of the radiation conversion panel of Modified Example 9.
Figure 35:
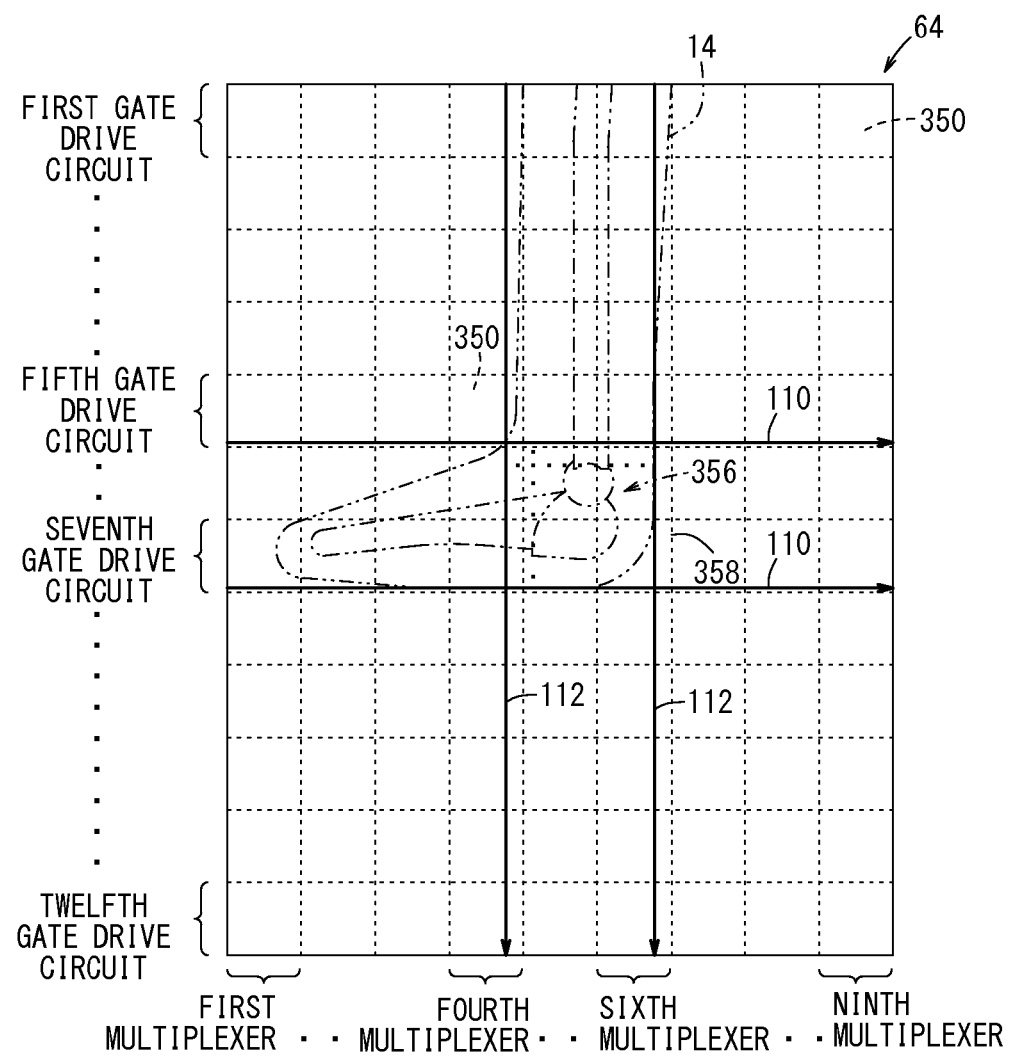
FIG. 35 is a schematic explanatory view of the radiation conversion panel of Modified Example 9.

In FIGS. 34 and 35, unlike FIGS. 32 and 33 utilizing the associated pixel regions 350 for capturing the image of the imaging area 352, 356, the cassette control device 122 acts to set (detect) two gate lines 110 and two signal lines 112 surrounding the imaging area 352, 356 as viewed in plan. The reading of the electric signals and the judgment of the emission start of the radiation 16 are performed only in the pixels 102 connectable with a plurality of the gate lines 110 between the two gate lines 110 and a plurality of the signal lines 112 between the two signal lines 112.

In FIG. 34, the cassette control device 122 (see FIG. 6) specifies two gate lines 110 and two signal lines 112 surrounding the imaging area 352 as viewed in plan based on the image capturing menu. Then, a plurality of the gate lines 110 between the specified two gate lines 110 are set as lines to which the gate drive circuits 150 should output the gate signals, and a plurality of the signal lines 112 between the specified two signal lines 112 are set as lines from which the multiplexers 152 should read the electric signals.

The cassette control device 122 acts to actuate the first to eighth gate drive circuits 150 corresponding to the setup gate lines 110 and the second to eighth multiplexers 152 corresponding to the setup signal lines 112 respectively. The cassette control device 122 controls the first readout control part 130 and the second readout control part 136 to read the electric signals only from the pixels 102 connected with the setup gate lines 110 and the setup signal lines 112, and controls the irradiation start judgment part 132 to judge the start of the emission of the radiation 16 only in these pixels 102.

Thus, in FIG. 34, the reading of the electric signals and the judgment of the emission start of the radiation 16 are performed only in the pixels 102 in the region surrounded by the two gate lines 110 and the two signal lines 112, and are not performed in the pixels 102 located outside the region. Therefore, the electric power consumption can be lowered in this case, like the cases of FIGS. 32 and 33, as compared with a case where the reading of the electric signals and the judgment of the emission start of the radiation 16 are performed in all the pixels 102. Furthermore, the radiographic image of the imaging area 352 can be reliably formed, and the time required to read the electric signals can be shortened.

In the case of FIG. 35, the ankle of the subject 14 is selected as the imaging area 356. The region surrounded by the two gate lines 110 and the two signal lines 112 is smaller than that for the imaging area 352 of the chest shown in FIG. 34. Also in this case, the reading of the electric signals and the judgment of the emission start of the radiation 16 are performed only in the pixels 102 in the above region, so that the radiographic image of the imaging area 356 can be reliably formed, and the above effects can be achieved in the same manner as FIG. 34.

In Modified Example 9, before the scan mode performed by the first readout control part 130, the second readout control part 136 may act to execute the reset operation or the offset signal readout mode for reading the electric signals stored in the pixels 102 in rows and columns corresponding to the imaging area 352, 356 as image correction offset signals (non-exposure signals) sequentially row by row. Also in this case, the electric charges can be reliably removed from the pixels 102 before the emission of the radiation 16, whereby the radiographic image can be obtained with high quality. In addition, the quality of the radiographic image can be further improved by performing the image correction processing using the offset signals.

Modified Example 10

In Modified Example 10, the image capturing menu also includes the image capturing history recorded in the recording unit 216 (see FIG. 10). The cassette control device 122 decides an electric charge readout mode to be performed before the emission of the radiation 16 based on the image capturing history and the like in the image capturing menu. Then, the cassette control device 122 controls the first readout control part 130 and the second readout control part 136 based on the decided readout mode, to read the electric charges from the pixels 102.

Figure 36:
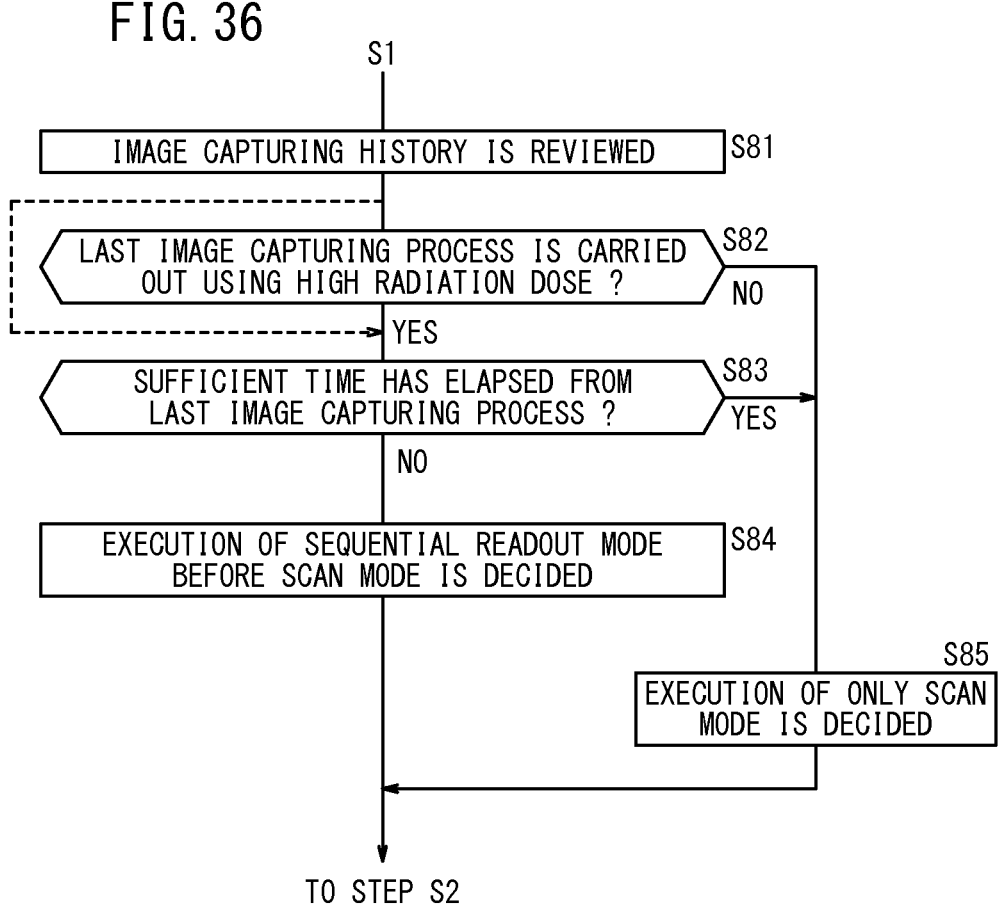
FIG. 36 is a flowchart for illustrating the operation of Modified Example 10.

After step S1 of FIG. 12, in step S81 of FIG. 36, the control unit 202 acts to display an image indicating also the image capturing history recorded in the recording unit 216 on the display unit 204. While watching the displayed image (image capturing history), when the last image capturing process is carried out using a relatively high radiation dose (step S82: YES) and only a short time has elapsed from the last image capturing process (step S83: NO), the user judges that residual electric charges generated in the last image capturing process may be stored in the pixels 102. Therefore, the user can decide to execute the sequential readout mode before the scan mode, and can operate the input unit 200 to enter the decision (step S84).

While watching the displayed image capturing history, when the last image capturing process is carried out using a relatively high radiation dose (step S82: YES) and a long time has elapsed from the last image capturing process (step S83: YES), the user judges that the residual electric charges to affect the next radiographic image are not stored in the pixels 102. Therefore, the user can decide to execute only the scan mode before the emission of the radiation 16, and can operate the input unit 200 to enter the decision (step S85).

While watching the displayed image capturing history, when the last image capturing process is carried out using a low radiation dose (step S82: NO), the user judges that the residual electric charges to affect the next radiographic image are not stored in the pixels 102. Therefore, the step S85 is carried out.

Furthermore, in Modified Example 10, after step S1, step S83 may be carried out without step S82 as shown by a dashed line in FIG. 36.

After step S84 or S85 is carried out in this manner, step S2 and following steps of FIG. 12 are performed. In this case, in step S4, the control unit 212 of the system controller 24 (see FIG. 10) sends the image capturing menu including the decision of step S84 or S85 and the image capturing history to the electronic cassette 20.

Figure 37:
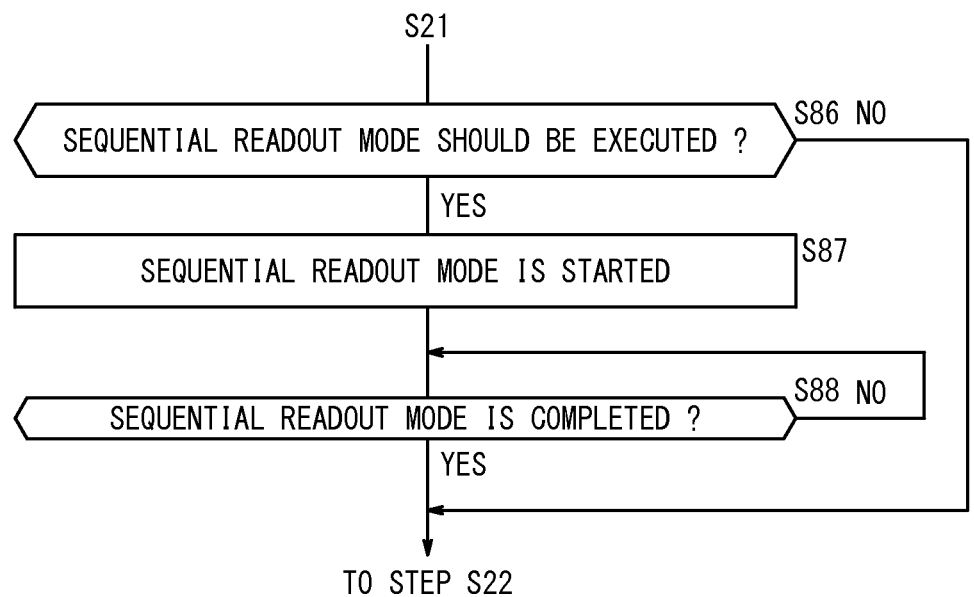
FIG. 37 is a flowchart for illustrating the operation of Modified Example 10.

In the electronic cassette 20, after the image capturing menu (including the image capturing conditions, the number of images, the decision, and the image capturing history) is received in step S21 of FIG. 13, the cassette control device 122 judges whether the sequential readout mode should be executed or not before the scan mode based on the image capturing menu (the image capturing history and the decision included therein) in step S86 of FIG. 37.

When the sequential readout mode should be executed (step S86: YES), the cassette control device 122 controls the second readout control part 136 to execute the sequential readout mode (step S87). If the sequential readout mode executed by the second readout control part 136 is completed in the pixels 102 (step S88: YES), the cassette control device 122 controls the first readout control part 130 to execute the scan mode in step S22 of FIG. 13, and the following steps are carried out. When the sequential readout mode is not completed, the cassette control device 122 remains in step S88.

On the other hand, when the sequential readout mode does not have to be executed (step S86: NO), the cassette control device 122 acts to perform step S22 and the following steps of FIG. 13.

In Modified Example 10, the electric charge readout mode (the scan mode or the sequential readout mode) to be executed before the emission of the radiation 16 is selected by the system controller 24 and the console 26 based on the image capturing history in the image capturing menu. The image capturing menu including the decision and the image capturing history are sent to the electronic cassette 20. The cassette control device 122 of the electronic cassette 20 controls the first readout control part 130 and the second readout control part 136 to execute the selected electric charge (electric signal) readout mode before the emission of the radiation 16 based on the decision and the image capturing history in the image capturing menu.

Consequently, the residual electric charges generated in the last image capturing process can be reliably removed from the pixels 102 before the emission of the radiation 16, and the radiographic image can be formed with a high quality without overlap of a residual image. Since the electric charge readout mode to be executed before the emission start of the radiation 16 can be selected based on the image capturing history including the condition (the high or low radiation dose) of the last image capturing process and the time from the last image capturing process, the residual electric charges in the pixels 102 can be efficiently removed.

In Modified Example 10, step S84 or S85 may be carried out depending on the conditions of the ongoing image capturing process. For example, when this image capturing process is carried out using a low radiation dose, the execution of the scan mode in a short time may be decided to increase the response speed for detecting the radiation 16 in the pixels 102 (step S85). When this image capturing process is carried out using a short irradiation time of the radiation 16, the execution of only the scan mode in a short time may be decided to avoid waste of time (step S85). In this case, the scan mode in a short time may be performed in all or part of the pixels 102 in the same manner as Modified Examples 4 to 6.

In Modified Example 10, the cassette control device 122 may change the interval between the rows, which are simultaneously read out in the scan mode, based on the radiation 16 irradiation time, the decision, and the image capturing history in the image capturing menu. For example, when this image capturing process is carried out under a short irradiation time of the radiation 16 to avoid waste of time, the cassette control device 122 may set a wide row interval and then control the first readout control part 130 to execute the scan mode. In this case, the scan mode can be completed in a short time.

In a case where only the pixels 102 in the predetermined rows are read out in the scan mode in the same manner as Modified Example 4, the cassette control device 122 may change the rows, which are read out in the scan mode, based on the radiation 16 irradiation time, the decision, and the image capturing history in the image capturing menu. In this case, the scan mode can be completed in a short time e.g. by increasing the interval between the predetermined rows.

Furthermore, in Modified Example 10, in step S84 or S85, the scan mode or the sequential readout mode may be decided to be executed only in the pixels 102 corresponding to the imaging area 352 or 356 in the same manner as Modified Example 9.

As described above, in steps S81 to S85, the user may decide the electric charge readout mode to be executed before the emission of the radiation 16 while watching the image on the display unit 204. Modified Example 10 is not limited thereto. The electric charge readout mode to be executed before the emission of the radiation 16 may be automatically decided by the control unit 212 based on the image capturing history recorded in the recording unit 216. Of course, the above effects can be achieved also in this case. It is to be understood that Modified Examples 1 to 9 may be further modified like Modified Example 10.

Modified Example 11

In the above embodiment and Modified Examples, the electric charges stored in the pixels 102 in a plurality of the rows (e.g. 12 rows) are simultaneously read out in the scan mode (the first readout mode). Therefore, the start of the emission of the radiation 16 can be rapidly and accurately judged.

In the scan mode, the irradiation start judgment part 132 judges whether or not the digital electric signals stored in the memory 124 are larger than the arbitrary settable threshold value (hereinafter referred to as the threshold value Th) (step S23). A significantly larger signal value is output from the charge amplifier 116 under the emission of the radiation 16 from the radiation source 34 to the electronic cassette 20 than without the emission of the radiation 16. Therefore, the digital electric signal stored in the memory 124 becomes larger than the threshold value Th under the emission of the radiation 16, whereby the start of the emission of the radiation 16 can be rapidly judged.

For example, the gains of the charge amplifiers 116 (hereinafter referred to as the gains G) may be controlled at a second readout gain G2 in the sequential readout mode. In a case where the charge amplifiers 116 are controlled at the second readout gain G2 in the simultaneous readout mode, 12 pixels 102 are simultaneously read out, the charge amplifiers 116 exhibit 12-fold signal values, and 12-fold digital electric signals are sent from the A/D converters 154 and stored in the memory 124. If the 12-fold digital electric signal becomes larger than the threshold value Th, the emission of the radiation 16 is judged to be started.

The gains G of the charge amplifiers 116 are designed such that the signals output from the charge amplifiers 116 have magnitudes within and closer to input dynamic ranges of the A/D converters 154 to improve the readout resolution (readout accuracy) in the sequential readout mode. Therefore, in a case where the gains G are not changed in the scan mode, the charge amplifiers 116 may be saturated, failing to ensure the high-speed operation.

In Modified Example 11, the charge amplifiers 116 are controlled at a first readout gain G1 by the first readout control part 130 in the scan mode, and are controlled at the second readout gain G2 by the second readout control part 136 in the sequential readout mode. The first readout gain G1 used in the scan mode is lower than the second readout gain G2 used in the sequential readout mode (G1<G2). For example, when 12 pixels in 12 rows are simultaneously read out in the scan mode, the first readout gain G1 may be 1/12 of the second readout gain G2 (G1=G2/12) to prevent the saturation of the charge amplifiers 116.

FIG. 38 is a detail view of the radiation conversion panel 64, the gate drive part 114, and the multiplexer part 118, equipped with the charge amplifiers 116. In each charge amplifier 116, the capacitor 158 connected to the input and output terminals of the operational amplifier 156 is replaced by a variable capacitor 158A to modify the gain G of the charge amplifier 116.

Figure 39A:
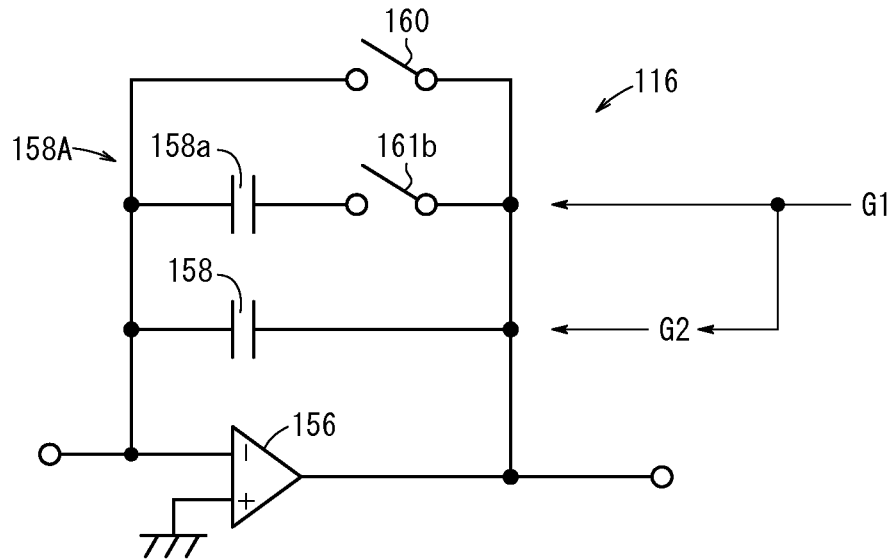
FIG. 39A is a circuit diagram of a charge amplifier with a two stage switchable gain.

As shown in FIG. 39A, the capacitance of the variable capacitor 158A can be switched by a switch 161*b*, which is controlled by the first readout control part 130 or the second readout control part 136. In a case where the switch 161*b* is in the off state and only the capacitor 158 is used as the feedback capacitor, the gain G of the charge amplifier 116 is controlled at the second readout gain G2 for the sequential readout mode. When the switch 161*b* is in the on state and the capacitors 158 and 158*a* are used in combination as the feedback capacitor, the gain G of the charge amplifier 116 is controlled at the first readout gain G1 for the scan mode (G1<G2). A voltage generated between terminals of a capacitor under an electric charge amount is inversely proportional to the capacitance value of the capacitor. Therefore, it should be noted that, as the capacitance value of the feedback capacitor is reduced, the terminal voltage under an electric charge amount is increased, resulting in a higher gain G of the charge amplifier 116. Thus, assuming a lossless condition to facilitate understanding, the gain G of the charge amplifier 116 satisfies the relation of G=Ca/Cf, in which Ca represents the equivalent capacitance value of the charge storage part 74 and Cf represents the capacitance value of the feedback capacitor of the charge amplifier 116.

As shown in FIG. 40, the gain G is controlled at the first readout gain G1 or a first readout gain G1' (to be hereinafter described) in the scan mode and is controlled at the second readout gain G2 in the sequential readout mode (G1'<G1<G2).

In the above embodiment and Modified Examples 1 to 10, among the setup image capturing conditions (including the irradiation time, the tube voltage, the tube current, and the like, stored in association with the imaging area and the diagnostic site in the table 218), at least the irradiation time is sent from the image capturing condition setting part 222 through the communication unit 214 to the electronic cassette 20. In Modified Example 11, at least the irradiation time and the tube current are sent to the electronic cassette 20. In Modified Example 11, the tube current is considered proportional to the radiation dose. In this sense, the image capturing condition setting part 222 acts as a radiation dose setting part.

In FIG. 40, the first readout gain G1', lower than the first readout gain G1, is used when a high radiation dose (a radiation dose higher than a predetermined value) of the emission of the radiation 16 is set by the image capturing condition setting part 222 (the radiation dose setting part). Thus, the first readout control part 130 can set the first readout gain G1' for the high radiation dose or the first readout gain G1 for the low radiation dose, the first readout gain G1' being lower than the first readout gain G1, so that the output saturation of the charge amplifier 116 can be prevented under both the high and low radiation doses.

In Modified Example 11, the first readout gain G is changed depending on the radiation dose in this manner. Therefore, as described above, among the image capturing conditions, the image capturing condition setting part 222 sends the irradiation time and further sends at least the tube current value corresponding to the radiation dose to the electronic cassette 20.

The electronic cassette 20 acts to store the sent irradiation time and tube current value corresponding to the radiation dose in the memory 124. The first readout control part 130 sets the scan mode gain (first readout gain) G1 or G1', based on the tube current value stored in the memory 124.

Figure 39B:
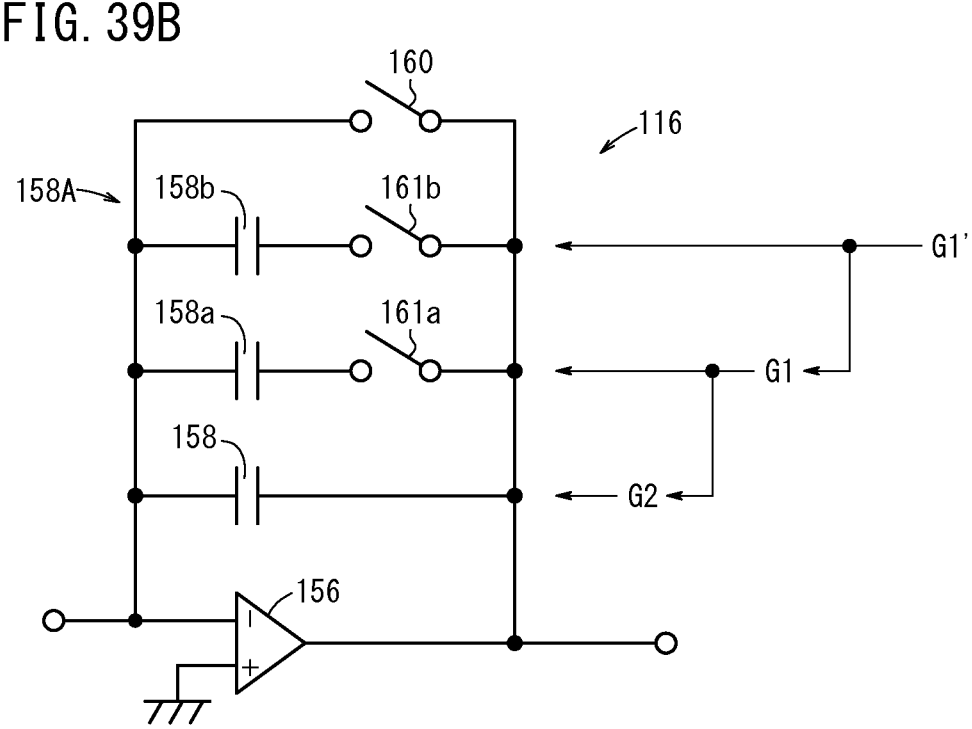
FIG. 39B is a circuit diagram of a charge amplifier with a three stage switchable gain.

FIG. 39B is a structural view of the charge amplifier 116 capable of switching the gain G into the second readout gain G2 for the sequential readout mode or the first readout gain (scan mode gain) G1 or G1'. When both of switches 161a and 161b are in the on states, the capacitor 158 can be connected in parallel to capacitors 158a and 158b to set the lowest scan mode gain G1' (G1'<G1<G2).

The first readout control part 130 and the second readout control part 136 may set the first readout gain G1 or G1' or the second readout gain G2 depending on the image capturing conditions (the imaging area and the diagnostic site) such as those of FIG. 11. In this case, when the user operates the input unit 200 of the console 26 to select the imaging area and the diagnostic site, the image capturing condition setting part 222 sends all the image capturing conditions corresponding thereto to the electronic cassette 20 through the communication unit 214.

With respect to the setting of the threshold value Th in the scan mode executed by the first readout control part 130, as shown in FIG. 40, a start threshold value Thi is set at the start of the scan mode and is used between timings t0 and t0' in the first cycle. In the first cycle, each plurality of the rows (e.g. 12 rows) is simultaneously read to obtain electric signal values Si. Furthermore, a normal threshold value Tha is set in the following cycles of the scan mode (after the timing t0'). The normal threshold value Tha is represented by Si+α, obtained by adding a predetermined value (small value) α to the electric signal value Si. The normal threshold value Tha is smaller than the start threshold value Thi (Si+α=Tha<Thi).

In this manner, the normal threshold value Tha set in the following cycles of the scan mode can be larger than but close to the noise level. Therefore, the emission of the radiation 16 can be detected more rapidly.

Figure 41:
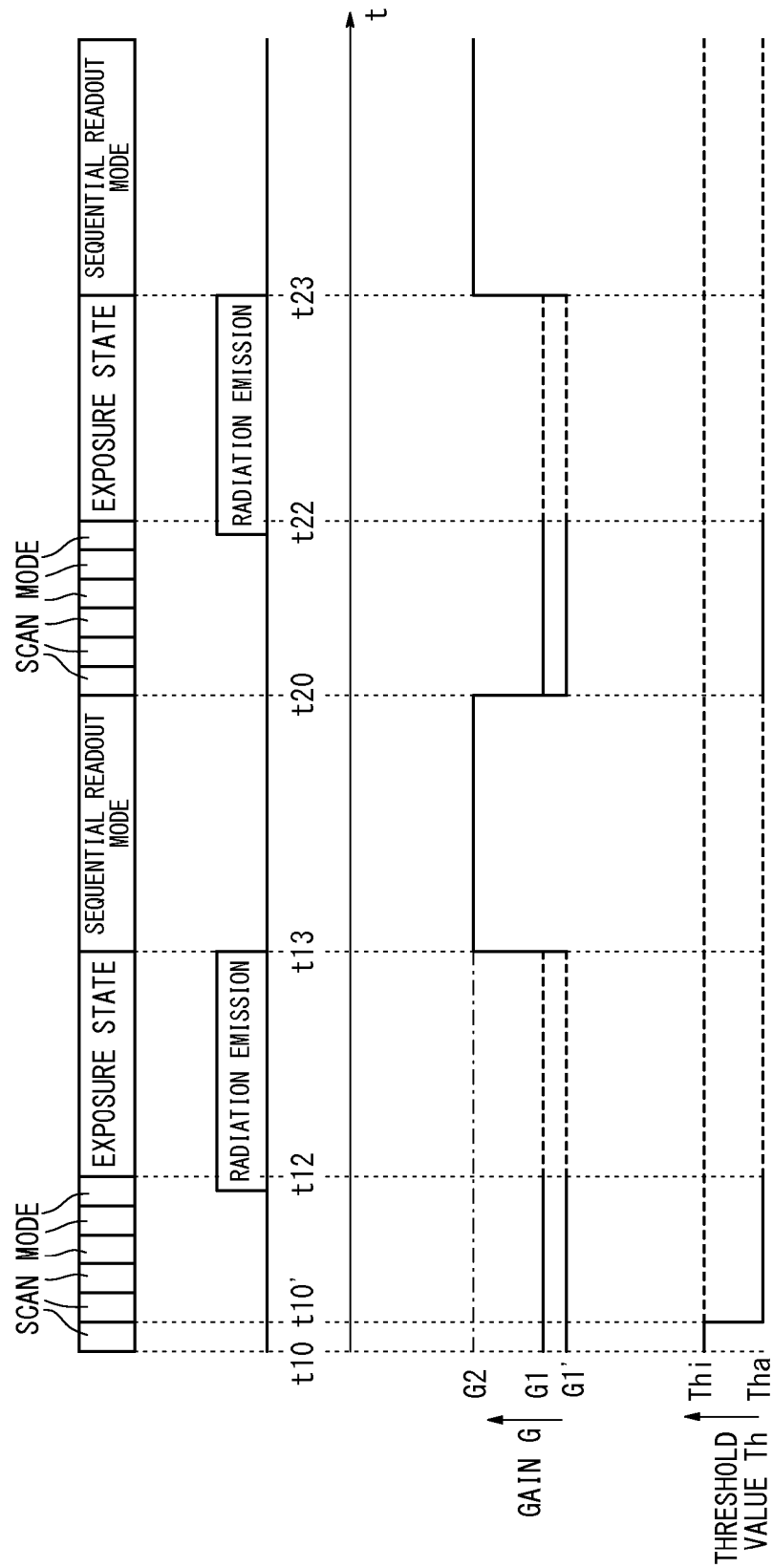
FIG. 41 is a time chart for illustrating charge amplifier gain switching and threshold value setting in a process of capturing two images.

In this case, the setup number of images may be 2 or more similarly to FIG. 15. As shown by a solid line in the bottom of FIG. 41, in the first image capturing process, the threshold value Th in the scan mode (first readout mode) is controlled such that the irradiation start judgment part 132 sets the start threshold value Thi between timings t10 and t10' and then sets the normal threshold value Tha between timings t10' to t12. In the second and following image capturing processes, the normal threshold value Tha is continuously used in the scan mode (first readout mode) as in the example of the timings t20 to t22. Thus, the emission of the radiation 16 can be rapidly detected even in the first cycle of the scan mode in the second and following image capturing processes.

Figure 42:
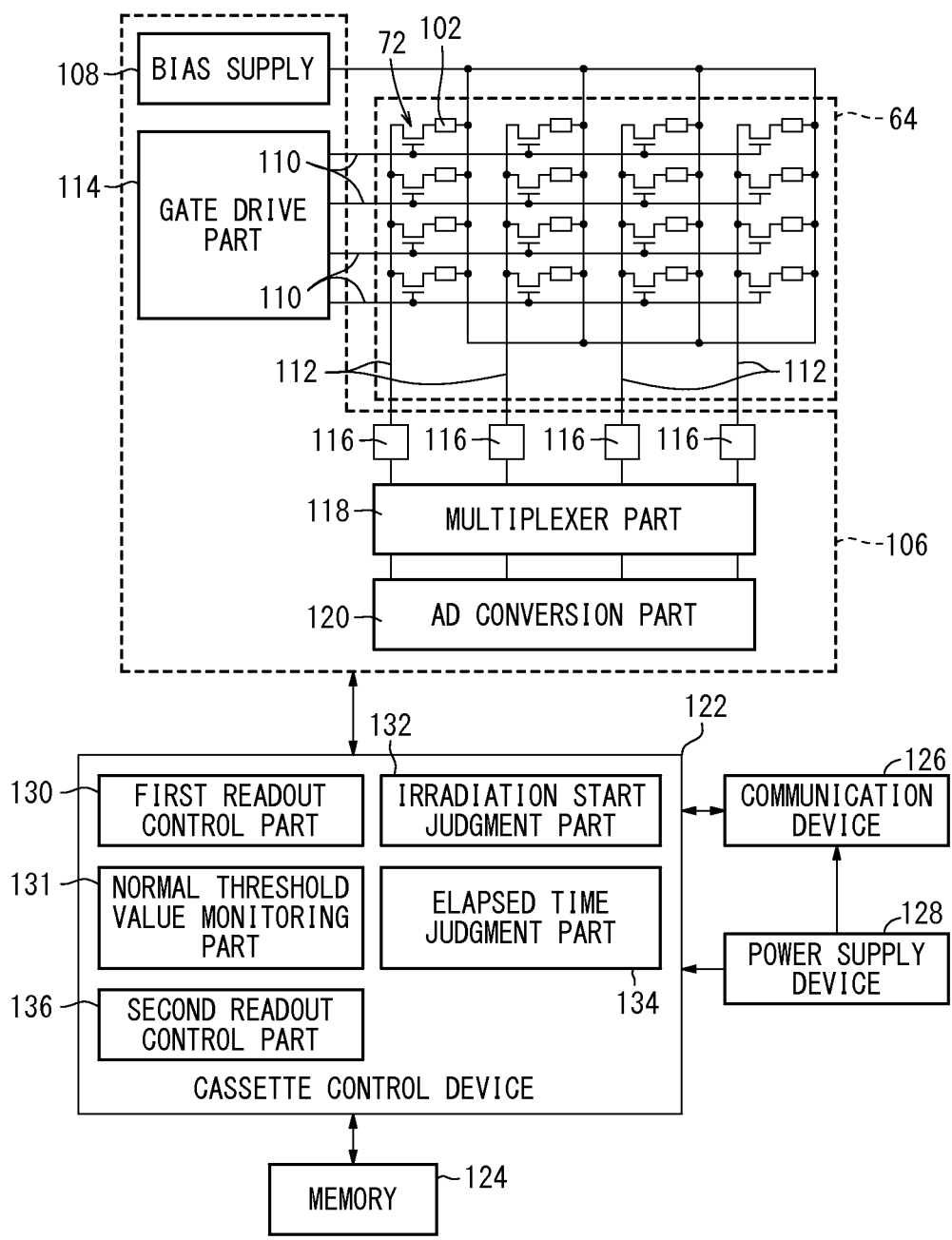
FIG. 42 is an explanatory view of an electronic cassette having a normal threshold value monitoring part.

As shown in FIG. 42, the cassette control device 122 has a normal threshold value monitoring part 131 for monitoring (logging) the normal threshold value Tha, which is set depending on the read noise level. If the monitored normal threshold value Tha (Si+α) based on the readout noise level becomes larger than a predetermined value (warning value), the normal threshold value monitoring part 131 sends a notice to at least one of a warning lamp (not shown) disposed on the electronic cassette 20 and the console 26 or the display device 28 through the communication device 126 and the system controller 24 (thereby providing a warning image or sound). Furthermore, the normal threshold value monitoring part 131 may send the notice directly from the console 26 or the electronic cassette 20 to a server in a maintenance center or the like through a communication link (not shown). In this case, at least one of the user and the outside maintenance center can predict a failure of the electronic cassette 20 containing the radiation conversion panel 64 via so-called remote maintenance.

As described above, in Modified Example 11, the electronic cassette 20 used as the radiographic image capturing apparatus has the image capturing panel having the radiation conversion panel 64 containing a plurality of the pixels 102 arranged in a matrix for converting the radiation 16 (which is emitted from the radiation source 34 and transmitted through the subject 14) into the electric signals and storing the electric signals, the first readout control part 130 for executing the first readout mode for reading the electric signals stored in the pixels 102 in a plurality of the rows simultaneously through the electric signal amplifiers of the charge amplifiers 116 set at the first readout gain G1, the irradiation start judgment part 132 for judging the start of the emission of the radiation 16 from the radiation source 34 to the image capturing panel having the radiation conversion panel 64, the emission of the radiation 16 being judged to be started in a case where a value of the electric signals read by the first readout control part 130 becomes larger than the arbitrarily settable threshold value Th, and the first readout control part 130 acting to stop the reading of the electric signals and to switch the image capturing panel having the radiation conversion panel 64 to the exposure state in a case where the emission of the radiation 16 is judged to be started by the irradiation start judgment part 132, the elapsed time judgment part 134 for judging whether the predetermined time has elapsed or not from the start of the emission of the radiation 16, and the second readout control part 136 for executing the second readout mode for reading the electric signals stored in the pixels sequentially row by row through the charge amplifiers 116 set at the second readout gain G2, the second readout mode being executed in a case where the predetermined time is judged to have elapsed by the elapsed time judgment part 134. The first readout gain G1 is lower than the second readout gain G2.

The charge amplifiers 116 are controlled at the lower gains in the first readout mode (scan mode). Therefore, even if the electric charges in a plurality of the pixels are simultaneously read out and the electric signal value becomes larger than the threshold value Th for detecting the start of the emission of the radiation 16, the output values of the charge amplifiers 116 are not excessively increased and are not saturated.

It should be noted that the first readout control part 130 can simultaneously read the electric signals stored in the pixels 102 in a plurality of the rows arranged at a predetermined row interval.

In addition, the image capturing condition setting part 222 is used as the radiation dose setting part for setting a low or high radiation dose of the radiation 16 to be emitted to the subject 14. The first readout control part 130 controls the first readout gain G based on information from the image capturing condition setting part 222 such that the first readout gain G1' for the high radiation dose is lower than the first readout gain G1 for the low radiation dose. Therefore, the output signals of the charge amplifiers 116 are not saturated under the high radiation dose and are sufficiently increased under the low radiation dose. Consequently, the emission of the radiation 16 can be rapidly detected.

The first readout control part 130 and the second readout control part 136 may set the first readout gain G1 (G1') and the second readout gain G2 based on the image capturing conditions (the imaging area and the diagnostic site).

Modified Example 12

Figure 43:
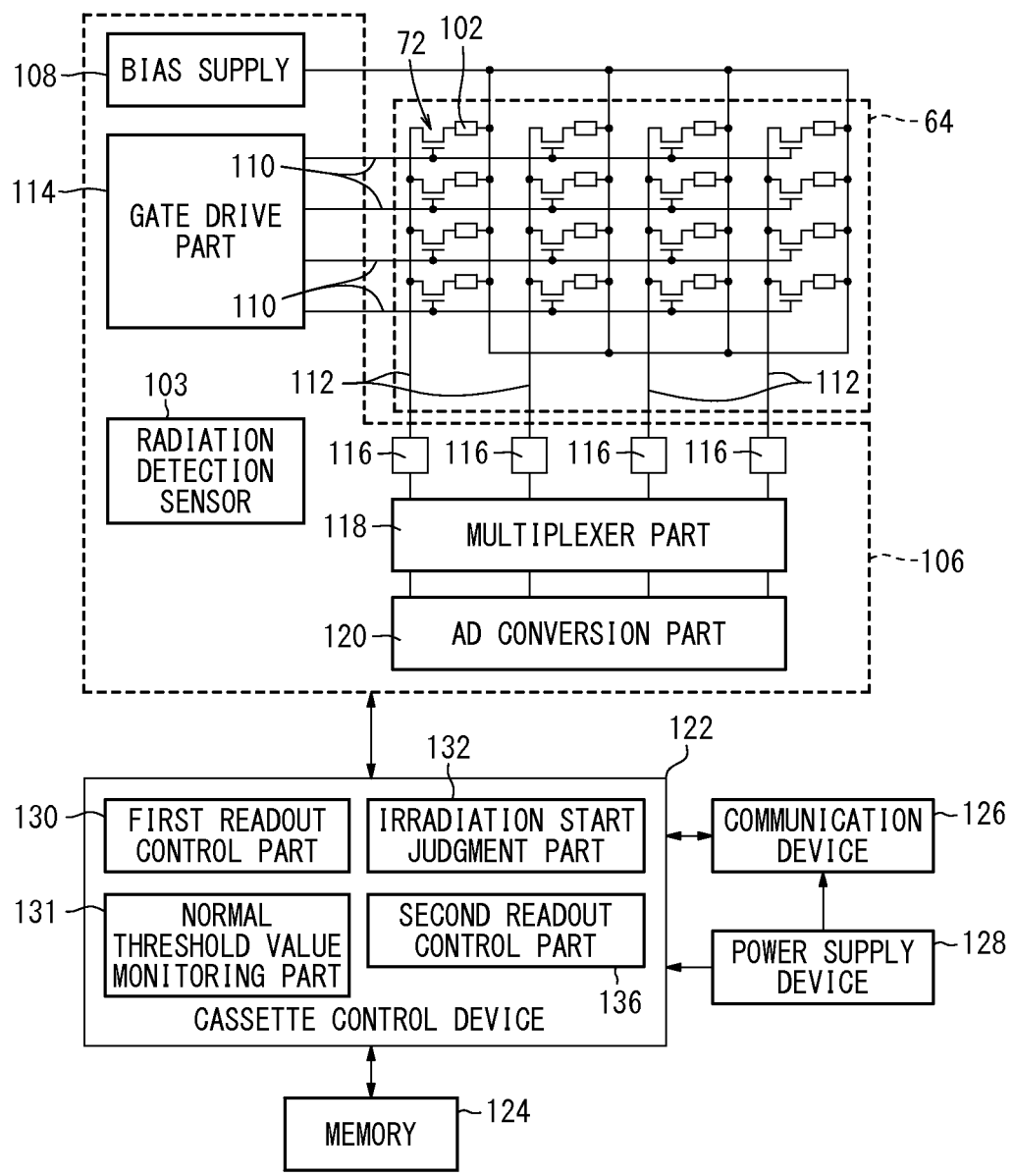
FIG. 43 is a detail view of a radiation conversion panel, a gate drive part, charge amplifiers, and a multiplexer part according to Modified Example 12, equipped with a radiation detection sensor as an emission completion judgment part.

In the above embodiment and Modified Examples 1 to 11, the elapsed time judgment part 134 is used for judging the completion of the emission of the radiation 16. Alternatively, as shown in FIG. 43, a radiation detection sensor (an emission completion judgment part or an exposure completion judgment part) 103 may be used for the judgment in the drive circuit device 106. The radiation detection sensor 103 may be a semiconductor sensor such as a photodiode, which outputs a signal only under the emission of the radiation 16.

In this case, if the radiation detection sensor 103 exhibits an output value of approximately zero, the emission of the radiation 16 is judged to be completed. If the emission of the radiation 16 is judged to be completed, the second readout control part 136 acts to execute the second readout mode for reading the electric signals stored in the pixels 102 sequentially row by row through the charge amplifiers 116 set at the second readout gain G2.

The radiation detection sensor 103 may be disposed on the image capturing surface 42 (see FIG. 2) of the panel unit 52, and may be located on each corner of the image capturable area 60.

Other than the semiconductor sensor such as the photodiode, the radiation detection sensor 103 may be such that another pixel and another TFT are formed in the radiation conversion panel 64, another charge amplifier (an operating amplifier, a feedback capacitor, and a reset switch) and another A/D converter are formed in the drive circuit device 106, and the second readout control part 136 directly controls the TFT, charge amplifier, and A/D converter. When the exposure is started, the reset switch is opened, the output of the charge amplifier is increased, and the increase is stopped (the output becomes constant), the emission of the radiation 16 can be judged to be completed. When the emission of the radiation 16 is judged to be completed, the reset switch is closed, so that the feedback capacitor in the charge amplifier is discharged.

Modified Example 13

Modified Examples 1 to 12 may be further modified as follows. An electronic cassette 20a according to Modified Example 13 will be described below with reference to FIGS. 44 to 46.

Figure 44:
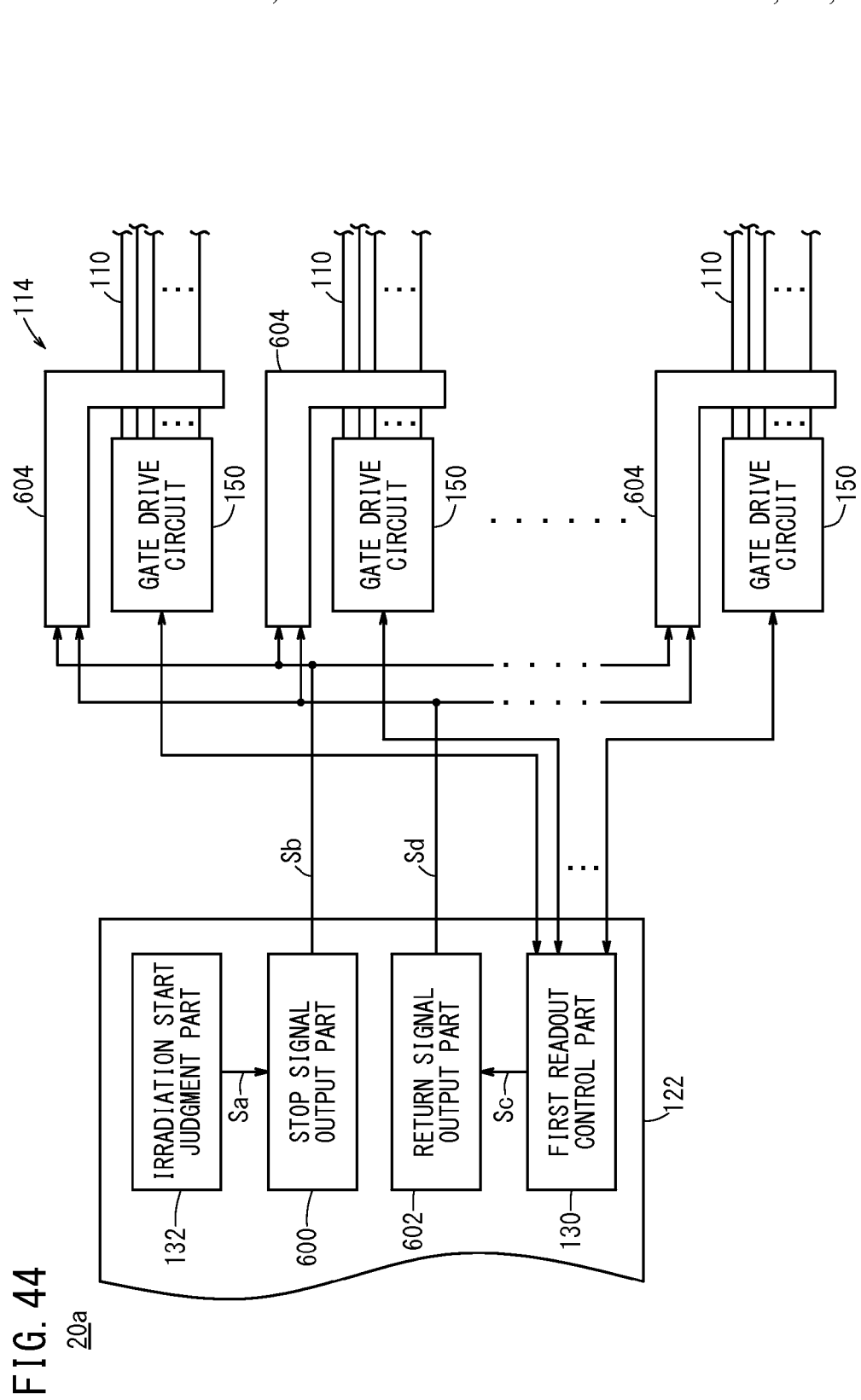
FIG. 44 is a partial block diagram of an electronic cassette according to Modified Example 13.

As shown in FIG. 44, the cassette control device 122 has a stop signal output part 600 for outputting a stop signal Sb based on a detection signal Sa from the irradiation start judgment part 132 (indicating the detection of the emission start of the radiation 16), and a return signal output part 602 for outputting a return signal Sd based on a scan end signal Sc from the first readout control part 130 (indicating the completion of the scan mode). The stop signal Sb and the return signal Sd are supplied to the gate drive part 114.

Figure 45:
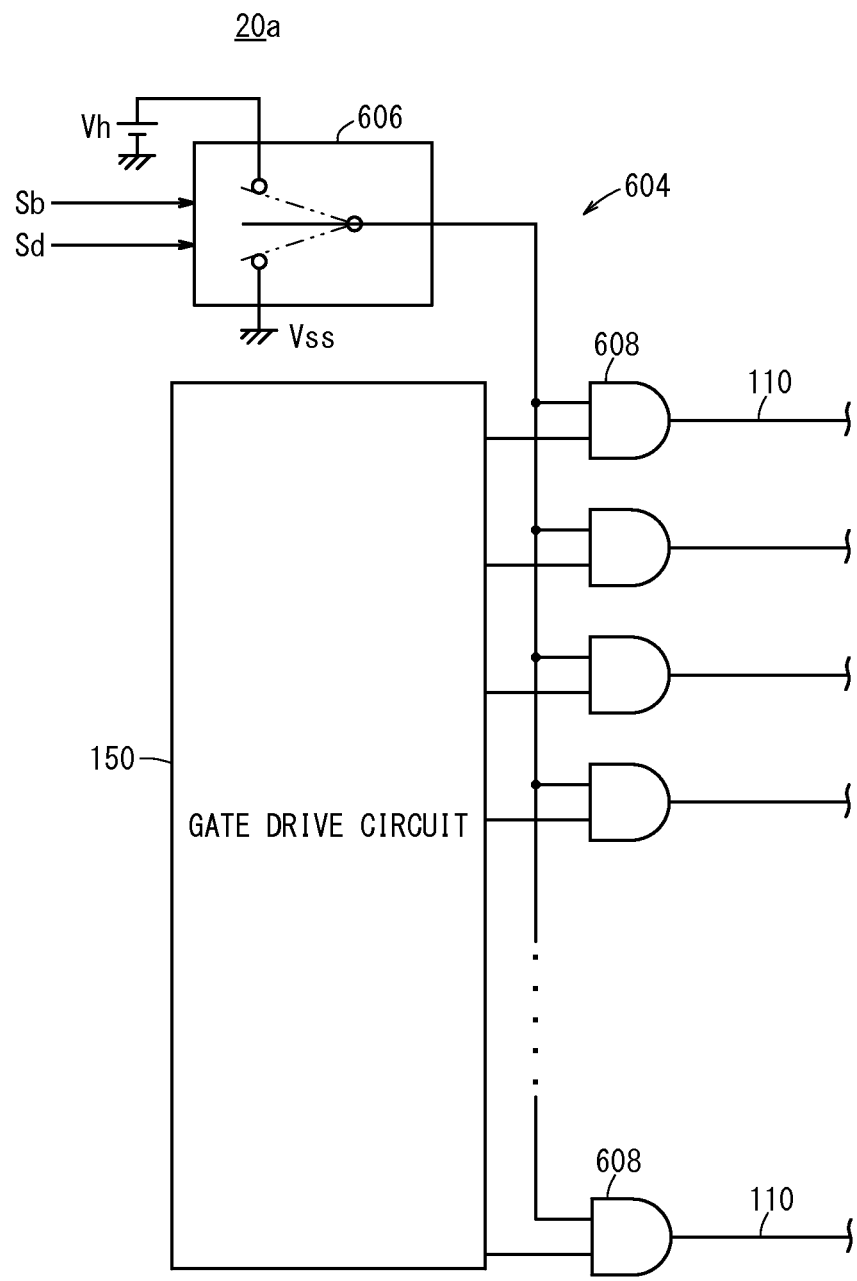
FIG. 45 is a circuit diagram of an example of a mask processing portion.

The gate drive part 114 has a mask processing portion 604 for each of the gate drive circuits 150. As shown in FIG. 45, the mask processing portion 604 has a first switch circuit 606, and further has AND circuits 608 corresponding to output terminals of the gate drive circuit 150.

The first switch circuit 606 outputs a high-level signal (Vh) at an early stage, outputs a low-level signal (Vss) based on the entered stop signal Sb, and outputs the high-level signal (Vh) based on the entered return signal Sd.

Each of the AND circuits 608 receives two types of signals from the gate drive circuit 150 and the first switch circuit 606, and outputs the logical product of the entered signals. The AND circuit 608 has an output line corresponding to the gate line 110. At the early stage and in a case where the return signal Sd is entered, the first switch circuit 606 outputs the high-level signal (Vh) to the AND circuit 608, so that the output from the gate drive circuit 150 is made effective, and the gate signal is sent to the selected gate line 110. In a case where the stop signal Sb is entered into the first switch circuit 606, until the return signal Sd is entered, the first switch circuit 606 outputs the low-level signal (Vss) to the AND circuit 608, so that the output from the gate drive circuit 150 is made ineffective, and the gate signal is not sent to the gate line 110.

When the start of the emission of the radiation 16 is detected, the cassette control device 122 sends the stop signal Sb to the gate drive circuits 150 to stop the reading. When the drive signals c1 to c12 are sent, the gate drive circuits 150 select the gate lines 110 sequentially, and output the gate signals to the selected gate lines 110 sequentially, to read the electric charges stored in the pixels 102 sequentially row by row. When the stop signal Sb is entered, the mask processing portions 604 act to perform a mask processing, and the gate drive circuits 150 do not output the gate signals. Thus, the first readout control part 130 stops the reading of the electric charges stored in the pixels 102 in the scan mode. In this case, when the stop signal Sb is sent, each of the gate drive circuits 150 continues to sequentially select the gate lines 110 (the scan mode is continued). However, since the mask processing is carried out, the gate signals are not sent to the selected gate lines 110. Therefore, the electronic cassette 20a can be switched into the exposure state at the timing of the detection of the radiation 16 (the judgment of the emission of the radiation 16 in the scan mode).

For example, even if the stop signal Sb is sent after the gate signal is sent to the gate line 110 of the 0th row, each of the gate drive circuits 150 continues to sequentially select the gate lines 110 of the first, second, ..., and final rows, but does not output the gate signals to the selected gate lines 110. In this case, even if the stop signal Sb is sent, the gate drive circuits 150 sequentially select the gate lines 110, and thereby output the end signals d1 to d12 after the gate lines 110 of the 239th rows are selected. When the end signals d1 to d12 are sent from the gate drive circuits 150, the first readout control part 130 acts to stop the scan mode.

Figure 46:
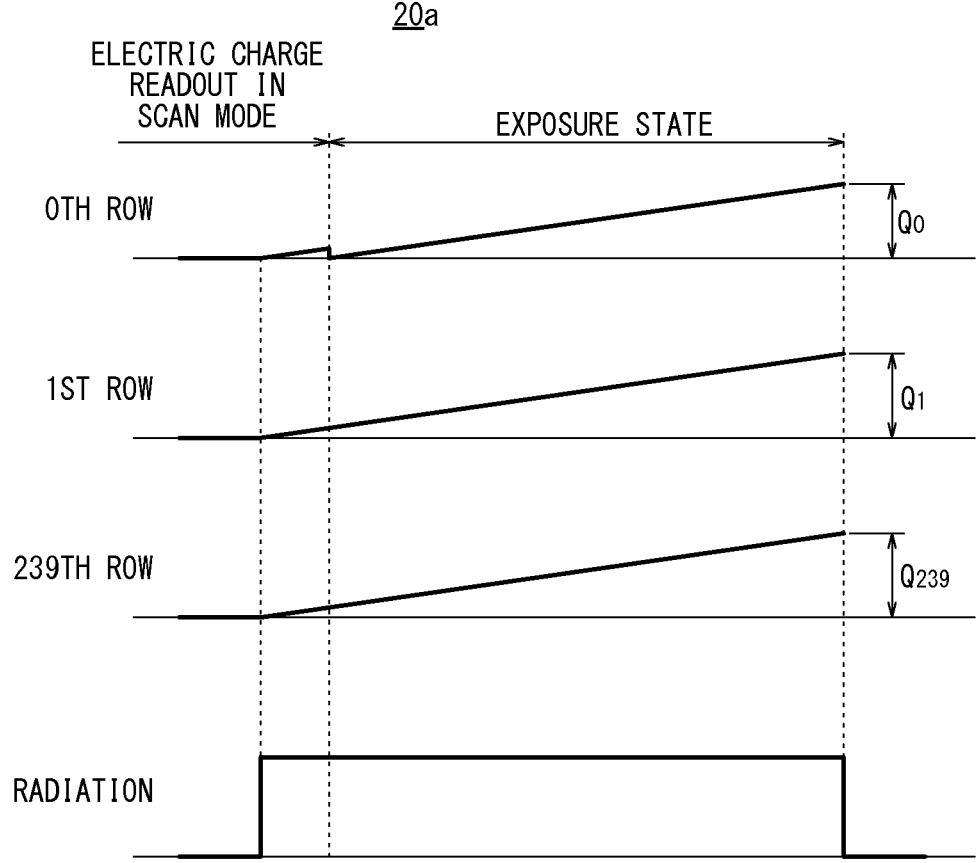
FIG. 46 is a diagram for illustrating electric charges stored in pixels in some rows in a case where the electronic cassette is switched into an accumulation state after a radiation is detected and then immediately the reading of the electric charges in the pixels in the scan mode is stopped.

FIG. 46 is a diagram for illustrating the electric charges stored in the pixels 102 in some rows in a case where the electronic cassette 20a is switched into the accumulation state after the radiation 16 is detected and then immediately the reading of the electric charges in the pixels 102 in the scan mode is stopped.

The electric charges in the pixels 102 in the some rows, stored in a case where the radiation 16 is detected in a process of reading the electric charges stored in the 0th row, are shown in FIG. 46. When the radiation 16 is detected, the cassette control device 122 sends the stop signal Sb to the gate drive circuits 150. Therefore, the electric charges stored in the pixels 102 in the second to final rows under the emission of the radiation 16 are not read out and remain in the rows. In this case, the amount Q0 of the electric charges stored in the pixels 102 in the 0th row by the exposure for capturing the radiographic image, the amount Q1 of the electric charges stored in the pixels 102 in the first row, and the amount Q239 of the electric charges stored in the pixels 102 in the 239th row satisfy the relation of Q0<Q1=Q239, and the difference between the amounts is not large. Thus, the exposure can be performed without wasting the radiation 16 with the image information, and the rows exhibit only small variations in the amounts of the electric charges.

The operation of the cassette control device 122 in Modified Example 13 is approximately equal to that shown in the flowchart of FIG. 13. However, in Modified Example 13, when the emission of the radiation 16 is judged to be started by the irradiation start judgment part 132 in step S24 of FIG. 13, the stop signal output part 600 sends the stop signal Sb to the gate drive circuits 150 to perform step S25, so that the electronic cassette 20a can be switched into the exposure state. Then, the first readout control part 130 judges whether the end signals d1 to d12 are sent or not from the gate drive circuits 150 in step S26. In a case where the end signals d1 to d12 are judged to be sent, the scan mode is stopped in step S27. At this time, the return signal output part 602 outputs the return signal Sd, and the mask processing by the mask processing portion 604 is stopped.

In this manner, when the emission of the radiation 16 is judged to be started, the electronic cassette 20a outputs the stop signal Sb to the gate drive circuits 150. Though the scan mode is continued until the one cycle is completed, the electric charges stored in the pixels 102 are not read out, whereby the radiation 16 with the image information are not wasted and are utilized for capturing the radiographic image.

In the above described example, the mask processing portion 604 for each gate drive circuit 150 is hardware containing the first switch circuit 606 and a plurality of the AND circuits 608. When the gate drive circuit 150 has a CPU, software (such as bit mask processing program) having the same function as the mask processing portion 604 may be embedded.

Modified Example 14

In an electronic cassette 20b according to Modified Example 14, in a case where the emission of the radiation 16 is detected and then the one cycle is completed in the scan mode, an all-line activation processing (all-pixel reset mode) for discarding excess charges in all the pixels 102 is carried out. In the all-line activation processing, the gate signals are sent to all the gate lines 110 to turn on all the TFTs 72 connected therewith.

The electronic cassette 20b of Modified Example 14 will be described specifically below with reference to FIGS. 47 to 50.

Figure 47:
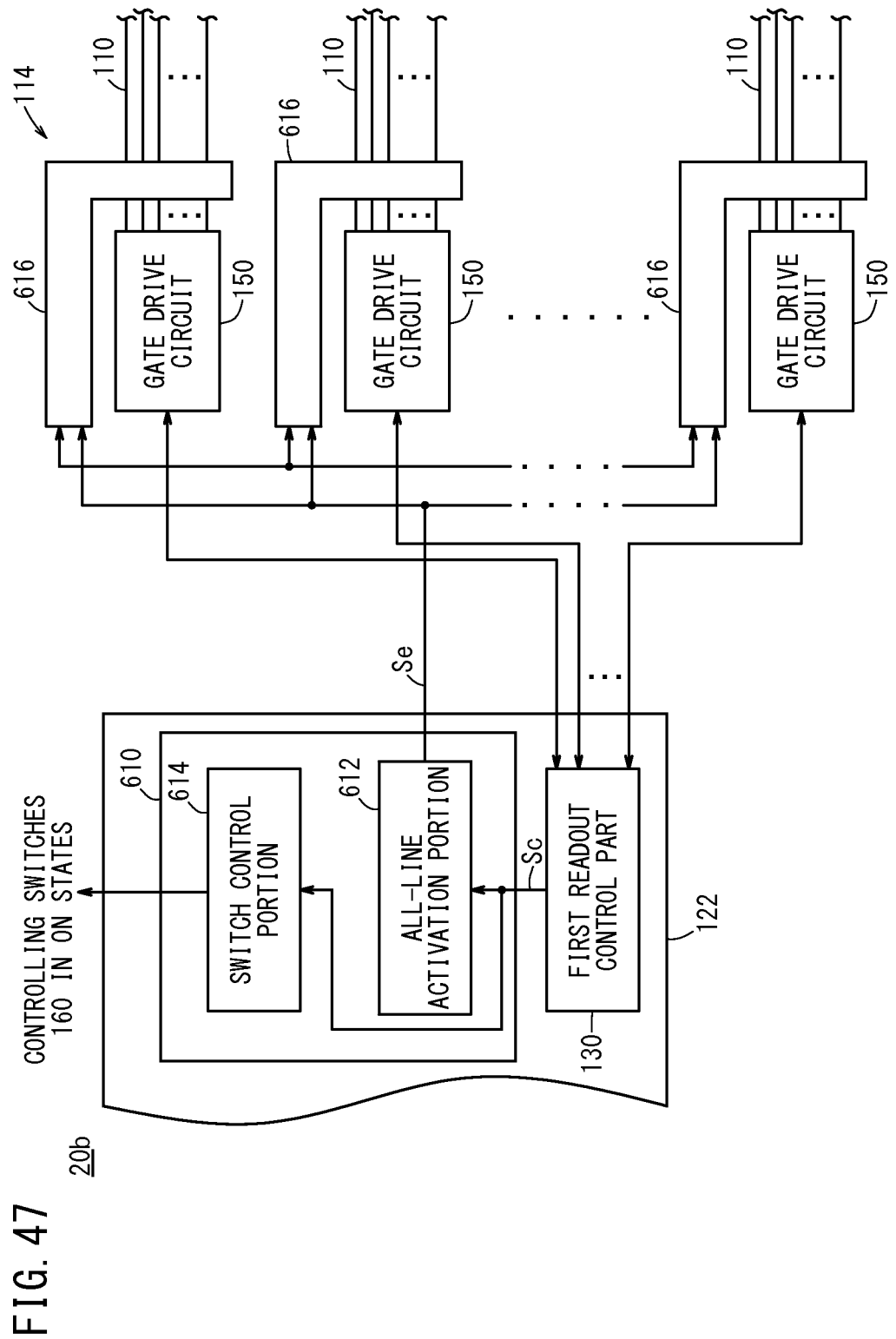
FIG. 47 is a partial block diagram of an electronic cassette according to Modified Example 14.

As shown in FIG. 47, the cassette control device 122 has an all-pixel reset control part 610. The all-pixel reset control part 610 has an all-line activation portion 612, which outputs a reset signal Se for activating all lines based on a signal indicating the completion of the scan mode (the scan end signal Sc) sent from the first readout control part 130. The all-pixel reset control part 610 further has a switch control portion 614, which controls the switches 160 of the charge amplifiers 116 (see FIG. 7) in the on states over a predetermined time (hereinafter referred to as the reset time) based on the scan end signal Sc.

Figure 48:
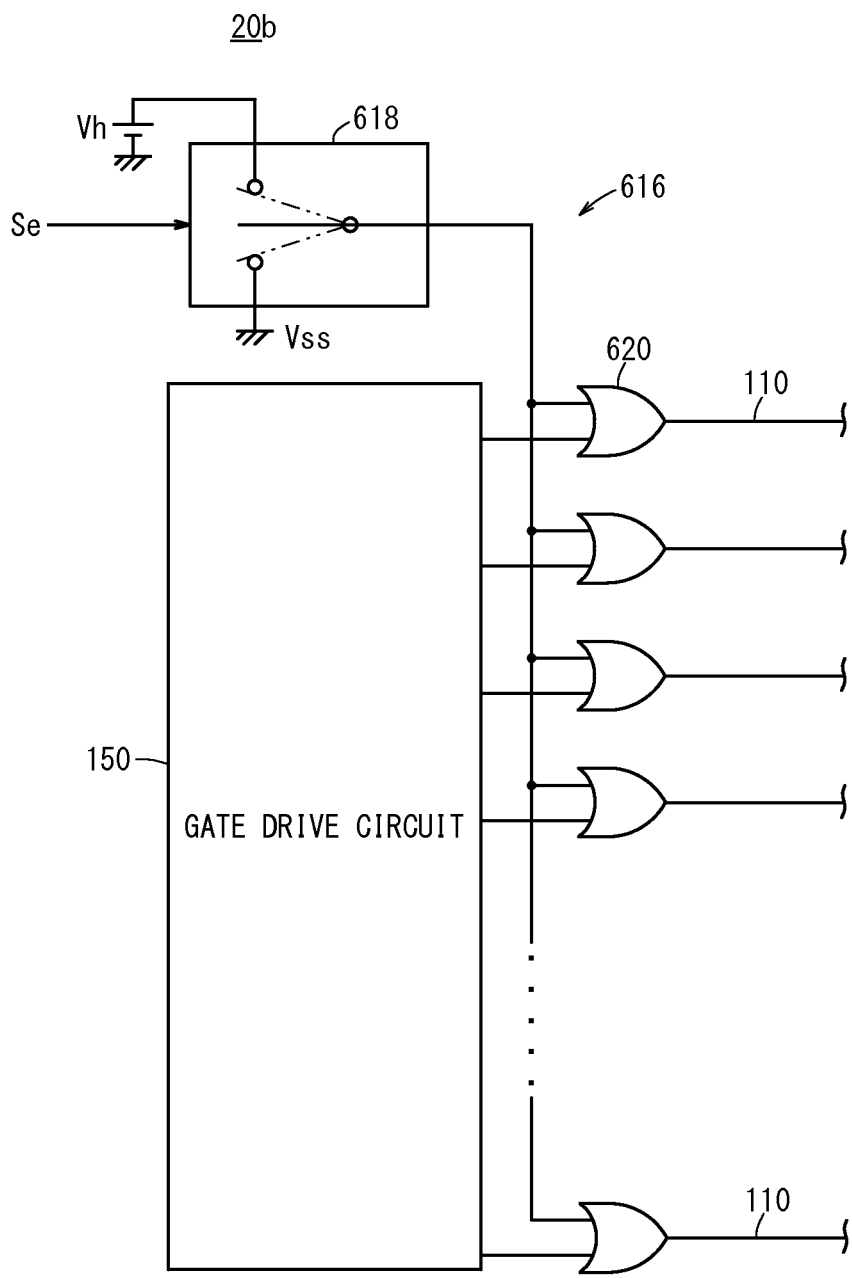
FIG. 48 is a circuit diagram of an example of an all-line activation circuit.

The gate drive part 114 has an all-line activation circuit 616 for each of the gate drive circuits 150. As shown in FIG. 48, the all-line activation circuit 616 has a second switch circuit 618, and further has OR circuits 620 corresponding to the output terminals of the gate drive circuit 150.

The second switch circuit 618 outputs a low-level signal (Vss) at an early stage, and outputs a high-level signal (Vh) over the reset time based on the entered reset signal Se. The output of the high-level signal (Vh) is synchronized with the control of the switches 160 of the charge amplifiers 116 in the on states by the switch control portion 614.

Each of the OR circuits 620 receives two types of signals from the gate drive circuit 150 and the second switch circuit 618, and outputs the logical sum of the entered signals. The OR circuit 620 has an output line corresponding to the gate line 110. When the scan mode is completed, the second switch circuit 618 outputs the high-level signal (Vh) to each OR circuit 620 over the reset time, so that the gate signals are sent to all the gate lines 110 (all the gate lines 110 are activated). At this time, the switches 160 of the charge amplifiers 116 are turned on. Consequently, the residual electric charges (excess charges) in all the pixels 102 are emitted through the switches 160 and the operational amplifiers 156 to GND (ground potential). The electric charges in the pixels 102 may be discarded onto the GND without modification, it being not necessary to convert the electric charges into the electric signals. Therefore, the reset time may be the sum of the one-row pixel readout time (e.g. 21 μsec) and a retardation time, and for example is 30 to 40 μsec.

On the other hand, when the second switch circuit 618 outputs the low-level signal (Vss), the output from the gate drive circuit 150 is effective, and the gate signal is sent to the selected gate line 110. It should be noted that the gate signals are not sent to the gate lines 110 in the exposure period.

Figure 49:
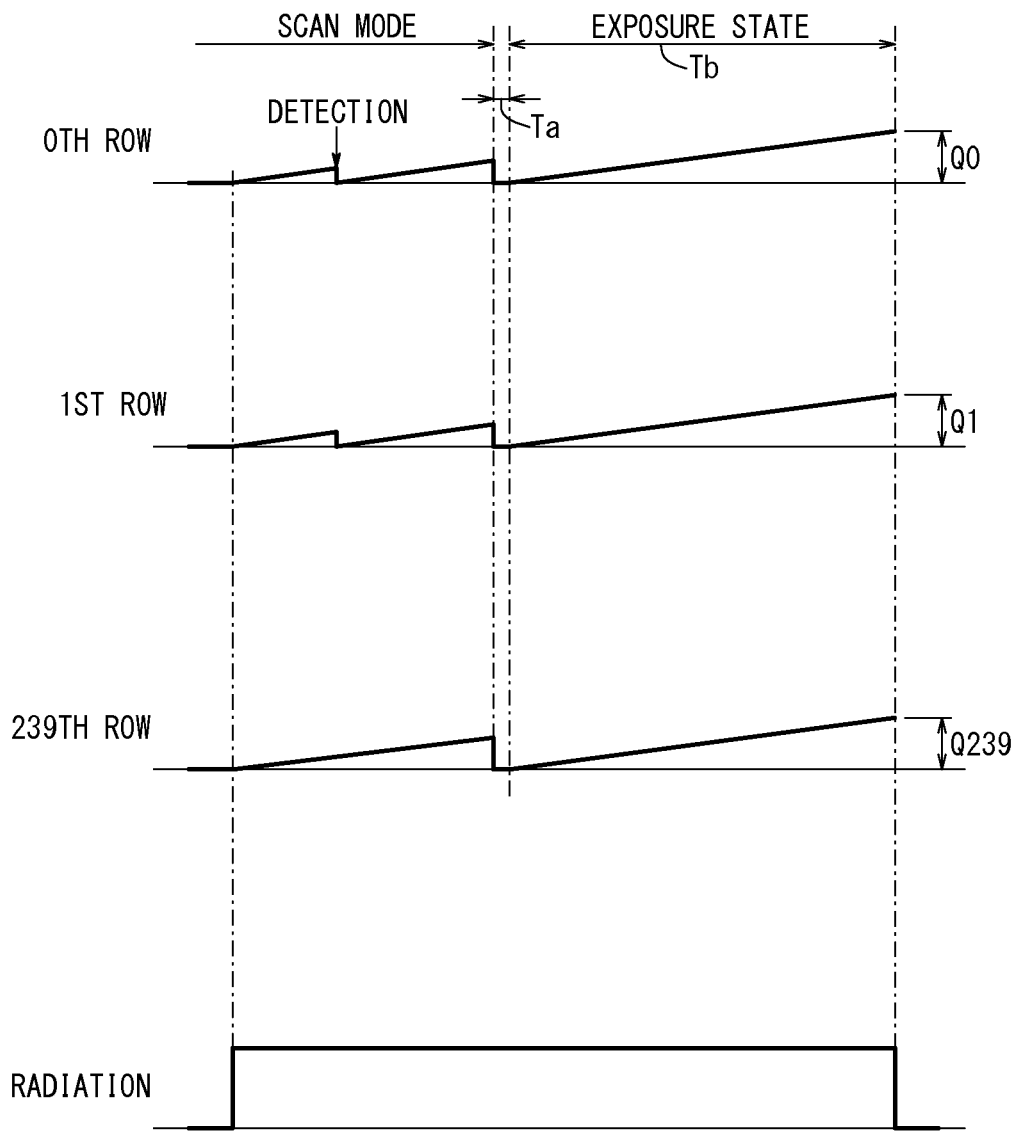
FIG. 49 is a diagram for illustrating electric charges stored in the pixels in some rows in a case where the electronic cassette is switched into an exposure state after a radiation is detected in a process of reading the electric charges in the 0th row, one cycle of the scan mode is completed, and then all pixels are reset.

FIG. 49 is a diagram for illustrating the electric charges stored in the pixels 102 in some rows in a case where the electronic cassette 20b is switched into the exposure state after the radiation 16 is detected in a process of reading the electric charges in the 0th row, the one cycle of the scan mode is completed, and then all the pixels 102 are reset. In the scan mode, each of the gate drive circuits 150 reads the electric charges stored in the pixels 102 in the 0th to final rows sequentially row by row. In this case, for example, even after a digital value obtained by reading the electric charges stored in the pixels 102 in the 0th row is judged to be larger than the threshold value to detect the radiation 16, the electric charges stored in the pixels 102 in the first to 239th rows are read sequentially row by row in the scan mode. When the electric charges stored in the pixels 102 in the 239th row are read out, the scan mode is completed. The electric charges remaining in all the pixels 102 are emitted to the GND (ground potential) in the reset time Ta after the completion, so that the electronic cassette 20b is switched into the exposure state after the reset time Ta. Thus, the all-pixel reset control part 610 acts to switch the radiation conversion panel 64 into the exposure state at the end of the all-pixel reset process. Consequently, at the start of the exposure period Tb, the amounts Q0, . . . , Q238, and Q239 of the electric charges in the pixels 102 can be approximately the same, and the difference between the amounts can be almost eliminated.

Figure 50:
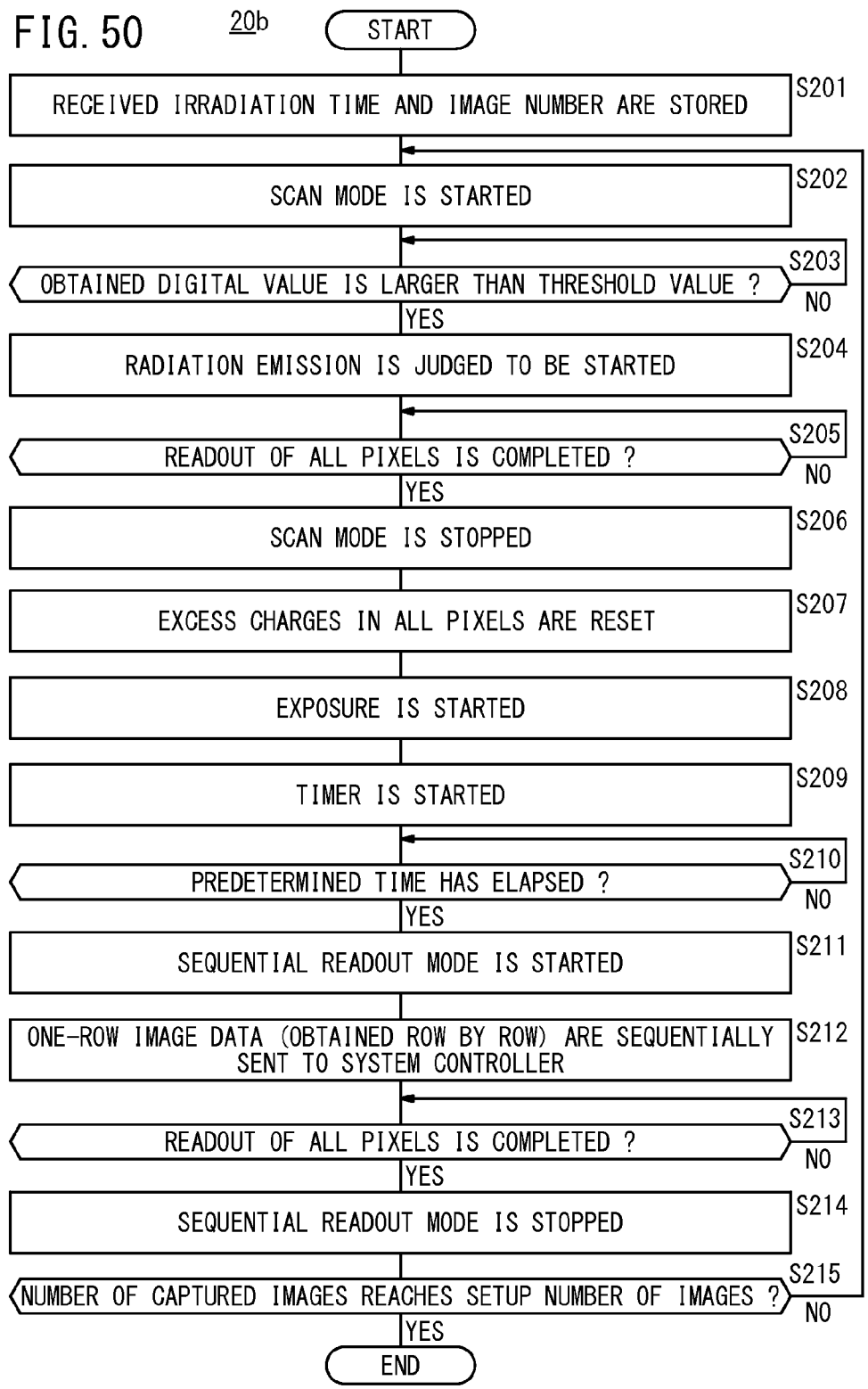
FIG. 50 is a flowchart of the operation of a cassette control device in the electronic cassette according to Modified Example 14.

The operation of the cassette control device 122 in Modified Example 14 is approximately equal to that shown in the flowchart of FIG. 13. As shown in FIG. 50, in Modified Example 14, steps S201 to S204 are carried out first in the same manner as steps S21 to S24 of FIG. 13. After the emission of the radiation 16 is judged to be started in step S204, the first readout control part 130 is in the standby state until the one cycle of the scan mode is completed (step S205). When the scan mode is completed, the first readout control part 130 outputs the scan end signal Sc, the all-line activation portion 612 outputs the reset signal Se to the all-line activation circuits 616 in the gate drive part 114, and the switch control portion 614 controls the switches 160 of the charge amplifiers 116 in the on states over the reset time Ta (see FIG. 7). Thus, the excess charges in all the pixels 102 are emitted to the GND to reset the pixels 102 (step S207). Then, when the reset time Ta has elapsed, the electronic cassette 20b is switched into the exposure state to start the exposure period Tb (step S208). At the start of the exposure period Tb, the cassette control device 122 acts to start a timer (step S209). In next step S210, the elapsed time judgment part 134 judges whether or not a predetermined time (equal to the exposure period Tb in this case) has elapsed from the start of the exposure period Tb. In a case where the predetermined time is judged to have elapsed in step S210, the exposure is completed (the exposure period Tb is stopped), and the second readout control part 136 acts to start the sequential readout mode to read the electric charges generated by the exposure with the radiation 16 (step S211). Steps S211 to S215 are carried out in the same manner as steps S29 to S33 of FIG. 13, and therefore explanations thereof are omitted.

In the electronic cassette 20b of Modified Example 14, the electric charge amount difference between the pixels 102 can be almost eliminated at the start of the exposure period Tb. Therefore, the image quality and the S/N ratio of the radiographic image can be improved.

In the above described example, the all-line activation circuit 616 for each gate drive circuit 150 is hardware containing the second switch circuit 618 and a plurality of the OR circuits 620. When the gate drive circuit 150 has a CPU, software having the same function as the all-line activation circuit 616 may be embedded.

Modified Example 15

In Modified Example 14, after the emission of the radiation 16 is detected in the scan mode, the step of discarding the excess charges in all the pixels 102 is not carried out until the one cycle is completed. Alternatively, the step of discarding the excess charges in all the pixels 102 may be carried out immediately after the detection of the emission of the radiation 16 in the scan mode.

An electronic cassette 20c according to Modified Example 15 will be described specifically below with reference to FIGS. 51 to 54.

Figure 51:
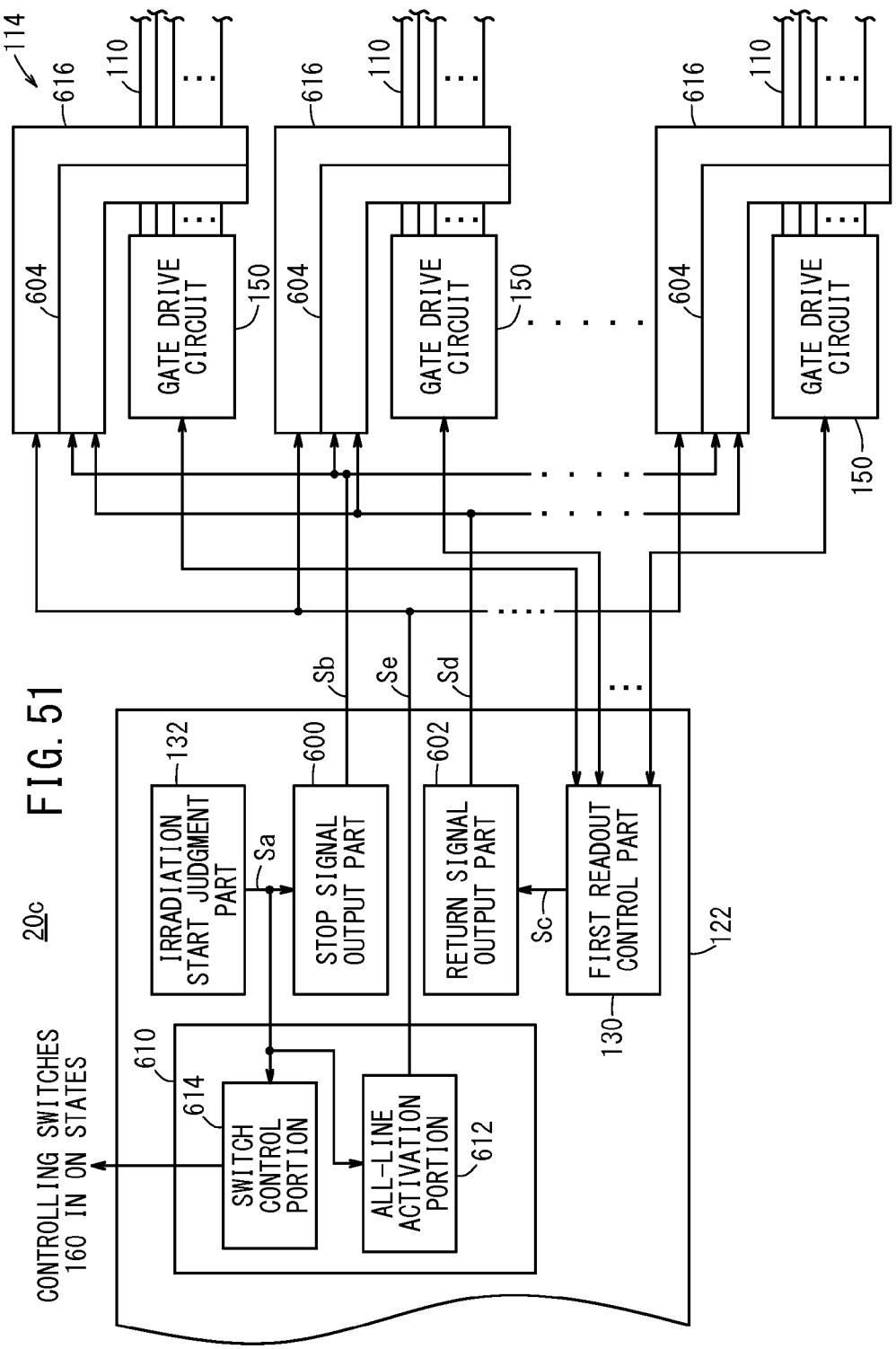
FIG. 51 is a partial block diagram of an electronic cassette according to Modified Example 15.

As shown in FIG. 51, the cassette control device 122 has the stop signal output part 600 and the return signal output part 602 as in Modified Example 13, and further has the all-pixel reset control part 610 (the all-line activation portion 612 and the switch control portion 614) as in Modified Example 14. In Modified Example 15, the all-line activation portion 612 outputs the reset signal Se for activating all lines based on the detection signal Sa from the irradiation start judgment part 132 (indicating the detection of the emission start of the radiation 16).

Figure 52:
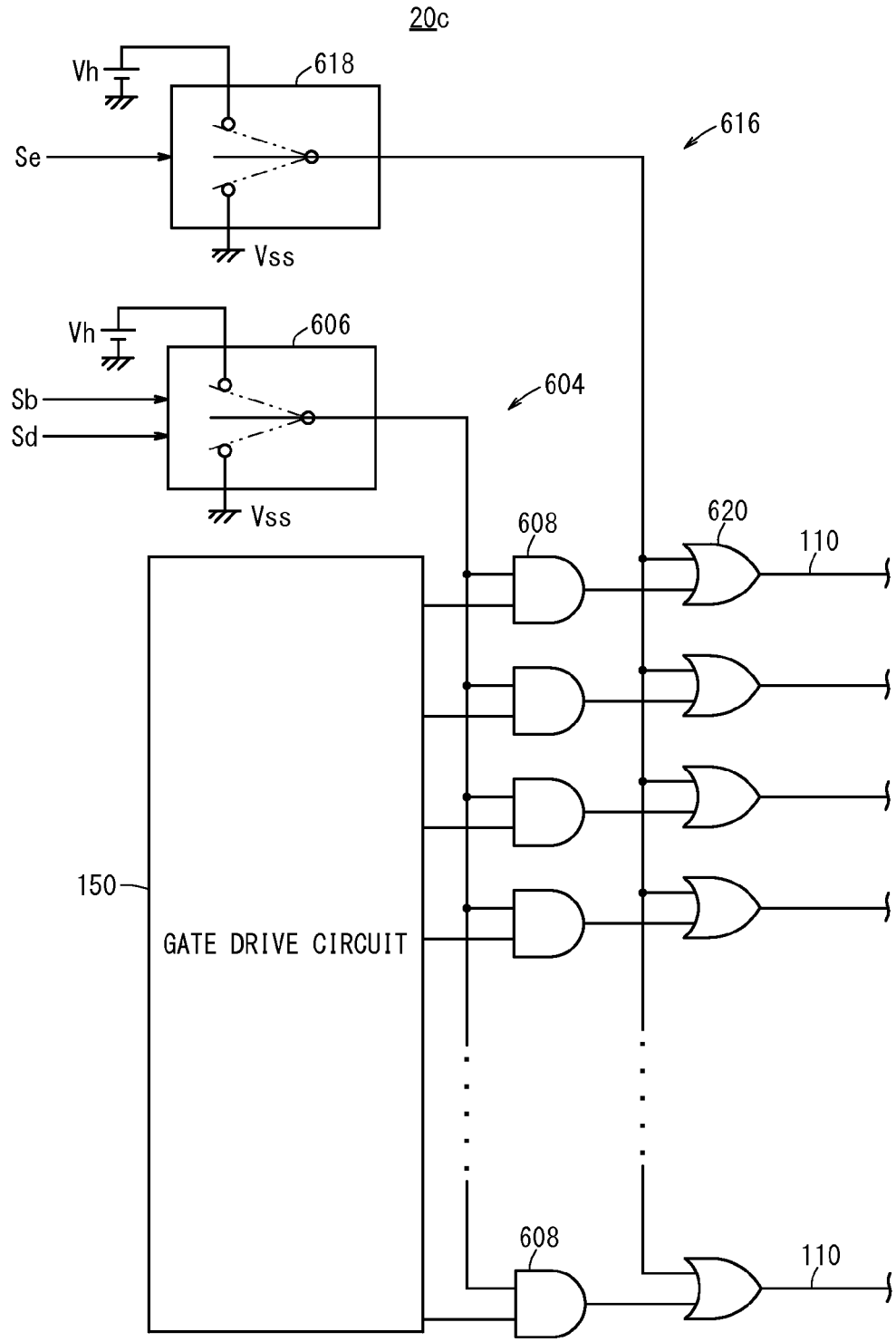
FIG. 52 is a circuit diagram of examples of a mask processing portion and an all-line activation circuit.

The gate drive part 114 has the mask processing portion 604 and the all-line activation circuit 616 for each of the gate drive circuits 150. As shown in FIG. 52, the mask processing portion 604 has the first switch circuit 606, and further has the AND circuits 608 corresponding to the output terminals of the gate drive circuit 150, as in Modified Example 13. The all-line activation circuit 616 has the second switch circuit 618, and further has the OR circuits 620 corresponding to the output terminals of the gate drive circuit 150, as in Modified Example 14.

Each of the AND circuits 608 receives the two types of signals from the gate drive circuit 150 and the first switch circuit 606, and outputs the logical product of the entered signals. Each of the OR circuits 620 receives the two types of signals from the associated AND circuit 608 and the second switch circuit 618, and outputs the logical sum of the entered signals. The OR circuit 620 has the output line corresponding to the gate line 110.

When the start of the emission of the radiation 16 is detected, the stop signal Sb is entered into the first switch circuit 606. Then, until the return signal Sd is entered, each AND circuit 608 outputs the low-level signals (Vss). Meanwhile, when the start of the emission of the radiation 16 is detected, the reset signal Se is entered into the second switch circuit 618. Then, the second switch circuit 618 outputs the high-level signal (Vh) over the reset time Ta, so that the gate signals are sent to all the gate lines 110 (all the gate lines 110 are activated). At this time, the switches 160 of the charge amplifiers 116 are turned on. Consequently, the residual electric charges (excess charges) in all the pixels 102 are emitted through the switches 160 and the operational amplifiers 156 to the GND (ground potential).

Figure 53:
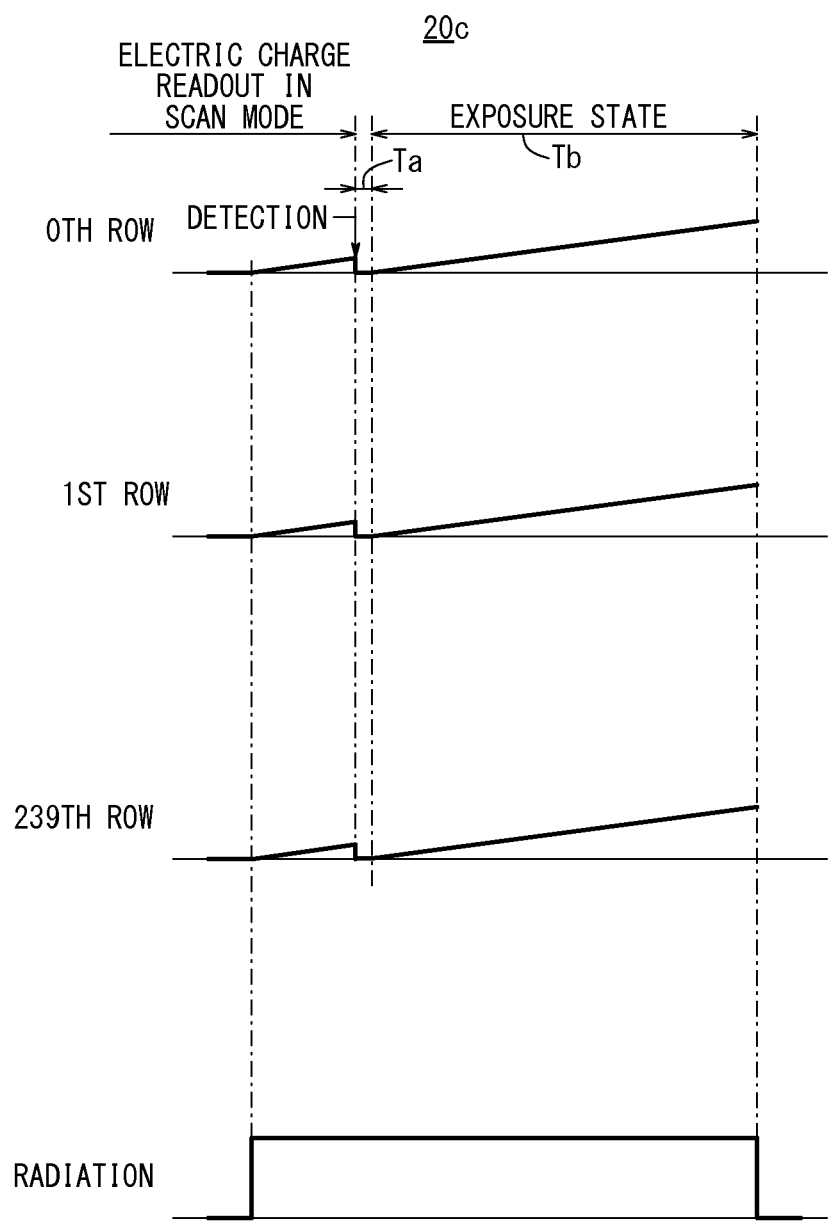
FIG. 53 is a diagram for illustrating electric charges stored in pixels in some rows in a case where the electronic cassette is switched into an exposure state after a radiation is detected, immediately the reading of the electric charges in the pixels in the scan mode is stopped, and all pixels are reset.

Modified Example 15 will be described below with reference to FIG. 53. In the scan mode, each of the gate drive circuits 150 reads the electric charges stored in the pixels 102 in the 0th to final rows sequentially row by row. In this case, for example, when a digital value obtained by reading the electric charges stored in the pixels 102 in the 0th row is judged to be larger than the threshold value to detect the radiation 16, the electric charges remaining in all the pixels 102 are emitted to the GND (ground potential) in the reset time Ta immediately after the judgment. After the reset time Ta has elapsed, though the scan mode is continued until the one cycle is completed, the electric charges stored in the pixels 102 are not read out. Therefore, when the reset time Ta has elapsed from the detection of the radiation 16 (the judgment of the emission of the radiation 16 in the scan mode), before the completion of the one cycle of the scan mode, the electronic cassette 20c can be switched into the exposure state.

Figure 54:
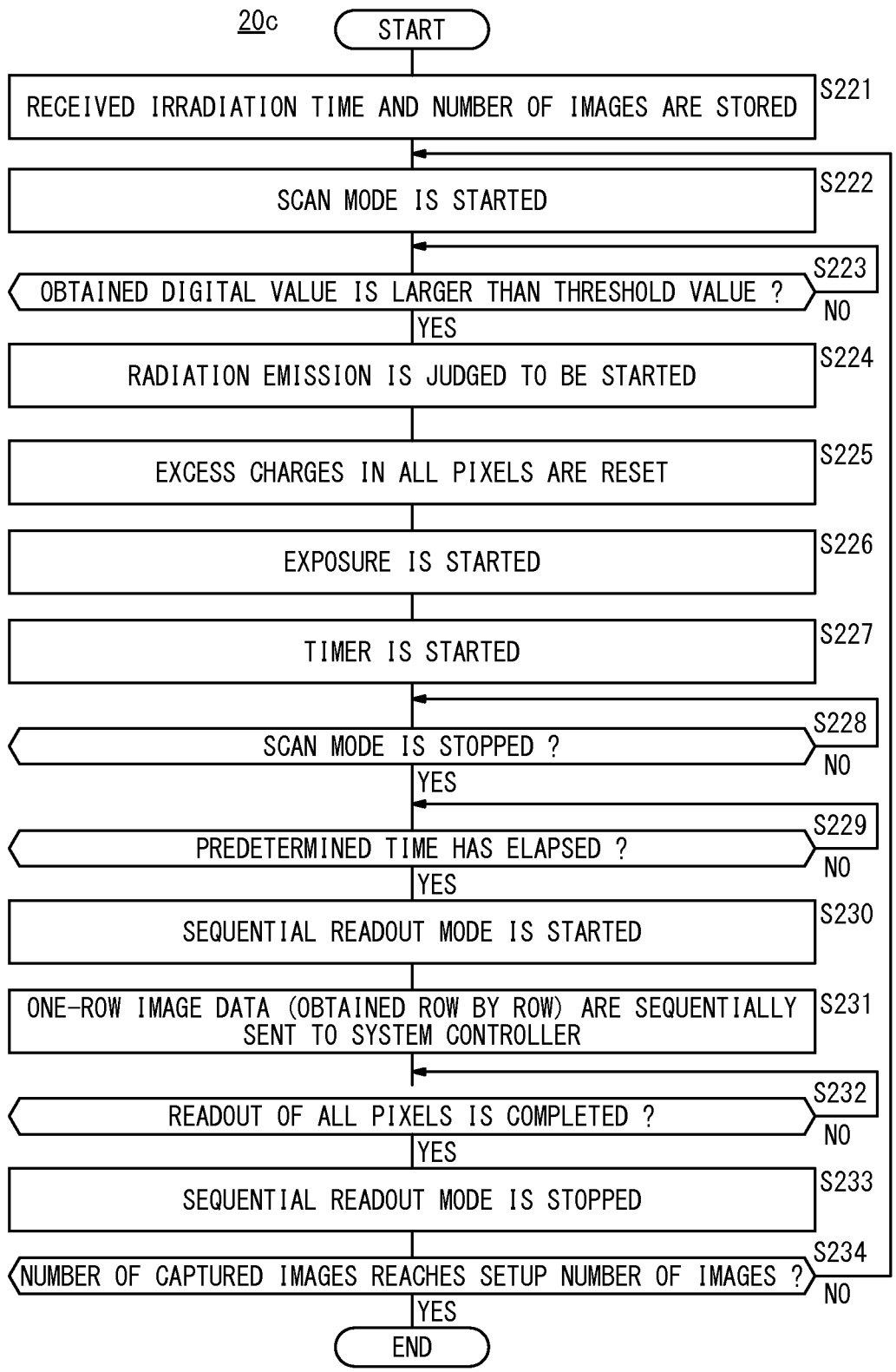
FIG. 54 is a flowchart of the operation of a cassette control device in the electronic cassette according to Modified Example 15.

The operation of the cassette control device 122 in Modified Example 15 is approximately equal to that shown in the flowchart of FIG. 13. As shown in FIG. 54, in Modified Example 15, steps S221 to S224 are carried out first in the same manner as steps S21 to S24 of FIG. 13. If the emission of the radiation 16 is judged to be started in step S224, the stop signal output part 600 sends the stop signal Sb to the gate drive circuits 150 to start the mask processing using the mask processing portion 604 (to stop the output from the gate drive circuits 150). Furthermore, as described above, when the emission of the radiation 16 is judged to be started, the all-line activation portion 612 outputs the reset signal Se to the all-line activation circuits 616 in the gate drive part 114, and the switch control portion 614 controls the switches 160 of the charge amplifiers 116 in the on states over the reset time Ta (see FIG. 7). Thus, the excess charges in all the pixels 102 are emitted to the GND to reset the pixels 102 (step S225). Then, when the reset time Ta has elapsed, the electronic cassette 20c is switched into the exposure state to start the exposure period Tb (step S226). At the start of the exposure period Tb, the cassette control device 122 acts to start a timer (step S227). The cassette control device 122 is in the standby state until the scan mode is completed in step S228. When the scan mode is completed, the return signal output part 602 outputs the return signal Sd, so that the mask processing using the mask processing portion 604 is completed. In next step S229, the elapsed time judgment part 134 judges whether a predetermined time (equal to the exposure period Tb also in this case) has elapsed or not from the start of the exposure period Tb. If the predetermined time is judged to have elapsed in step S229, the exposure is completed (the exposure period Tb is stopped), and the second readout control part 136 acts to start the sequential readout mode to read the electric charges generated by the exposure with the radiation 16 (step S230). Steps 230 to S234 are carried out in the same manner as steps S29 to S33 of FIG. 13, and therefore explanations thereof are omitted.

In Modified Example 15, the advantageous effects of both of Modified Examples 13 and 14 can be achieved. Thus, at the start of the exposure period Tb, the amounts Q0, . . . , Q238, and Q239 of the electric charges in the pixels 102 can be approximately the same, and the difference between the amounts can be almost eliminated. Therefore, the image quality and the S/N ratio of the radiographic image can be improved. Furthermore, the radiation 16 with the image information is not wasted and is utilized for capturing the radiographic image.

In the above described example, the mask processing portion 604 and the all-line activation circuit 616 for each gate drive circuit 150 are hardware containing the first switch circuit 606 and a plurality of the AND circuits 608 and hardware containing the second switch circuit 618 and a plurality of the OR circuits 620 respectively. When the gate drive circuit 150 has a CPU, software having the same functions as the mask processing portion 604 and the all-line activation circuit 616 may be embedded.

Modified Example 16

In the above embodiment and Modified Examples 1 to 15, one electronic cassette 20 is used and described. In general, various types and specifications of the electronic cassettes 20 are used depending on the requirements of the image capturing conditions and the like. For example, in a case where the electronic cassette 20 is a so-called indirect type apparatus using a scintillator, its specification depends on the sensitivity, the pixel size, and the like of the scintillator. Furthermore, the electronic cassettes 20 are relatively costly. Therefore, as is often the case, a plurality of the electronic cassettes 20 are not placed in each of a plurality of image capturing rooms, but are shared by the image capturing rooms. When a plurality of the electronic cassettes 20 are shared by a plurality of the image capturing rooms, a radiation technician may make a mistake in selecting the electronic cassette 20.

Thus, a radiographic image capturing system 10 according to Modified Example 16 has a structure containing a plurality of the electronic cassettes 20, which can be appropriately used even if the mistake is made in the selection of the electronic cassette 20.

Figure 55:
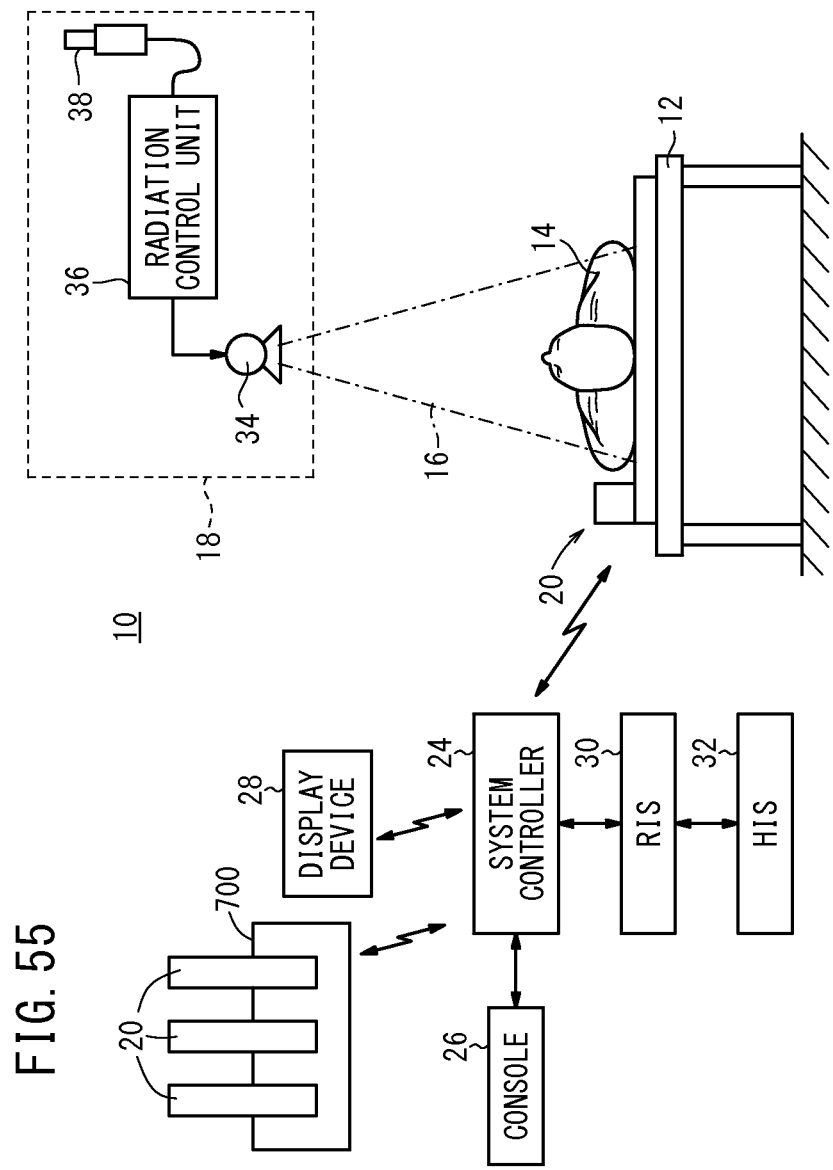
FIG. 55 is a schematic view of a radiographic image capturing system according to Modified Example 16.

FIG. 55 is a schematic view of the radiographic image capturing system 10 of Modified Example 16. As shown in FIG. 55, the radiographic image capturing system 10 has the electronic cassette 20 that is practically used in the image capturing process, and further has a plurality of the electronic cassettes 20 arranged on a cradle 700. The electronic cassettes 20 may have the same or different specifications. The electronic cassettes 20 arranged on the cradle 700 can be charged up by the cradle 700.

Figure 56:
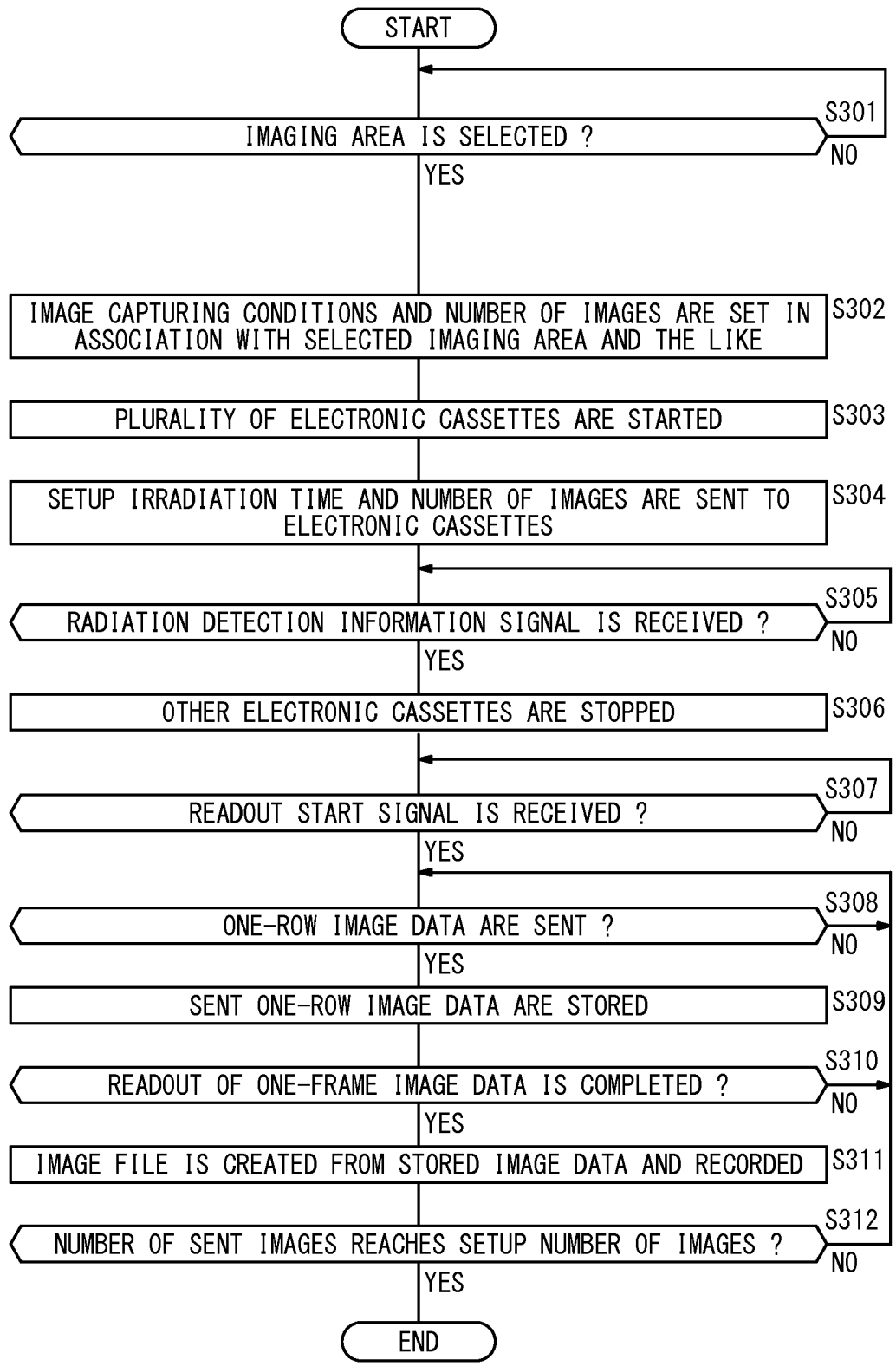
FIG. 56 is a flowchart of the operation of a system controller and a console in the radiographic image capturing system of Modified Example 16.
Figure 57:
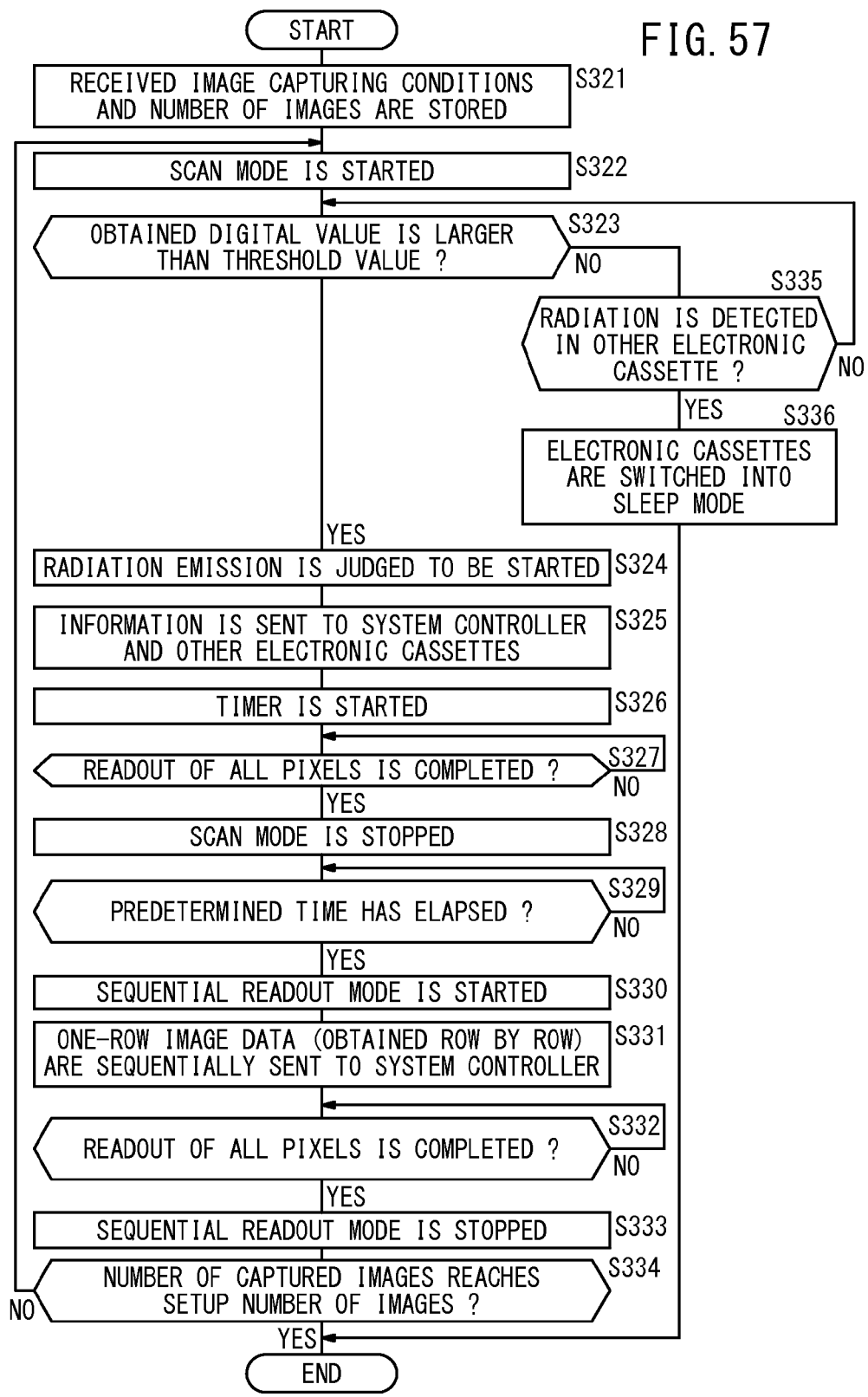
FIG. 57 is a flowchart of the operation of a cassette control device according to Modified Example 16.

FIG. 56 is a flowchart of the operation of the system controller 24 and the console 26 in the radiographic image capturing system 10 of Modified Example 16, and FIG. 57 is a flowchart of the operation of the cassette control device 122 of Modified Example 16 (see FIG. 6).

The operation of each component in Modified Example 16 is substantially equal to that in the above embodiment (FIGS. 12 and 13). However, Modified Example 16 is different from the above embodiment in that any one of a plurality of the electronic cassettes 20 can be used in the image capturing process.

In the operation of the system controller 24 and the console 26 in the radiographic image capturing system 10, steps S301 and S302 of FIG. 56 are carried out in the same manner as steps S1 and S2 of FIG. 12. After the image capturing conditions are set, in next step S303, the control unit 212 sends the startup signal to a plurality of the electronic cassettes 20 through the communication unit 214, whereby the electronic cassettes 20 are started up. The electronic cassettes 20 are in the sleep states until the startup signal is sent. Furthermore, the control unit 212 acts to send identification information of one or more electronic cassettes 20 usable in this image capturing process to the console 26, and to display the identification information on the display unit 204.

Though the one or more electronic cassettes 20 usable in this image capturing process are identified as described above, all the electronic cassettes 20 in the radiographic image capturing system 10 are started up. Alternatively, the control unit 212 may select the electronic cassettes 20 depending on the setup image capturing conditions, and may send the startup signal only to the selected electronic cassettes 20.

When the startup signal is received, a plurality of the electronic cassettes 20 are switched from the sleep mode to the scan mode. The electronic cassettes 20 may act to perform the reset operation before the scan mode. In the sleep mode, electric power is supplied only to essential components (such as the cassette control device 122 and the communication device 126), and is not supplied to the other components.

The image capturing condition setting part 222 and the image number setting part 224 in the control unit 212 (see FIG. 10) send the setup irradiation time and the setup number of images to the started electronic cassettes 20 through the communication unit 214 (step S304).

The control unit 212 judges whether a radiation detection information signal is received or not from any one of the electronic cassettes 20 (step S305). The radiation detection information signal includes a notice of the detection of the radiation 16 in the electronic cassette 20, and includes identification information for identifying the electronic cassette 20.

If the radiation detection information signal is judged to be not received in step S305, the radiographic image capturing system 10 remains in step S305 until it is received. If the radiation detection information signal is judged to be received, the control unit 212 acts to switch the electronic cassettes 20, other than the electronic cassette 20 sending the radiation detection information signal, into the sleep mode, thereby stopping the other electronic cassettes 20 (step S306). Thus, the control unit 212 outputs a stop signal to the electronic cassettes 20, other than the electronic cassette 20 sending the radiation detection information signal. The stop signal includes an instruction to stop the scan mode and switch into the sleep mode. When the stop signal is received, the other electronic cassettes 20 are switched from the scan mode into the sleep mode. Alternatively, the other electronic cassettes 20 may be shut down or switched into a standby mode. In the standby mode, electric power is supplied only to components (such as the memory 124 and the pixels 102) other than the essential components. In a case where the electric power is supplied from the bias supply 108 to the pixels 102 in the standby mode, the electric charges are stored in the pixels 102 but do not read out.

Steps S308 to S312 are carried out in the same manner as steps S6 to S10 of FIG. 12. To judge whether or not the data are sent to the electronic cassette 20, from which the radiation detection information signal is sent, the data may include the identification information of the electronic cassette 20.

The operation of the cassette control device 122 is shown in FIG. 57 as described above. It should be noted that, in Modified Example 16, not one but a plurality of the cassette control devices 122 in all the electronic cassettes 20 that received the startup signal act to perform the operation of FIG. 57.

Steps S321 to S324 of FIG. 57 are carried out in the same manner as steps S21 to S24 of FIG. 13. One cassette control device 122 detects the emission of the radiation 16, and then sends the radiation detection information signal to the control unit 212 in the system controller 24 and the other cassette control devices 122 in the other electronic cassettes 20 in next step S325. The one cassette control device 122 may send the radiation detection information signal only to the control unit 212 or the other cassette control devices 122.

Steps S326 to S334 are carried out in the same manner as steps S25 to S33 of FIG. 13.

When the irradiation start judgment part 132 judges in step S323 that the digital electric signals stored in the memory 124 are not larger than the threshold value (S323: NO), the other cassette control devices 122 judge whether the radiation 16 is detected or not in the other electronic cassettes 20 (step S335). This judgment is made based on the stop signal from the system controller 24 or the radiation detection information signal from the other electronic cassette 20. Thus, in a case where the stop signal or the radiation detection information signal is received, the cassette control device 122 judges that the radiation 16 is detected in the other electronic cassette 20. On the other hand, in a case where the stop signal and the radiation detection information signal are not received, the cassette control device 122 judges that the radiation 16 is not detected in the other electronic cassettes 20.

When the radiation 16 is not detected in the other electronic cassettes 20 (S335: NO), the radiographic image capturing system 10 is returned to step S323. When the radiation 16 is detected in the other electronic cassette 20 (S335: YES), the cassette control devices 122 act to stop the scan mode and are switched into the sleep mode (step S336). Alternatively, as described above, the cassette control devices 122 may be shut down or switched into the standby mode.

As described above, in Modified Example 16, a plurality of the electronic cassettes 20 can be used in the radiographic image capturing process. Therefore, the radiographic image can be obtained even if the user (such as the radiation technician) makes the mistake in selecting the electronic cassette 20. Since the radiation 16 is detected by the radiation conversion panel 64, a radiation detection means other than the radiation conversion panel 64 is not required, and the electronic cassette 20 can be reduced in size.

Furthermore, the electric charges stored in the pixels in a plurality of the rows are simultaneously read out in the scan mode, whereby the start of the emission of the radiation 16 can be judged rapidly and accurately. Since the electric charges stored in the pixels are summed up and read out, a significantly larger value is obtained under the emission of the radiation 16 than without the emission of the radiation 16, whereby the start of the emission of the radiation 16 can be rapidly judged. Therefore, the electronic cassette 20 can be readily switched from the scan mode for simultaneously reading the electric charges in a plurality of the rows to the sequential readout mode for reading the electric charges row by row. Consequently, the start of the emission of the radiation 16 can be judged in a shorter irradiation time (using a smaller amount of the radiation 16), so that the energy of the radiation 16 can be efficiently utilized.

Since a plurality of the rows are simultaneously read out in the scan mode, each row can be controlled in a shorter period in the scan mode than in a row-by-row reading mode. At the start of acquiring the radiographic image information (which is practically used as the radiographic image), the electric charge difference between the pixels is smaller in a case where the electronic cassette 20 is switched from the scan mode to the sequential readout mode than in a case where the start of the emission of the radiation 16 is detected in the second readout mode. Thus, in Modified Example 16, generation of artifacts can be reduced.

Consequently, in Modified Example 16, the radiographic image can be more appropriately captured even if the user makes the mistake in selecting the electronic cassette 20.

In Modified Example 16, when a plurality of the electronic cassettes 20 execute the scan mode and one electronic cassette 20 detects the radiation 16, the one electronic cassette 20 sends the detection information to the other electronic cassettes 20 directly or through the system controller 24. The other electronic cassettes 20 act to stop the scan mode in a case where they receive the detection information. In this case, the electronic cassettes 20 other than the one electronic cassette 20 (which has detected the radiation 16) can reduce the subsequent power consumption.

Though the other electronic cassettes 20 act to stop the scan mode and are switched into the sleep mode based on the stop signal from the system controller 24 or the radiation detection information signal from the one electronic cassette 20 in the above example, Modified Example 16 is not limited thereto. For example, only one of the stop signal and the radiation detection information signal may be utilized. Alternatively, the readout start signal from the electronic cassette 20 may be used instead of the radiation detection information signal. In addition, the system controller 24 may send the stop signal to the other electronic cassettes 20 depending on the readout start signal. In this case, the readout start signal is used also as the radiation detection information signal, so that the processing of the electronic cassette 20 can be simplified.

The contents of Modified Example 16 may be used in combination with Modified Examples 1 to 15. For example, in Modified Example 16, the electric charges may be read only from part of the pixels in the scan mode in the same manner as Modified Example 4. In this case, the electric power consumption or the calculation amount in the scan mode can be reduced.

Modified Example 17

In Modified Example 16, the radiographic image capturing process is performed in all the electronic cassettes 20 that receive the startup signal. However, in some cases, the electronic cassette 20 selected by mistake by the radiation technician do not satisfy the image capturing conditions at all.

Thus, in Modified Example 17, the electronic cassettes 20, which satisfy the image capturing conditions, act to perform the image capturing process after the scan mode. On the other hand, the electronic cassettes 20, which do not satisfy the image capturing conditions, do not perform the image capturing process, though they are switched into the scan mode.

The radiographic image capturing system 10 of Modified Example 17 has the same structure as that of Modified Example 16 (FIG. 55). The operation of the system controller 24 and the console 26 in the radiographic image capturing system 10 in Modified Example 17 is substantially equal to that in Modified Example 16 (FIG. 56). However, in step S302 of FIG. 56, the control unit 212 acts to identify a plurality of the electronic cassettes 20 corresponding to the image capturing conditions and the number of images (the electronic cassettes 20 usable for the image capturing process). Then, in step S303, the control unit 212 sends, to the usable electronic cassettes 20, a startup signal (first startup signal) for instructing the execution of the sequential readout mode after the scan mode. Meanwhile, the control unit 212 sends, to the unusable electronic cassettes 20, a startup signal (second startup signal) for instructing the execution of the sleep mode after the scan mode.

In Modified Example 17, the operation of each cassette control device 122, to which the first startup signal is sent from the control unit 212, is performed in the same manner as Modified Example 16 (FIG. 57). Meanwhile, the operation of each cassette control device 122, to which the second startup signal is sent from the control unit 212, is performed as shown in FIG. 58.

Steps S341 to S345, S347, and S348 of FIG. 58 are carried out in the same manner as steps S321 to S325, S335, and S336 of FIG. 57.

The cassette control device 122 sends the radiation detection information signal in step S345, and is switched from the scan mode into the sleep mode in next step S346. The cassette control device 122 may be switched into the sleep mode after it receives a radiation detection information signal receipt acknowledgment from the system controller 24 or the other electronic cassette 20.

In Modified Example 17, the following effect can be achieved in addition to the advantageous effects of Modified Example 16. In Modified Example 17, the system controller 24 receives the entered radiographic image capturing conditions, and selects the electronic cassettes 20 suitable for the image capturing conditions from a plurality of the electronic cassettes 20. Then, if the radiation 16 is detected in the scan mode, the system controller 24 sends, to the selected electronic cassette 20 suitable for the image capturing conditions, an instruction to execute the sequential readout mode. Meanwhile, if the radiation 16 is detected in the scan mode, the system controller 24 sends, to the electronic cassettes 20 unsuitable for the image capturing conditions, an instruction not to execute the sequential readout mode but to send the radiation 16 detection information to the system controller 24. If the radiation 16 detection information is sent from the electronic cassette 20 unsuitable for the image capturing conditions, the system controller 24 provides a warning to the user (such as the radiation technician) through the display device 28.

Consequently, in a case where the electronic cassette 20 unsuitable for the image capturing conditions is selected by mistake, the system controller 24 can encourage the user to restart the image capturing process.

The contents of Modified Example 17 may be used in combination with Modified Examples 1 to 15. For example, in Modified Example 17, the electric charges may be read only from part of the pixels in the scan mode in the same manner as Modified Example 4. In this case, the electric power consumption or the calculation amount in the scan mode can be reduced.

The technical scope of the present invention is not limited to the above description of the embodiment. It will be apparent to those skilled in the art that various changes and modifications may be made therein. Such changes and modifications are to be understood as included within the scope of the present invention as defined by the appended claims.

The invention claimed is:

1. A radiographic image capturing apparatus comprising:
   an image capturing panel containing a plurality of pixels arranged in a matrix for converting a radiation that is emitted from a radiation source and transmitted through a subject, into electric signals and storing the electric signals,
   a first readout control part configured to execute a first readout mode for reading the electric signals stored in the pixels in a plurality of rows simultaneously,
   an irradiation start judgment part configured to judge start of emission of the radiation from the radiation source to the image capturing panel, the emission of the radiation being judged to be started in a case where a value of the electric signals read by the first readout control part becomes larger than an arbitrarily settable threshold value,
   an elapsed time judgment part configured to judge whether or not a predetermined time has elapsed after the start of the emission of the radiation, and
   a second readout control part configured to execute a second readout mode for reading the electric signals stored in the pixels sequentially row by row, the second readout mode being executed in a case where the predetermined time is judged to have elapsed by the elapsed time judgment part,
   wherein in a case where the emission of the radiation is judged to be started by the irradiation start judgment part, the first readout control part acts to stop the reading of the electric signals and to switch the image capturing panel to an exposure state, and
   wherein a readout time for reading the electric signals stored in the pixels in one row under the first readout mode is not equal to a readout time for reading the electric signals stored in the pixels in one row under the second readout mode.

2. The radiographic image capturing apparatus according to claim 1, further comprising a plurality of gate drive circuits configured to read the electric signals stored in the pixels,
wherein the gate drive circuits are associated with reading of the electric signals in the pixels in different rows and reads associated pixels sequentially row by row,
the first readout control part simultaneously controls the gate drive circuits each to read the associated pixels sequentially row by row, so as to execute the first readout mode for reading the electric signals stored in the pixels in the plurality of rows simultaneously, and
the second readout control part sequentially controls the gate drive circuits each to read the associated pixels sequentially row by row, so as to execute the second readout mode for reading the electric signals stored in the pixels sequentially row by row.

3. The radiographic image capturing apparatus according to claim 1, wherein the readout time for reading the electric signals stored in the pixels in one row under the first readout mode is shorter than the readout time for reading the electric signals stored in the pixels in one row under the second readout mode.

4. The radiographic image capturing apparatus according to claim 1, further comprising:
a first readout mode stop judgment part configured to stop the first readout mode in a case where the value of the electric signals does not reach the threshold value even after a predetermined time has elapsed from start of the first readout mode.

5. The radiographic image capturing apparatus according to claim 1, comprising:
a mode switch judgment part configured to judge whether the first readout mode is started or not, and
a first announcement device configured to announce a judgment result from the mode switch judgment part to an outside in a case where the first readout mode is judged to be started by the mode switch judgment part,
wherein in the first readout mode executed by the first readout control part, the electric signals stored in the pixels are read based on an image capturing menu associated with the emission of the radiation.

6. The radiographic image capturing apparatus according to claim 1, wherein
in the first readout mode executed by the first readout control part, the electric signals stored in the pixels corresponding to an image region of the subject set in an image capturing menu associated with the emission of the radiation are read out, and
in the second readout mode executed by the second readout control part, the electric signals stored in the pixels corresponding to the image region are read out.

7. The radiographic image capturing apparatus according to claim 1, further comprising an all-pixel reset control part configured to perform an all-pixel reset process of discarding the electric signals stored in all the pixels in a case where the emission of the radiation is judged to be started by the irradiation start judgment part,
wherein the image capturing panel is switched to an exposure state at a stage where the all-pixel reset process is completed.

* * * * *

UNITED STATES PATENT AND TRADEMARK OFFICE
CERTIFICATE OF CORRECTION

| | | |
|---|---|---|
| PATENT NO. | : 8,933,413 B2 | Page 1 of 1 |
| APPLICATION NO. | : 14/267192 | |
| DATED | : January 13, 2015 | |
| INVENTOR(S) | : Kitano et al. | |

It is certified that error appears in the above-identified patent and that said Letters Patent is hereby corrected as shown below:

On the title page, under Related U.S. Application Data, it should read--

Continuation of application No. 13/742,111, filed on January 15, 2013, now Patent No. 8,841,628, which is a continuation of application No. PCT/JP2011/062518, filed on May 31, 2011.

Signed and Sealed this
Fifth Day of May, 2015

Michelle K. Lee
*Director of the United States Patent and Trademark Office*